US012396444B2

(12) United States Patent
Mujica et al.

(10) Patent No.: US 12,396,444 B2
(45) Date of Patent: *Aug. 26, 2025

(54) MOUSE COMPRISING A HUMANIZED TRKB LOCUS

(71) Applicant: Regeneron Pharmaceuticals, Inc., Tarrytown, NY (US)

(72) Inventors: Alexander O. Mujica, Elmsford, NY (US); Yajun Tang, White Plains, NY (US); Jeffrey D. Lee, New York, NY (US); Min Gao, Woodcliff Lake, NJ (US); Susan D. Croll, New Paltz, NY (US); Lynn Macdonald, Harrison, NY (US); Ying Hu, Scarsdale, NY (US); Carmelo Romano, Tarrytown, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 195 days.

This patent is subject to a terminal disclaimer.

(21) Appl. No.: 17/810,029

(22) Filed: Jun. 30, 2022

(65) Prior Publication Data
US 2022/0361464 A1 Nov. 17, 2022

Related U.S. Application Data

(63) Continuation of application No. 16/206,330, filed on Nov. 30, 2018, now Pat. No. 11,419,318.

(60) Provisional application No. 62/661,373, filed on Apr. 23, 2018, provisional application No. 62/592,905, filed on Nov. 30, 2017.

(51) Int. Cl.
*A01K 67/0278* (2024.01)
*A01K 67/0271* (2024.01)
*A61K 49/00* (2006.01)
*C12N 5/10* (2006.01)
*C12N 9/12* (2006.01)

(52) U.S. Cl.
CPC ...... *A01K 67/0278* (2013.01); *A01K 67/0271* (2013.01); *A61K 49/0008* (2013.01); *C12N 5/10* (2013.01); *C12N 9/12* (2013.01); *C12Y 207/10001* (2013.01); *A01K 2207/15* (2013.01); *A01K 2217/072* (2013.01); *A01K 2227/105* (2013.01); *A01K 2267/03* (2013.01); *A01K 2267/0318* (2013.01); *C07K 2319/02* (2013.01); *C07K 2319/03* (2013.01); *C07K 2319/033* (2013.01); *C07K 2319/035* (2013.01)

(58) Field of Classification Search
None
See application file for complete search history.

(56) References Cited

U.S. PATENT DOCUMENTS

| | | |
|---|---|---|
| 5,942,435 A | 8/1999 | Wheeler |
| 6,586,251 B2 | 7/2003 | Economides et al. |
| 7,060,429 B2 * | 6/2006 | Krueger ........... C07K 14/70571 |
| | | 435/325 |
| 7,294,754 B2 | 11/2007 | Poueymirou et al. |
| 7,576,259 B2 | 8/2009 | Poueymirou et al. |
| 7,659,442 B2 | 2/2010 | Poueymirou et al. |
| 10,329,582 B2 | 6/2019 | Lee et al. |
| 10,385,359 B2 | 8/2019 | Lee et al. |
| 11,419,318 B2 | 8/2022 | Mujica et al. |
| 2002/0146416 A1 | 10/2002 | Presta et al. |
| 2008/0078000 A1 | 3/2008 | Poueymirou et al. |
| 2013/0111616 A1 | 5/2013 | Macdonald et al. |
| 2013/0111617 A1 | 5/2013 | Macdonald et al. |
| 2013/0117873 A1 | 5/2013 | Wang et al. |
| 2014/0134662 A1 | 5/2014 | Flavell et al. |
| 2014/0178879 A1 | 6/2014 | Economides et al. |
| 2014/0235933 A1 | 8/2014 | Lee et al. |
| 2014/0245466 A1 | 8/2014 | Macdonald et al. |
| 2014/0310828 A1 | 10/2014 | Lee et al. |
| 2015/0089678 A1 | 3/2015 | Murphy et al. |
| 2015/0143558 A1 | 5/2015 | McWhirter et al. |
| 2015/0143559 A1 | 5/2015 | McWhirter et al. |
| 2015/0282463 A1 | 10/2015 | Murphy et al. |
| 2015/0320021 A1 | 11/2015 | Wang et al. |

(Continued)

FOREIGN PATENT DOCUMENTS

| | | |
|---|---|---|
| CN | 101157730 A | 4/2008 |
| CN | 105829542 A | 8/2016 |

(Continued)

OTHER PUBLICATIONS

Patil et al.,Indian Journal of Public Health research & Development, vol. 2, No. 1, 106-109 (Year: 2011).*

(Continued)

*Primary Examiner* — Anoop K Singh
(74) *Attorney, Agent, or Firm* — Alston & Bird LLP

(57) ABSTRACT

Non-human animal genomes, non-human animal cells, and non-human animals comprising a humanized TRKB locus and methods of making and using such non-human animal genomes, non-human animal cells, and non-human animals are provided. Non-human animal cells or non-human animals comprising a humanized TRKB locus express a human TRKB protein or a chimeric transthyretin protein, fragments of which are from human TRKB. Methods are provided for using such non-human animals comprising a humanized TRKB locus to assess in vivo efficacy of human-TRKB-targeting reagents such as nuclease agents designed to target human TRKB.

14 Claims, 16 Drawing Sheets

Specification includes a Sequence Listing.

(56) References Cited

U.S. PATENT DOCUMENTS

| | | | |
|---|---|---|---|
| 2015/0327524 | A1 | 11/2015 | Murphy et al. |
| 2015/0342163 | A1 | 12/2015 | Voronina et al. |
| 2015/0366174 | A1 | 12/2015 | Burova et al. |
| 2015/0376628 | A1 | 12/2015 | Schoenherr et al. |
| 2015/0376651 | A1 | 12/2015 | Frendewey et al. |
| 2016/0145646 | A1 | 5/2016 | Frendewey et al. |
| 2016/0157469 | A1 | 6/2016 | Burova et al. |
| 2016/0157470 | A1* | 6/2016 | Gurer ............... C07K 16/2803 800/21 |
| 2016/0345549 | A1 | 12/2016 | Gurer et al. |
| 2017/0164588 | A1 | 6/2017 | Olson et al. |
| 2018/0139940 | A1 | 5/2018 | Macdonald et al. |
| 2019/0159436 | A1 | 5/2019 | Mujica et al. |
| 2019/0290783 | A1 | 9/2019 | Voronina et al. |
| 2020/0015462 | A1 | 1/2020 | Murphy et al. |

FOREIGN PATENT DOCUMENTS

| | | | | |
|---|---|---|---|---|
| RU | 2425880 C2 | 7/2009 | | |
| WO | WO 2002/003071 A2 | 1/2002 | | |
| WO | WO 2009/053442 A1 | 4/2009 | | |
| WO | WO 2014/130706 A1 | 8/2014 | | |
| WO | WO 2014/172489 A2 | 10/2014 | | |
| WO | WO 2015/088643 A1 | 6/2015 | | |
| WO | WO-2015127158 A1 * | 8/2015 | ....... | A61K 39/39558 |
| WO | WO 2015/200334 A1 | 12/2015 | | |
| WO | WO 2015/200805 A2 | 12/2015 | | |
| WO | WO 2016/044745 A1 | 3/2016 | | |
| WO | WO 2016/081923 A2 | 5/2016 | | |
| WO | WO 2017/087780 A1 | 5/2017 | | |
| WO | WO 2019/108983 A1 | 6/2019 | | |
| WO | WO 2015/042557 A1 | 11/2022 | | |

OTHER PUBLICATIONS

Zhu, F Nature communications 10.1., 1-13 (Year: 2019).*
Perreault et al PLOS One, e62616, 1-13 (Year: 2013).*
Koponen et al Mol. Cell. Neurosci. 26, 166-181 (Year: 2004).*
Harari et al PLOS One, 9, e84259, 1-12 (Year: 2014).*
Luberg et al (ournal of Neurochemistry, 113, 952-964 (Year: 2010).*
Barthold, "Genetically altered mice: phenotypes, no phenotypes, and Faux phenotypes," Genetica, 122(1):75-88, (2004).
Birling, et al., "Modeling human disease in rodents by CRISPR/Cas9 genome editing," Mamm. Genome, 28(7-8):291-301, (2017).
Brevini, et al., "No shortcuts to pig embryonic stem cells," Theriogenology, 74(4):544-550, (2010).
Brevini, et al., "Porcine embryonic stem cells: Facts, challenges and hopes," Theriogenology, 68 Suppl. 1:S206-S213, (2007).
Burova, et al., "Characterization of the Anti-PD-1 Antibody REGN2810 and Its Antitumor Activity in Human PD-1 Knock-In Mice," Mol. Cancer Ther., 16(5):861-870, (2017).
Cao, et al., "Isolation and Culture of Primary Bovine Embryonic Stem Cell Colonies by a Novel Method," J. Exp. Zool. A. Ecol. Genet. Physiol., 311(5):368-376, (2009).
Chen, et al., "Neuroprotective effect of TrkB agonist antibody in humanized TrkB rat," Invest. Ophthalmol. Vis. Sci., 59(9):6134, (2018).
Clark, et al., "A future for transgenic livestock," Nat. Rev. Genet., 4(10):825-833, (2003).
Dechiara, T.M., et al., "VelociMouse: Fully ES Cell-Derived FO-Generation Mice Obtained from the Injection of ES Cells into Eight-Cell-Stage Embryos," Jan. 1, 2009, Methods in Molecular Biology, 530(16): 311-324.
Dennis, "Welfare Issues of Genetically Modified Animals," ILAR J., 43(2):100-109, (2002).
Ezashi et al., "Pluripotent Stem Cells From Domesticated Mammals," Annu. Rev. Anim. Biosci., 4:223-253, (2016).
Frendewey, et al., "The Loss-of-Allele Assay for ES Cell Screening and Mouse Genotyping," Methods Enzymol., 476:295-307, (2010).

Geiger, et al., "Functional Characterization of Human Cancer-Derived TRKB Mutations," PLoS One, 6(2):e16871, 1-12, (2011).
Genoway, "Humanized Mouse Model," retrieved from https://www.genoway.com/services/customized-mouse/knockin-models/humanisation.htm on May 12, 2018.
Glik B., Pasternak Dzh. Moleculyarnaya biotehnologiya. Printsipy i primeneniye. Moscow: Mir, 2002, English Translation.
Gomez, et al., "Derivation of cat embryonic stem-like cells from in vitro-produced blastocysts lon homologous and heterologous feeder cells," Theriogenology, 74(4): 498-515, (2010).
Graham, et al., "Resources for the design of CRISPR gene editing experiments," Genome Biol., 16:260, (2015).
Guo et al., "Targeted Genome Editing in Primate Embryos," Cell Res., 25(7):767-768, (2015).
Haniu, et al., "Interactions between Brain-derived Neurotrophic Factor and the TRKB Receptor: Identification of Two Ligand Binding Domains in Soluble TRKB by Affinity Separation and Chemical Cross-Linking," J. Biol. Chem., 272(40):25296-25308, (1997).
Harari, et al., "Bridging the Species Divide: Transgenic Mice Humanization for Type-1 Interferon Response," PLoS One, 9(1):e84259, 1-12, (2014).
Herndler-Brandstetter, et al., "Humanized mouse model supports development, function, and tissue residency of human natural killer cells," Proc. Natl. Acad. Sci. U.S.A., 114(45):E9626-E9634, (2017).
Hofker Marten H., et al., Transgenic mouse methods and protocols, Methods in molecular biology, 209, p. 51-58, 2002-2003.
Hong et al., "Derivation and Characterization of Embryonic Stem Cell Lines Derived from Transgenic Fischer 344 and Dark Agouti Rats," Stem Cells Dev., 21(9):1571-1586, (2012).
Houdebine, "Methods to Generate Transgenic Animals," pp. 31-48 in "Genetic Engineering in Livestock: New Applications and Interdisciplinary Perspectives," Ed. Engelhard et al., (2009).
Hsu et al., "DNA Targeting Specificity of RNA-guided Cas9 Nucleases," Nat. Biotechnol., 31(9):827-832, (2013).
Hutchison, "Mice with a Conditional Deletion of the Neurotrophin Receptor TrkB Are Dwarfed, and Are Similar to Mice with a MAPK14 Deletion," PLoS One, 8(6):e66206, 1-10, (2013).
Jean, et al., "Pluripotent genes in avian stem cells," Dev. Growth Differ., 55(1): 41-51, (2013).
Kawamata, et al., "Generation of genetically modified rats from embryonic stem cells," Proc. Natl. Acad. Sci. U.S.A., 7(32):14223-14228, (2010).
Khodarovich et al., "Expression of Eukaryotic Recombinant Proteins and Deriving Them from the Milk of Transgenic Animals," Applied Biochemistry and Microbiology, 49(9):711-722, (2013).
Koponen et al., "Transgenic mice overexpressing the full-length neurotrophin receptor trkB exhibit increased activation of the trkB-PLCgamma pathway, reduced anxiety, and facilitated learning," Mol. Cell. Neurosci. 26(1):166-181, (2004).
Kumar, et al., "Transgenic Mouse Technology: Principles and Methods," Methods Mol. Biol., 590:335-362, (2009).
Lee et al., "Developing genetically engineered mouse models using engineered nucleases: Current status, challenges, and the way forward," Drug Discovery Today: Disease Models, 20:13-20, (2016).
Lin, et al., "Appetite Enhancement and Weight Gain by Peripheral Administration of TrkB Agonists in Non-Human Primates," PLoS ONE, 3(4):e1900, 1-7, (2008).
Liu, et al., "7,8-dihydroxyflavone, a small molecular TrkB agonist, is useful for treating various BDNF-implicated human disorders," Transl. Neurodegener., 5:2, pp. 2-9, (2016).
Luberg et al., "Human TrkB Gene: Novel Alternative Transcripts, Protein Isoforms and Expression Pattern in the Prefrontal Cerebral Cortex During Postnatal Development," J. Neurochem., 113(4):952-964, (2010).
Luikart, et al., "In Vivo Role of Truncated TrkB Receptors During Sensory Ganglion Neurogenesis," Neuroscience, 117(4):847-858, (2003).
Lute, et al., "Human CTLA4 knock-in mice unravel the quantitative link between tumor immunity and autoimmunity induced by anti-CTLA-4 antibodies," Blood, 106(9):3127-3133, (2005).
Maksimenko et al., "Use of transgenic animals in biotechnology: prospects and problems," Acta Naturae, 5(1):33-46, (2013).

(56) References Cited

OTHER PUBLICATIONS

Massa, et al., "Small molecule BDNF mimetics activate TrkB signaling and prevent neuronal degeneration in rodents," J. Clin. Invest., 120(5):1774-1785, (2010).
Medina, et al., "TrkB regulates neocortex formation through the Shc/PLCγ-mediated control of neuronal migration," EMBO J., 23(19):3803-3814, (2004).
Mullins, et al., "Transgenesis in the rat and larger mammals," J. Clin. Invest. 97(7):1557-1560, (1996).
Munoz et al., "Constraints to progress in embryonic stem cells from domestic species," Stem Cell Rev. Rep., 5(1):6-9, (2009).
Munoz, et al., "Conventional pluripotency markers are unspecific for bovine embryonic-derived cell-lines," Theriogenology, 69(9): 1159-1164, (2008).
Nadal-Nicolás, et al., "Brn3a as a Marker of Retinal Ganglion Cells: Qualitative and Quantitative Time Course Studies in Naïve and Optic Nerve-Injured Retinas," Invest. Ophthalmol. Vis. Sci., 50(8):3860-3868, (2009).
NCBI Accession No. NP_001269890.1, (2017).
NCBI Accession No. NP_006171.2, (2017).
NCBI Accession No. NP_036863.1, (2017).
Niemann, "Transgenic farm animals get off the ground. Transgenic Animals in Agriculture, Conference Tahoe City, California, USA. Aug. 24-27, 1997." Transgenic Res., 7(1): 73-75, (1998).
O'Leary, et al., "Design of Potent Peptide Mimetics of Brain-derived Neurotrophic Factor," J. Biol. Chem., 278(28):25738-25744, (2008).
Paris, et al., "Equine embryos and embryonic stem cells: defining reliable markers of pluripotency," Theriogenology, 74(4): 516-524, (2010).
Patil et al., "Transgenic animals and drug development: A review," Indian Journal of Public Health Research and Development, 2(1):106-109, (2011).
PCT International Search Report and Written Opinion of the International Searching Authority for application PCT/US2018/063390 mailed Feb. 26, 2019.
Perreault, et al., "Activation of TrkB with TAM-163 Results in Opposite Effects on Body Weight in Rodents and Non-Human Primates," PLoS One, 8(5):e62616, 1-13, (2013).
Poueymirou, et al., "F0 generation mice fully derived from gene-targeted embryonic stem cells allowing immediate phenotypic analyses," Nat. Biotechnol., 25(1):91-99, (2007).
Qian, et al., "Novel Agonist Monoclonal Antibodies Activate TrkB Receptors and Demonstrate Potent Neurotrophic Activities," J. Neurosci., 26(37):9394-9403, (2006).
Rezza, et al., "Unexpected genomic rearrangements at targeted loci associated with CRISPR/Cas9-mediated knock-in," Sci. Rep., 9(1):3486, (2019).
Rios, "BDNF and the central control of feeding: accidental bystander or essential player?," Trends Neurosci., 36(2):83-90, (2013).
Ristevski, "Making better transgenic models: conditional, temporal, and spatial approaches," Mol. Biotechnol., 29(2):153-163, (2005).
Rogalski, et al., "TrkB Activation by Brain-derived Neurotrophic Factor Inhibits the G Protein-gated Inward Rectifier Kir3 by Tyrosine Phosphorylation of the Channel," J. Biol. Chem., 275(33):25082-25088, (2000).
Rogers, et al., "Disruption of the CFTR Gene Produces a Model of Cystic Fibrosis in Newborn Pigs," Science, 321(5897):1837-1841, (2008).
Rybchin V.N., Osnovy geneticheskoy inzhenerii, Saint Petersburg, SHbGTU Publishing House, 2002, p. 411-413, English translation.
Selsby et al., "Porcine models of muscular dystrophy," ILAR J., 56(1):116-126, (2015).
Sigmund, "Viewpoint: Are Studies in Genetically Altered Mice Out of Control?," Arterioscler. Thromb. Vasc. Biol., 20(6):1425-1429, (2000).
U.S. Appl. No. 16/206,330, Advisory Action mailed Feb. 19, 2021.
U.S. Appl. No. 16/206,330, Final Office Action mailed Jan. 14, 2022.
U.S. Appl. No. 16/206,330, Final Office Action mailed Nov. 6, 2020.
U.S. Appl. No. 16/206,330, Non-Final Office Action mailed Apr. 30, 2020.
U.S. Appl. No. 16/206,330, Non-Final Office Action mailed Jul. 2, 2021.
U.S. Appl. No. 16/206,330, Requirement for Restriction/Election mailed Nov. 15, 2019.
Valenzuela, et al., "High-throughput engineering of the mouse genome coupled with high-resolution expression analysis," Nat. Biotechnol., 21(6):652-659, (2003).
Wakchaure, et al., "Transgenic Animals: A Review on its Various Dimensions and Applications in Animal Biotechnology," International Journal of Emerging Technology and Advanced Engineering, 5(11):210-213, (2015).
Webster, et al., "Small molecule activators of the Trk receptors for neuroprotection," BMC Neurosci., 9(Suppl 2):S1, (2008).
Xu, et al., "Brain-derived neurotrophic factor regulates energy balance downstream of melanocortin-4 receptor," Nat. Neurosci, 6(7):736-742, (2003).
Yang et al., "Mutant PFN1 Causes ALS Phenotypes and Progressive Motor Neuron Degeneration in Mice by a Gain of Toxicity," Proc. Natl. Acad. Sci. U.S.A., 113(41):E6209-E6218, (2016).
Yang, et al., "A small molecule TrkB/TrkC neurotrophin receptor co-activator with distinctive effects on neuronal survival and process outgrowth," Neuropharmacology, 110(Pt A):343-361, (2016).
Zhao, et al., "Inconsistency between hepatic expression and serum concentration of transthyretin in mice humanized at the transthyretin locus," Genes to Cells, 13:1257-1268, (2008).
Zhou, et al., "Developing tTA transgenic rats for inducible and reversible gene expression," Int. J. Biol. Sci., 5(2):171-181, (2009).
Zhu et al., "Humanising the mouse genome piece by piece," Nat. Commun. 10(1):1845, (Apr. 23, 2019).
Zörner, et al., "Forebrain-Specific trkB-Receptor Knockout Mice: Behaviorally More Hyperactive Than 'Depressive'," Biol. Psychiatry, 54(1):972-982, (2003).
U.S. Appl. No. 62/592,905, filed Nov. 30, 2017, Expired.
U.S. Appl. No. 62/661,373, filed Apr. 23, 2018, Expired.
U.S. Appl. No. 16/206,330, filed Nov. 30, 2018, now U.S. Pat. No. 11,419,318, Issued.
PCT/US2018/063390, Nov. 30, 2018, WO 2019/108983, Expired.
EP 23207807.1 Extended European Search Report mailed Feb. 28, 2024.

* cited by examiner

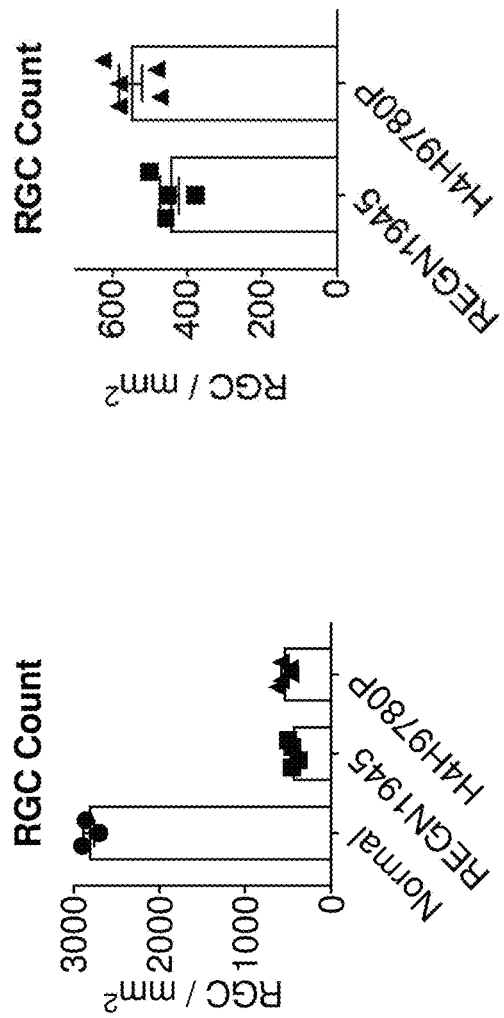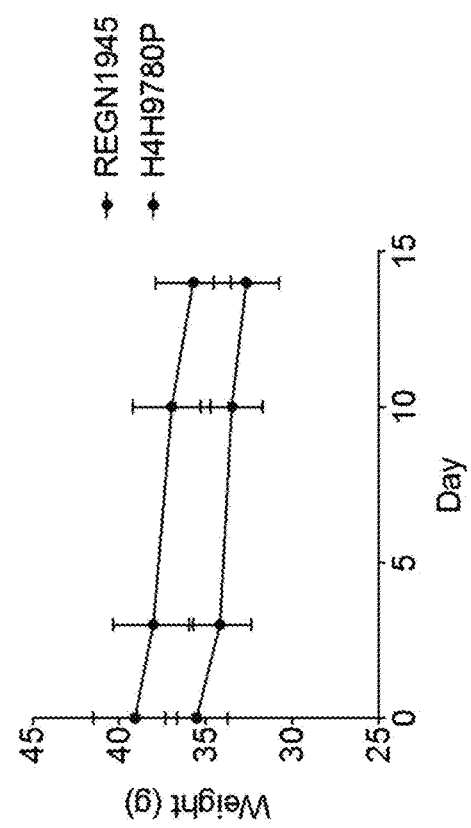
FIG. 17A
FIG. 17B
FIG. 17C

MOUSE COMPRISING A HUMANIZED TRKB LOCUS

CROSS-REFERENCE TO RELATED APPLICATIONS

This application is a continuation of U.S. application Ser. No. 16/206,330, filed Nov. 30, 2018, which claims the benefit of U.S. Application No. 62/592,905, filed Nov. 30, 2017, and U.S. Application No. 62/661,373, filed Apr. 23, 2018, each of which is herein incorporated by reference in its entirety for all purposes.

REFERENCE TO A SEQUENCE LISTING SUBMITTED AS A TEXT FILE VIA EFS WEB

The Sequence Listing written in file 580552SEQLIST.txt is 154 kilobytes, was created on Jun. 29, 2022, and is hereby incorporated by reference.

BACKGROUND

Tropomyosin receptor kinase B (TRKB) is a promising target for neuroprotection in neurodegenerative diseases such as glaucoma. TRKB is one of the most widely distributed neurotrophic receptors (NTRs) in the brain, which is highly enriched in the neocortex, hippocampus, striatum, and brainstem. Binding of brain-derived neurotrophic factor (BDNF) to TRKB receptor triggers its dimerization through conformational changes and autophosphorylation of tyrosine residues in the intracellular domain, resulting in activation of signaling pathways involving mitogen-activated protein kinase (MAPK), phosphatidylinositol 3-kinase (PI3K), and phospholipase C-γ (PLC-γ).

TRKB is important for neuronal survival, differentiation, and function, and TRKB agonists could have therapeutic potential in numerous neurological, mental, and metabolic disorders. However, there remains a need for suitable non-human animals providing the true human target or a close approximation of the true human target of human-TRKB-targeting reagents, thereby enabling testing of the efficacy and mode of action of such agents in live animals as well as pharmacokinetic and pharmacodynamics studies.

SUMMARY

Non-human animals comprising a humanized TRKB locus are provided, as well as methods of using such non-human animals. Non-human animal genomes or cells comprising a humanized TRKB locus are also provided.

In one aspect, provided are non-human animal genomes, non-human animal cells, or non-human animals comprising a humanized TRKB locus. Such non-human animal genomes, non-human animal cells, or non-human animals can comprise a genetically modified endogenous TrkB locus encoding a TRKB protein, wherein the TRKB protein comprises a cytoplasmic domain, a transmembrane domain, and an extracellular domain, and all or part of the extracellular domain is encoded by a segment of the endogenous TrkB locus that has been deleted and replaced with an orthologous human TRKB sequence.

In one aspect, provided are non-human animals comprising a humanized TrkB locus. Such non-human animals can comprise a genetically modified endogenous TrkB locus encoding a TRKB protein, wherein the TRKB protein comprises a cytoplasmic domain, a transmembrane domain, and an extracellular domain, and all or part of the extracellular domain is encoded by a segment of the endogenous TrkB locus that has been deleted and replaced with an orthologous human TRKB sequence.

In another aspect, provided are non-human animal cells comprising in their genome a genetically modified endogenous TrkB locus encoding a TRKB protein, wherein the TRKB protein comprises a cytoplasmic domain, a transmembrane domain, and an extracellular domain, and all or part of the extracellular domain is encoded by a segment of the endogenous TrkB locus that has been deleted and replaced with an orthologous human TRKB sequence.

In another aspect, provided are non-human animal genomes comprising a genetically modified endogenous TrkB locus encoding a TRKB protein, wherein the TRKB protein comprises a cytoplasmic domain, a transmembrane domain, and an extracellular domain, and all or part of the extracellular domain is encoded by a segment of the endogenous TrkB locus that has been deleted and replaced with an orthologous human TRKB sequence In some such non-human animal genomes, non-human animal cells, or non-human animals, the TRKB protein comprises a human TRKB extracellular domain. Optionally, the extracellular domain comprises the sequence set forth in SEQ ID NO: 60. Optionally, all of the extracellular domain is encoded by the segment of the endogenous TrkB locus that has been deleted and replaced with the orthologous human TRKB sequence, optionally wherein the coding sequence for the extracellular domain comprises the sequence set forth in SEQ ID NO: 72.

In some such non-human animal genomes, non-human animal cells, or non-human animals, the TRKB protein comprises an endogenous signal peptide. Optionally, the signal peptide comprises the sequence set forth in SEQ ID NO: 51 or 55. Optionally, all of the signal peptide is encoded by an endogenous TrkB sequence, optionally wherein the coding sequence for the signal peptide comprises the sequence set forth in SEQ ID NO: 63 or 67.

In some such non-human animal genomes, non-human animal cells, or non-human animals, the TRKB protein comprises an endogenous TRKB transmembrane domain. Optionally, the transmembrane domain comprises the sequence set forth in SEQ ID NO: 53 or 57. Optionally, all of the transmembrane domain is encoded by an endogenous TrkB sequence, optionally wherein the coding sequence for the transmembrane domain comprises the sequence set forth in SEQ ID NO: 65 or 69.

In some such non-human animal genomes, non-human animal cells, or non-human animals, the TRKB protein comprises an endogenous TRKB cytoplasmic domain. Optionally, the cytoplasmic domain comprises the sequence set forth in SEQ ID NO: 54 or 58. Optionally, all of the cytoplasmic domain is encoded by an endogenous TrkB sequence, optionally wherein the coding sequence for the cytoplasmic domain comprises the sequence set forth in SEQ ID NO: 66 or 70.

In some such non-human animal genomes, non-human animal cells, or non-human animals, the TRKB protein comprises an endogenous TRKB signal peptide, an endogenous TRKB transmembrane domain, and an endogenous TRKB cytoplasmic domain. Optionally, the signal peptide comprises the sequence set forth in SEQ ID NO: 51, the transmembrane domain comprises the sequence set forth in SEQ ID NO: 53, and the cytoplasmic domain comprises the sequence set forth in SEQ ID NO: 54. Optionally, the signal peptide comprises the sequence set forth in SEQ ID NO: 55, the transmembrane domain comprises the sequence set forth in SEQ ID NO: 57, and the cytoplasmic domain comprises the sequence set forth in SEQ ID NO: 58. Optionally, all of the signal peptide, all of the transmembrane domain, and all of the cytoplasmic domain are encoded by an endogenous TrkB sequence. Optionally, the coding sequence for the signal peptide comprises the sequence set forth in SEQ ID NO: 63, the coding sequence for the transmembrane domain comprises the sequence set forth in SEQ ID NO: 65, and the coding sequence for the cytoplasmic domain comprises the sequence set forth in SEQ ID NO: 66. Optionally, the coding sequence for the signal peptide comprises the sequence set forth in SEQ ID NO: 67, the coding sequence for the transmembrane domain comprises the sequence set forth in SEQ ID NO: 69, and the coding sequence for the cytoplasmic domain comprises the sequence set forth in SEQ ID NO: 70.

In some such non-human animal genomes, non-human animal cells, or non-human animals, the TRKB protein is a chimeric non-human animal/human TRKB protein. Optionally, the extracellular domain is a human TRKB extracellular domain, the transmembrane domain is an endogenous TRKB protein transmembrane domain, and the cytoplasmic domain is an endogenous TRKB protein cytoplasmic domain. Optionally, the TRKB protein comprises the sequence set forth in SEQ ID NO: 4 or 5. Optionally, the coding sequence of the genetically modified TrkB locus encoding the TRKB protein comprises the sequence set forth in SEQ ID NO: 12 or 13.

Some such non-human animal genomes, non-human animal cells, or non-human animals are heterozygous for the genetically modified endogenous TrkB locus. Some such non-human animal genomes, non-human animal cells, or non-human animals are homozygous for the genetically modified endogenous TrkB locus.

Some such non-human animals or mammals. Optionally, the non-human animal is a rodent. Optionally, the rodent is a rat or mouse.

Some such non-human animals are rats. Optionally, the TRKB protein comprises the sequence set forth in SEQ ID NO: 5. Optionally, the coding sequence of the genetically modified TrkB locus encoding the TRKB protein comprises the sequence set forth in SEQ ID NO: 13.

Some such non-human animals are mice. Optionally, the TRKB protein comprises the sequence set forth in SEQ ID NO: 4. Optionally, the coding sequence of the genetically modified TrkB locus encoding the TRKB protein comprises the sequence set forth in SEQ ID NO: 12.

In another aspect, provided are methods of assessing the activity of a human-TRKB-targeting reagent in vivo using the above non-human animals. Some such methods comprise: (a) administering the human-TRKB-targeting reagent to the non-human animal; and (b) assessing the activity of the human-TRKB-targeting reagent in the non-human animal.

In some such methods, the assessed activity is neuroprotective activity.

In some such methods, step (a) comprises injecting the human-TRKB-targeting reagent to the non-human animal.

In some such methods, step (b) comprises assessing changes in one or more or all of body weight, body composition, metabolism, and locomotion relative to a control-non-human animal. Optionally, the assessing changes in body composition comprises assessing lean mass and/or fat mass relative to a control non-human animal. Optionally, assessing changes in metabolism comprises assessing changes in food consumption and/or water consumption.

In some such methods, step (b) comprises assessing TRKB phosphorylation and/or activation of the MAPK/ERK and PI3K/Akt pathways relative to a control non-human animal.

In some such methods, step (b) comprises assessing neuroprotective activity. In some such methods, step (b) comprises assessing neuroprotective activity, and the non-human animal is a rat. In some such methods, step (b) comprises assessing retinal ganglion cell viability. Optionally, assessing retinal ganglion cell viability comprises assessing retinal ganglion cell density. Optionally, retinal ganglion cell density is measured in dissected retinas stained for retinal ganglion cells. Optionally, retinal ganglion cell viability is assessed in a complete optic nerve transection model after optic nerve injury. Optionally, retinal ganglion cell viability is assessed in an optic nerve crush model.

In some such methods, the human-TRKB-targeting reagent is an antigen-binding protein. Optionally, the antigen-binding protein is a human TRKB agonist antibody. In some such methods, the human-TRKB-targeting reagent is a small molecule. Optionally, the small molecule is a human TRKB agonist.

In another aspect, provided are targeting vectors for generating a genetically modified endogenous TrkB locus encoding a TRKB protein, wherein the TRKB protein comprises a cytoplasmic domain, a transmembrane domain, and an extracellular domain, and all or part of the extracellular domain is encoded by a segment of the endogenous TrkB locus that has been deleted and replaced with an orthologous human TRKB sequence, and wherein the targeting vector comprises an insert nucleic acid comprising the orthologous human TRKB sequence flanked by a 5' homology arm targeting a 5' target sequence at the endogenous TrkB locus and a 3' homology arm targeting a 3' target sequence at the endogenous TrkB locus.

In another aspect, provided are methods of making any of the non-human animals described above. Some such methods can comprise (a) introducing into a non-human animal pluripotent cell that is not a one-cell stage embryo: (i) an exogenous repair template comprising an insert nucleic acid flanked by a 5' homology arm that hybridizes to a 5' target sequence at the endogenous TrkB locus and a 3' homology arm that hybridizes to a 3' target sequence at the endogenous TrkB locus, wherein the insert nucleic acid comprises the orthologous human TRKB sequence; and (ii) a nuclease agent targeting a target sequence within the endogenous TrkB locus, wherein the genome is modified to comprise the genetically modified endogenous TrkB locus; (b) introducing the modified non-human animal pluripotent cell into a host embryo; and (c) implanting the host embryo into a surrogate mother to produce a genetically modified F0 generation non-human animal comprising the genetically modified endogenous TrkB locus. Optionally, the pluripotent cell is an embryonic stem (ES) cell. Optionally, the nuclease agent is a Cas9 protein and a guide RNA that targets a guide RNA target sequence within the endogenous TrkB locus. Optionally, step (a) further comprises introducing into the non-human animal pluripotent cell a second guide RNA that targets a second guide RNA target sequence within the endogenous TrkB locus. Optionally, the exogenous repair template is a large targeting vector that is at least 10 kb in length, or wherein the exogenous repair template is a large targeting vector in which the sum total of the 5' homology arm and the 3' homology arm is at least 10 kb in length.

Some such methods comprise: (a) introducing into a non-human animal one-cell stage embryo: (i) an exogenous repair template comprising an insert nucleic acid flanked by a 5' homology arm that hybridizes to a 5' target sequence at the endogenous TrkB locus and a 3' homology arm that hybridizes to a 3' target sequence at the endogenous TrkB locus, wherein the insert nucleic acid comprises the orthologous human TRKB sequence; and (ii) a nuclease agent targeting a target sequence within the endogenous TrkB locus, wherein the genome is modified to comprise the genetically modified endogenous TrkB locus; and (b) implanting the modified non-human animal one-cell stage embryo into a surrogate mother to produce a genetically modified F0 generation non-human animal comprising the genetically modified endogenous TrkB locus. Optionally, the nuclease agent is a Cas9 protein and a guide RNA that targets a guide RNA target sequence within the endogenous TrkB locus. Optionally, step (a) further comprises introducing into the non-human one-cell stage embryo a second guide RNA that targets a second guide RNA target sequence within the endogenous TrkB locus.

BRIEF DESCRIPTION OF THE FIGURES

FIG. 12A shows BDNF dose response in an optic nerve crush (ONC) model in WT mice. FIG. 12B shows BDNF dose response in an optic nerve transection model in WT rat from 0.13 µg to 30 µg.

FIG. 15A includes a naïve control (noninjured contralateral eye), and FIG. 15B does not.

FIGS. 17A and 17B show retinal ganglion cell density in retinas dissected and stained for retinal ganglion cells in human TRKB homozygous mice given TrkB agonist antibody (H4H9780P) or isotype control antibody (REGN1945) intravitreally at 3 and 10 days after optic nerve transection. Retinas were dissected 14 days after transection. FIG. 17A includes a normal control (noninjured contralateral eye), and FIG. 17B does not.

FIG. 17C shows the body weight of the human TRKB homozygous mice given TrkB agonist antibody (H4H9780P) or isotype control antibody (REGN1945).

DEFINITIONS

Figure 1:
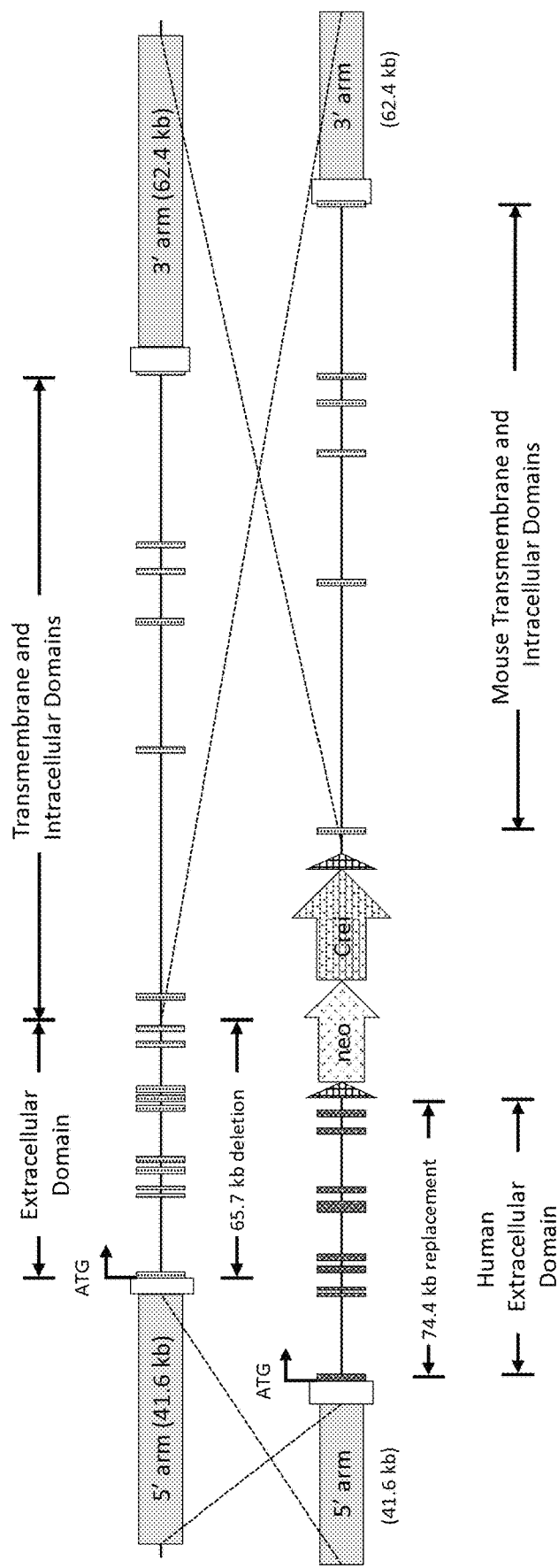
FIG. 1 (not to scale) shows a schematic of the targeting scheme for humanization of the region of the mouse TrkB (mouse Ntrk2) locus encoding the extracellular domain of TRKB. The top portion of the figure shows the endogenous mouse TrkB (mouse Ntrk2) locus, and the bottom portion of the figure shows the large targeting vector.

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones. The term "domain" refers to any part of a protein or polypeptide having a particular function or structure.

Proteins are said to have an "N-terminus" and a "C-terminus." The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

The term "genomically integrated" refers to a nucleic acid that has been introduced into a cell such that the nucleotide sequence integrates into the genome of the cell and is capable of being inherited by progeny thereof. Any protocol may be used for the stable incorporation of a nucleic acid into the genome of a cell.

The term "targeting vector" refers to a recombinant nucleic acid that can be introduced by homologous recombination, non-homologous-end-joining-mediated ligation, or any other means of recombination to a target position in the genome of a cell.

The term "viral vector" refers to a recombinant nucleic acid that includes at least one element of viral origin and includes elements sufficient for or permissive of packaging into a viral vector particle. The vector and/or particle can be utilized for the purpose of transferring DNA, RNA, or other nucleic acids into cells either ex vivo or in vivo. Numerous forms of viral vectors are known.

The term "wild type" includes entities having a structure and/or activity as found in a normal (as contrasted with mutant, diseased, altered, or so forth) state or context. Wild type genes and polypeptides often exist in multiple different forms (e.g., alleles).

The term "endogenous" refers to a nucleic acid sequence that occurs naturally within a cell or non-human animal. For example, an endogenous TrkB sequence of a non-human animal refers to a native TrkB sequence that naturally occurs at the TrkB locus in the non-human animal.

"Exogenous" molecules or sequences include molecules or sequences that are not normally present in a cell in that form. Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence, or can include a sequence corresponding to an endogenous sequence within the cell but in a different form (i.e., not within a chromosome). In contrast, endogenous molecules or sequences include molecules or sequences that are normally present in that form in a particular cell at a particular developmental stage under particular environmental conditions.

The term "heterologous" when used in the context of a nucleic acid or a protein indicates that the nucleic acid or protein comprises at least two portions that do not naturally occur together in the same molecule. For example, the term "heterologous," when used with reference to portions of a nucleic acid or portions of a protein, indicates that the nucleic acid or protein comprises two or more sub-sequences that are not found in the same relationship to each other (e.g., joined together) in nature. As one example, a "heterologous" region of a nucleic acid vector is a segment of nucleic acid within or attached to another nucleic acid molecule that is not found in association with the other molecule in nature. For example, a heterologous region of a nucleic acid vector could include a coding sequence flanked by sequences not found in association with the coding sequence in nature. Likewise, a "heterologous" region of a protein is a segment of amino acids within or attached to another peptide molecule that is not found in association with the other peptide molecule in nature (e.g., a fusion protein, or a protein with a tag). Similarly, a nucleic acid or protein can comprise a heterologous label or a heterologous secretion or localization sequence.

"Codon optimization" takes advantage of the degeneracy of codons, as exhibited by the multiplicity of three-base pair codon combinations that specify an amino acid, and generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a nucleic acid encoding a Cas9 protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) *Nucleic Acids Research* 28:292, herein incorporated by reference in its entirety for all purposes. Computer algorithms for codon optimization of a particular sequence for expression in a particular host are also available (see, e.g., Gene Forge).

The term "locus" refers to a specific location of a gene (or significant sequence), DNA sequence, polypeptide-encoding sequence, or position on a chromosome of the genome of an organism. For example, a "TrkB locus" may refer to the specific location of a TrkB gene, TrkB DNA sequence, TrkB-encoding sequence, or TrkB position on a chromosome of the genome of an organism that has been identified as to where such a sequence resides. A "TrkB locus" may comprise a regulatory element of a TrkB gene, including, for example, an enhancer, a promoter, 5' and/or 3' untranslated region (UTR), or a combination thereof.

The term "gene" refers to a DNA sequence in a chromosome that codes for a product (e.g., an RNA product and/or a polypeptide product) and includes the coding region interrupted with non-coding introns and sequence located adjacent to the coding region on both the 5' and 3' ends such that the gene corresponds to the full-length mRNA (including the 5' and 3' untranslated sequences). The term "gene" also includes other non-coding sequences including regulatory sequences (e.g., promoters, enhancers, and transcription factor binding sites), polyadenylation signals, internal ribosome entry sites, silencers, insulating sequence, and matrix attachment regions. These sequences may be close to the coding region of the gene (e.g., within 10 kb) or at distant sites, and they influence the level or rate of transcription and translation of the gene.

The term "allele" refers to a variant form of a gene. Some genes have a variety of different forms, which are located at the same position, or genetic locus, on a chromosome. A diploid organism has two alleles at each genetic locus. Each pair of alleles represents the genotype of a specific genetic locus. Genotypes are described as homozygous if there are two identical alleles at a particular locus and as heterozygous if the two alleles differ.

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. The promoter sequences disclosed herein modulate transcription of an operably linked polynucleotide. A promoter can be active in one or more of the cell types disclosed herein (e.g., a eukaryotic cell, a non-human mammalian cell, a human cell, a rodent cell, a pluripotent cell, a one-cell stage embryo, a differentiated cell, or a combination thereof). A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772, herein incorporated by reference in its entirety for all purposes.

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

The term "variant" refers to a nucleotide sequence differing from the sequence most prevalent in a population (e.g., by one nucleotide) or a protein sequence different from the sequence most prevalent in a population (e.g., by one amino acid).

The term "fragment" when referring to a protein means a protein that is shorter or has fewer amino acids than the full-length protein. The term "fragment" when referring to a nucleic acid means a nucleic acid that is shorter or has fewer nucleotides than the full-length nucleic acid. A fragment can be, for example, an N-terminal fragment (i.e., removal of a portion of the C-terminal end of the protein), a C-terminal fragment (i.e., removal of a portion of the N-terminal end of the protein), or an internal fragment.

"Sequence identity" or "identity" in the context of two polynucleotides or polypeptide sequences makes reference to the residues in the two sequences that are the same when aligned for maximum correspondence over a specified comparison window. When percentage of sequence identity is used in reference to proteins, residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

"Percentage of sequence identity" includes the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized below.

| Alanine | Ala | A | Nonpolar | Neutral | 1.8 |
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

A "homologous" sequence (e.g., nucleic acid sequence) includes a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence. Homologous sequences can include, for example, orthologous sequence and paralogous sequences. Homologous genes, for example, typically descend from a common ancestral DNA sequence, either through a speciation event (orthologous genes) or a genetic duplication event (paralogous genes). "Orthologous" genes include genes in different species that evolved from a common ancestral gene by speciation. Orthologs typically retain the same function in the course of evolution. "Paralogous" genes include genes related by duplication within a genome. Paralogs can evolve new functions in the course of evolution.

The term "in vitro" includes artificial environments and to processes or reactions that occur within an artificial environment (e.g., a test tube). The term "in vivo" includes natural environments (e.g., a cell or organism or body) and to processes or reactions that occur within a natural environment. The term "ex vivo" includes cells that have been removed from the body of an individual and to processes or reactions that occur within such cells.

The term "reporter gene" refers to a nucleic acid having a sequence encoding a gene product (typically an enzyme) that is easily and quantifiably assayed when a construct comprising the reporter gene sequence operably linked to a heterologous promoter and/or enhancer element is introduced into cells containing (or which can be made to contain) the factors necessary for the activation of the promoter and/or enhancer elements. Examples of reporter genes include, but are not limited, to genes encoding beta-galactosidase (lacZ), the bacterial chloramphenicol acetyltransferase (cat) genes, firefly luciferase genes, genes encoding beta-glucuronidase (GUS), and genes encoding fluorescent proteins. A "reporter protein" refers to a protein encoded by a reporter gene.

The term "fluorescent reporter protein" as used herein means a reporter protein that is detectable based on fluorescence wherein the fluorescence may be either from the reporter protein directly, activity of the reporter protein on a fluorogenic substrate, or a protein with affinity for binding to a fluorescent tagged compound. Examples of fluorescent proteins include green fluorescent proteins (e.g., GFP, GFP-2, tagGFP, turboGFP, eGFP, Emerald, Azami Green, Monomeric Azami Green, CopGFP, AceGFP, and ZsGreenl), yellow fluorescent proteins (e.g., YFP, eYFP, Citrine, Venus, YPet, PhiYFP, and ZsYellowl), blue fluorescent proteins (e.g., BFP, eBFP, eBFP2, Azurite, mKalamal, GFPuv, Sapphire, and T-sapphire), cyan fluorescent proteins (e.g., CFP, eCFP, Cerulean, CyPet, AmCyanl, and Midoriishi-Cyan), red fluorescent proteins (e.g., RFP, mKate, mKate2, mPlum, DsRed monomer, mCherry, mRFP1, DsRed-Express, DsRed2, DsRed-Monomer, HcRed-Tandem, HcRedl, AsRed2, eqFP611, mRaspberry, mStrawberry, and Jred), orange fluorescent proteins (e.g., mOrange, mKO, Kusabira-Orange, Monomeric Kusabira-Orange, mTangerine, and tdTomato), and any other suitable fluorescent protein whose presence in cells can be detected by flow cytometry methods.

The term "recombination" includes any process of exchange of genetic information between two polynucleotides and can occur by any mechanism. Recombination in response to double-strand breaks (DSBs) occurs principally through two conserved DNA repair pathways: non-homologous end joining (NHEJ) and homologous recombination (HR). See Kasparek & Humphrey (2011) Seminars in Cell & Dev. Biol. 22:886-897, herein incorporated by reference in its entirety for all purposes. Likewise, repair of a target nucleic acid mediated by an exogenous donor nucleic acid can include any process of exchange of genetic information between the two polynucleotides.

NHEJ includes the repair of double-strand breaks in a nucleic acid by direct ligation of the break ends to one another or to an exogenous sequence without the need for a homologous template. Ligation of non-contiguous sequences by NHEJ can often result in deletions, insertions, or translocations near the site of the double-strand break. For example, NHEJ can also result in the targeted integration of an exogenous donor nucleic acid through direct ligation of the break ends with the ends of the exogenous donor nucleic acid (i.e., NHEJ-based capture). Such NHEJ-mediated targeted integration can be preferred for insertion of an exogenous donor nucleic acid when homology directed repair (HDR) pathways are not readily usable (e.g., in non-dividing cells, primary cells, and cells which perform homology-based DNA repair poorly). In addition, in contrast to homology-directed repair, knowledge concerning large regions of sequence identity flanking the cleavage site is not needed, which can be beneficial when attempting targeted insertion into organisms that have genomes for which there is limited knowledge of the genomic sequence. The integration can proceed via ligation of blunt ends between the exogenous donor nucleic acid and the cleaved genomic sequence, or via ligation of sticky ends (i.e., having 5' or 3' overhangs) using an exogenous donor nucleic acid that is flanked by overhangs that are compatible with those generated by a nuclease agent in the cleaved genomic sequence. See, e.g., US 2011/020722, WO 2014/033644, WO 2014/089290, and Maresca et al. (2013) *Genome Res.* 23(3):539-546, each of which is herein incorporated by reference in its entirety for all purposes. If blunt ends are ligated, target and/or donor resection may be needed to generation regions of microhomology needed for fragment joining, which may create unwanted alterations in the target sequence.

Recombination can also occur via homology directed repair (HDR) or homologous recombination (HR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. See Wang et al. (2013) *Cell* 153:910-918; Mandalos et al. (2012) *PLOS ONE* 7:e45768:1-9; and Wang et al. (2013) *Nat Biotechnol.* 31:530-532, each of which is herein incorporated by reference in its entirety for all purposes.

The term "antigen-binding protein" includes any protein that binds to an antigen. Examples of antigen-binding proteins include an antibody, an antigen-binding fragment of an antibody, a multispecific antibody (e.g., a bi-specific antibody), an scFV, a bis-scFV, a diabody, a triabody, a tetrabody, a V-NAR, a VHH, a VL, a F(ab), a F(ab)$_2$, a DVD (dual variable domain antigen-binding protein), an SVD (single variable domain antigen-binding protein), a bispecific T-cell engager (BiTE), or a Davisbody (U.S. Pat. No. 8,586,713, herein incorporated by reference herein in its entirety for all purposes).

As used herein, the expression "anti-TRKB antibody" includes both monovalent antibodies with a single specificity, as well as bispecific antibodies comprising a first arm that binds TRKB and a second arm that binds a second (target) antigen, wherein the anti-TRKB arm comprises, for example, any of the HCVR/LCVR or CDR sequences as set forth in Table 22 herein. The expression "anti-TrkB antibody" also includes antibody-drug conjugates (ADCs) comprising an anti-TRKB antibody or antigen-binding portion thereof conjugated to a drug or toxin (i.e., cytotoxic agent). The expression "anti-TRKB antibody" also includes antibody-radionuclide conjugates (ARCs) comprising an anti-TRKB antibody or antigen-binding portion thereof conjugated to a radionuclide.

The term "anti-TRKB antibody" as used herein means any antigen-binding molecule or molecular complex comprising at least one complementarity determining region (CDR) that specifically binds to or interacts with TRKB or a portion of TRKB. The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-TRKB antibody (or antigen-binding portion thereof) may be identical to the human germline sequences, or may be naturally or artificially modified. An amino acid consensus sequence may be defined based on a side-by-side analysis of two or more CDRs.

The term "antibody" as used herein also includes antigen-binding fragments of full length antibody molecules. The terms "antigen-binding portion" of an antibody, "antigen-binding fragment" of an antibody, and the like, as used herein, include any enzymatically obtainable, synthetic, or genetically engineered polypeptide or glycoprotein that specifically binds an antigen to form a complex. Antigen-binding fragments of an antibody may be derived, for example, from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, and so forth.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed within the expression "antigen-binding fragment" as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "specifically binds," or "binds specifically to," or the like, means that an antibody or antigen-binding fragment thereof forms a complex with an antigen that is relatively stable under physiologic conditions. Specific binding can be characterized by an equilibrium dissociation constant of at least about $1\times10^{-6}$ M or less (e.g., a smaller $K_D$ denotes a tighter binding). Methods for determining whether two molecules specifically bind are well-known and include, for example, equilibrium dialysis, surface plasmon resonance, and the like. As described herein, antibodies have been identified by surface plasmon resonance, e.g., BIA-CORE™, which bind specifically to TRKB. Moreover, multi-specific antibodies that bind to TRKB protein and one or more additional antigens or a bi-specific that binds to two different regions of TRKB are nonetheless considered antibodies that "specifically bind," as used herein.

The anti-TRKB antibodies disclosed herein may comprise one or more amino acid substitutions, insertions and/or deletions in the framework and/or CDR regions of the heavy and light chain variable domains. Such mutations can be readily ascertained by comparing the amino acid sequences disclosed herein to sequences available from, for example, public antibody sequence databases. Once obtained, antibodies and antigen-binding fragments that contain one or more mutations can be easily tested for one or more desired property such as, improved binding specificity, increased binding affinity, improved or enhanced antagonistic or agonistic biological properties (as the case may be), reduced immunogenicity, and so forth. Antibodies and antigen-binding fragments obtained in this general manner are included.

Also included are anti-TRKB antibodies comprising variants of any of the HCVR, LCVR, and/or CDR amino acid sequences disclosed herein having one or more conservative substitutions. For example, the present invention includes anti-TRKB antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 22.

The term "substantial identity" or "substantially identical," when referring to a nucleic acid or fragment thereof in the context of anti-TRKB antibodies, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides in the context of anti-TRKB antibodies, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" as applied to polypeptides in the context of anti-TRKB antibodies is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference in its entirety for all purposes. Examples of groups of amino acids that have side chains with similar chemical properties include: (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate; and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256:1443-1445, herein incorporated by reference in its entirety for all purposes. A "moderately conservative" replacement is any change having a nonnegative value in the PAM250 log-likelihood matrix.

Compositions or methods "comprising" or "including" one or more recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

"Optional" or "optionally" means that the subsequently described event or circumstance may or may not occur and that the description includes instances in which the event or circumstance occurs and instances in which it does not.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The term "and/or" refers to and encompasses any and all possible combinations of one or more of the associated listed items, as well as the lack of combinations when interpreted in the alternative ("or").

The term "or" refers to any one member of a particular list and also includes any combination of members of that list.

The singular forms of the articles "a," "an," and "the" include plural references unless the context clearly dictates otherwise. For example, the term "a protein" or "at least one protein" can include a plurality of proteins, including mixtures thereof.

Statistically significant means p≤0.05.

DETAILED DESCRIPTION

I. Overview

Disclosed herein are non-human animal genomes, non-human animal cells, and non-human animals comprising a humanized TRKB locus and methods of using such non-human animal cells and non-human animals. Non-human animal cells or non-human animals comprising a humanized TRKB locus express a human TRKB protein or an chimeric TRKB protein comprising one or more fragments of a human TRKB protein (e.g., all or part of the human TRKB extracellular domain).

A humanized TRKB allele (e.g., resulting from replacing all or part of the non-human animal genomic DNA one-for-one with orthologous human genomic DNA) will provide the true human target or a close approximation of the true human target of human-TRKB-targeting reagents (e.g., agonist antibodies or agonist small molecules designed to target human TRKB), thereby enabling testing of the efficacy and mode of action of such agents in live animals as well as pharmacokinetic and pharmacodynamics studies. For example, as shown in the working examples disclosed herein, intravitreal administration of human-TRKB-agonist antibodies has a significant neuroprotective effect after optic nerve injury in humanized TrkB rats.

II. Non-Human Animals Comprising a Humanized TRKB Locus

The non-human animal genomes, non-human animal cells, and non-human animals disclosed herein comprise a humanized TRKB locus. Cells or non-human animals comprising a humanized TRKB locus express a human TRKB protein or a partially humanized, chimeric TRKB protein in which one or more fragments of the native TRKB protein have been replaced with corresponding fragments from human TRKB (e.g., all or part of the extracellular domain).

A. TRKB

The cells and non-human animals described herein comprise a humanized TRKB locus. TRKB (also known as BDNF-NT-3 growth factors receptor, GP145-TrkB, Trk-B, TrkB, neurotrophic tyrosine kinase receptor type 2, TrkB tyrosine kinase, tropomyosin-related kinase B, tropomyosin receptor kinase B, neurotrophic receptor tyrosine kinase 2, and NTRK2) is encoded by the TRKB gene (also known as NTRK2, OBHD, TRK-B, and GP 145-TRKB). TRKB is a receptor tyrosine kinase involved in the development and maturation of the central and the peripheral nervous systems through regulation of neuron survival, proliferation, migration, differentiation, and synapse formation and plasticity. TRKB is a receptor for BDNF/brain-derived neurotrophic factor and NTF4/neurotrophin-4. Alternatively, TRKB can also bind NTF3/neurotrophin-3, which is less efficient in activating the receptor but regulates neuron survival through TRKB. Upon ligand-binding, TRKB undergoes homodimerization, autophosphorylation, and activation. The canonical isoform of TRKB is expressed in the central and peripheral nervous system. In the central nervous system (CNS), expression is observed in the cerebral cortex, hippocampus, thalamus, choroid plexus, granular layer of the cerebellum, brain stem, and spinal cord. In the peripheral nervous system, it is expressed in many cranial ganglia, the ophthalmic nerve, the vestibular system, multiple facial structures, the submaxillary glands, and dorsal root ganglia.

Human TRKB maps to human 9q21.33 on chromosome 9 (NCBI RefSeq Gene ID 4915; Assembly GRCh38.p7; location NC_000009.12 (84668368 . . . 85027070)). The gene has been reported to have 23 exons. The wild type human TRKB protein has been assigned UniProt accession number Q16620. At least seven isoforms are known (Q16620-1 through Q16620-7). The sequence for one isoform, Q16620-4 (identical to NCBI Accession No. NP_006171.2), is set forth in SEQ ID NO: 3. An mRNA (cDNA) encoding the canonical isoform is assigned NCBI Accession No. AF410899.1 and is set forth in SEQ ID NO: 8. Another example of an mRNA (cDNA) encoding a human TRKB isoform is assigned RefSeq mRNA ID NM_006180.4. An exemplary coding sequence (CDS) is set forth in SEQ ID NO: 11. The full-length human TRKB protein set forth in SEQ ID NO: 3 has 838 amino acids, including a signal peptide (amino acids 1-31), an extracellular domain (amino acids 32-430), a transmembrane domain (amino acids 431-454), and a cytoplasmic domain (amino acids 455-838). Delineations between these domains are as designated in UniProt. Reference to human TRKB includes the canonical (wild type) forms as well as all allelic forms and isoforms. Any other forms of human TRKB have amino acids numbered for maximal alignment with the wild type form, aligned amino acids being designated the same number. An example of another isoform of human TRKB is Q16620-1 (identical to NCBI Accession No. NP_001018074.1), set forth in SEQ ID NO: 75. An mRNA (cDNA) encoding this isoform is assigned NCBI Accession No. NM_001018064.2 and is set forth in SEQ ID NO: 76. An exemplary coding sequence (CDS) for this isoform (CCDS ID CCDS35050.1) is set forth in SEQ ID NO: 77.

Rat TrkB maps to rat 17p14 on chromosome 17 (NCBI RefSeq Gene ID 25054; Assembly Rnor_6.0; location NC_005116.4 (5934651 . . . 6245778, complement)). The gene has been reported to have 23 exons. The wild type rat TRKB protein has been assigned UniProt accession number Q63604. At least three isoforms are known (Q63604-1 through Q63604-3). The sequence for the canonical isoform, Q63604-1 (identical to NCBI Accession No. NP_036863.1), is set forth in SEQ ID NO: 2. An mRNA (cDNA) encoding the canonical isoform is assigned NCBI Accession No. NM_012731.2 and is set forth in SEQ ID NO: 7. Another example of an mRNA (cDNA) encoding a rat TRKB isoform is assigned RefSeq mRNA ID M55291. An exemplary coding sequence (CDS) is set forth in SEQ ID NO: 10. The canonical full-length rat TRKB protein set forth in SEQ ID NO: 2 has 821 amino acids, including a signal peptide (amino acids 1-31), an extracellular domain (amino acids 32-429), a transmembrane domain (amino acids 430-453), and a cytoplasmic domain (amino acids 454-821). Delineations between these domains are as designated in UniProt. Reference to rat TRKB includes the canonical (wild type) forms as well as all allelic forms and isoforms. Any other forms of rat TRKB have amino acids numbered for maximal alignment with the wild type form, aligned amino acids being designated the same number.

Mouse TrkB maps to mouse 13 B1; 13 31.2 cM on chromosome 12 (NCBI RefSeq Gene ID 18212; Assembly GRCm38.p4 (GCF_000001635.24); location NC_000079.6 (58806569 . . . 59133970)). The gene has been reported to have 23 exons. The wild type mouse TRKB protein has been assigned UniProt accession number P15209. At least four isoforms are known (P15209-1 through P15209-4). The sequence for the canonical isoform, P15209-1 (identical to NCBI Accession Nos. NP_001020245.1 and NP_001269890.1), is set forth in SEQ ID NO: 1. An exemplary mRNA (cDNA) isoform encoding the canonical isoform is assigned NCBI Accession No. NM_001025074.2 and is set forth in SEQ ID NO: 6. An exemplary coding sequence (CDS) (CCDS ID CCDS26573.1) is set forth in SEQ ID NO: 9. The canonical full-length mouse TRKB protein set forth in SEQ ID NO: 1 has 821 amino acids, including a signal peptide (amino acids 1-31), an extracellular domain (amino acids 32-429), a transmembrane domain (amino acids 430-453), and a cytoplasmic domain (amino acids 454-821). Delineations between these domains are as designated in UniProt. Reference to mouse TRKB includes the canonical (wild type) forms as well as all allelic forms and isoforms. Any other forms of mouse TRKB have amino acids numbered for maximal alignment with the wild type form, aligned amino acids being designated the same number.

B. Humanized TRKB Loci

A humanized TRKB locus can be a TrkB locus in which the entire TrkB gene is replaced with the corresponding orthologous human TRKB sequence, or it can be a TrkB locus in which only a portion of the TrkB gene is replaced with the corresponding orthologous human TRKB sequence (i.e., humanized). Optionally, the corresponding orthologous human TRKB sequence is modified to be codon-optimized based on codon usage in the non-human animal. Replaced (i.e., humanized) regions can include coding regions such as an exon, non-coding regions such as an intron, an untranslated region, or a regulatory region (e.g., a promoter, an enhancer, or a transcriptional repressor-binding element), or any combination thereof. As one example, exons corresponding to 1, 2, 3, 4, 5, 6, 7, 8, 9, 10, 11, 12, 13, 14, 15, 16, 17, 18, 19, 20, 21, 22, or all 23 exons of the human TRKB gene can be humanized. For example, exons corresponding to exons 3-10 of the human TRKB gene can be humanized, including the segment of exon 2 (coding exon 1) from the codon encoding amino acid 33, beginning just after the signal peptide. Alternatively, a region of TrkB encoding an epitope recognized by an anti-human-TRKB antigen-binding protein or a region targeted by human-TRKB-targeting reagent (e.g., a small molecule) can be humanized. Likewise, introns corresponding to 1, 2, 3, 4, 5, 6, 7, 8, 9, 10, 11, 12, 13, 14, 15, 16, 17, 18, 19, 20, 21, or all 22 introns of the human TRKB gene can be humanized or can remain endogenous. For example, introns corresponding to the introns between exons 2 and 10 (i.e., introns 2-9, between coding exon 1 and exon 10) of the human TRKB gene can be humanized, optionally including part of the intron following exon 10 (i.e., intron 10). Flanking untranslated regions including regulatory sequences can also be humanized or remain endogenous. For example, the 5' untranslated region (UTR), the 3' UTR, or both the 5' UTR and the 3' UTR can be humanized, or the 5' UTR, the 3' UTR, or both the 5' UTR and the 3' UTR can remain endogenous. In a specific example, both the 5' UTR and the 3' UTR remain endogenous. Depending on the extent of replacement by orthologous sequences, regulatory sequences, such as a promoter, can be endogenous or supplied by the replacing human orthologous sequence. For example, the humanized TRKB locus can include the endogenous non-human animal TrkB promoter.

One or more or all of the regions encoding the signal peptide, the cytoplasmic domain, the transmembrane domain, or the extracellular can be humanized, or one or more of such regions can remain endogenous. Exemplary coding sequences for a mouse TRKB signal peptide, extracellular domain, transmembrane domain, and cytoplasmic domain are set forth in SEQ ID NOS: 63-66, respectively. Exemplary coding sequences for a rat TRKB signal peptide, extracellular domain, transmembrane domain, and cytoplasmic domain are set forth in SEQ ID NOS: 67-70, respectively. Exemplary coding sequences for a human TRKB signal peptide, extracellular domain, transmembrane domain, and cytoplasmic domain are set forth in SEQ ID NOS: 71-74, respectively.

For example, all or part of the region of the TrkB locus encoding the signal peptide can be humanized, and/or all or part of the region of the TrkB locus encoding the extracellular domain can be humanized, and/or all or part of the region of the TrkB locus encoding the transmembrane domain can be humanized, and/or all or part of the region of the TrkB locus encoding the cytoplasmic domain can be humanized. In one example, all or part of the region of the TrkB locus encoding the extracellular domain is humanized. Optionally, the CDS of the human TRKB extracellular domain comprises, consists essentially of, or consists of a sequence that is at least 85%, 90%, 95%, 96%, 97%, 98%, 99%, or 100% identical to SEQ ID NO: 72 (or degenerates thereof). The TRKB protein can retain the activity of the native TRKB (e.g., retains the ability to become phosphorylated, retains the ability to activate downstream signaling pathways such as the PI3K/AKT and MAPK/ERK pathways, or retains the ability to regulate neuron survival, proliferation, migration, differentiation, or synapse formation and plasticity or produce any of the phenotypes disclosed elsewhere herein). For example, the region of the TrkB locus encoding the extracellular domain can be humanized such that a chimeric TRKB protein is produced with an endogenous signal peptide, an endogenous cytoplasmic domain, an endogenous transmembrane domain, and a humanized extracellular domain.

One or more of the regions encoding the signal peptide, the cytoplasmic domain, the transmembrane domain, or the extracellular can remain endogenous. For example, the region encoding the signal peptide and/or the cytoplasmic domain and/or the transmembrane domain can remain endogenous. Optionally, the CDS of the endogenous TRKB signal peptide comprises, consists essentially of, or consists of a sequence that is at least 85%, 90%, 95%, 96%, 97%, 98%, 99%, or 100% identical to SEQ ID NO: 63 or 67 (or degenerates thereof). Optionally, the CDS of the endogenous TRKB transmembrane domain comprises, consists essentially of, or consists of a sequence that is at least 85%, 90%, 95%, 96%, 97%, 98%, 99%, or 100% identical to SEQ ID NO: 65 or 69 (or degenerates thereof). Optionally, the CDS of the endogenous TRKB cytoplasmic domain comprises, consists essentially of, or consists of a sequence that is at least 85%, 90%, 95%, 96%, 97%, 98%, 99%, or 100% identical to SEQ ID NO: 66 or 70 (or degenerates thereof). In each case, the TRKB protein can retain the activity of the native TRKB.

The TRKB protein encoded by the humanized TRKB locus can comprise one or more domains that are from a human TRKB protein and/or one or more domains that are from an endogenous (i.e., native) TRKB protein. Exemplary amino acid sequences for a mouse TRKB signal peptide, extracellular domain, transmembrane domain, and cytoplasmic domain are set forth in SEQ ID NOS: 51-54, respectively. Exemplary amino acid sequences for a rat TRKB signal peptide, extracellular domain, transmembrane domain, and cytoplasmic domain are set forth in SEQ ID NOS: 55-58, respectively. Exemplary amino acid sequences for a human TRKB signal peptide, extracellular domain, transmembrane domain, and cytoplasmic domain are set forth in SEQ ID NOS: 59-62, respectively.

The TRKB protein can comprise one or more or all of a human TRKB signal peptide, a human TRKB extracellular domain, a human TRKB transmembrane domain, and a human TRKB cytoplasmic domain. As one example, the TRKB protein can comprise a human TRKB extracellular domain.

The TRKB protein encoded by the humanized TRKB locus can also comprise one or more domains that are from the endogenous (i.e., native) non-human animal TRKB protein. As one example, the TRKB protein encoded by the humanized TRKB locus can comprise a signal peptide from the endogenous (i.e., native) non-human animal TRKB protein and/or a cytoplasmic domain from the endogenous (i.e., native) non-human animal TRKB protein and/or a transmembrane domain from the endogenous (i.e., native) non-human animal TRKB protein.

Domains in a chimeric TRKB protein that are from a human TRKB protein can be encoded by a fully humanized sequence (i.e., the entire sequence encoding that domain is replaced with the orthologous human TRKB sequence) or can be encoded by a partially humanized sequence (i.e., some of the sequence encoding that domain is replaced with the orthologous human TRKB sequence, and the remaining endogenous (i.e., native) sequence encoding that domain encodes the same amino acids as the orthologous human TRKB sequence such that the encoded domain is identical to that domain in the human TRKB protein). Likewise, domains in a chimeric protein that are from the endogenous TRKB protein cay be encoded by a fully endogenous sequence (i.e., the entire sequence encoding that domain is the endogenous TrkB sequence) or can be encoded by a partially humanized sequence (i.e., some of the sequence encoding that domain is replaced with the orthologous human TRKB sequence, but the orthologous human TRKB sequence encodes the same amino acids as the replaced endogenous TrkB sequence such that the encoded domain is identical to that domain in the endogenous TRKB protein). For example part of the region of the TrkB locus encoding the transmembrane domain (e.g., encoding the N-terminal region of the transmembrane domain) can be replaced with orthologous human TRKB sequence, wherein the amino acid sequence of the region of the transmembrane domain encoded by the orthologous human TRKB sequence is identical to the corresponding endogenous amino acid sequence.

As one example, the TRKB protein encoded by the humanized TRKB locus can comprise a human TRKB extracellular domain. Optionally, the human TRKB extracellular domain comprises, consists essentially of, or consists of a sequence that is at least 85%, 90%, 95%, 96%, 97%, 98%, 99%, or 100% identical to SEQ ID NO: 60. The TRKB protein retains the activity of the native TRKB (e.g., retains the ability to become phosphorylated, retains the ability to activate downstream signaling pathways such as the PI3K/AKT and MAPK/ERK pathways, or retains the ability to regulate neuron survival, proliferation, migration, differentiation, or synapse formation and plasticity or produce any of the phenotypes disclosed elsewhere herein). As another example, the TRKB protein encoded by the humanized TRKB locus can comprise an endogenous non-human animal TRKB cytoplasmic domain (e.g., a mouse TRKB cytoplasmic domain or a rat TRKB cytoplasmic domain). Optionally, the non-human animal TRKB cytoplasmic domain comprises, consists essentially of, or consists of a sequence that is at least 85%, 90%, 95%, 96%, 97%, 98%, 99%, or 100% identical to SEQ ID NO: 54 or 58. As another example, the TRKB protein encoded by the humanized TRKB locus can comprise an endogenous non-human animal TRKB transmembrane domain (e.g., a mouse TRKB transmembrane domain or a rat TRKB transmembrane domain). Optionally, the non-human animal TRKB transmembrane domain comprises, consists essentially of, or consists of a sequence that is at least 85%, 90%, 95%, 96%, 97%, 98%, 99%, or 100% identical to SEQ ID NO: 53 or 57. As another example, the TRKB protein encoded by the humanized TRKB locus can comprise an endogenous non-human animal TRKB signal peptide (e.g., a mouse TRKB signal peptide or a rat TRKB signal peptide). Optionally, the non-human animal TRKB signal peptide comprises, consists essentially of, or consists of a sequence that is at least 85%, 90%, 95%, 96%, 97%, 98%, 99%, or 100% identical to SEQ ID NO: 51 or 55. In each case, the TRKB protein can retain the activity of the native TRKB. For example, the TRKB protein encoded by the humanized TRKB locus can comprise, consist essentially of, or consist of a sequence that is at least 85%, 90%, 95%, 96%, 97%, 98%, 99%, or 100% identical to SEQ ID NO: 4 or 5. Optionally, the TRKB CDS encoded by the humanized TRKB locus can comprise, consist essentially of, or consist of a sequence that is at least 85%, 90%, 95%, 96%, 97%, 98%, 99%, or 100% identical to SEQ ID NO: 12 or 13 (or degenerates thereof). In each case, the TRKB protein can retain the activity of the native TRKB.

Optionally, a humanized TRKB locus can comprise other elements. Examples of such elements can include selection cassettes, reporter genes, recombinase recognition sites, or other elements. Alternatively, the humanized TRKB locus can lack other elements (e.g., can lack a selection marker or selection cassette). Examples of suitable reporter genes and reporter proteins are disclosed elsewhere herein. Examples of suitable selection markers include neomycin phosphotransferase (neo$_r$), hygromycin B phosphotransferase (hyg$_r$), puromycin-N-acetyltransferase (puro$_r$), blasticidin S deaminase (bsr$_r$), xanthine/guanine phosphoribosyl transferase (gpt), and herpes simplex virus thymidine kinase (HSV-k). Examples of recombinases include Cre, Flp, and Dre recombinases. One example of a Cre recombinase gene is Crei, in which two exons encoding the Cre recombinase are separated by an intron to prevent its expression in a prokaryotic cell. Such recombinases can further comprise a nuclear localization signal to facilitate localization to the nucleus (e.g., NLS-Crei). Recombinase recognition sites include nucleotide sequences that are recognized by a site-specific recombinase and can serve as a substrate for a recombination event. Examples of recombinase recognition sites include FRT, FRT11, FRT71, attp, att, rox, and lox sites such as loxP, lox511, lox2272, lox66, lox71, loxM2, and lox5171.

Other elements such as reporter genes or selection cassettes can be self-deleting cassettes flanked by recombinase recognition sites. See, e.g., U.S. Pat. No. 8,697,851 and US 2013/0312129, each of which is herein incorporated by reference in its entirety for all purposes. As an example, the self-deleting cassette can comprise a Crei gene (comprises two exons encoding a Cre recombinase, which are separated by an intron) operably linked to a mouse Prm1 promoter and a neomycin resistance gene operably linked to a human ubiquitin promoter. By employing the Prm1 promoter, the self-deleting cassette can be deleted specifically in male germ cells of F0 animals. The polynucleotide encoding the selection marker can be operably linked to a promoter active in a cell being targeted. Examples of promoters are described elsewhere herein. As another specific example, a self-deleting selection cassette can comprise a hygromycin resistance gene coding sequence operably linked to one or more promoters (e.g., both human ubiquitin and EM7 promoters) followed by a polyadenylation signal, followed by a Crei coding sequence operably linked to one or more promoters (e.g., an mPrm1 promoter), followed by another polyadenylation signal, wherein the entire cassette is flanked by loxP sites.

The humanized TRKB locus can also be a conditional allele. For example, the conditional allele can be a multifunctional allele, as described in US 2011/0104799, herein incorporated by reference in its entirety for all purposes. For example, the conditional allele can comprise: (a) an actuating sequence in sense orientation with respect to transcription of a target gene; (b) a drug selection cassette (DSC) in sense or antisense orientation; (c) a nucleotide sequence of interest (NSI) in antisense orientation; and (d) a conditional by inversion module (COIN, which utilizes an exon-splitting intron and an invertible gene-trap-like module) in reverse orientation. See, e.g., US 2011/0104799. The conditional allele can further comprise recombinable units that recombine upon exposure to a first recombinase to form a conditional allele that (i) lacks the actuating sequence and the DSC; and (ii) contains the NSI in sense orientation and the COIN in antisense orientation. See, e.g., US 2011/0104799.

Figure 4:
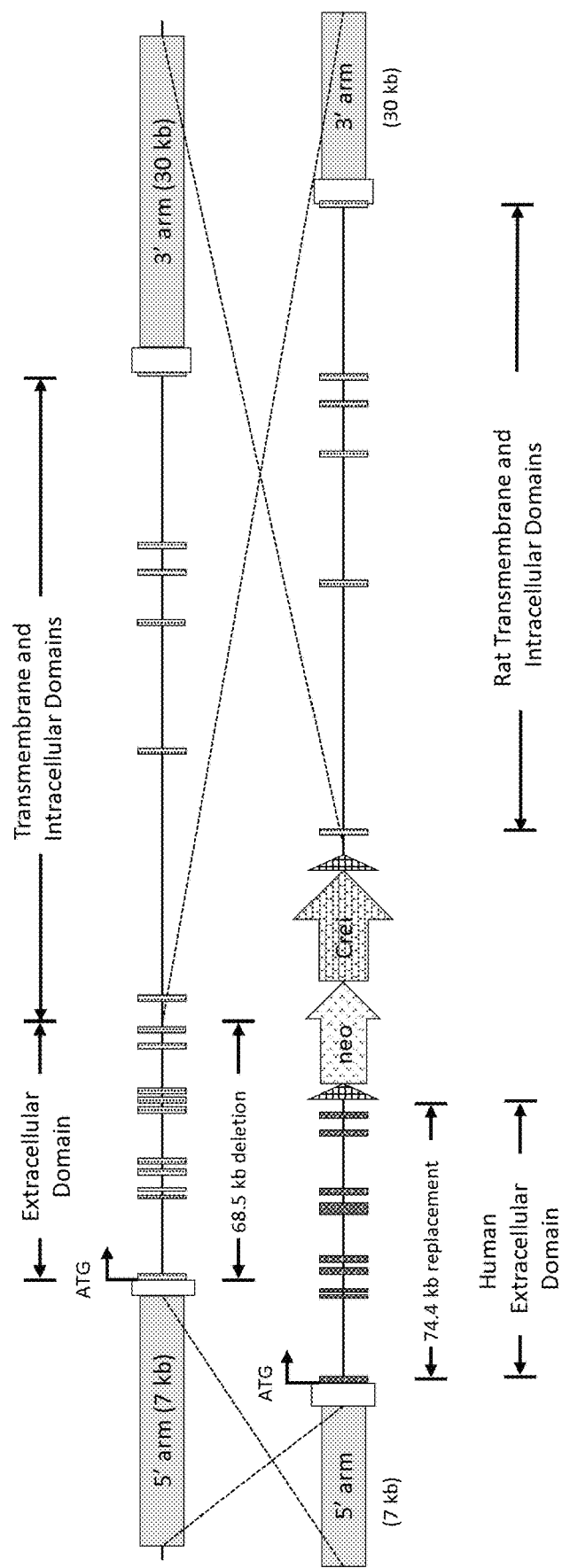
FIG. 4 (not to scale) shows a schematic of the targeting scheme for humanization of the region of the rat TrkB (rat Ntrk2) locus encoding the extracellular domain of TRKB. The top portion of the figure shows the endogenous rat TrkB (rat Ntrk2) locus, and the bottom portion of the figure shows the large targeting vector.

One exemplary humanized TRKB locus (e.g., a humanized mouse TrkB locus or a humanized rat TrkB locus) is one in which a region in exon 2/coding exon 1 from the codon encoding amino acid 33, beginning just after the signal peptide (or the codon corresponding to the codon encoding amino acid 33 in mouse TrkB, rat TrkB, or human TRKB when optimally aligned with the mouse TrkB, rat TrkB, or human TRKB CDS, respectively) through exon 10 (or the exon corresponding to mouse TrkB, rat TrkB, or human TRKB exon 10 when optimally aligned with the mouse TrkB, rat TrkB, or human TRKB CDS, respectively), optionally including a portion of intron 10, is replaced with the corresponding human sequence. The replaced region encodes the extracellular domain of TRKB. See FIGS. 1 and 4 and SEQ ID NOS: 4 and 5.

C. Non-Human Animal Genomes, Non-Human Animal Cells, and Non-Human Animals Comprising a Humanized TRKB Locus Non-human animal genomes, non-human animal cells, and non-human animals comprising a humanized TRKB locus as described elsewhere herein are provided. The genomes, cells, or non-human animals can be male or female. The genomes, cells, or non-human animals can be heterozygous or homozygous for the humanized TRKB locus. A diploid organism has two alleles at each genetic locus. Each pair of alleles represents the genotype of a specific genetic locus. Genotypes are described as homozygous if there are two identical alleles at a particular locus and as heterozygous if the two alleles differ.

The non-human animal genomes or cells provided herein can be, for example, any non-human animal genome or cell comprising a TrkB locus or a genomic locus homologous or orthologous to the human TRKB locus. The genomes can be from or the cells can be eukaryotic cells, which include, for example, fungal cells (e.g., yeast), plant cells, animal cells, mammalian cells, non-human mammalian cells, and human cells. The term "animal" includes any member of the animal kingdom, including, for example, mammals, fishes, reptiles, amphibians, birds, and worms. A mammalian cell can be, for example, a non-human mammalian cell, a rodent cell, a rat cell, a mouse cell, or a hamster cell. Other non-human mammals include, for example, non-human primates, monkeys, apes, orangutans, cats, dogs, rabbits, horses, bulls, deer, bison, livestock (e.g., bovine species such as cows, steer, and so forth; ovine species such as sheep, goats, and so forth; and porcine species such as pigs and boars). Birds include, for example, chickens, turkeys, ostrich, geese, ducks, and so forth. Domesticated animals and agricultural animals are also included. The term "non-human" excludes humans.

The cells can also be any type of undifferentiated or differentiated state. For example, a cell can be a totipotent cell, a pluripotent cell (e.g., a human pluripotent cell or a non-human pluripotent cell such as a mouse embryonic stem (ES) cell or a rat ES cell), or a non-pluripotent cell. Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

The cells provided herein can also be germ cells (e.g., sperm or oocytes). The cells can be mitotically competent cells or mitotically-inactive cells, meiotically competent cells or meiotically-inactive cells. Similarly, the cells can also be primary somatic cells or cells that are not a primary somatic cell. Somatic cells include any cell that is not a gamete, germ cell, gametocyte, or undifferentiated stem cell. For example, the cells can be neurons, such as hippocampal neurons or cortical neurons.

Suitable cells provided herein also include primary cells. Primary cells include cells or cultures of cells that have been isolated directly from an organism, organ, or tissue. Primary cells include cells that are neither transformed nor immortal. They include any cell obtained from an organism, organ, or tissue which was not previously passed in tissue culture or has been previously passed in tissue culture but is incapable of being indefinitely passed in tissue culture. Such cells can be isolated by conventional techniques and include, for example, hippocampal neurons or cortical neurons.

Other suitable cells provided herein include immortalized cells. Immortalized cells include cells from a multicellular organism that would normally not proliferate indefinitely but, due to mutation or alteration, have evaded normal cellular senescence and instead can keep undergoing division. Such mutations or alterations can occur naturally or be intentionally induced. A specific example of an immortalized cell line is a neuroblastoma cell line such as N18TG2 or T48 or a cell line such as the NIH-3T3 cell line. Numerous types of immortalized cells are well known. Immortalized or primary cells include cells that are typically used for culturing or for expressing recombinant genes or proteins.

The cells provided herein also include one-cell stage embryos (i.e., fertilized oocytes or zygotes). Such one-cell stage embryos can be from any genetic background (e.g., BALB/c, C57BL/6, 129, or a combination thereof for mice), can be fresh or frozen, and can be derived from natural breeding or in vitro fertilization.

The cells provided herein can be normal, healthy cells, or can be diseased or mutant-bearing cells.

Non-human animals comprising a humanized TRKB locus as described herein can be made by the methods described elsewhere herein. The term "animal" includes any member of the animal kingdom, including, for example, mammals, fishes, reptiles, amphibians, birds, and worms. In a specific example, the non-human animal is a non-human mammal. Non-human mammals include, for example, non-human primates, monkeys, apes, orangutans, cats, dogs, horses, bulls, deer, bison, sheep, rabbits, rodents (e.g., mice, rats, hamsters, and guinea pigs), and livestock (e.g., bovine species such as cows and steer; ovine species such as sheep and goats; and porcine species such as pigs and boars). Birds include, for example, chickens, turkeys, ostrich, geese, and ducks. Domesticated animals and agricultural animals are also included. The term "non-human animal" excludes humans. Preferred non-human animals include, for example, rodents, such as mice and rats.

The non-human animals can be from any genetic background. For example, suitable mice can be from a 129 strain, a C57BL/6 strain, a mix of 129 and C57BL/6, a BALB/c strain, or a Swiss Webster strain. Examples of 129 strains include 129P1, 129P2, 129P3, 129X1, 129S1 (e.g., 129S1/SV, 129S1/Svlm), 129S2, 129S4, 129S5, 129S9/SvEvH, 129S6 (129/SvEvTac), 129S7, 129S8, 129T1, and 129T2. See, e.g., Festing et al. (1999) Mammalian Genome 10:836, herein incorporated by reference in its entirety for all purposes. Examples of C57BL strains include C57BL/A, C57BL/An, C57BL/GrFa, C57BL/Kal_wN, C57BL/6, C57BL/6J, C57BL/6ByJ, C57BL/6NJ, C57BL/10, C57BL/10ScSn, C57BL/10Cr, and C57BL/Ola. Suitable mice can also be from a mix of an aforementioned 129 strain and an aforementioned C57BL/6 strain (e.g., 50% 129 and 50% C57BL/6). Likewise, suitable mice can be from a mix of aforementioned 129 strains or a mix of aforementioned BL/6 strains (e.g., the 129S6 (129/SvEvTac) strain).

Similarly, rats can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rats can also be obtained from a strain derived from a mix of two or more strains recited above. For example, a suitable rat can be from a DA strain or an ACI strain. The ACI rat strain is characterized as having black agouti, with white belly and feet and an $RT1^{av1}$ haplotype. Such strains are available from a variety of sources including Harlan Laboratories. The Dark Agouti (DA) rat strain is characterized as having an agouti coat and an $RT1^{av1}$ haplotype. Such rats are available from a variety of sources including Charles River and Harlan Laboratories. Some suitable rats can be from an inbred rat strain. See, e.g., US 2014/0235933, herein incorporated by reference in its entirety for all purposes.

III. Methods of Using Non-Human Animals Comprising a Humanized TRKB Locus for Assessing Efficacy of Human-TRKB-Targeting Reagents In Vivo or Ex Vivo Various methods are provided for using the non-human animals comprising a humanized TRKB locus as described elsewhere herein for assessing or optimizing delivery or efficacy of human-TRKB-targeting reagents (e.g., therapeutic agonist molecules) in vivo or ex vivo. Because the non-human animals comprise a humanized TRKB locus, the non-human animals will more accurately reflect the efficacy of a human-TRKB-targeting reagent.

A. Methods of Testing Efficacy of Human-TRKB-Targeting Reagents In Vivo or Ex Vivo Various methods are provided for assessing delivery or efficacy of human-TRKB-targeting reagents in vivo using non-human animals comprising a humanized TRKB locus as described elsewhere herein. Such methods can comprise: (a) introducing into the non-human animal a human-TRKB-targeting reagent; and (b) assessing the activity of the human-TRKB-targeting reagent.

The human-TRKB-targeting reagent can be a human-TRKB-targeting antibody or antigen-binding protein or any other large molecule or small molecule that targets human TRKB. Alternatively, the human-TRKB-targeting reagent can be any biological or chemical agent that targets the human TRKB locus (the human TRKB gene), the human TRKB mRNA, or the human TRKB protein. Examples of human-TRKB-targeting reagents are disclosed elsewhere herein.

Such human-TRKB-targeting reagents can be administered by any delivery method (e.g., injection, AAV, LNP, or HDD) as disclosed in more detail elsewhere herein and by any route of administration. Means of delivering therapeutic molecules and routes of administration are disclosed in more detail elsewhere herein. In particular methods, the reagents are delivered via injection (e.g., direct hippocampal injection, subcutaneous injection, or intravitreal injection).

Methods for assessing activity of the human-TRKB-targeting reagent are well-known and are provided elsewhere herein. In some methods, assessing activity of the human-TRKB-targeting reagent (e.g., agonist activity or inhibitory activity) comprises assessing TRKB activity (e.g., TRKB phosphorylation, TRKB-mediated activation of downstream signaling pathways, or TRKB-induced phenotypes) as disclosed elsewhere herein. Assessment of activity can be in any cell type, any tissue type, or any organ type as disclosed elsewhere herein. In some methods, assessment of activity is in brain tissue (e.g., hippocampus or striatum) or neurons (e.g., retinal ganglion cells, hippocampal neurons, or cortical neurons).

If the TRKB-targeting reagent is a genome editing reagent (e.g., a nuclease agent), such methods can comprise assessing modification of the humanized TRKB locus. For example, the assessing can comprise sequencing the humanized TRKB locus in one or more cells isolated from the non-human animal (e.g., next-generation sequencing). Assessment can comprise isolating a target organ (e.g., brain) or tissue from the non-human animal and assessing modification of humanized TRKB locus in the target organ or tissue. Assessment can also comprise assessing modification of humanized TRKB locus in two or more different cell types within the target organ or tissue. Similarly, assessment can comprise isolating a non-target organ or tissue (e.g., two or more non-target organs or tissues) from the non-human animal and assessing modification of humanized TRKB locus in the non-target organ or tissue.

Such methods can also comprise measuring expression levels of the mRNA produced by the humanized TRKB locus, or by measuring expression levels of the protein encoded by the humanized TRKB locus. For example, protein levels can be measured in a particular cell, tissue, or organ type (e.g., brain), or secreted levels can be measured in the serum. Methods for assessing expression of TRKB mRNA or protein expressed from the humanized TRKB locus are provided elsewhere herein and are well-known.

The various methods provided above for assessing activity in vivo can also be used to assess the activity of human-TRKB-targeting reagents ex vivo as described elsewhere herein.

B. Methods of Optimizing Delivery or Efficacy of Human-TRKB-Targeting Reagent In Vivo or Ex Vivo Various methods are provided for optimizing delivery of human-TRKB-targeting reagents to a cell or non-human animal or optimizing the activity or efficacy of human-TRKB-targeting reagents in vivo. Such methods can comprise, for example: (a) performing the method of testing the efficacy of a human-TRKB-targeting reagent as described above a first time in a first non-human animal or first cell; (b) changing a variable and performing the method a second time in a second non-human animal (i.e., of the same species) or a second cell with the changed variable; and (c) comparing the activity of the human-TRKB-targeting reagent in step (a) with the activity of the human-TRKB-targeting reagent in step (b), and selecting the method resulting in the higher efficacy or activity.

Methods of measuring delivery, efficacy, or activity of human-TRKB-targeting reagents are disclosed elsewhere herein. Higher efficacy can mean different things depending on the desired effect within the non-human animal or cell. For example, higher efficacy can mean higher activity and/or higher specificity. Higher activity can be, for example, activity in activating TRKB or activity in inhibiting TRKB. It can refer to a higher percentage of cells being targeted within a particular target cell type (e.g., neurons such as retinal ganglion cells) or within a particular target tissue or organ (e.g., brain). Higher specificity can refer to higher specificity with respect to TRKB as compared to off-target effects, higher specificity with respect to the cell type targeted, or higher specificity with respect to the tissue or organ type targeted.

The variable that is changed can be any parameter. As one example, the changed variable can be the packaging or the delivery method by which the human-TRKB-targeting reagent or reagents are introduced into the cell or non-human animal. Examples of delivery methods are disclosed elsewhere herein. As another example, the changed variable can be the route of administration for introduction of the human-TRKB-targeting reagent or reagents into the cell or non-human animal. Examples of routes of administration are disclosed elsewhere herein.

As another example, the changed variable can be the concentration or amount of the human-TRKB-targeting reagent or reagents introduced. As another example, the changed variable can be the timing of introducing the human-TRKB-targeting reagent or reagents relative to the timing of assessing the activity or efficacy of the reagents. As another example, the changed variable can be the number of times or frequency with which the human-TRKB-targeting reagent or reagents are introduced. As another example, the changed variable can be the human-TRKB-targeting reagent or reagents that are introduced (e.g., comparing one reagent to a different reagent).

C. Human-TRKB-Targeting Reagents

A human-TRKB-targeting reagent can be any reagent that targets a human TRKB protein, a human TRKB gene, or a human TRKB mRNA. A human-TRKB-targeting reagent can be, for example, an agonist (i.e., a molecule that indirectly or directly activates human TRKB) or it can be an antagonist (i.e., an inhibitor or inhibitory reagent that blocks human TRKB activity). In a specific example, the human-TRKB-targeting reagent is a TRKB agonist. Human-TRKB-targeting reagents in the methods disclosed herein can be known human-TRKB-targeting reagents, can be putative human-TRKB-targeting reagents (e.g., candidate reagents designed to target human TRKB), or can be reagents being screened for human-TRKB-targeting activity.

For example, a human-TRKB-targeting reagent can be an antigen-binding protein (e.g., agonist antibody) targeting an epitope of a human TRKB protein. An example of such a reagent is the TRKB agonist antibody H4H9816P2. Other anti-TRKB antibodies are disclosed elsewhere herein. In some cases, the anti-TRKB antibodies bind human TRKB with a $K_D$ of less than about 200 nM as measured by surface plasmon resonance at 25° C. or at 37° C. In other cases, the anti-TRKB antibodies bind human TRKB with a $K_D$ of less than about 600 pM, less than about 300 pM, less than about 200 pM, less than about 150 pM, less than about 100 pM, less than about 80 pM, less than about 50 pM, less than about 40 pM, less than about 30 pM, less than about 20 pM, less than about 10 pM, less than about 5 pM, less than about 3 pM, or less than about 1 pM. In some cases, the anti-TRKB antibodies bind human TRKB with a dissociative half-life (t½) of greater than about 10 minutes as measured by surface plasmon resonance at 25° C. or 37° C. In other cases, the anti-TRKB antibodies bind human TRKB with a t½ of greater than about 20 minutes, greater than about 50 minutes, greater than about 100 minutes, greater than about 120 minutes, greater than about 150 minutes, greater than about 300 minutes, greater than about 350 minutes, greater than about 400 minutes, greater than about 450 minutes, greater than about 500 minutes, greater than about 550 minutes, greater than about 600 minutes, greater than about 700 minutes, greater than about 800 minutes, greater than about 900 minutes, greater than about 1000 minutes, greater than about 1100 minutes, or greater than about 1200 minutes. As a specific example, the anti-TRKB antibody can comprise a set of six CDRs (HCDR1-HCDR2-HCDR3-LCDR1-LCDR2-LCDR3) selected from the groups set forth in Table 22 or substantially similar sequences having at least 90%, at least 95%, at least 98%, or at least 99% sequence identity thereto.

Other human-TRKB-targeting reagents include small molecules (e.g., agonists) targeting a human TRKB protein. Examples of small molecule TRKB agonists include 7,8-Dihydroxyflavone (7,8-DHF), deoxygedunin, LM22A-4 (N,N',N"-tris(2-hydroxyethyl)-1,3,5-benzenetricarboxamide), and LM22B-10 (2-[[4-[[4-[Bis-(2-hydroxyethyl)-amino]-phenyl]-(4-chloro-phenyl)-methyl]-phenyl]-(2-hydroxy-ethyl)-amino]-ethanol). See, e.g., Liu et al. (2015) *Translational Neurodegeneration* 5:2; Massa et al. (2010) *J. Clin. Invest.* 120(5):1774-1785; and Yang et al. (2016) *Neuropharmacology* 110:343-361, each of which is herein incorporated by reference in its entirety for all purposes. An example of a TRKB-targeting reagent that is an inhibitor is K252a. See, e.g., Yang et al. (2016) *Neuropharmacology* 110:343-361, herein incorporated by reference in its entirety for all purposes.

Other human-TRKB-targeting reagents include peptides or peptide mimetics (e.g., agonists) targeting a human TRKB protein. Examples of peptide mimetics that serve as human TRKB agonists are disclosed, e.g., in O'Leary et al. (2003) *J. Biol. Chem.* 278(28):25738-25744, herein incorporated by reference in its entirety for all purposes.

Other human-TRKB-targeting reagents can include genome editing reagents such as a nuclease agent (e.g., a Clustered Regularly Interspersed Short Palindromic Repeats (CRISPR)/CRISPR-associated (Cas) (CRISPR/Cas) nuclease, a zinc finger nuclease (ZFN), or a Transcription Activator-Like Effector Nuclease (TALEN)) that cleaves a recognition site within the human TRKB gene. Likewise, a human-TRKB-targeting reagent can be an exogenous donor nucleic acid (e.g., a targeting vector or single-stranded oligodeoxynucleotide (ssODN)) designed to recombine with the human TRKB gene).

Other human-TRKB-targeting reagents can include antisense oligonucleotides (e.g., siRNA or shRNA) targeting a human TRKB mRNA. Antisense oligonucleotides (ASOs) or antisense RNAs are short synthetic strings of nucleotides designed to prevent the expression of a targeted protein by selectively binding to the RNA that encodes the targeted protein and thereby preventing translation. These compounds bind to RNA with high affinity and selectivity through well characterized Watson-Crick base pairing (hybridization). RNA interference (RNAi) is an endogenous cellular mechanism for controlling gene expression in which small interfering RNAs (siRNAs) that are bound to the RNA-induced silencing complex (RISC) mediate the cleavage of target messenger RNA (mRNA).

The activity of any other known or putative human-TRKB-targeting reagent can also be assessed using the non-human animals disclosed herein. Similarly, any other molecule can be screened for human-TRKB-targeting activity using the non-human animals disclosed herein.

D. Administering Human-TRKB-Targeting Reagents to Non-Human Animals or Cells

The methods disclosed herein can comprise introducing into a non-human animal or cell various molecules (e.g., human-TRKB-targeting reagents such as antibodies or small molecules), including nucleic acids, proteins, nucleic-acid-protein complexes, peptide mimetics, antigen-binding proteins, or small molecules. "Introducing" includes presenting to the cell or non-human animal the molecule (e.g., nucleic acid or protein or small molecule) in such a manner that it gains access to the interior of the cell or to the interior of cells within the non-human animal. The introducing can be accomplished by any means. If multiple components are introduced, they can be introduced simultaneously or sequentially in any combination. In addition, two or more of the components can be introduced into the cell or non-human animal by the same delivery method or different delivery methods. Similarly, two or more of the components can be introduced into a non-human animal by the same route of administration or different routes of administration.

Molecules introduced into the non-human animal or cell can be provided in compositions comprising a carrier increasing the stability of the introduced molecules (e.g., prolonging the period under given conditions of storage (e.g., −20° C., 4° C., or ambient temperature) for which degradation products remain below a threshold, such below 0.5% by weight of the starting nucleic acid or protein; or increasing the stability in vivo). Non-limiting examples of such carriers include poly(lactic acid) (PLA) microspheres, poly(D,L-lactic-coglycolic-acid) (PLGA) microspheres, liposomes, micelles, inverse micelles, lipid cochleates, and lipid microtubules.

Various methods and compositions are provided herein to allow for introduction of a human-TRKB-targeting reagent into a cell or non-human animal. Methods for introducing nucleic acids into various cell types are known and include, for example, stable transfection methods, transient transfection methods, and virus-mediated methods.

Transfection protocols as well as protocols for introducing nucleic acid sequences into cells may vary. Non-limiting transfection methods include chemical-based transfection methods using liposomes; nanoparticles; calcium phosphate (Graham et al. (1973) *Virology* 52 (2): 456-67, Bacchetti et al. (1977) *Proc. Natl. Acad. Sci. USA* 74 (4): 1590-4, and Kriegler, M (1991). Transfer and Expression: A Laboratory Manual. New York: W. H. Freeman and Company. pp. 96-97); dendrimers; or cationic polymers such as DEAE-dextran or polyethylenimine. Non-chemical methods include electroporation, Sono-poration, and optical transfection. Particle-based transfection includes the use of a gene gun, or magnet-assisted transfection (Bertram (2006) *Current Pharmaceutical Biotechnology* 7, 277-28). Viral methods can also be used for transfection.

Introduction of human-TRKB-targeting reagents into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In one example, nucleofection is performed using the LONZA® NUCLEOFECTOR™ system.

Introduction of human-TRKB-targeting reagents into a cell (e.g., a zygote) can also be accomplished by microinjection. In zygotes (i.e., one-cell stage embryos), microinjection can be into the maternal and/or paternal pronucleus or into the cytoplasm. If the microinjection is into only one pronucleus, the paternal pronucleus is preferable due to its larger size. Microinjection of an mRNA is preferably into the cytoplasm (e.g., to deliver mRNA directly to the translation machinery), while microinjection of a protein or a polynucleotide encoding a protein or encoding an RNA is preferable into the nucleus/pronucleus. Alternatively, microinjection can be carried out by injection into both the nucleus/pronucleus and the cytoplasm: a needle can first be introduced into the nucleus/pronucleus and a first amount can be injected, and while removing the needle from the one-cell stage embryo a second amount can be injected into the cytoplasm. If a protein is injected into the cytoplasm and needs to be targeted to the nucleus, it can comprise a nuclear localization signal to ensure delivery to the nucleus/pronucleus. Methods for carrying out microinjection are well known. See, e.g., Nagy et al. (Nagy A, Gertsenstein M, Vintersten K, Behringer R., 2003, Manipulating the Mouse Embryo. Cold Spring Harbor, New York Cold Spring Harbor Laboratory Press); see also Meyer et al. (2010) *Proc. Natl. Acad. Sci. USA* 107:15022-15026 and Meyer et al. (2012) *Proc. Natl. Acad. Sci. USA* 109:9354-9359.

Other methods for introducing human-TRKB-targeting reagents into a cell or non-human animal can include, for example, vector delivery, particle-mediated delivery, exosome-mediated delivery, lipid-nanoparticle-mediated delivery, cell-penetrating-peptide-mediated delivery, or implantable-device-mediated delivery. As specific examples, a nucleic acid or protein can be introduced into a cell or non-human animal in a carrier such as a poly(lactic acid) (PLA) microsphere, a poly(D,L-lactic-coglycolic-acid) (PLGA) microsphere, a liposome, a micelle, an inverse micelle, a lipid cochleate, or a lipid microtubule. Some specific examples of delivery to a non-human animal include hydrodynamic delivery, virus-mediated delivery (e.g., adeno-associated virus (AAV)-mediated delivery), and lipid-nanoparticle-mediated delivery.

Introduction of human-TRKB-targeting reagents into cells or non-human animals can be accomplished by hydrodynamic delivery (HDD). Hydrodynamic delivery has emerged as a method for intracellular DNA delivery in vivo. For gene delivery to parenchymal cells, only essential DNA sequences need to be injected via a selected blood vessel, eliminating safety concerns associated with current viral and synthetic vectors. When injected into the bloodstream, DNA is capable of reaching cells in the different tissues accessible to the blood. Hydrodynamic delivery employs the force generated by the rapid injection of a large volume of solution into the incompressible blood in the circulation to overcome the physical barriers of endothelium and cell membranes that prevent large and membrane-impermeable compounds from entering parenchymal cells. In addition to the delivery of DNA, this method is useful for the efficient intracellular delivery of RNA, proteins, and other small compounds in vivo. See, e.g., Bonamassa et al. (2011) *Pharm. Res.* 28(4): 694-701, herein incorporated by reference in its entirety for all purposes.

Introduction of human-TRKB-targeting reagents can also be accomplished by virus-mediated delivery, such as AAV-mediated delivery or lentivirus-mediated delivery. Other exemplary viruses/viral vectors include retroviruses, adenoviruses, vaccinia viruses, poxviruses, and herpes simplex viruses. The viruses can infect dividing cells, non-dividing cells, or both dividing and non-dividing cells. The viruses can integrate into the host genome or alternatively do not integrate into the host genome. Such viruses can also be engineered to have reduced immunity. The viruses can be replication-competent or can be replication-defective (e.g., defective in one or more genes necessary for additional rounds of virion replication and/or packaging). Viruses can cause transient expression, long-lasting expression (e.g., at least 1 week, 2 weeks, 1 month, 2 months, or 3 months), or permanent expression. Exemplary viral titers (e.g., AAV titers) include $10^{12}$, $10^{13}$, $10^{14}$, $10^{15}$, and $10^{16}$ vector genomes/mL.

The ssDNA AAV genome consists of two open reading frames, Rep and Cap, flanked by two inverted terminal repeats that allow for synthesis of the complementary DNA strand. When constructing an AAV transfer plasmid, the transgene is placed between the two ITRs, and Rep and Cap can be supplied in trans. In addition to Rep and Cap, AAV can require a helper plasmid containing genes from adenovirus. These genes (E4, E2a, and VA) mediated AAV replication. For example, the transfer plasmid, Rep/Cap, and the helper plasmid can be transfected into HEK293 cells containing the adenovirus gene E1+ to produce infectious AAV particles. Alternatively, the Rep, Cap, and adenovirus helper genes may be combined into a single plasmid. Similar packaging cells and methods can be used for other viruses, such as retroviruses.

Multiple serotypes of AAV have been identified. These serotypes differ in the types of cells they infect (i.e., their tropism), allowing preferential transduction of specific cell types. Serotypes for CNS tissue include AAV1, AAV2, AAV4, AAV5, AAV8, and AAV9. Serotypes for heart tissue include AAV1, AAV8, and AAV9. Serotypes for kidney tissue include AAV2. Serotypes for lung tissue include AAV4, AAV5, AAV6, and AAV9. Serotypes for pancreas tissue include AAV8. Serotypes for photoreceptor cells include AAV2, AAV5, and AAV8. Serotypes for retinal pigment epithelium tissue include AAV1, AAV2, AAV4, AAV5, and AAV8. Serotypes for skeletal muscle tissue include AAV1, AAV6, AAV7, AAV8, and AAV9. Serotypes for liver tissue include AAV7, AAV8, and AAV9, and particularly AAV8.

Tropism can be further refined through pseudotyping, which is the mixing of a capsid and a genome from different viral serotypes. For example AAV2/5 indicates a virus containing the genome of serotype 2 packaged in the capsid from serotype 5. Use of pseudotyped viruses can improve transduction efficiency, as well as alter tropism. Hybrid capsids derived from different serotypes can also be used to alter viral tropism. For example, AAV-DJ contains a hybrid capsid from eight serotypes and displays high infectivity across a broad range of cell types in vivo. AAV-DJ8 is another example that displays the properties of AAV-DJ but with enhanced brain uptake. AAV serotypes can also be modified through mutations. Examples of mutational modifications of AAV2 include Y444F, Y500F, Y730F, and S662V. Examples of mutational modifications of AAV3 include Y705F, Y731F, and T492V. Examples of mutational modifications of AAV6 include S663V and T492V. Other pseudotyped/modified AAV variants include AAV2/1, AAV2/6, AAV2/7, AAV2/8, AAV2/9, AAV2.5, AAV8.2, and AAV/SASTG.

To accelerate transgene expression, self-complementary AAV (scAAV) variants can be used. Because AAV depends on the cell's DNA replication machinery to synthesize the complementary strand of the AAV's single-stranded DNA genome, transgene expression may be delayed. To address this delay, scAAV containing complementary sequences that are capable of spontaneously annealing upon infection can be used, eliminating the requirement for host cell DNA synthesis.

To increase packaging capacity, longer transgenes may be split between two AAV transfer plasmids, the first with a 3' splice donor and the second with a 5' splice acceptor. Upon co-infection of a cell, these viruses form concatemers, are spliced together, and the full-length transgene can be expressed. Although this allows for longer transgene expression, expression is less efficient. Similar methods for increasing capacity utilize homologous recombination. For example, a transgene can be divided between two transfer plasmids but with substantial sequence overlap such that co-expression induces homologous recombination and expression of the full-length transgene.

Introduction of human-TRKB-targeting reagents can also be accomplished by lipid nanoparticle (LNP)-mediated delivery. Lipid formulations can protect biological molecules from degradation while improving their cellular uptake. Lipid nanoparticles are particles comprising a plurality of lipid molecules physically associated with each other by intermolecular forces. These include microspheres (including unilamellar and multilamellar vesicles, e.g., liposomes), a dispersed phase in an emulsion, micelles, or an internal phase in a suspension. Such lipid nanoparticles can be used to encapsulate one or more nucleic acids or proteins for delivery. Formulations which contain cationic lipids are useful for delivering polyanions such as nucleic acids. Other lipids that can be included are neutral lipids (i.e., uncharged or zwitterionic lipids), anionic lipids, helper lipids that enhance transfection, and stealth lipids that increase the length of time for which nanoparticles can exist in vivo. Examples of suitable cationic lipids, neutral lipids, anionic lipids, helper lipids, and stealth lipids can be found in WO 2016/010840 A1, herein incorporated by reference in its entirety for all purposes. An exemplary lipid nanoparticle can comprise a cationic lipid and one or more other components. In one example, the other component can comprise a helper lipid such as cholesterol. In another example, the other components can comprise a helper lipid such as cholesterol and a neutral lipid such as DSPC. In another example, the other components can comprise a helper lipid such as cholesterol, an optional neutral lipid such as DSPC, and a stealth lipid such as S010, S024, S027, S031, or S033.

The mode of delivery can be selected to decrease immunogenicity. For example, if multiple components are delivered, they may be delivered by different modes (e.g., bimodal delivery). These different modes may confer different pharmacodynamics or pharmacokinetic properties on the subject delivered molecule. For example, the different modes can result in different tissue distribution, different half-life, or different temporal distribution. Some modes of delivery (e.g., delivery of a nucleic acid vector that persists in a cell by autonomous replication or genomic integration) result in more persistent expression and presence of the molecule, whereas other modes of delivery are transient and less persistent (e.g., delivery of an RNA or a protein).

Administration in vivo can be by any suitable route including, for example, parenteral, intravenous, oral, subcutaneous, intra-arterial, intracranial, intrathecal, intraperitoneal, topical, intranasal, or intramuscular. Systemic modes of administration include, for example, oral and parenteral routes. Examples of parenteral routes include intravenous, intraarterial, intraosseous, intramuscular, intradermal, subcutaneous, intranasal, and intraperitoneal routes. A specific example is intravenous infusion. Nasal instillation and intravitreal injection are other specific examples. Local modes of administration include, for example, intrathecal, intracerebroventricular, intraparenchymal (e.g., localized intraparenchymal delivery to the striatum (e.g., into the caudate or into the putamen), cerebral cortex, precentral gyrus, hippocampus (e.g., into the dentate gyrus or CA3 region), temporal cortex, amygdala, frontal cortex, thalamus, cerebellum, medulla, hypothalamus, tectum, tegmentum, or substantia nigra), intraocular, intraorbital, subconjuctival, intravitreal, subretinal, and transscleral routes. Significantly smaller amounts of the components (compared with systemic approaches) may exert an effect when administered locally (for example, intraparenchymal or intravitreal) compared to when administered systemically (for example, intravenously). Local modes of administration may also reduce or eliminate the incidence of potentially toxic side effects that may occur when therapeutically effective amounts of a component are administered systemically. In a specific example, a human-TRKB-targeting reagents is administered via direct hippocampal injection, subcutaneous injection, or intravitreal injection.

Compositions comprising human-TRKB-targeting reagents can be formulated using one or more physiologically and pharmaceutically acceptable carriers, diluents, excipients or auxiliaries. The formulation can depend on the route of administration chosen. The term "pharmaceutically acceptable" means that the carrier, diluent, excipient, or auxiliary is compatible with the other ingredients of the formulation and not substantially deleterious to the recipient thereof.

The frequency of administration and the number of dosages can be depend on the half-life of the human-TRKB-targeting reagents and the route of administration among other factors. The introduction of human-TRKB-targeting reagents into the cell or non-human animal can be performed one time or multiple times over a period of time. For example, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

E. Measuring Delivery, Activity, or Efficacy of Human-TRKB-Targeting Reagents In Vivo or Ex Vivo The methods disclosed herein can further comprise detecting or measuring activity of human-TRKB-targeting reagents. Measuring the activity of such reagents (e.g., agonist activity or inhibitor activity) can comprise measuring TRKB activity. TRKB activity can be measured by any known means. For example, TRKB phosphorylation can be assessed (e.g., in the brain or neurons), activation of downstream pathways such as PI3K/AKT and MAPK/ERK by TRKB can be assessed (e.g., in the brain or neurons, such as primary cortical neurons), or cell survival can be assessed (e.g., neuron cell survival, such as retinal ganglion cell survival). For example, phosphorylation or activation of downstream signaling pathways can be assessed at 15 minutes, 30 minutes, 1 hour, 2 hours, 4 hours, or 18 hours post-dosing. Increases in TRKB phosphorylation, activation of downstream signaling pathways, or cell survival can be indications of TRKB activation, whereas decreases can be indications of TRKB inhibition.

In non-human animals, the assessing can comprise assessing one or more or all of body weight, body composition, metabolism, and locomotion relative to a control-non-human animal (e.g., at 12 hours, 24 hours, 48 hours, 72 hours, 96 hours, or 120 hours post-dosing). See, e.g., Lin et al. (2008) *PLoS ONE* 3(4):e1900; Rios et al. (2013) *Trends in Neurosciences* 36(2):83-90; and Zorner et al. (2003) *Biol. Psychiatry* 54:972-982, each of which is herein incorporated by reference in its entirety for all purposes. Assessing changes in body composition can comprise, for example, assessing lean mass and/or fat mass. Assessing changes in metabolism can comprise, for example, assessing changes in food consumption and/or water consumption. Decreases in body weight, fat mass, lean mass, food intake, and water intake can be indications of TRKB activation, whereas increases can be indications of TRKB inhibition. Increases in locomotion can be indications of TRKB activation, whereas decreases can be indications of TRKB inhibition.

The assessing can comprise assessing neuroprotective activity. As one example, cell survival can be assessed in non-human animals. For example, rodent retinal ganglion cells (RGCs) are often used to study neurodegenerative processes associated with axonal lesion as well as to assay neuroprotective therapies. See, e.g., Nadal-Nicolás et al. (2009) *Invest. Ophthalmol. Vis. Sci.* 50(8):3860-3868, herein incorporated by reference in its entirety for all purposes. Retinal ganglion cell survival/viability can be assessed (e.g., in a complete optic nerve transection model after optic nerve injury) following treatment with a human-TRKB targeting reagent relative to a control non-human animal. For example, retinal ganglion cell survival/viability can be assessed in a complete optic nerve transection model after optic nerve injury. See, e.g., Nadal-Nicolás et al. (2009) *Invest. Ophthalmol. Vis. Sci.* 50(8):3860-3868, herein incorporated by reference in its entirety for all purposes. As another example, retinal ganglion cell survival/viability can be assessed in an optic nerve crush model. In this model, the crush injury to the optic nerve leads to gradual retinal ganglion cells apoptosis. See., e.g., Tang et al. (2011) *J. Vis. Exp.* 50:2685, herein incorporated by reference in its entirety for all purposes. Retinal ganglion cell survival/viability can be assessed, for example, by measuring retinal ganglion cell density (e.g., in retinas dissected and stained for retinal ganglion cells). Increased survival/viability can be an indication of TRKB activation, whereas decreased survival/viability can be an indication of TRKB inhibition.

If the human-TRKB-targeting reagent is a genome editing reagent, the measuring can comprise assessing the humanized TRKB locus for modifications. Various methods can be used to identify cells having a targeted genetic modification. The screening can comprise a quantitative assay for assessing modification of allele (MOA) of a parental chromosome. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence. Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, herein incorporated by reference in its entirety for all purposes). Next-generation sequencing (NGS) can also be used for screening. Next-generation sequencing can also be referred to as "NGS" or "massively parallel sequencing" or "high throughput sequencing." NGS can be used as a screening tool in addition to the MOA assays to define the exact nature of the targeted genetic modification and whether it is consistent across cell types or tissue types or organ types.

The assessing in a non-human animal can be in any cell type from any tissue or organ. For example, the assessment can be in multiple cell types from the same tissue or organ (e.g., the brain) or in cells from multiple locations within the tissue or organ (e.g., hippocampus and striatum). This can provide information about which cell types within a target tissue or organ are being targeted or which sections of a tissue or organ are being reached by the human-TRKB-targeting reagent. As another example, the assessment can be in multiple types of tissue or in multiple organs. In methods in which a particular tissue, organ, or cell type is being targeted, this can provide information about how effectively that tissue or organ is being targeted and whether there are off-target effects in other tissues or organs.

If the reagent is designed to inactivate the humanized TRKB locus, affect expression of the humanized TRKB locus, or prevent translation of the humanized TRKB mRNA, the measuring can comprise assessing humanized TRKB mRNA or protein expression. This measuring can be within the brain or particular cell types (e.g., neurons such as retinal ganglion cells).

IV. Methods of Making Non-Human Animals Comprising a Humanized TRKB Locus

Various methods are provided for making a non-human animal genome, non-human animal cell, or non-human animal comprising a humanized TRKB locus as disclosed elsewhere herein. Any convenient method or protocol for producing a genetically modified organism is suitable for producing such a genetically modified non-human animal. See, e.g., Cho et al. (2009) *Current Protocols in Cell Biology* 42:19.11:19.11.1-19.11.22 and Gama Sosa et al. (2010) *Brain Strutt. Funct.* 214(2-3):91-109, each of which is herein incorporated by reference in its entirety for all purposes. Such genetically modified non-human animals can be generated, for example, through gene knock-in at a targeted TrkB locus.

For example, the method of producing a non-human animal comprising a humanized TRKB locus can comprise: (1) modifying the genome of a pluripotent cell to comprise the humanized TRKB locus; (2) identifying or selecting the genetically modified pluripotent cell comprising the humanized TRKB locus; (3) introducing the genetically modified pluripotent cell into a non-human animal host embryo; and (4) implanting and gestating the host embryo in a surrogate mother. For example, the method of producing a non-human animal comprising a humanized TRKB locus can comprise: (1) modifying the genome of a pluripotent cell to comprise the humanized TRKB locus; (2) identifying or selecting the genetically modified pluripotent cell comprising the humanized TRKB locus; (3) introducing the genetically modified pluripotent cell into a non-human animal host embryo; and (4) gestating the host embryo in a surrogate mother. Optionally, the host embryo comprising modified pluripotent cell (e.g., a non-human ES cell) can be incubated until the blastocyst stage before being implanted into and gestated in the surrogate mother to produce an F0 non-human animal. The surrogate mother can then produce an F0 generation non-human animal comprising the humanized TRKB locus.

The methods can further comprise identifying a cell or animal having a modified target genomic locus. Various methods can be used to identify cells and animals having a targeted genetic modification.

The step of modifying the genome can, for example, utilize exogenous repair templates (e.g., targeting vectors) to modify a TrkB locus to comprise a humanized TRKB locus disclosed herein. As one example, the targeting vector can be for generating a humanized TRKB gene at an endogenous TrkB locus (e.g., endogenous non-human animal TrkB locus), wherein the targeting vector comprises a 5' homology arm targeting a 5' target sequence at the endogenous TrkB locus and a 3' homology arm targeting a 3' target sequence at the endogenous TrkB locus. Exogenous repair templates can also comprise nucleic acid inserts including segments of DNA to be integrated in the TrkB locus. Integration of a nucleic acid insert in the TrkB locus can result in addition of a nucleic acid sequence of interest in the TrkB locus, deletion of a nucleic acid sequence of interest in the TrkB locus, or replacement of a nucleic acid sequence of interest in the TrkB locus (i.e., deletion and insertion). The homology arms can flank an insert nucleic acid comprising human TRKB sequence to generate the humanized TRKB locus (e.g., for deleting a segment of the endogenous TrkB locus and replacing with an orthologous human TRKB sequence).

The exogenous repair templates can be for non-homologous-end-joining-mediated insertion or homologous recombination. Exogenous repair templates can comprise deoxyribonucleic acid (DNA) or ribonucleic acid (RNA), they can be single-stranded or double-stranded, and they can be in linear or circular form. For example, a repair template can be a single-stranded oligodeoxynucleotide (ssODN).

Exogenous repair templates can also comprise a heterologous sequence that is not present at an untargeted endogenous TrkB locus. For example, an exogenous repair template can comprise a selection cassette, such as a selection cassette flanked by recombinase recognition sites.

Some exogenous repair templates comprise homology arms. If the exogenous repair template acid also comprises a nucleic acid insert, the homology arms can flank the nucleic acid insert. For ease of reference, the homology arms are referred to herein as 5' and 3' (i.e., upstream and downstream) homology arms. This terminology relates to the relative position of the homology arms to the nucleic acid insert within the exogenous repair template. The 5' and 3' homology arms correspond to regions within the TrkB locus, which are referred to herein as "5' target sequence" and "3' target sequence," respectively.

A homology arm and a target sequence "correspond" or are "corresponding" to one another when the two regions share a sufficient level of sequence identity to one another to act as substrates for a homologous recombination reaction. The term "homology" includes DNA sequences that are either identical or share sequence identity to a corresponding sequence. The sequence identity between a given target sequence and the corresponding homology arm found in the exogenous repair template can be any degree of sequence identity that allows for homologous recombination to occur. For example, the amount of sequence identity shared by the homology arm of the exogenous repair template (or a fragment thereof) and the target sequence (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a corresponding region of homology between the homology arm and the corresponding target sequence can be of any length that is sufficient to promote homologous recombination. In some targeting vectors, the intended mutation in the endogenous TrkB locus is included in an insert nucleic acid flanked by the homology arms.

In cells other than one-cell stage embryos, the exogenous repair template can be a "large targeting vector" or "LTVEC," which includes targeting vectors that comprise homology arms that correspond to and are derived from nucleic acid sequences larger than those typically used by other approaches intended to perform homologous recombination in cells. LTVECs also include targeting vectors comprising nucleic acid inserts having nucleic acid sequences larger than those typically used by other approaches intended to perform homologous recombination in cells. For example, LTVECs make possible the modification of large loci that cannot be accommodated by traditional plasmid-based targeting vectors because of their size limitations. For example, the targeted locus can be (i.e., the 5' and 3' homology arms can correspond to) a locus of the cell that is not targetable using a conventional method or that can be targeted only incorrectly or only with significantly low efficiency in the absence of a nick or double-strand break induced by a nuclease agent (e.g., a Cas protein). LTVECs can be of any length and are typically at least 10 kb in length. The sum total of the 5' homology arm and the 3' homology arm in an LTVEC is typically at least 10 kb.

The screening step can comprise, for example, a quantitative assay for assessing modification of allele (MOA) of a parental chromosome. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence.

Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, incorporated herein by reference in its entirety for all purposes).

An example of a suitable pluripotent cell is an embryonic stem (ES) cell (e.g., a mouse ES cell or a rat ES cell). The modified pluripotent cell can be generated, for example, through recombination by (a) introducing into the cell one or more exogenous donor nucleic acids (e.g., targeting vectors) comprising an insert nucleic acid flanked, for example, by 5' and 3' homology arms corresponding to 5' and 3' target sites, wherein the insert nucleic acid comprises a human TRKB sequence to generate a humanized TRKB locus; and (b) identifying at least one cell comprising in its genome the insert nucleic acid integrated at the endogenous TrkB locus (i.e., identifying at least one cell comprising the humanized TRKB locus). The modified pluripotent cell can be generated, for example, through recombination by (a) introducing into the cell one or more targeting vectors comprising an insert nucleic acid flanked by 5' and 3' homology arms corresponding to 5' and 3' target sites, wherein the insert nucleic acid comprises a humanized TRKB locus; and (b) identifying at least one cell comprising in its genome the insert nucleic acid integrated at the target genomic locus.

Alternatively, the modified pluripotent cell can be generated by (a) introducing into the cell: (i) a nuclease agent, wherein the nuclease agent induces a nick or double-strand break at a target site within the endogenous TrkB locus; and (ii) one or more exogenous donor nucleic acids (e.g., targeting vectors) optionally comprising an insert nucleic acid flanked by, for example, 5' and 3' homology arms corresponding to 5' and 3' target sites located in sufficient proximity to the nuclease target site, wherein the insert nucleic acid comprises a human TRKB sequence to generate a humanized TRKB locus; and (c) identifying at least one cell comprising in its genome the insert nucleic acid integrated at the endogenous TrkB locus (i.e., identifying at least one cell comprising the humanized TRKB locus). Alternatively, the modified pluripotent cell can be generated by (a) introducing into the cell: (i) a nuclease agent, wherein the nuclease agent induces a nick or double-strand break at a recognition site within the target genomic locus; and (ii) one or more targeting vectors comprising an insert nucleic acid flanked by 5' and 3' homology arms corresponding to 5' and 3' target sites located in sufficient proximity to the recognition site, wherein the insert nucleic acid comprises the humanized TRKB locus; and (c) identifying at least one cell comprising a modification (e.g., integration of the insert nucleic acid) at the target genomic locus. Any nuclease agent that induces a nick or double-strand break into a desired recognition site can be used. Examples of suitable nucleases include a Transcription Activator-Like Effector Nuclease (TALEN), a zinc-finger nuclease (ZFN), a meganuclease, and Clustered Regularly Interspersed Short Palindromic Repeats (CRISPR)/CRISPR-associated (Cas) systems (e.g., CRISPR/Cas9 systems) or components of such systems (e.g., CRISPR/Cas9). See, e.g., US 2013/0309670 and US 2015/0159175, each of which is herein incorporated by reference in its entirety for all purposes.

The donor cell can be introduced into a host embryo at any stage, such as the blastocyst stage or the pre-morula stage (i.e., the 4 cell stage or the 8 cell stage). Progeny that are capable of transmitting the genetic modification though the germline are generated. See, e.g., U.S. Pat. No. 7,294,754, herein incorporated by reference in its entirety for all purposes.

Alternatively, the method of producing the non-human animals described elsewhere herein can comprise: (1) modifying the genome of a one-cell stage embryo to comprise the humanized TRKB locus using the methods described above for modifying pluripotent cells; (2) selecting the genetically modified embryo; and (3) implanting and gestating the genetically modified embryo into a surrogate mother. Alternatively, the method of producing the non-human animals described elsewhere herein can comprise: (1) modifying the genome of a one-cell stage embryo to comprise the humanized TRKB locus using the methods described above for modifying pluripotent cells; (2) selecting the genetically modified embryo; and (3) gestating the genetically modified embryo in a surrogate mother. Progeny that are capable of transmitting the genetic modification though the germline are generated.

Nuclear transfer techniques can also be used to generate the non-human mammalian animals. Briefly, methods for nuclear transfer can include the steps of: (1) enucleating an oocyte or providing an enucleated oocyte; (2) isolating or providing a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods, oocytes are generally retrieved from deceased animals, although they may be isolated also from either oviducts and/or ovaries of live animals. Oocytes can be matured in a variety of well-known media prior to enucleation. Enucleation of the oocyte can be performed in a number of well-known manners. Insertion of the donor cell or nucleus into the enucleated oocyte to form a reconstituted cell can be by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell can be activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, can be cultured in well-known media and then transferred to the womb of an animal. See, e.g., US 2008/0092249, WO 1999/005266, US 2004/0177390, WO 2008/017234, and U.S. Pat. No. 7,612,250, each of which is herein incorporated by reference in its entirety for all purposes.

The various methods provided herein allow for the generation of a genetically modified non-human F0 animal wherein the cells of the genetically modified F0 animal comprise the humanized TRKB locus. It is recognized that depending on the method used to generate the F0 animal, the number of cells within the F0 animal that have the humanized TRKB locus will vary. The introduction of the donor ES cells into a pre-morula stage embryo from a corresponding organism (e.g., an 8-cell stage mouse embryo) via for example, the VELOCIMOUSE® method allows for a greater percentage of the cell population of the F0 animal to comprise cells having the nucleotide sequence of interest comprising the targeted genetic modification. For example, at least 50%, 60%, 65%, 70%, 75%, 85%, 86%, 87%, 87%, 88%, 89%, 90%, 91%, 92%, 93%, 94%, 95%, 96%, 97%, 98%, 99% or 100% of the cellular contribution of the non-human F0 animal can comprise a cell population having the targeted modification.

The cells of the genetically modified F0 animal can be heterozygous for the humanized TRKB locus or can be homozygous for the humanized TRKB locus.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. When a nucleotide sequence encoding an amino acid sequence is provided, it is understood that codon degenerate variants thereof that encode the same amino acid sequence are also provided. The amino acid sequences follow the standard convention of beginning at the amino terminus of the sequence and proceeding forward (i.e., from left to right in each line) to the carboxy terminus.

TABLE 1

Description of Sequences.

| SEQ ID NO | Type | Description |
|---|---|---|
| 1 | Protein | Mouse TRKB/NTRK2 protein (P15209-1; NP_001020245.1; NP_001269890.1) |
| 2 | Protein | Rat TRKB/NTRK2 protein (Q63604-1; NP_036863.1) |
| 3 | Protein | Human TRKB/NTRK2 protein (Q16620-4; NP_006171.2) |
| 4 | Protein | Mouse/Human Hybrid TRKB/NTRK2 protein |
| 5 | Protein | Rat/Human Hybrid TRKB/NTRK2 protein |
| 6 | DNA | Mouse TrkB/Ntrk2 cDNA (NM_001025074.2) |
| 7 | DNA | Rat TrkB/Ntrk2 cDNA (NM_012731.2) |
| 8 | DNA | Human TRKB/NTRK2 cDNA (AF410899.1) |
| 9 | DNA | Mouse TrkB/Ntrk2 CDS (CCDS ID CCDS26573.1) |
| 10 | DNA | Rat TrkB/Ntrk2 CDS |
| 11 | DNA | Human TRKB/NTRK2 CDS |
| 12 | DNA | Mouse/Human TRKB/NTRK2 CDS |
| 13 | DNA | Rat/Human TRKB/NTRK2 CDS |
| 14 | DNA | 7138 hU Fwd |
| 15 | DNA | 7138 hU Probe(FAM) |
| 16 | DNA | 7138hU Rev |
| 17 | DNA | 7138 hD Fwd |
| 18 | DNA | 7138 hD Probe(Cal) |
| 19 | DNA | 7138 hD Rev |
| 20 | DNA | 7138U Fwd |
| 21 | DNA | 7138U Probe(FAM) |
| 22 | DNA | 7138U Rev |
| 23 | DNA | 7138D Fwd |
| 24 | DNA | 7138D Probe(Cal) |
| 25 | DNA | 7138D Rev |
| 26 | DNA | rnoTU Fwd |
| 27 | DNA | rnoTU Probe (FAM) |
| 28 | DNA | rnoTU Rev |
| 29 | DNA | rnoTD Fwd |
| 30 | DNA | rnoTD Probe (Cal-Orange) |
| 31 | DNA | rnoTD Rev |
| 32 | DNA | rnoTM Fwd |
| 33 | DNA | rnoTM Probe (FAM) |
| 34 | DNA | rnoTM Rev |
| 35 | DNA | rnoTAU2 Fwd |
| 36 | DNA | rnoTAU2 Probe(FAM) |
| 37 | DNA | rnoTAU2 Rev |
| 38 | DNA | rnoTAD Fwd |
| 39 | DNA | rnoTAD Probe(Cal) |
| 40 | DNA | rnoTAD Rev |
| 41 | DNA | rnoGU Guide Target |
| 42 | DNA | rnoGU2 Guide Target |
| 43 | DNA | rnoGD Guide Target |

TABLE 1-continued

Description of Sequences.

| SEQ ID NO | Type | Description |
|---|---|---|
| 44 | DNA | rnoGD2 Guide Target |
| 45 | DNA | rnoTGU Fwd |
| 46 | DNA | rnoTGU Probe(FAM) |
| 47 | DNA | rnoTGU Rev |
| 48 | DNA | rnoTGD Fwd |
| 49 | DNA | rnoTGD Probe(Cal) |
| 50 | DNA | rnoTGD Rev |
| 51 | Protein | Mouse TRKB/NTRK2 Signal Peptide |
| 52 | Protein | Mouse TRKB/NTRK2 Extracellular Domain |
| 53 | Protein | Mouse TRKB/NTRK2 Transmembrane Domain |
| 54 | Protein | Mouse TRKB/NTRK2 Cytoplasmic Domain |
| 55 | Protein | Rat TRKB/NTRK2 Signal Peptide |
| 56 | Protein | Rat TRKB/NTRK2 Extracellular Domain |
| 57 | Protein | Rat TRKB/NTRK2 Transmembrane Domain |
| 58 | Protein | Rat TRKB/NTRK2 Cytoplasmic Domain |
| 59 | Protein | Human TRKB/NTRK2 Signal Peptide |
| 60 | Protein | Human TRKB/NTRK2 Extracellular Domain |
| 61 | Protein | Human TRKB/NTRK2 Transmembrane Domain |
| 62 | Protein | Human TRKB/NTRK2 Cytoplasmic Domain |
| 63 | DNA | Mouse TrkB/Ntrk2 Signal Peptide CDS |
| 64 | DNA | Mouse TrkB/Ntrk2 Extracellular Domain CDS |
| 65 | DNA | Mouse TrkB/Ntrk2 Transmembrane Domain CDS |
| 66 | DNA | Mouse TrkB/Ntrk2 Cytoplasmic Domain CDS |
| 67 | DNA | Rat TrkB/Ntrk2 Signal Peptide CDS |
| 68 | DNA | Rat TrkB/Ntrk2 Extracellular Domain CDS |
| 69 | DNA | Rat TrkB/Ntrk2 Transmembrane Domain CDS |
| 70 | DNA | Rat TrkB/Ntrk2 Cytoplasmic Domain CDS |
| 71 | DNA | Human TRKB/NTRK2 Signal Peptide CDS |
| 72 | DNA | Human TRKB/NTRK2 Extracellular Domain CDS |
| 73 | DNA | Human TRKB/NTRK2 Transmembrane Domain CDS |
| 74 | DNA | Human TRKB/NTRK2 Cytoplasmic Domain CDS |
| 75 | Protein | Human TRKB/NTRK2 protein (Q16620-1; NP_001018074.1) |
| 76 | DNA | Human TRKB/NTRK2 cDNA (NM_001018064.2) |
| 77 | DNA | Human TRKB/NTRK2 CDS (CCDS ID CCDS35050.1) |
| 78-125 | DNA/Protein | Heavy and Light Chain Variable Regions and CDRs of Selected Anti-TRKB Antibodies in Table 22 and Table 23 |

EXAMPLES

Example 1. Generation of Mice Comprising a Humanized TRKB Locus

A large targeting vector (LTVEC) comprising a 5' homology arm comprising 41.6 kb of the mouse TrkB locus and 3' homology arm comprising 62.4 kb of the mouse TrkB locus was generated to replace a region of 65.7 kb from the mouse TrkB gene encoding the mouse TRKB extracellular domain with 74.4 kb of the corresponding human sequence of TRKB. Information on mouse and human TRKB is provided in Table 2. A description of the generation of the large targeting vector is provided in Table 3. Generation and use of large targeting vectors (LTVECs) derived from bacterial artificial chromosome (BAC) DNA through bacterial homologous recombination (BHR) reactions using VELOCIGENE® genetic engineering technology is described, e.g., in U.S. Pat. No. 6,586,251 and Valenzuela et al. (2003) *Nat. Biotechnol.* 21(6):652-659, each of which is herein incorporated by reference in its entirety for all purposes. Generation of LTVECs through in vitro assembly methods is described, e.g., in US 2015/0376628 and WO 2015/200334, each of which is herein incorporated by reference in its entirety for all purposes.

TABLE 2

Mouse and Human TRKB/NTRK2.

| | Official Symbol | NCBI Gene ID | Primary Source | RefSeq mRNA ID | UniProt ID | Genomic Assembly | Location |
|---|---|---|---|---|---|---|---|
| Mouse | Ntrk2 | 18212 | MGI: 97384 | NM_001025074 | P15209 | GRCm38/mm10 | Chr 13: 58,806,569-59,133,970 (+) |
| Human | Ntrk2 | 4915 | HGNC: 8032 | AF410899 | Q16620 | GRCh38/hg38 | Chr 9: 84,669,778-85,027,070 (+) |

TABLE 3

Mouse TrkB/Ntrk2 Large Targeting Vector.

| | Genome Build | Start | End | Length (bp) |
|---|---|---|---|---|
| 5' Mouse Arm | GRCm38/mm10 | Chr13: 58,767,209 | Chr13: 58,808,821 | 41,613 |
| Human Insert | GRCh38/hg38 | Chr9: 84,670,730 | Chr9: 84,745,139 | 74,409 |
| 3' Mouse Arm | GRCm38/mm10 | Chr13: 58,874,563 | Chr13: 58,936,986 | 62,424 |

Specifically, a region starting in exon 2 (coding exon 1; from amino acid 32, preserving signal peptide) through exon 10, including the first 137 base pairs of intron 10 and all introns between exons 2 and 10 (i.e., between coding exon 1 and exon 10) was deleted from the mouse TrkB locus (preserving the mouse transmembrane domain encoded by exons 10 and 11). A region including exon 2/coding exon 1 (from amino acid 32, beginning after the signal peptide) through exon 10, including the first 177 base pairs of intron 10 and all introns between exons 2 and 10 (i.e., between coding exon 1 and exon 10) was inserted in place of the deleted mouse region (preserving the mouse transmembrane domain encoded by exons 10 and 11).

Figure 6:
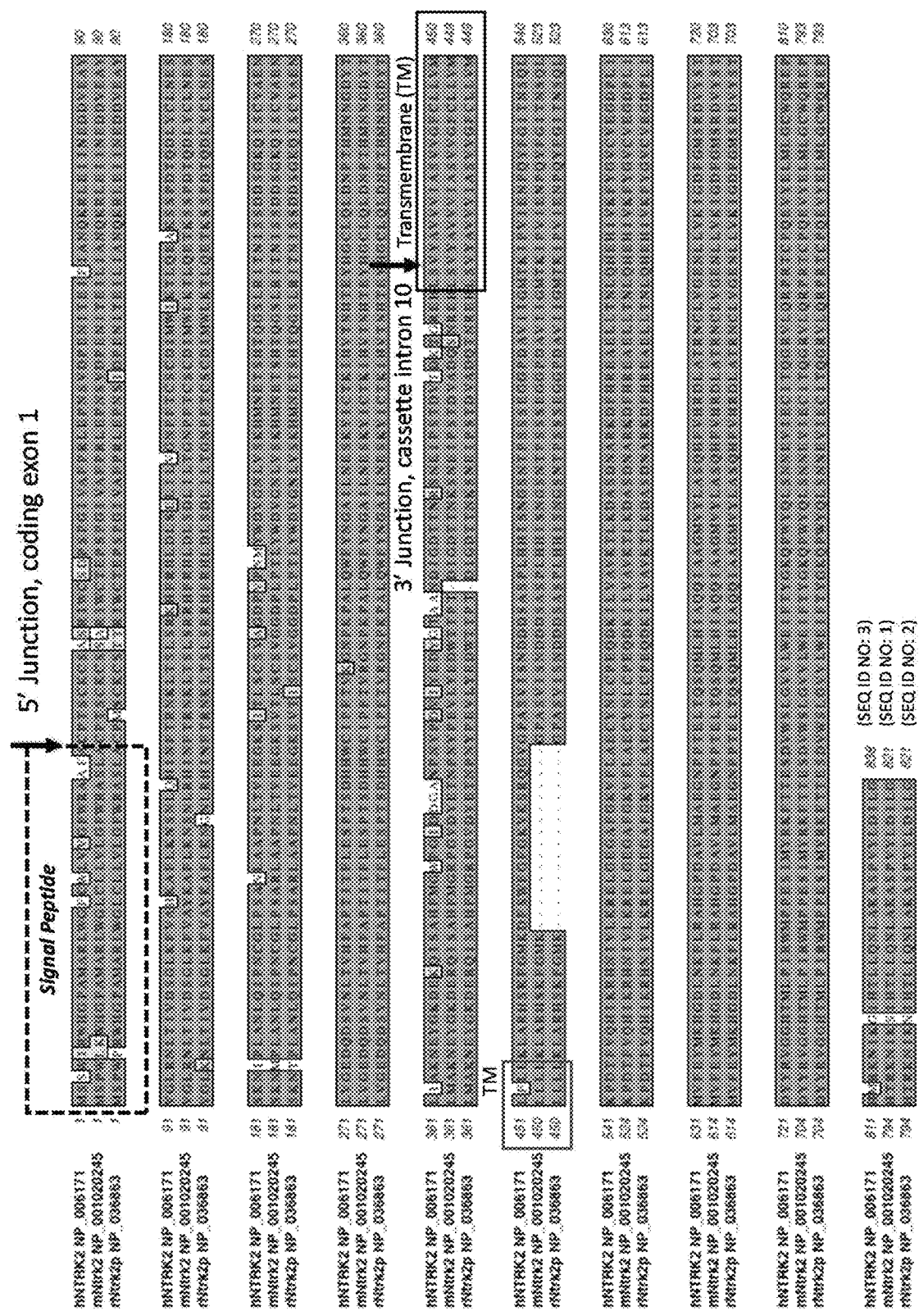
FIG. 6 shows an alignment of the mouse, rat, and human TRKB (NTRK2) proteins.

Sequences for the mouse TRKB signal peptide, extracellular domain, transmembrane domain, and cytoplasmic domain are set forth in SEQ ID NOS: 51-54, respectively, with the corresponding coding sequence set forth in SEQ ID NOS: 63-66, respectively. Sequences for the human TRKB signal peptide, extracellular domain, transmembrane domain, and cytoplasmic domain are set forth in SEQ ID NOS: 59-62, respectively, with the corresponding coding sequences set forth in SEQ ID NOS: 71-74, respectively. The expected encoded chimeric TRKB protein is has mouse TRKB transmembrane and intracellular domains, a mouse TRKB signal peptide, and a human TRKB extracellular domain. See FIG. 1. An alignment of the mouse and human TRKB proteins in FIG. 6. The mouse and human TrkB/TRKB coding sequences are set forth in SEQ ID NOS: 9 and 11, respectively. The mouse and human TRKB protein sequences are set forth in SEQ ID NOS: 1 and 3, respectively. The sequences for the expected chimeric mouse/human TRKB coding sequence and the expected chimeric mouse/human TRKB protein are set forth in SEQ ID NOS: 12 and 4, respectively.

Figure 2:
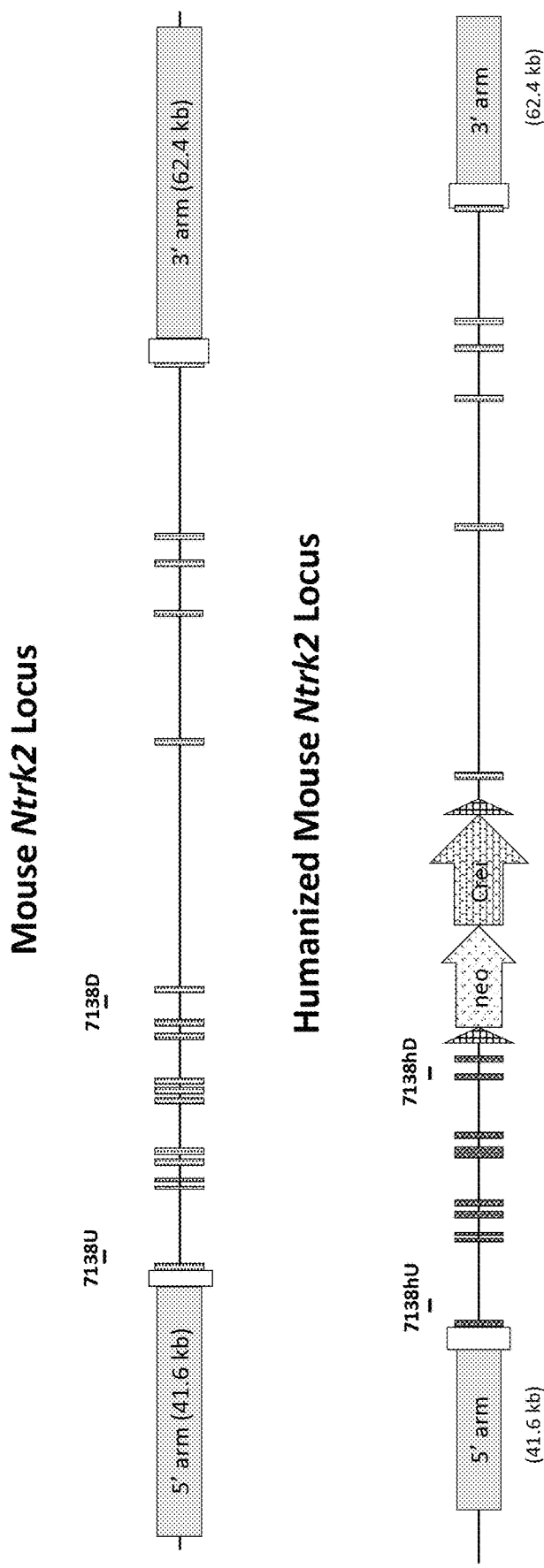
FIG. 2 (not to scale) shows a schematic of the TAQMAN® assays for screening humanization of the mouse TrkB (mouse Ntrk2) locus. Gain-of-allele (GOA) assays include 7138hU and 7138hD. Loss-of-allele (LOA) assays include 7138U and 7138D.

To generate the mutant allele, the large targeting vector was introduced into F1H4 mouse embryonic stem cells. Following antibiotic selection, colonies were picked, expanded, and screened by TAQMAN®. See FIG. 2. Loss-of-allele assays were performed to detect loss of the endogenous mouse allele, and gain-of-allele assays were performed to detect gain of the humanized allele using the primers and probes set forth in Table 4.

TABLE 4

Screening Assays.

| Assay | Description | Primer/Probe | Sequence |
|---|---|---|---|
| 7138 hU | Upstream Human Insertion | Fwd | AGGTGGGTAGGTCCTGGAAGTG (SEQ ID NO: 14) |
| | | Probe (FAM) | AATGCTGTCCCAAGAGTGGG (SEQ ID NO: 15) |
| | | Rev | GTCCTGCATCCCTTGTCTTTG (SEQ ID NO: 16) |
| 7138 hD | Downstream Human Insertion | Fwd | ATGTGGGCGTTGTGCAGTCTC (SEQ ID NO: 17) |
| | | Probe (Cal) | CGCTGCAGTGCATTGAACTCAGCA (SEQ ID NO: 18) |
| | | Rev | CTGTGGAGGGACGTGACCAG (SEQ ID NO: 19) |
| 7138U | Upstream Mouse LOA | Fwd | TCCGCTAGGATTTGGTGTACTG (SEQ ID NO: 20) |
| | | Probe (FAM) | AGCCTTCTCCAGGCATCGTGGCAT (SEQ ID NO: 21) |
| | | Rev | TCCGGGTCAACGCTGTTAG (SEQ ID NO: 22) |
| 7138D | Downstream Mouse LOA | Fwd | TCCTGCGAGGGTTCTGAC (SEQ ID NO: 23) |
| | | Probe (Ca) | TGGGTGCTCATATGCCAGAGAAATTGTCA (SEQ ID NO: 24) |
| | | Rev | CGATCTGTGATGGCCTGCTTAC (SEQ ID NO: 25) |

Modification-of-allele (MOA) assays including loss-of-allele (LOA) and gain-of-allele (GOA) assays are described, for example, in US 2014/0178879; US 2016/0145646; WO 2016/081923; and Frendewey et al. (2010) *Methods Enzymol.* 476:295-307, each of which is herein incorporated by reference in its entirety for all purposes. The loss-of-allele (LOA) assay inverts the conventional screening logic and quantifies the number of copies in a genomic DNA sample of the native locus to which the mutation was directed. In a correctly targeted heterozygous cell clone, the LOA assay detects one of the two native alleles (for genes not on the X or Y chromosome), the other allele being disrupted by the targeted modification. The same principle can be applied in reverse as a gain-of-allele (GOA) assay to quantify the copy number of the inserted targeting vector in a genomic DNA sample.

F0 mice were generated using the VELOCIMOUSE® method. See, e.g., U.S. Pat. Nos. 7,576,259; 7,659,442; 7,294,754; US 2008/0078000; and Poueymirou et al. (2007) *Nat. Biotechnol.* 25(1):91-99, each of which is herein incorporated by reference in its entirety for all purposes. In the VELOCIMOUSE method, targeted mouse embryonic stem (ES) cells are injected through laser-assisted injection into pre-morula stage embryos, e.g., eight-cell-stage embryos, which efficiently yields F0 generation mice that are fully ES-cell-derived. All experiments performed in humanized TRKB mice as described below were performed in mice in which the self-deleting selection cassette was self-deleted.

Example 2. In Vivo Comparison of Effect of H4H9816 and Isotype Control REGN1945 Antibodies on Body Weight and Metabolism in TrkB$^{hu/hu}$ Mice (MAID7139)

Experimental Procedure

To determine the effect of a TRKB agonist antibody, H4H9816P2, on body weight and composition, a metabolic study of mice homozygous for the expression of human TRKB receptor in place of the mouse TRKB receptor (TrkB$^{hu/hu}$ mice) was conducted following a single sub-cutaneous antibody injection. These studies were undertaken in part based on previous studies of TrkB agonists and TrkB-knockout mice. See, e.g., Lin et al. (2008) *PLoS ONE* 3(4):e1900; Rios et al. (2013) *Trends in Neurosciences* 36(2):83-90; and Zorner et al. (2003) *Biol. Psychiatry* 54:972-982, each of which is herein incorporated by reference in its entirety for all purposes. TrkB$^{hu/hu}$ mice (male, 20 weeks old) were first transferred from group-cage to single-cage housing for two weeks of acclimatization. After this period, mice were transferred to metabolic cages (CLAMS, Columbus Instruments) to assess changes in food and water consumption, locomotion, energy expenditure, and respiration following antibody administration. Regular powdered chow was stored in a floor chamber on a spring-loaded scale (Mettler Toledo, PL602E) to measure food consumption via changes in total chow weight. Water was accessible via a cage-top spout and intake was measured by tracking changes in pump-line volume (Oxymax®/CLAMS Liquid Unit). CLAMS metabolic cages measured each of these parameters in continuous, 16-18 minute intervals throughout the duration of the study. Metabolic data were analyzed in single measures and summarized in 24-hour intervals containing one complete dark and light cycle using OXYMAX®/CLAMS software (Columbus instruments, v5.35). After acclimating to the cages for two weeks, TrkB$^{hu/hu}$ mice received a single 50 mg/kg sub-cutaneous dose of either a TRKB agonist antibody, H4H9816P2, or an IgG4 isotype control antibody in PBS at pH7.2. A group of naïve control TrkB$^{hu/hu}$ mice did not receive an injection. Mice were weighed immediately prior to dosing, and at 24, 48, 72, 96, and 120 hours post-dosing. In order to measure each mouse's body composition, Nuclear Magnetic Resonance Relaxometry, also referred to as Quantitative Magnetic Resonance, was performed using an EchoMRI™-500 Analyzer (EchoMRI LLC). Prior to dosing, mice were placed in a clear plastic holder and inserted into the NMR-MRI device to measure each subject's lean mass, fat mass, and hydration status. Measurements were performed over the course of 0.5-3.2 minutes per mouse, and were taken again approximately 120 hours after dosing.

Results and Conclusions

Daily body weight monitoring was performed to determine whether a single subcutaneous injection of H4H9816P2 induces weight loss in TrkB$^{hu/hu}$ mice. Prior to dosing, there were no significant differences in the average body weight of the three treatment groups, as each had an average pre-dose body weight of 28.39-29.85 g (Table 5). At 48 hours post-dosing, however, H4H9816P2-treated TrkB$^{hu/hu}$ mice lost an average of 1.70 g, or 5.96% of their pre-dose body weight. At the same time point, naïve and isotype control antibody-treated TrkB$^{hu/hu}$ mice gained between 1.79-2.37% of their pre-dose body weight. H4H9816P2-treated TrkB$^{hu/hu}$ mice continued to lose weight throughout the full time course of the study, and by 72 and 96 hours post-dosing these mice had lost an average of 8.42% and 11.80% of their pre-dose body weight, respectively. At 120 hours post-dosing, H4H9816P2-treated TrkB$^{hu/hu}$ mice had lost an average of 12.67% of their pre-dose body weight. Conversely, naïve and isotype control-treated TrkB$^{hu/hu}$ mice did not exhibit any loss in pre-dose body weight throughout the study. As body weight in H4H9816P2-treated TrkB$^{hu/hu}$ mice was significantly reduced relative to both naïve and isotype controls at 48, 72, 96, and 120 hours post-dosing, it was determined that TRKB agonist antibody H4H9816P2 induced significant body weight loss in TrkB$^{hu/hu}$ mice.

TABLE 5

Body Weight of TrkB$^{hu/hu}$ Mice after Dosing with TRKB Agonist Antibody H4H9816P2.

| Experimental group | Mean pre-dose body weight (g) (±SD) Percent change from pre-dose body weight (+/−SD) | Mean body weight (g) 24 hours post-dose (±SD) Percent change from pre-dose body weight (+/−SD) | Mean body weight (g) 48 hours post-dose (±SD) Percent change from pre-dose body weight (+/−SD) | Mean body weight (g) 72 hours post-dose (±SD) Percent change from pre-dose body weight (+/−SD) | Mean body weight (g) 96 hours post-dose (±SD) Percent change from pre-dose body weight (+/−SD) | Mean body weight (g) 120 hours post-dose (±SD) Percent change from pre-dose body weight (+/−SD) |
|---|---|---|---|---|---|---|
| Naïve (n = 3) | 28.85 (+/−0.81) N/A | 29.69 (+/−0.97) +2.91% (+/−0.62) | 29.36 (+/−1.10) +1.79% (+/−1.62) | 29.32 (+/−1.29) +1.65% (+/−2.24) | 29.29 (+/−1.10) +1.54% (+/−1.22) | 28.88 (+/−1.04) +0.10% (+/−1.05) |

TABLE 5-continued

Body Weight of TrkB$^{hu/hu}$ Mice after Dosing with TRKB Agonist Antibody H4H9816P2.

| Experimental group | Mean pre-dose body weight (g) (±SD) Percent change from pre-dose body weight (+/−SD) | Mean body weight (g) 24 hours post-dose (±SD) Percent change from pre-dose body weight (+/−SD) | Mean body weight (g) 48 hours post-dose (±SD) Percent change from pre-dose body weight (+/−SD) | Mean body weight (g) 72 hours post-dose (±SD) Percent change from pre-dose body weight (+/−SD) | Mean body weight (g) 96 hours post-dose (±SD) Percent change from pre-dose body weight (+/−SD) | Mean body weight (g) 120 hours post-dose (±SD) Percent change from pre-dose body weight (+/−SD) |
|---|---|---|---|---|---|---|
| Isotype control (n = 4) | 29.21 (+/−2.68) N/A | 30.27 (+/−2.51) +3.61% (+/−1.68) | 29.90 (+/−2.63) +2.37% (+/−1.50) | 30.08 (+/−2.69) +2.98% (+/−1.09) | 29.87 (+/−2.52) +2.25% (+/−1.56) | 29.69 (+/−2.68) +1.65% (+/−0.81) |
| H4H9816P2 (n = 4) | 28.39 (+/−1.35) N/A | 27.87 (+/−1.29) −1.83% (+/−0.56) | 26.69 (+/−0.87) −5.96% (+/−1.88) | 26.00* (+/−0.98) −8.42% (+/−1.85) | 25.04** (+/−1.03) −11.80% (+/−1.52) | 24.79** (+/−1.36) −12.67% (+/−1.66) |

Statistical significance determined by two-way ANOVA with Tukey's multiple comparison post-hoc test is indicated (*= p < 0.05, = p < 0.01, * = p < 0.001, **** = p < 0.0001, compared to isotype control group: TrkB$^{hu/hu}$ mice dosed with 50 mg/kg isotype control antibody.

The effect of TRKB agonist antibody H4H9816P2 injection on body composition was also measured by performing NMR-MRI on each subject before and after dosing. Prior to dosing, the three treatment groups of TrkB$^{hu/hu}$ mice did not exhibit any significant differences in fat mass or lean mass, as each group had an average of 4.19-4.75 g of fat mass and 21.32-21.70 g of lean mass (Table 6). Following antibody administration, however, TrkB$^{hu/hu}$ mice dosed with H4H9816P2 lost an average of 48.90% of their total body fat mass over the course of the study (Table 6). Naïve and isotype control antibody-treated TrkB$^{hu/hu}$ mice lost an average of 8.49% and 9.48% of their pre-dose fat mass, respectively, which was significantly less than H4H9816P2-treated subjects (Table 6). Furthermore, H4H9816P2-treated TrkB$^{hu/hu}$ mice lost an average of 7.84% of their lean mass throughout the study, which was significantly greater than the 2.41% and 1.75% of average pre-dose lean mass lost by naïve and isotype control antibody-treated groups, respectively (Table 6). As such, the described body weight loss could be explained by a significant loss of fat mass and a modest loss of lean mass following injection of TRKB agonist antibody H4H9816P2 in TrkB$^{hu/hu}$ mice.

TABLE 6

Body Composition of TrkB$^{hu/hu}$ Mice after Dosing with TRKB Agonist Antibody H4H9816P2.

| Experimental group | Mean pre-dose fat mass (%) (±SD) | Mean fat mass (%) 120 hours post-dose (±SD) | Mean fat mass change (%) 120 hours post-dose (±SD) | Mean pre-dose lean mass (%) (±SD) | Mean lean mass (%) 120 hours post-dose (±SD) | Mean lean mass change (%) 120 hours post-dose (±SD) |
|---|---|---|---|---|---|---|
| Naive (n = 3) | 4.65 (+/−0.32) | 4.27 (+/−0.55) | −8.49 (+/−7.18) | 21.45 (+/−0.79) | 20.94 (+/−0.98) | −2.41 (+/−1.81) |
| Isotype control (n = 4) | 4.75 (+/−2.98) | 4.40 (+/−2.98) | −9.48 (+/−6.00) | 21.70 (+/−0.50) | 21.32 (+/−0.35) | −1.75 (+/−0.98) |
| H4H9816P2 (n = 4) | 4.19 (+/−1.15) | 2.14 (+/−0.64) | −48.90**** (+/−5.06) | 21.32 (+/−1.87) | 19.64 (+/−1.69) | −7.84*** (+/−0.94) |

Statistical significance determined by Kruskal-Wallis One-way ANOVA with Tukey's multiple comparison post-hoc test is indicated (* = p < 0.05,  = p < 0.01, * = p < 0.001, **** = p < 0.0001, compared to isotype control group: TrkB$^{hu/hu}$ mice dosed with 50 mg/kg isotype control antibody.

In addition to assessing the effects of TRKB agonist antibody H4H9816P2 injection on body weight and composition in TrkB$^{hu/hu}$ mice, feeding, drinking, and locomotor activity were continuously measured by metabolic cages. Prior to dosing, TrkB$^{hu/hu}$ mice consumed an average of 3.49-3.73 g of chow per day. Within 24 hours of dosing, however, H4H9816P2-treated TrkB$^{hu/hu}$ mice significantly reduced their food intake to 2.20 g of chow per day. The average level of food intake in H4H9816P2-treated TrkB$^{hu/hu}$ mice did not exceed 2.49 g of chow per day throughout the remainder of the study, while naïve and isotype antibody-treated TrkB$^{hu/hu}$ mice consistently consumed an average of 3.62-4.07 g of chow per day (Table 7).

Similarly, there were no significant differences in daily water consumption between treatment groups prior to dosing. TrkB$^{hu/hu}$ mice consumed an average of 4.67-5.55 mL of water per day in each treatment group (Table 8). After dosing, H4H9816P2-treated TrkB$^{hu/hu}$ mice reduced their water intake to 2.05-3.24 mL of water per day. This was significantly lower than naïve and isotype control antibody-treated TrkB$^{hu/hu}$ mice, which consistently consumed 4.50-5.77 mL of water per day throughout the study (Table 8). Thus, injection of the TRKB agonist antibody, H4H9816P2, appeared to result in a significant reduction of both food and water intake in TrkB$^{hu/hu}$ mice relative to both naïve and isotype controls.

TABLE 7

Food Consumption of TrkB$^{hu/hu}$ Mice after Dosing with TRKB Agonist Antibody H4H9816P2.

| Experimental group | Mean total food intake (g) 0-24 hours pre-dose (±SD) | Mean total food intake (g) 0-24 hours post-dose (±SD) | Mean total food intake (g) 24-48 hours post-dose (±SD) | Mean total food intake (g) 48-72 hours post-dose (±SD) | Mean total food intake (g) 72-96 hours post-dose (±SD) |
|---|---|---|---|---|---|
| Naive (n = 3) | 3.51 (+/−0.53) | 3.98 (+/−0.08) | 3.76 (+/−0.19) | 3.62 (+/−0.35) | 3.91 (+/−0.18) |
| Isotype control (n = 4) | 3.73 (+/−0.48) | 4.07 (+/−0.23) | 3.99 (+/−0.17) | 3.89 (+/−0.22) | 3.80 (+/−0.22) |
| H4H9816P2 (n = 4) | 3.49 (+/−1.07) | 2.20**** (+/−0.16) | 2.08**** (+/−0.36) | 2.18**** (+/−0.37) | 2.49*** (+/−0.47) |

Statistical significance determined by Kruskal-Wallis One-way ANOVA with Tukey's multiple comparison post-hoc test is indicated (*= p < 0.05, = p < 0.01, *= p < 0.001, ****= p < 0.0001, compared to isotype control group: TrkB$^{hu/hu}$ mice dosed with 50 mg/kg isotype control antibody.

TABLE 8

Water Consumption of TrkB$^{hu/hu}$ Mice after Dosing with TrkB Agonist Antibody H4H9816P2.

| Experimental group | Mean total water intake (mL) 0-24 hours pre-dose (±SD) | Mean total water intake (mL) 0-24 hours post-dose (±SD) | Mean total water intake (mL) 24-48 hours post-dose (±SD) | Mean total water intake (mL) 48-72 hours post-dose (±SD) | Mean total water intake (mL) 72-96 hours post-dose (±SD) |
|---|---|---|---|---|---|
| Naive (n = 3) | 4.79 (+/−0.21) | 5.42 (+/−0.94) | 4.96 (+/−0.91) | 4.57 (+/−0.56) | 4.88 (+/−0.32) |
| Isotype control (n = 4) | 5.55 (+/−1.23) | 4.50 (+/−1.08) | 5.08 (+/−1.39) | 5.09 (+/−1.10) | 5.77 (+/−1.62) |
| H4H9816P2 (n = 4) | 4.67 (+/−1.13) | 2.25** (+/−0.55) | 3.24* (+/−1.10) | 2.05*** (+/−0.29) | 2.25**** (+/−0.24) |

Statistical significance determined by Kruskal-Wallis One-way ANOVA with Tukey's multiple comparison post-hoc test is indicated (*= p < 0.05, = p < 0.01, *= p < 0.001, ****= p < 0.0001, compared to isotype control group: TrkB$^{hu/hu}$ mice dosed with 50 mg/kg isotype control antibody.

To determine the effects of antibody treatment on activity, locomotion was analyzed by OXYMAX®/CLAMS software (Columbus instruments, v5.35), which continuously measured the total number of x-plane ambulations of each mouse. One mouse exhibited hyperactivity prior to dosing and was removed from post-dose statistical analysis. While naïve and isotype antibody-treated subjects consistently registered an average of 11,000-15,000 ambulations per day throughout the study, H4H9816P2-treated TrkB$^{hu/hu}$ mice registered 28,260 ambulations between 24-48 hours post-dosing, and registered 21,193 and 27,028 ambulations from 48-72 and 72-96 hours post-dosing, respectively (Table 9). H4H9816P2-treated TrkB$^{hu/hu}$ mice registered more total ambulation counts at each time point following antibody administration, suggesting hyperactivity to be an additional effect of H4H9816P2 injection. In combination, these effects suggest that a single subcutaneous injection of the TRKB agonist antibody, H4H9816P2, induced significant changes in body weight, body composition, metabolism, and locomotion in TrkB$^{hu/hu}$ mice.

TABLE 9

Locomotion of TrkB$^{hu/hu}$ Mice after Dosing with TrkB Agonist Antibody H4H9816P2.

| Experimental group | Mean total ambulations (counts) 0-24 hours pre-dose (±SD) | Mean total ambulations (counts) 0-24 hours post-dose (±SD) | Mean total ambulations (counts) 24-48 hours post-dose (±SD) | Mean total ambulations (counts) 48-72 hours post-dose (±SD) | Mean total ambulations (counts) 72-96 hours post-dose (±SD) |
|---|---|---|---|---|---|
| Naive (n = 3) | 16562 (+/−3380) | 14692 (+/−2792) | 14387 (+/−6126) | 13279 (+/−3607) | 12525 (+/−4121) |
| Isotype Control REGN1945 (n = 4) | 18105 (+/−4085) | 13380 (+/−2730) | 13049 (+/−3376) | 11371 (+/−2552) | 11468 (+/−2088) |
| H4H9816P2 (n = 4) | 13292 (+/−5294) | 16575 (+/−6836) | 28260 (+/−19874) | 21193 (+/−6668) | 27028* (+/−10969) |

Statistical significance determined by Kruskal-Wallis One-way ANOVA with Tukey's multiple comparison post-hoc test is indicated (*= $p < 0.05$, = $p < 0.01$, *= $p < 0.001$, ****= $p < 0.0001$, compared to isotype control group: TrkB$^{hu/hu}$ mice dosed with 50 mg/kg isotype control antibody.

Example 3. In Vivo Comparison of the Effect of TRKB Agonist Antibody H4H9816P2 and IgG4 Isotype Control REGN1945 on TRKB Phosphorylation in the Brain Following Stereotaxic Injection in TrkB$^{hu/hu}$ Mice (MAID 7139)

Experimental Procedure

Tyrosine receptor kinase B (TRKB) is activated through binding of its ligand brain-derived neurotrophic factor (BDNF) at the extracellular receptor domain, which induces the dimerization and autophosphorylation of tyrosine residues in the intracellular receptor domain and subsequent activation of cytoplasmic signaling pathways. See, e.g., Haniu et al. (1997) *J. Biol. Chem.* 272(40):25296-25303 and Rogalski et al. (2000) *J. Biol. Chem.* 275(33):25082-25088, each of which is herein incorporated by reference in its entirety for all purposes. In order to determine the effect of a TRKB agonist antibody, H4H9816P2, on TRKB activation kinetics, a time-course study of TRKB phosphorylation following direct hippocampal injection was performed in mice homozygous for a chimeric mouse/human TRKB receptor in which the extracellular domain has been humanized (MAID 7139) (referred to as TrkB$^{hu/hu}$ mice). TrkB$^{hu/hu}$ mice (N=48) received bilateral stereotaxic injections of either with 2 µL of either vehicle (PBS), REGN1945 hereby noted as IgG4 isotype control antibody (27.5 mg/mL final concentration), or TRKB agonist antibody H4H9816P2 (27.5 mg/mL final concentration) into the hippocampus, −2 mm posterior and +1.5 mm lateral to bregma. In order to minimize tissue damage, injection and needle removal were both performed gradually over 5-minute intervals. TrkB$^{hu/hu}$ mice were then sacrificed by $CO_2$ euthanasia approximately 30 minutes, 1 hour, 4 hours, or 18 hours post-injection. A terminal bleed was performed via cardiac puncture to collect blood, and mice were then transcardially perfused with cold heparinized saline. The brain was carefully removed from the skull, and a 2 mm$^3$ section of tissue surrounding the injection site was dissected, collected in an Eppendorf tube and stored on ice. The brain section was then lysed in 300 µL of RIPA lysis buffer (ThermoFisher Scientific, Cat #89901) containing 2× protease and phosphatase inhibitors (ThermoFisher Scientific, Cat #78444) and stored on ice. The lysed tissue was then homogenized for further processing, aliquoted and stored at −80° C.

To assess TRKB phosphorylation in the brain tissue, immuno-precipitation and western blotting was performed. Anti-human TRKB antibody H4H10108N that does not compete for binding with H4H9816P2 was coupled to NHS-activated Sepharose beads (prepared using manufacturer's protocol; GE Healthcare, Cat #17-0906) and washed with DPBS three times to remove any residual preservation solution. Homogenized brain lysates were thawed on ice and diluted to a concentration of 1 mg/mL (brain weight to buffer volume) in a buffer composed of 1% NP-40, 0.1% Tween-20, protease and phosphatase inhibitors in TBST. The protein concentration of the homogenized brain lysate was quantified by performing a standard BCA assay per manufacturer's instructions (Thermo Scientific Pierce, Cat #23225). For every 100 µg of protein, 15 µL of anti-human TRKB antibody (H4H10108N) NHS-activated Sepharose beads were added to the brain lysate solution and the mixture was incubated overnight at 4° C. with gentle shaking 20 rpm (Thermo rotator). The next day, samples were centrifuged at 1000× g for one minute, and the supernatant was then carefully removed. Beads were subsequently washed twice with 400 μL of Tris-buffered saline (Bio-Rad, Cat #1706435) with 1% Tween-20 (Sigma Aldrich, Cat #P9416) (TBST). After carefully aspirating the wash buffer, 60 μL of 0.1% Trifluoroacetic acid (TFA; Sigma-Aldrich, T62200) in water at pH 3.0 was added to each sample. The solution was mixed and allowed to stand for two minutes before being collected and transferred into a separate tube. This process was repeated with another 60 μL of 0.1% TFA at pH 3.0. The two 0.1% TFA solutions for each sample were then combined, and 2 μL of 1M Tris-HCl (ThermoFisher Scientific, Cat #15567-027), at pH 8.5, was added.

The solution was dried using a speed vacuum and then re-suspended and reduced with a mixture of 20 μL of 1× Laemmli Buffer (Bio-Rad, Cat #1610737) plus 355 nM 2-mercaptoethanol (BME; Gibco, Cat #21985-023). Samples were boiled at 95° C. for 10 minutes and loaded onto a 10-well, Mini-Protean 4-15% Tris-Glycine gel (Bio-Rad, Cat #4561086). After electrophoresis, protein samples were transferred from the Tris-Glycine gel onto a PVDF membrane (Bio-Rad, Cat #170-4156) via the Trans-Blot Turbo Transfer System (Bio-Rad, Cat #1704156) over the course of 30 minutes at a constant rate of 1.3 A and 25 V. After the transfer, the membrane was blocked with 2.5% milk (Bio-Rad, Cat #170-6406) in TBST for one hour at room temperature, and subsequently probed overnight with either an anti-phospho-TRKB antibody (Novus, Cat #NB100-92656) diluted 1:1000 in a solution of 2.5% BSA or anti-TRKB primary antibody (Cell Signaling, Cat #4603) diluted to 1:1000 in 2.5% milk TBST at 4° C. on a shaker at 30 rpm. The next day, blots were washed with TBST and incubated with an anti-rabbit IgG antibody conjugated with horseradish peroxidase (Jackson, Cat #111-035-144) at 1:1000 in 1% milk in TBST for 1 hour at room temperature. Blots were then washed again, developed with ECL solution (PerkinElmer, Inc. Cat #RPN2106), and subsequent image exposures were taken every 30 seconds.

Results and Conclusions

Figure 3:
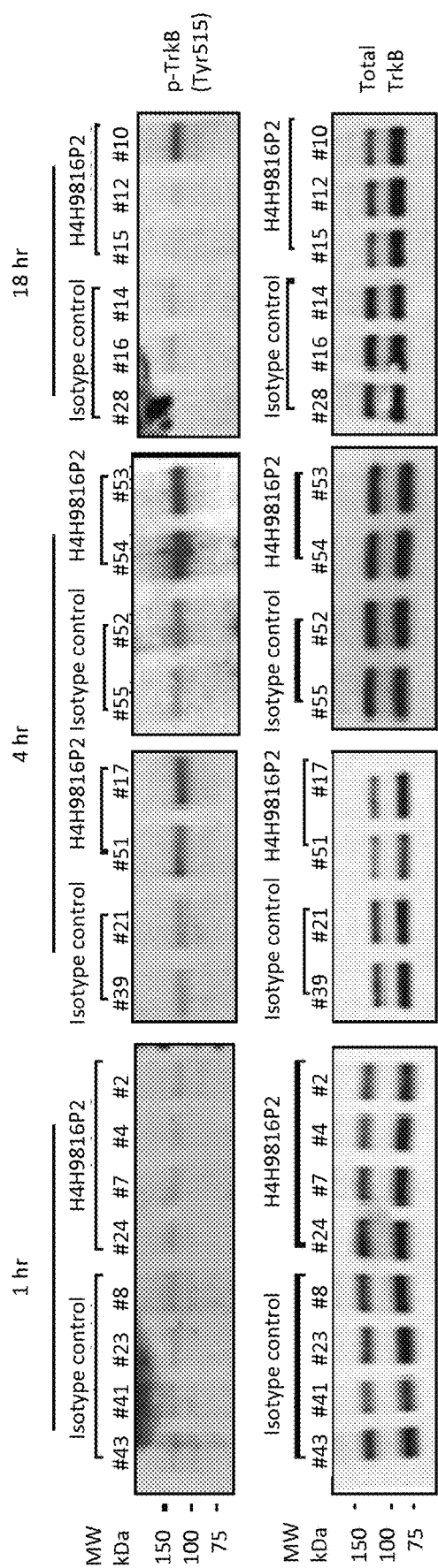
FIG. 3 shows western blots assessing total TRKB levels and phospho-TRKB levels in homozygous humanized TRKB mice at 1 hour, 4 hours, and 18 hours following direct hippocampal injection of TRKB agonist antibody H4H9816P2 or isotype control antibody.

Immunoprecipitation and subsequent western blotting of protein derived from TrkB$^{hu/hu}$ mouse brain lysates demonstrated that hippocampal TRKB phosphorylation was detectable in mice injected with a TRKB agonist antibody, H4H9816P2, but not in mice treated with vehicle or isotype control antibody, as shown FIG. 3. Among the time points assessed, TRKB phosphorylation peaked at 4 hours after stereotaxic injection in mice dosed with H4H9816P2. TRKB phosphorylation was also detected by western blot at 18 hours post-dosing in some, but not all mice. Conversely, injection of vehicle and IgG4 isotype control antibody did not induce TRKB phosphorylation at any time point. Western blotting also indicated that the total TRKB receptor levels were downregulated in some, but not all TrkB$^{hu/hu}$ mice dosed with H4H9816P2 relative to vehicle and isotype control treated mice. Total TRKB levels appeared to be slightly downregulated in H4H9816P2-treated subjects at 18 hours post-dosing. Thus, these results indicate that direct injection of the TRKB agonist antibody, H4H9816P2, induces phosphorylation of hippocampal TRJB receptors in TrkB$^{hu/hu}$ mice.

Example 4. Activation of Downstream Signaling Pathways by TrkB Agonist Antibodies in Primary Cortical Neurons from Postnatal Day 1 TrkB$^{hu/hu}$ Mice Experimental Procedure All procedures were conducted in accordance with the ARVO Statement for Use of Animals in Ophthalmic and Vision Research and the Regeneron Pharmaceuticals, Inc. IACUC. Primary mouse cortical neurons were isolated and cultured from humanized TrkB mice (MAID 7139). See, e.g., Beaudoin et al. (2012) *Nat. Protoc.* 7(9):1741-1754, herein incorporated by reference in its entirety for all purposes. Western blots were performed to determine the effects of TrkB agonist antibodies on the downstream pathways of Akt and Erk (p-Akt, p-Erk1/2). Primary cortical neurons from postnatal day 1 (P1) humanized TrkB mouse pups were cultured for 4 days (DIV-4) in NeuralQ Basal Medium (Global Stem, cat. #GSM-9420) supplemented with GS21 Neural Supplement (Global Stem, cat. #GSM-3100), Glutamax (Invitrogen, cat. #35050-061) and Penicillin/Streptomycin. Cells were treated with TrkB agonist antibody H4H9816P-L1 (10 μg/mL), TrkB agonist antibody H4H9780P-L1 (10 μg/mL), TrkB agonist antibody H4H9814P-L1 (10 μg/mL), IgG4 isotype control REGN1945 (10 μg/mL), control antibody H1M8037C-L1 (10 μg/mL), or BDNF (1 μg/mL), for 15 minutes or 2 hours. Western blots were performed to determine if the agonists have a difference in downstream signaling maintenance and strength. Treated cells were rinsed and scraped in cold PBS containing 1% protease and phosphatase inhibitors (Sigma). Protein concentration was determined by Bradford protein assay (Pierce). Samples (50 μg) were separated by SDS-PAGE in 3-8% Tris-Acetate reduced gels (Novex) and transferred to a nitrocellulose membrane (Bio-Rad).

The membrane was incubated for 1 hour in blocking solution containing 5% milk and 0.1% Tween-20, pH 7.6. This was followed by overnight incubation at 4° C. in the blocking buffer containing 5% BSA, 0.1% Tween-20, and rabbit anti-phosphoTrk (Cell Signaling, cat. #9141, 1:500), rabbit anti-phospho-Akt (Cell Signaling, cat. #9271, 1:1000), or rabbit anti-phospho-ERK1/2 antibody (Sigma, cat. #E7028, 1:5000). Subsequently, the labeled proteins were visualized by incubation with a horseradish peroxidase (HRP) conjugated anti-goat, mouse or rabbit IgG followed by development with a chemiluminescence substrate for HRP (Pierce). To determine the amounts of total TrkB, MAPK or Akt present in each lane, the nitrocellulose membranes were stripped of the antibodies in stripping buffer (Pierce) for 20 min and incubated with rabbit anti-TrkB (Cell Signaling, cat. #4603, 1:1000), rabbit anti-Erk1/2 (Cell Signaling, cat. #06-182, 1:1000), or rabbit anti-Akt antibody (Cell Signaling, cat. #9272, 1:1000) and then visualized as described above. Beta-Actin (Sigma, cat. #A5316, 1:20000 and GAPDH (Sigma, cat. #G9295) were probed as sample loading control.

Materials

TABLE 10

| mAB Clone IDs. | | |
|---|---|---|
| REGN | AbPID | Lot |
| REGN1945 | H4H9816P | L1 |
| | H4H9780P | L1 |
| | H4H9814P | L1 |
| | H1M8037C | L1 |
| | Comparator, Control antibody | |

TABLE 11

Reagents.

| Reagent/Equipment | Source | Identifier | Lot # |
|---|---|---|---|
| Penicillin/Streptomycin | Invitrogen | 15140 | |
| Fetal Bovine Serum | Invitrogen | 10082-147 | |
| GS21 Neural Supplement (50X) | GlobalStem | GSM-3100 | 18130001 |
| NeuralQ Basal Medium | GlobalStem | GSM-9420 | 18190001 |
| Glutamax | Invitrogen | 35050-061 | |
| Protease Inhibitor Cocktail | Sigma | P8340 | |
| Phosphatase Inhibitor Cocktail 3 | Sigma | P0044 | 034M4010V |
| RIPA lysis buffer 1x | Rockland | MB-030-0250 | 24805 |
| BSA | Sigma | A8806 | |
| Tris-Acetate 4-8% reduced gels | Invitrogen | WG1602BX10 | 14022684 |
| BCA Protein Assay Kit | Pierce | 23227 | |
| ECL | Pierce | 32209 | |
| Restore Western Blot Stripping Buffer | Pierce | 21059 | |
| Nitrocellulose membrane | Bio-Rad Laboratories | 1620112 | |

TABLE 12

Neurobasal Medium.

NeuralQ Basal Medium (Global Stem, GSM-9420) 50 mL
GS21 Neural Supplement (50X) (Global Stem, GSM-3100) 10 mL
Glutamax (Invitrogen, 35050-061) 0.5 mL
Penicillin/Streptomycin 5 mL

TABLE 13

Antibodies.

H4H9816P lot1 (10 µg/mL)
H4H9780P lot1 (10 µg/mL)
H4H9814P lot1 (10 µg/mL)
REGN1945 human IgG4 lot1 (10 µg/mL)
C2 H1M8037C lot1 (10 µg/mL)

TABLE 14

Western Blots.

p-Trk (Cell Signaling, 9141) Rb, 1:500
total TrkB (Cell Signaling, 4603) Rb 1:1000
p-Akt (Cell Signaling, 9271) Rb 1:1000
total-Akt (Cell Signaling, 9272) Rb 1:1000
p-Erk1/2 (Sigma, E7028) 1:5000
total Erk1/2 (Cell Signaling, 06-182) Rb 1:1000
b-Actin (Sigma, A5316) Ms 1:20000
GAPDH (Sigma, G9295) HRP conjugated 1:20000

Results and Conclusions

Figure 7:
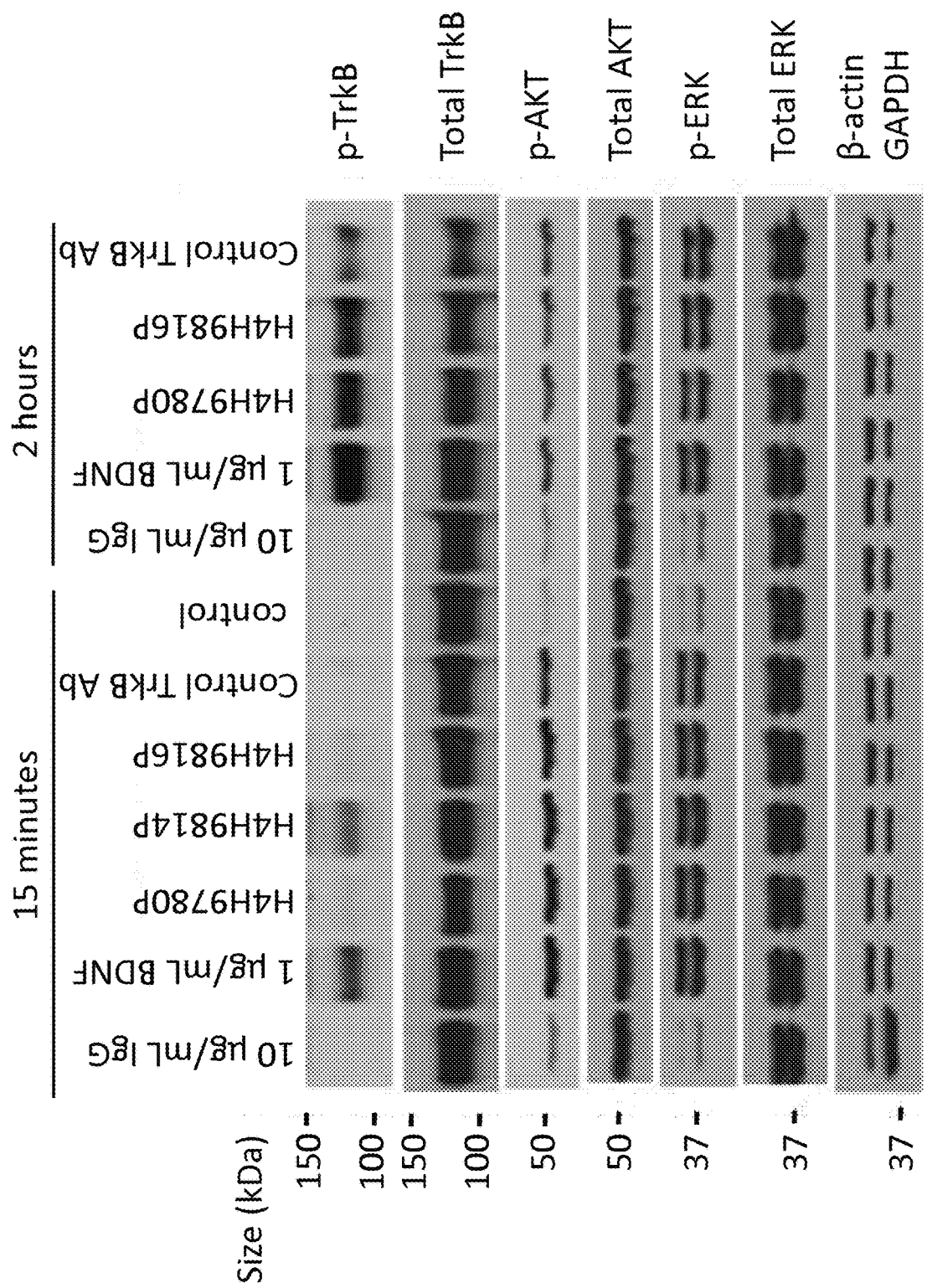
FIG. 7 shows western blots of phospho-TrkB, total TrkB, phospho-Akt, total AKT, phospho-ERK, and total ERK at 15 minutes and 2 hours after treatment of primary cortical neurons isolated from postnatal day 1 homozygous humanized TRKB mouse pups with various TrkB agonist antibodies or BDNF.

As shown in FIG. 7, while all the TrkB agonist antibodies showed activation of the MAPK/ERK and PI3K/Akt pathways at 15 minutes after the incubation, only BDNF and H4H9814P showed TrkB phosphorylation. At 2 hours after incubation, all the TrkB agonist antibodies showed activation of TrkB.

Example 5. Pharmacokinetic Assessment of an Anti-TrkB Antibody in Humanized TrkB and Wild Type Mice Experimental Procedure Evaluation of the pharmacokinetics of an anti-TrkB antibody, H4H9816P2 (Lot H4H9816P2-L7), was conducted in humanized TrkB (mice homozygous for chimeric mouse/human TrkB expression, TrkB$^{hu/hu}$) (MAID7139) and wild type (WT) mice. Cohorts contained 5 mice per mouse strain. All mice received a single sub-cutaneous (SC) 10 mg/kg dose. Blood samples were collected at 6 hours and 1, 2, 3, 6, 9, 16, 21, and 30 days post-dosing. Blood was processed into serum and frozen at −80° C. until analyzed.

Circulating antibody concentrations were determined by total human IgG4/hIgG1 antibody analysis using the Gyrolab xPlore™ (Gyros, Uppsala, Sweden). Briefly, biotinylated mouse anti-human IgG4/IgG1-specific monoclonal antibody (REGN2567; Lot RSCH15088)) diluted to 100 µg/mL in antibody dilution buffer (0.05% Tween-20+PBS) was captured on a Gyrolab Bioaffy 200 CD, which contained affinity columns preloaded with streptavidin-coated beads (Dynospheres™). The standard used for calibration in this assay was H4H9816P at concentrations ranging from 0.488 to 2000 ng/mL in dilution buffer (0.5% BSA+PBS) containing 0.1% normal mouse serum (NMS). Serum samples were diluted 1:100 in the antibody dilution buffer. Human IgG captured on the anti-REGN2567-coated affinity columns on the CD, run at room temperature, was detected by addition of 0.5 µg/mL Alexa-647-conjugated mouse anti-human kappa monoclonal antibody (REGN654; Lot RSCH13067) diluted in detection buffer (Rexxip F buffer); and the resultant fluorescent signal was recorded in response units (RU) by the GyroLab xPlore instrument. Sample concentrations were determined by interpolation from a standard curve that was fit using a 5-parameter logistic curve fit using the Gyrolab Evaluator Software. Average concentrations from 2 replicate experiments were used for subsequent PK analysis.

PK parameters were determined by non-compartmental analysis (NCA) using Phoenix® WinNonlin® software Version 6.3 (Certara, L. P., Princeton, NJ) and an extravascular dosing model. Using the respective mean concentration values for each antibody, all PK parameters including observed maximum concentration in serum ($C_{max}$), estimated half-life observed ($t_{1/2}$), and area under the concentration curve versus time up to the last measurable concentration ($AUC_{last}$) were determined using a linear trapezoidal rule with linear interpolation and uniform weighting.

Results and Conclusions

Following 10 mg/kg s.c. administration of anti-TrkB antibody, H4H9816P2, similar maximum concentrations ($C_{max}$) of antibody were observed by day 1 or 2 in both TrkB$^{hu/hu}$ and WT mice (135 and 131 µg/mL, respectively). By day 9, H4H9816P2 exhibited steeper drug elimination in TrkB$^{hu/hu}$ mice than in WT mice, indicating a target-mediated effect. Day 30 antibody concentrations were about 35-fold less in TrkB$^{hu/hu}$ mice. Antibody exposure ($AUC_{last}$) for H4H9816P2 in WT mice was ~1.7-fold higher than seen in TrkB$^{hu/hu}$ mice (1730 and 1020 d*µg/mL, respectively). WT mice also exhibited about a 3-fold increase in half-life ($T_{1/2}$) over TrkB$^{hu/hu}$ mice (8.4 and 2.9 days, respectively).

Figure 8:
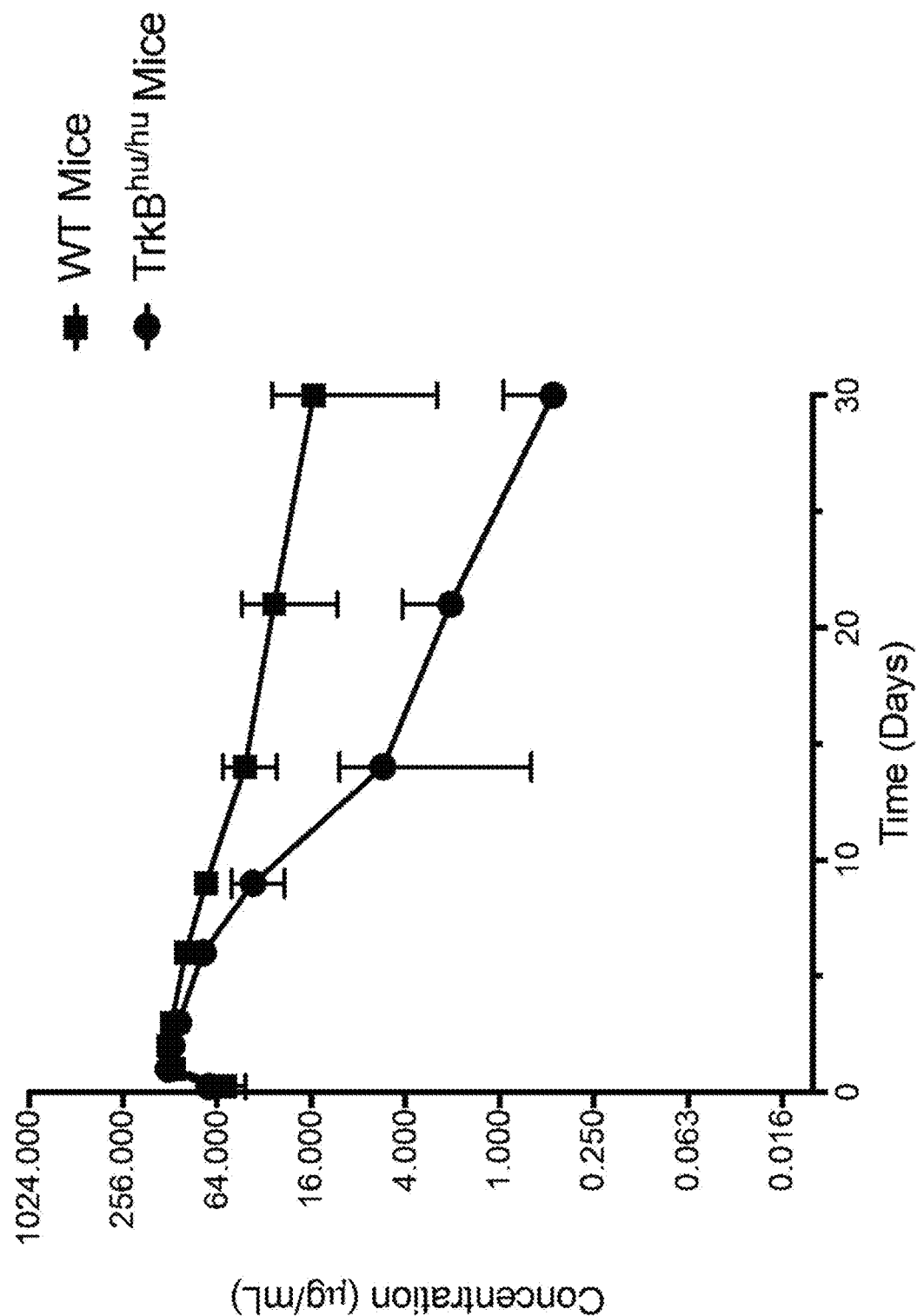
FIG. 8 shows pharmacokinetic profiles of anti-TrkB antibody in H4H9816P2 in homozygous TrkB$^{hu/hu}$ and wild type mice.

A summary of the data for total anti-TrkB antibody concentrations are summarized in Table 15, mean PK parameters are described in Table 16 and mean total antibody concentrations versus time are shown in FIG. 8. In FIG. 8, mice were administered a single 10 mg/kg subcutaneous dose on day 0. Concentrations of total H4H9816P2 in serum were measured using a Gyros immunoassay. Data points on post-dose 6 hours, 1, 2, 3, 6, 9, 16, 21, and 30 days indicate the mean concentration of antibody. Total antibody concentrations of H4H9816P2 are represented as solid circles for TrkB$^{hu/hu}$ mice and solid squares for wild type mice. Data are plotted as mean±SD.

TABLE 15

Mean Concentrations (±SD) of Total IgG in Serum Following a Single 10 mg/kg Sub-Cutaneous Injection of H4H9816P2 in TrkB$^{hu/hu}$ and Wild Type Mice over Time.

| Antibody | Time (d) | Total mAb Concentration in Mouse Serum 10 mg/kg | |
|---|---|---|---|
| | | Mean (µg/mL) | +/−SD |
| TrkB$^{hu/hu}$ Mice | 0.25 | 72.42 | 4.06 |
| | 1 | 132.0 | 18.0 |
| | 2 | 124.9 | 15.9 |
| | 3 | 113.4 | 11.8 |
| | 6 | 78.72 | 9.98 |
| | 9 | 37.74 | 14.0 |
| | 16 | 5.592 | 4.97 |
| | 21 | 2.060 | 2.11 |
| | 30 | 0.447 | 0.506 |
| WT Mice | 0.25 | 56.73 | 14.5 |
| | 1 | 120.8 | 6.26 |
| | 2 | 131.2 | 7.54 |
| | 3 | 125.7 | 7.46 |
| | 6 | 101.9 | 11.4 |
| | 9 | 75.94 | 7.06 |
| | 16 | 42.61 | 16.1 |
| | 21 | 27.75 | 16.9 |
| | 30 | 15.52 | 13.0 |

Abbreviations: Time = time in days post single-dose injection; d = day of study; SD = standard deviation.

TABLE 16

Summary of Pharmacokinetic Parameters.

| Parameter | Units | H4H9816P2 | |
|---|---|---|---|
| | | TrkB$^{hu/hu}$ Mice | WT Mice |
| $C_{max}$ | µg/mL | 135 ± 15 | 131 ± 7.5 |
| $T_{1/2}$ | d | 2.94 ± 1.1 | 8.36 ± 3.9 |
| $AUC_{last}$ | d·µg/mL | 1020 ± 150 | 1730 ± 310 |

PK parameters were derived from mean concentration versus time profiles. $T_{1/2}$ and $AUC_{last}$ are based on concentrations out to day 30.
Abbreviations: $C_{max}$ = peak concentration; AUC = area under the concentration-time curve; $AUC_{last}$ = AUC computed from time zero to the time of the last positive concentration; $T_{1/2}$ = terminal half-life of elimination.

Example 6. Generation of Rats Comprising a Humanized TRKB Locus

A large targeting vector comprising a 5' homology arm comprising 7 kb of the rat TrkB locus and 3' homology arm comprising 47 kb of the rat TrkB locus was generated to replace a region of 68.5 kb from the rat TrkB gene encoding the rat TRKB extracellular domain with 74.4 kb of the corresponding human sequence of TRKB. Generation and use of large targeting vectors (LTVECs) derived from bacterial artificial chromosome (BAC) DNA through bacterial homologous recombination (BHR) reactions using VELOCIGENE® genetic engineering technology is described, e.g., in U.S. Pat. No. 6,586,251 and Valenzuela et al. (2003) Nat. Biotechnol. 21(6):652-659, each of which is herein incorporated by reference in its entirety for all purposes. Generation of LTVECs through in vitro assembly methods is described, e.g., in US 2015/0376628 and WO 2015/200334, each of which is herein incorporated by reference in its entirety for all purposes. Information on rat and human TRKB is provided in Table 17. A description of the generation of the large targeting vector is provided in Table 18.

TABLE 17

Rat and Human TRKB/NTRK2.

| | Official Symbol | NCBI GeneID | Primary Source | RefSeq mRNA ID | UniProt ID | Genomic Assembly | Location |
|---|---|---|---|---|---|---|---|
| Rat | Ntrk2 | 25054 | RGD: 3213 | NM_012731.2 | Q63604 | RGSC 5.0/rn5 | Chr 17: 8,156,432-8,464,507 (−) |
| Human | Ntrk2 | 4915 | HGNC: 8032 | AF410899 | Q16620 | GRCh38/hg38 | Chr 9: 84,669,778-85,027,070 (+) |

TABLE 18

Rat TrkB/Ntrk2 Large Targeting Vector.

| | Genome Build | Start | End | Length (bp) |
|---|---|---|---|---|
| 5' Rat Arm | RGSC 5.0/rn5 | Chr17: 8,470,615 | Chr17: 8,463,379 | 7,236 |
| Human Insert | GRCh38/hg38 | Chr9: 84,670,730 | Chr9: 84,745,139 | 74,409 |
| 3' Rat Arm | RGSC 5.0/rn5 | Chr17: 8,394,967 | Chr17: 8,347,889 | 47,078 |

Specifically, a region starting in exon 2 (coding exon 1; from amino acid 32, preserving signal peptide) through exon 10, including the first 50 base pairs of intron 10 and all introns between exons 2 and 10 (i.e., between coding exon 1 and exon 10) was deleted from the rat TrkB locus (preserving the rat transmembrane domain encoded by exons 10 and 11). A region including exon 2/coding exon 1 (from amino acid 32, beginning after the signal peptide) through exon 10, including the first 66 base pairs of intron 10 and all introns between exons 2 and 10 (i.e., between coding exon 1 and exon 10) was inserted in place of the deleted rat region (preserving the rat transmembrane domain encoded by exons 10 and 11).

Sequences for the rat TRKB signal peptide, extracellular domain, transmembrane domain, and cytoplasmic domain are set forth in SEQ ID NOS: 55-58, respectively, with the corresponding coding sequence set forth in SEQ ID NOS: 67-70, respectively. Sequences for the human TRKB signal peptide, extracellular domain, transmembrane domain, and cytoplasmic domain are set forth in SEQ ID NOS: 59-62, respectively, with the corresponding coding sequence set forth in SEQ ID NOS: 71-74, respectively. The expected encoded chimeric TRKB protein is has rat TRKB transmembrane and intracellular domains, a rat TRKB signal peptide, and a human TRKB extracellular domain. See FIG. 4. An alignment of the rat and human TRKB proteins in FIG. 6. The rat and human TrkB/TRKB coding sequences are set forth in SEQ ID NOS: 10 and 11, respectively. The rat and human TRKB protein sequences are set forth in SEQ ID NOS: 2 and 3, respectively. The sequences for the expected chimeric rat/human TRKB coding sequence and the expected chimeric rat/human TRKB protein are set forth in SEQ ID NOS: 13 and 5, respectively.

Figure 5:
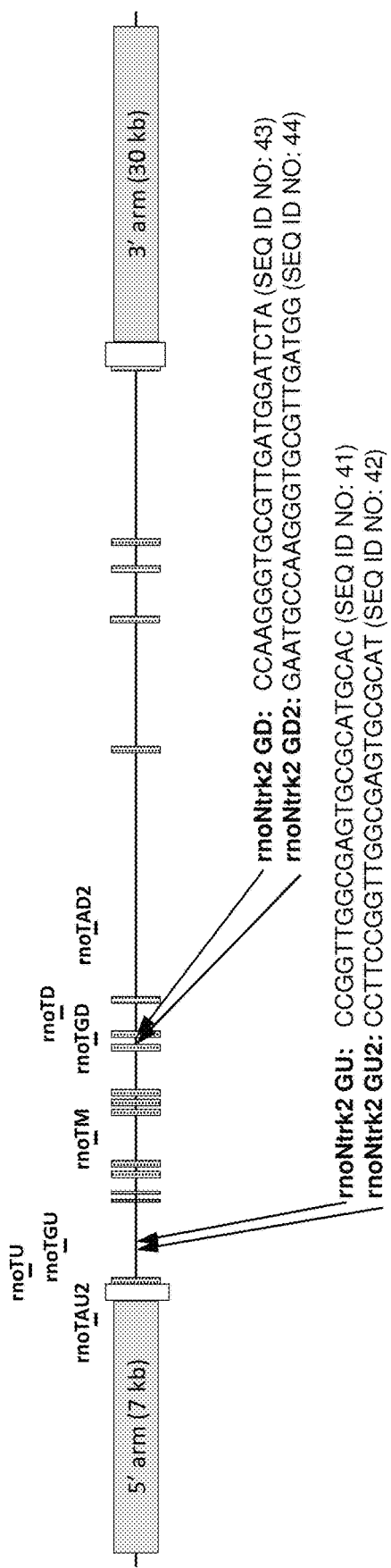
FIG. 5 (not to scale) shows a schematic of the TAQMAN® assays for screening humanization of the rat TrkB (rat Ntrk2) locus and the guide RNA positions (guide target sequences set forth in SEQ ID NOS: 41-44) for targeting the rat TrkB (rat Ntrk2) locus. Gain-of-allele (GOA) assays include 7138hU and 7138hD. Loss-of-allele (LOA) assays include rnoTU, rnoTM, and rnoTD. CRISPR assays designed to cover the region that is disrupted by CRISPR/Cas9 targeting include rnoTGU and rnoTGD. Retention assays include rnoTAU2 and rnoTAD2.
Figure 5:
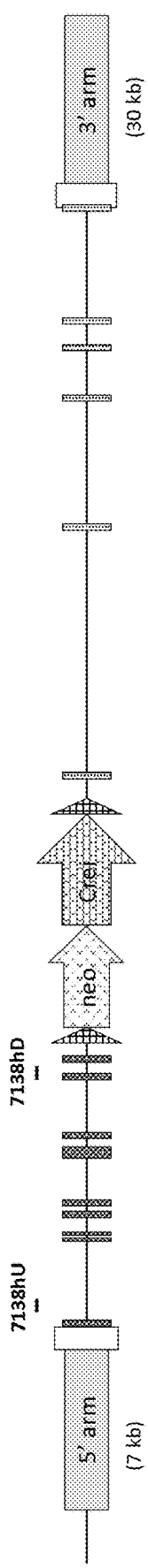

To generate the mutant allele, CRISPR/Cas9 components including four guide RNAs (guide RNA target sequences set forth in SEQ ID NOS: 41-44) were introduced into rat embryonic stem cells together with the large targeting vector. Specifically, 4×10$^6$ rat ES cells (Dark Agouti line DA2B) were electroporated with the following: 2 mg TrkB LTVEC; 5 mg Cas9 expression plasmid; and 5 mg each of the gRNAs: gU, gU2, gD and gD2. The electroporation conditions were: 400 V voltage; 100 mF capacitance; and 0 W resistance. Antibiotic selection was performed using G418 at a concentration of 75 mg/mL. Colonies were picked, expanded, and screened by TAQMAN®. See FIG. 5. Loss-of-allele assays were performed to detect loss of the endogenous rat allele, gain-of-allele assays were performed to detect gain of the humanized allele, and CRISPR and retention assays were performed using the primers and probes set forth in Table 19.

TABLE 19

Screening Assays.

| Assay | Description | Primer/ Probe | Sequence |
|---|---|---|---|
| moTU | Upstream LOA | Fwd | GGGCTCAGGCAGGTATATGTTG (SEQ ID NO: 26) |
|  |  | Probe (FAM) | ACAGATGCTGTCCCAAACATAGCAAGA (SEQ ID NO: 27) |
|  |  | Rev | CCAACCCTAAGCCAGTGAAACAG (SEQ ID NO: 28) |
| moTM | Middle LOA | Fwd | GCAGACACTGGATGGGTCA (SEQ ID NO: 32) |
|  |  | Probe (FAM) | CCATTCGCGAGTTATGAGAAGCTGCA (SEQ ID NO: 33) |
|  |  | Rev | ACAGGGTTAGCTGGTGAATGGA (SEQ ID NO: 34) |
| moTD | Downstream LOA | Fwd | GTGCTGGAGACCAGGAGACT (SEQ ID NO: 29) |
|  |  | Probe (Cal-Orange) | TGCCATACTCAGTTTATACGGTGCTGAC (SEQ ID NO: 30) |
|  |  | Rev | GCCTGGTGGCTCAGTCAATG (SEQ ID NO: 31) |
| 7138 hU | Upstream Human Insertion | Fwd | AGGTGGGTAGGTCCTGGAAGTG (SEQ ID NO: 14) |
|  |  | Probe (FAM) | AATGCTGTCCCAAGAGTGGG (SEQ ID NO: 15) |
|  |  | Rev | GTCCTGCATCCCTTGTCTTTG (SEQ ID NO: 16) |
| 7138 hD | Downstream Human Insertion | Fwd | ATGTGGGCGTTGTGCAGTCTC (SEQ ID NO: 17) |
|  |  | Probe (Cal) | CGCTGCAGTGCATTGAACTCAGCA (SEQ ID NO: 18) |
|  |  | Rev | CTGTGGAGGGACGTGACCAG (SEQ ID NO: 19) |
| rnoTAU2 | Upstream Retention | Fwd | TCGGAGCACAGGACTACAG (SEQ ID NO: 35) |
|  |  | Probe (FAM) | CAAGAGGAACTGTGTCCAGGAAAGC (SEQ ID NO: 36) |
|  |  | Rev | AGCGTGCCTCACCTAACCTCTA (SEQ ID NO: 37) |
| rnoTAD2 | Downstream Retention | Fwd | GCACAGCACTGTAAAGGCA (SEQ ID NO: 38) |
|  |  | Probe (Cal) | ACGGAACTCGAAGGAATTGGTATTGTTGT (SEQ ID NO: 39) |
|  |  | Rev | ACACAGCTATGGGAGAAAGACTG (SEQ ID NO: 40) |
| rnoTGU | Upstream CRISPR Assay | Fwd | CTGGGTGATTGGGACTGAGAAAG (SEQ ID NO: 45) |
|  |  | Probe (FAM) | CAGCCTTGAAAGTATGGCTTGGGC (SEQ ID NO: 46) |
|  |  | Rev | GCACTCGCCAACCGGAAG (SEQ ID NO: 47) |

TABLE 19-continued

Screening Assays.

| Assay | Description | Primer/ Probe | Sequence |
|---|---|---|---|
| rnoTGD | Downstream CRISPR Assay | Fwd | GACCAGCTCACCCTTACTTATGG (SEQ ID NO: 48) |
| | | Probe (Cal) | ACTGAATGCCAAGGGTGCGTTGA (SEQ ID NO: 49) |
| | | Rev | TCTTGGAAATCCGCTGAAGAGTT (SEQ ID NO: 50) |

Modification-of-allele (MOA) assays including loss-of-allele (LOA) and gain-of-allele (GOA) assays are described, for example, in US 2014/0178879; US 2016/0145646; WO 2016/081923; and Frendewey et al. (2010) *Methods Enzymol.* 476:295-307, each of which is herein incorporated by reference in its entirety for all purposes. The loss-of-allele (LOA) assay inverts the conventional screening logic and quantifies the number of copies in a genomic DNA sample of the native locus to which the mutation was directed. In a correctly targeted heterozygous cell clone, the LOA assay detects one of the two native alleles (for genes not on the X or Y chromosome), the other allele being disrupted by the targeted modification. The same principle can be applied in reverse as a gain-of-allele (GOA) assay to quantify the copy number of the inserted targeting vector in a genomic DNA sample.

Retention assays are described in US 2016/0145646 and WO 2016/081923, each of which is herein incorporated by reference in its entirety for all purposes. Retention assays distinguish between correct targeted insertions of a nucleic acid insert into a target genomic locus from random transgenic insertions of the nucleic acid insert into genomic locations outside of the target genomic locus by assessing copy numbers of DNA templates from 5' and 3' target sequences corresponding to the 5' and 3' homology arms of the targeting vector, respectively. Specifically, retention assays determine copy numbers in a genomic DNA sample of a 5' target sequence DNA template intended to be retained in the modified target genomic locus and/or the 3' target sequence DNA template intended to be retained in the modified target genomic locus. In diploid cells, correctly targeted clones will retain a copy number of two. Copy numbers greater than two generally indicate transgenic integration of the targeting vector randomly outside of the target genomic locus rather than at the target genomic locus. Copy numbers of less than generally indicate large deletions extending beyond the region targeted for deletion.

CRISPR assays are TAQMAN® assays designed to cover the region that is disrupted by the CRISPR gRNAs. When a CRISPR gRNA cuts and creates an indel (insertion or deletion), the TAQMAN® assay will fail to amplify and thus reports CRISPR cleavage.

The positive clone CB1 was thawed, expanded, and reconfirmed by TAQMAN®. CB1 was also confirmed by successful PCR from the 5' end of the human replacement sequence to the flanking rat genomic sequence, beyond the end of the 5' homology arm. The PCR amplicon was confirmed as correct by sequencing of the ends.

F0 and F1 rats were generated using methods as described in US 2014/0235933, US 2014/0310828, WO 2014/130706, and WO 2014/172489, each of which is herein incorporated by reference in its entirety for all purposes. In such methods, confirmed targeted rat ES cell clones (e.g., Dark Agouti ES cell clones) are microinjected into blastocysts (e.g., Sprague Dawley (SD) blastocysts), which are then transferred to pseudopregnant recipient females (e.g., SD recipient females) for gestation using standard techniques. Chimeras are identified (e.g., by coat color), and male F0 chimeras are bred to female wild-type rats of the same strain (e.g., SD females). Germline (e.g., agouti) F1 pups are then genotyped for the presence of the targeted allele. All experiments performed in humanized TRKB rats as described below were performed in rats in which the self-deleting selection cassette was self-deleted.

Example 7. In Vivo Comparison of the Effect of TRKB Agonist Antibody H4H9816P2 and IgG4 Isotype Control REGN1945 on Retinal Ganglion Cell (RGC) Survival TrkBhuihu Rats Experimental Procedure All procedures were conducted in accordance with the ARVO Statement for Use of Animals in Ophthalmic and Vision Research and the Regeneron Pharmaceutical Inc. IACUC. Adult female TrkB humanized rats (MAID100010), 8-10 weeks old, each weighing 200-250 g, were used. All surgical procedures on rats were performed under general anesthesia using an intraperitoneal injection of ketamine (63 mg/kg) and xylazine (6.0 mg/kg). Eye ointment containing erythromycin (0.5%, Bausch & Lomb) was applied to protect the cornea.

Intraorbital Optic Nerve Axotomy and Intravitreal Injection. The left optic nerve (ON) was exposed intraorbitally, its dura was opened. ON was transected about 1.5 mm behind the globe. Care was taken to avoid damaging the blood supply to the retina. Intravitreal injections were performed just posterior to the pars plana with a pulled glass pipette connected to a 50 µL Hamilton syringe. Care was taken not to damage the lens. Rats with any significant postoperative complications (e.g., retinal ischemia, cataract) were excluded from further analysis. Animals were allocated to different experimental groups. One control group received intravitreal injections of 3 µL isotype control REGN1945 (46.6 µg/µL); the other group received injection of 3 µL anti-human TRKB antibody H4H9816P2 (45.7 µg/µL) at 3 and 10 days after ON axotomy.

Immunohistochemical Staining and Counting of Viable Retinal Ganglion Cells (RGCs). BRN3A (brain-specific homeobox/POU domain protein 3A) was used as a marker for surviving retinal ganglion cells (RGCs), because it has been shown to be an efficient and reliable method for selective labelling of viable RGCs in retinal whole mounts after ON injury. See, e.g., Nadal-Nicolás et al. (2009) *Invest. Ophthalmol. Vis. Sic.* 50(8):3860-3868, herein incorporated by reference in its entirety for all purposes. To immunostain for BRN3A, retinas were blocked in 10% normal donkey serum and 0.5% Triton X-100 for 1 hr, then incubated in the same medium with BRN3A antibody (1:400; Cat #:

sc-31984, Santa Cruz) 2 hr at room temperature. After further washes retinas were incubated with Alexa594-conjugated donkey anti-goat secondary antibody (1:400; Cat #: A-11058, Invitrogen) overnight at 4° C.

Results and Conclusions

To assess the effect of the TRKB agonist antibody on RGC survival in vivo, we used a complete optic nerve transection model. TRKB agonist antibody (H4H9816P2) or isotype control antibody was applied at 3 and 10 days after surgery. Animals were euthanized 14 days after axotomy. The RGC density in the uninjured contralateral eye is similar in the three TRKB genotypes (homozygous humanized, heterozygous humanized, and wild type), averaging around 1600 per mm$^2$ as shown in Table 20. The density of surviving RGCs was assessed in retinal whole mounts using BRN3A staining. We found that in homozygous TrkB$^{hu/hu}$ humanized rats, TRKB agonist antibody (H4H9816P2) significantly ($p<0.01$, Mann-Whitney test) increased RGC survival compared with controls (685±106 vs. 255±66 RGCs per mm$^2$). In heterozygous TrkB$^{hu/+}$ humanized rats, there is also significant ($p<0.05$, Mann-Whitney test) survival effect of TrkB agonist Ab (444±90 vs. 208±50 RGCs per mm$^2$). In wild type rats, there was a slight but not significant increase of RGC number in rats treated with TRKB agonist antibody compared to isotype control (Table 21). In conclusion, the TRKB agonist antibody (H4H9816P2) significantly increased RGC survival in TrkB$^{hu/hu}$ humanized rats.

TABLE 20

RGC Quantification (RGCs/mm$^2$) in Uninjured Control Eye.

| hu/hu | hu/+ | +/+ |
|---|---|---|
| 1637.3 | 1720.4 | 1636.3 |
| 1551.5 | 2064.6 | 1670.2 |
| 1651.4 | 1738.8 | 1873.4 |
| 1628.2 | 2029.8 | 1725.4 |
| 1804.7 | 1929.6 | 1973.4 |
| 1741.3 | 1645.9 | |
| 1739.7 | 1761.5 | |
| 1698.8 | 1787.5 | |
| 1862.5 | 1914.0 | |
| 1779.4 | | |

TABLE 21

RGC Quantification (RGCs/mm$^2$) after Optic Nerve Injury.

| | H4H9816P2 | | | | | Isotype control Ab | | | | |
|---|---|---|---|---|---|---|---|---|---|---|
| | A: Y1 | A: Y2 | A: Y3 | A: Y4 | A: Y5 | B: Y1 | B: Y2 | B: Y3 | B: Y4 | B: Y5 |
| Hu/Hu | 790.1 | 737.1 | 756.3 | 587.8 | 555.7 | 322.8 | 295.0 | 286.9 | 171.3 | 197.9 |
| Hu/+ | 530.4 | 457.5 | 522.9 | 390.6 | 319.2 | 231.0 | 184.6 | 265.1 | 151.3 | |
| +/+ | 320.9 | 355.5 | 256.9 | 342.7 | | 112.3 | | | | |

Example 8. Heavy and Light Chain Variable Region Amino Acid Sequences of Anti-TRKB Antibodies Used in Examples Several fully human anti-TRKB antibodies (i.e., antibodies possessing human variable domains and human constant domains) were tested in the examples, including those designated as H4H9780P, H4H9814P, and H4H9816P2. Table 22 sets forth the amino acid sequence identifiers of the heavy and light chain variable regions and CDRs of selected anti-TRKB antibodies used in the examples. Table 23 sets forth the nucleic acid sequence identifiers of the heavy and light chain variable regions and CDRs of selected anti-TRKB antibodies used in the examples. These antibodies are described in more detail in U.S. patent application Ser. No. 16/202,881, filed Nov. 28, 2018, which is herein incorporated by reference in its entirety for all purposes.

TABLE 22

Amino Acid SEQ ID NOS for Anti-TRKB Antibodies.

| Ab Name | VH | HCDR1 | HCDR2 | HCDR3 | VK | LCDR1 | LCDR2 | LCDR3 |
|---|---|---|---|---|---|---|---|---|
| H4H9780P | 79 | 81 | 83 | 85 | 87 | 89 | 91 | 93 |
| H4H9814P | 95 | 97 | 99 | 101 | 103 | 105 | 107 | 109 |
| H4H9816P2 | 111 | 113 | 115 | 117 | 119 | 121 | 123 | 125 |

TABLE 23

Nucleic Acid SEQ ID NOS for Anti-TRKB Antibodies.

| Ab Name | VH | HCDR1 | HCDR2 | HCDR3 | VK | LCDR1 | LCDR2 | LCDR3 |
|---|---|---|---|---|---|---|---|---|
| H4H9780P | 78 | 80 | 82 | 84 | 86 | 88 | 90 | 92 |
| H4H9814P | 94 | 96 | 98 | 100 | 102 | 104 | 106 | 108 |
| H4H9816P2 | 110 | 112 | 114 | 116 | 118 | 120 | 122 | 124 |

Antibodies are typically referred to herein according to the following nomenclature: Fc prefix (e.g., "H4H"), followed by a numerical identifier (e.g., "9780," "9816," etc., as shown in Table 22), followed by a "P" or "P2" suffix. The H4H prefix in the antibody designations indicates the particular Fc region isotype of the antibody. Thus, according to this nomenclature, an antibody may be referred to herein as, e.g., "H4H9780P," which indicates a human IgG4 Fc region. Variable regions are fully human if denoted by the first "H" in the antibody designation. As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Table 22—will remain the same, and the binding properties to antigen are expected to be identical or substantially similar regardless of the nature of the Fc domain.

Example 9. Neuroprotective Effect of Anti-Human TrkB Agonist Antibodies in Humanized TrkB Rats The experiments below were undertaken to evaluate the neuroprotective effect of the endogenous TRKB agonist, brain-derived neurotrophic factor (BDNF), and a TRKB agonist monoclonal antibody (mAb) in wild-type (WT) mice and rats and in humanized TrkB mice and rats.

Figures 9, 10:
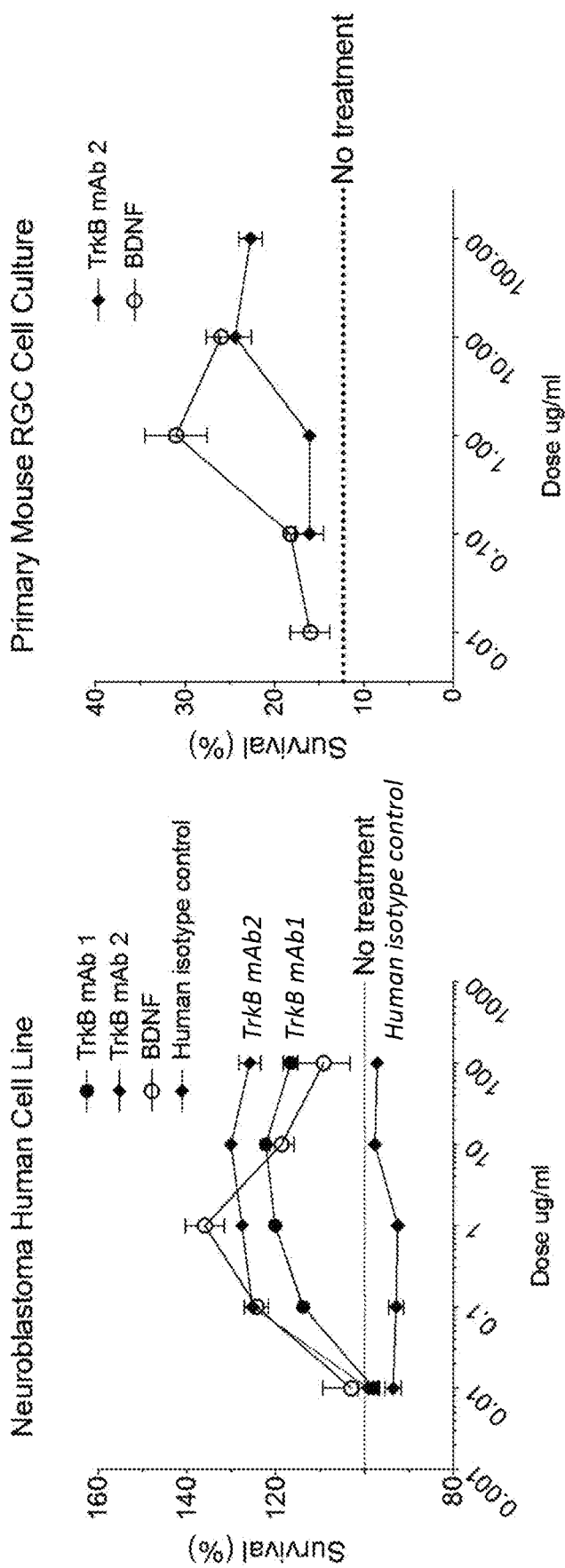
FIG. 9 shows cell survival in differentiated human neuroblastoma SH-SY5Y cells treated with different doses of TrkB agonist antibodies or BDNF. TrkB mAb1 is H4H9816P2; TrkB mAb2 is a control TrkB agonist antibody with affinity for human TrkB, rat TrkB, and mouse TrkB. A human isotype control antibody was used as a negative control. Data were normalized to the serum-free media without antibodies.
FIG. 10 shows cell survival in primary mouse retinal ganglion cells treated with different doses of TrkB agonist antibody or BDNF. TrkB mAb2 is a control TrkB agonist antibody with affinity for human TrkB, rat TrkB, and mouse TrkB. Data were normalized to the serum-free media without antibodies.

The in vitro effects of BDNF and TRKB Ab were quantified by cell survival assays using differentiated human neuroblastoma cell line SH-SY5Y. In vitro, BDNF or TRKB Ab significantly increased cell survival in retinoic-acid-differentiated SH-SY5Y cells. The effects showed bell shaped dose responses with the optimal dose of 1 µg/mL for BDNF or 10 µg/mL for TRKB Ab. Neuroblastoma cell line SH-SY5Y was cultured in differentiation media containing all-trans 10 µM retinoic acid for 4 days. The culture was changed to serum-free differentiation media containing different dose of antibodies (0.01-100 µg/mL). Two days later, CCK8 reagent was added, plates were incubated for 3-4 hours, and OD450 was measured to determine percentage of surviving cells. Data were normalized to the serum-free media without antibodies. As shown in FIG. 9, TRKB mAbs (TrkB mAb1 is H4H9816P2; TrkB mAb2 is a control TrkB agonist antibody) dose-dependently increased the survival of SH-SY5Y cells. Human isotype control had no effect on SH-SY5Y cell survival. Serum-free media without antibodies resulted in 100% survival.

Retinas from P2 C57BL/6J mice were then dissected and dissociated. Retinal ganglion cells were purified by immuno-panning and cultured in a 96-well plate with treatment or no treatment. After 24 hours, MTT (3-(4,5-dimethylthiazol-2-yl)-2,5-diphenyltetrazolium bromide) was added to each well to calculate cell survival for each group. As shown in FIG. 10, BDNF had a bell-shaped response curve and optimal dose at 1 µg/mL. TrkB mAb2 (a control TrkB agonist antibody with affinity for human TrkB, mouse TrkB, and rat TrkB) may have a bell-shaped curve as well at higher doses but shows neuroprotective effect.

To test the in vivo neuroprotective effect, WT and humanized TrkB mice and rats were used. Animals received intravitreal (IVT) injections of BDNF or TRKB mAb day 3 and 10 post-optic-nerve transection (ONT). Retinal ganglion cell (RGC) number was quantified using HALO software (Indica Labs) at 1 week for mouse or 2 weeks for rat after optic nerve transection by Brn3a IHC on retinal flat mounts.

RGC death in TrkB$^{hu/hu}$ mice was similar to WT mice at 1 or 2 weeks after optic nerve transection. BDNF or TRKB Ab had small or no significant neuroprotective effect in WT or TrkB$^{hu/hu}$ mice. In contrast, there was significant RGC neuroprotection in TrkB$^{hu/hu}$ rats with IVT TRKB Ab. A decrease in body weight was observed in TrkB$^{hu/hu}$ mice but not rats after IVT TRKB Ab treatment. BDNF had no effect on body weight in either mouse or rat.

Figure 11B:
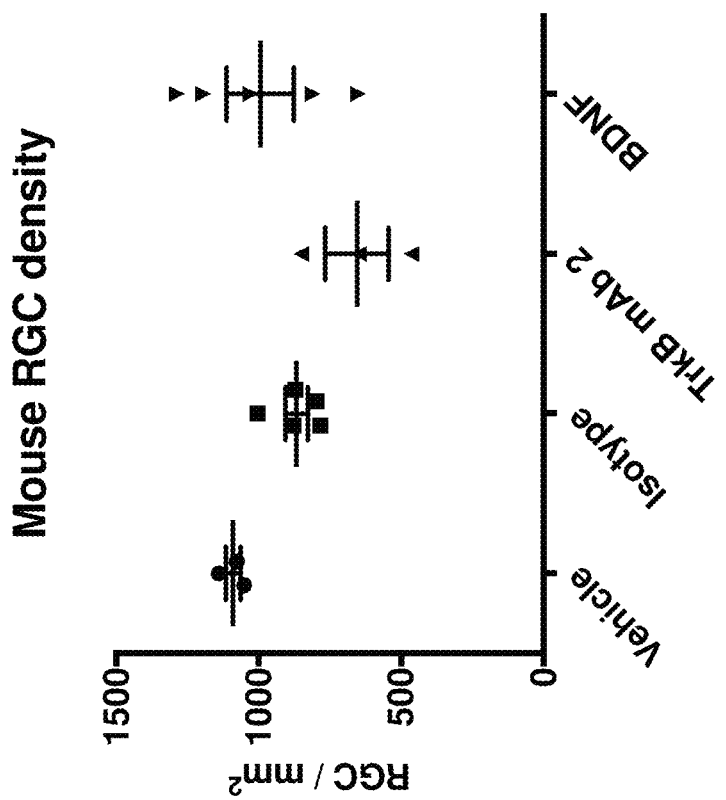
FIGS. 11A and 11B show retinal ganglion cell density in retinas dissected and stained for retinal ganglion cells in wild type rats and mice, respectively, following optic nerve transection and treatment with BDNF, TrkB agonist antibody, isotype control antibody, or vehicle control. Rats were given BDNF (2.5 µg), TrkB agonist antibody (18 µg), isotype control antibody (18 µg), or vehicle control intravitreally at 3 days and 10 days after optic nerve transection. Mice were given BDNF (2.5 µg), TrkB agonist antibody (10 µg), isotype control antibody (10 µg), or vehicle control intravitreally at 3 days and 10 days after optic nerve transection. TrkB mAb2 is a control TrkB agonist antibody with affinity for human TrkB, rat TrkB, and mouse TrkB.
Figure 11A:
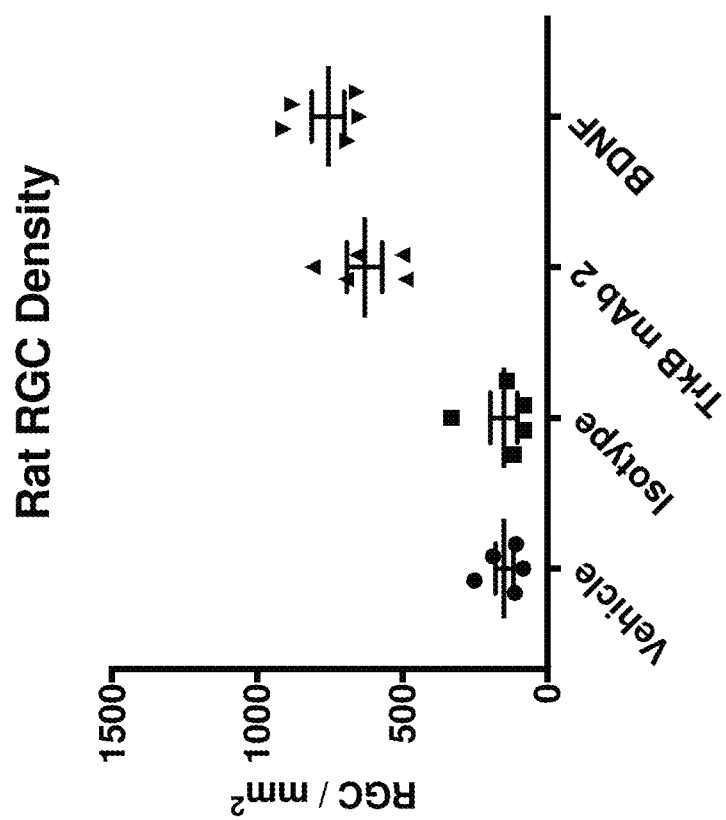

FIGS. 11A and 11B show the results of an experiment assessing neuroprotection in an optic nerve transection model in WT mice and rats. In FIG. 11A, 8-9 week old Dark Agouti rats were given BDNF (5 µg), TrkB mAb2 (18 µg), isotype control antibody (18 µg), or vehicle control intravitreally at 3 days and 10 days after transection. TrkB mAb2 is a control TrkB agonist antibody with affinity for human TrkB, mouse TrkB, and rat TrkB. Retinas were dissected and stained for retinal ganglion cells 14 days after transection. BDNF and TRKB mAb showed significant neuroprotection as measured by retinal ganglion cell (RGC) density. In FIG. 11B, 8-week-old C57BL/6J WT mice were given BDNF (2.5 µg), TrkB mAb2 (10 µg), isotype control antibody (10 µg), or vehicle control intravitreally at 3 days and 10 days after transection. TrkB mAb2 is a control TrkB agonist antibody with affinity for human TrkB, mouse TrkB, and rat TrkB. There was no significant neuroprotection. Thus, BDNF and TRKB mAb treatment resulted in significant increases in RGC density in dissected retinas in wild type rats after optic nerve transection, whereas no significant effect on RGC density was observed in the same model in wild type mice.

Figure 12B:
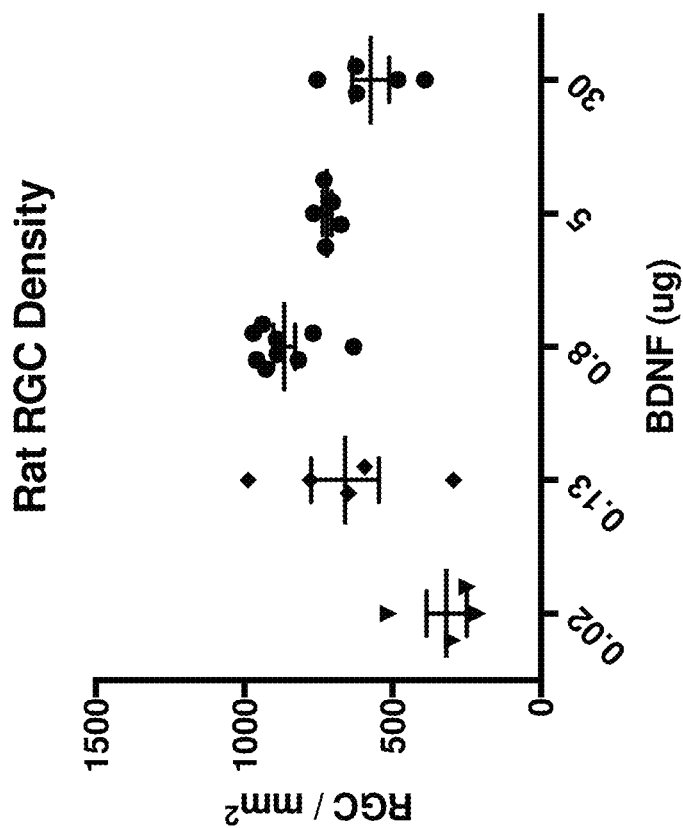
FIGS. 12A and 12B show retinal ganglion cell density in retinas dissected and stained for retinal ganglion cells in wild type mice and rats, respectively, following optic nerve transection or optic nerve crush and treatment with various doses of BDNF.
Figure 12A:
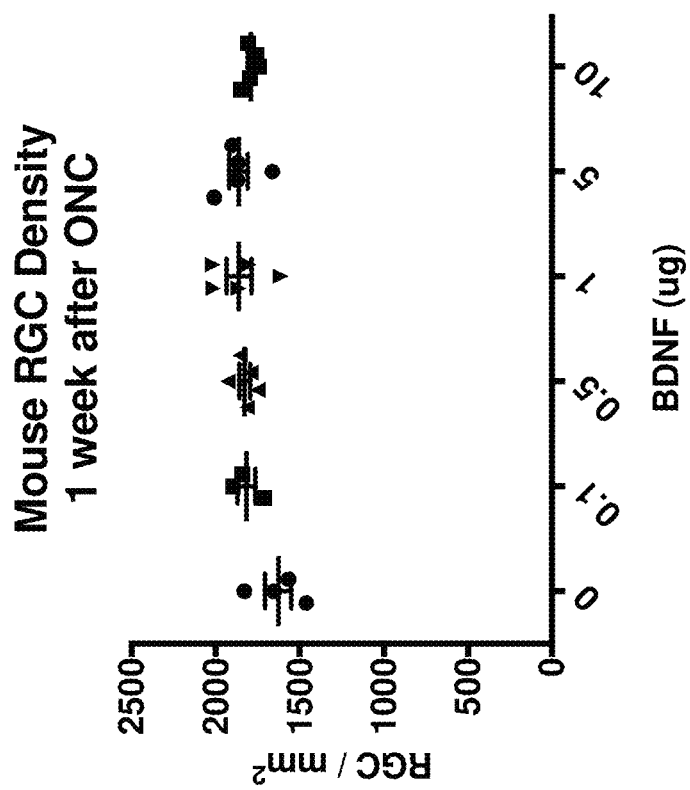

FIGS. 12A and 12B show BDNF dose response in WT mice and rats. In FIG. 12A, BDNF dose response in an optic nerve crush (ONC) model in WT mice shows a small window of neuroprotection. FIG. 12B shows a BDNF dose response in an optic nerve transection model in WT rat from 0.13 µg to 30 µg. There is bell-shaped response similar to the in vitro data, with the optimal dose at 0.8 µg. Retinas were dissected and stained for retinal ganglion cells 14 days after transection. Thus, BDNF treatment resulted in much more pronounced dose response curve as measured by RGC density in dissected retinas in wild type rats after optic nerve transection compared to the much less pronounced BDNF dose response curve in as measured by RGC density in dissected retinas in wild type mice after optic nerve crush.

Figures 13A, 13B:
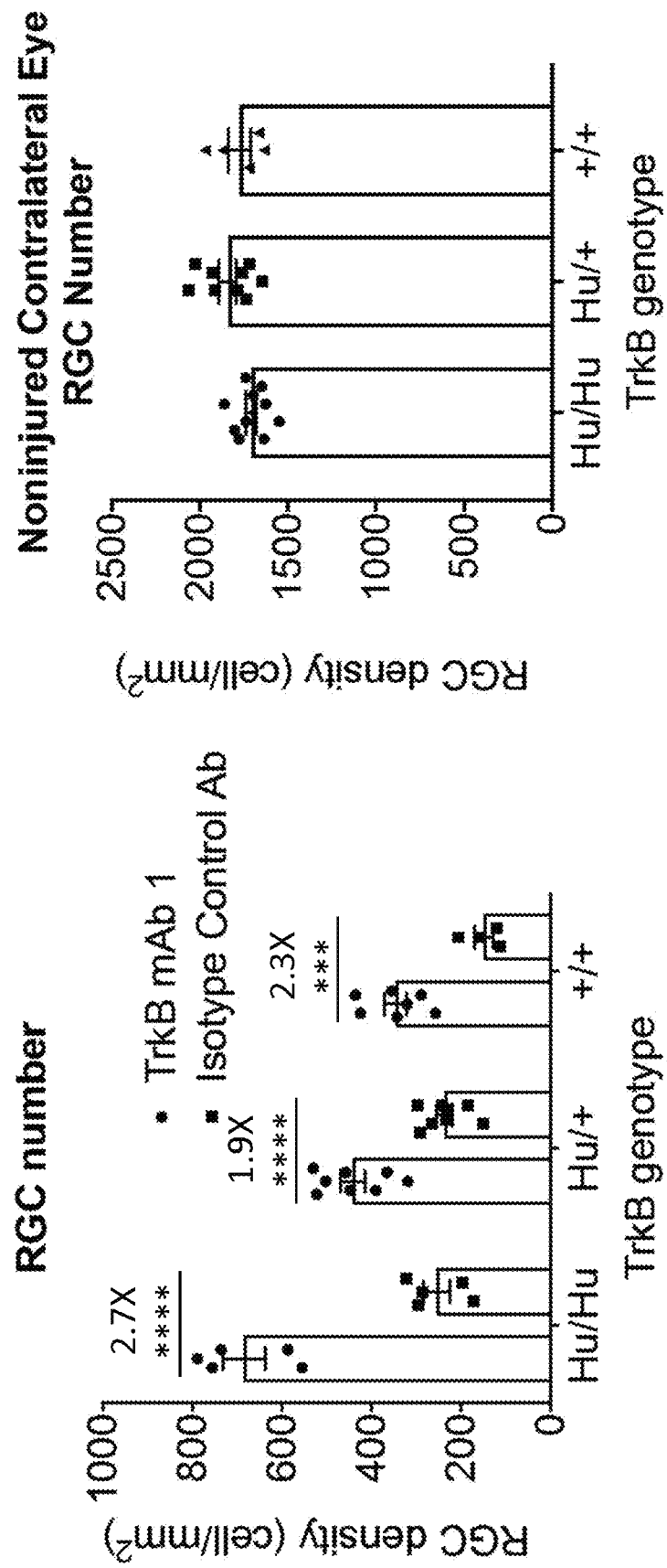
FIG. 13A shows retinal ganglion cell density in retinas dissected and stained for retinal ganglion cells in homozygous, heterozygous, or wild-type TrkB rats given either TrkB agonist antibody or isotype control antibody intravitreally at 3 and 10 days after optic nerve transection (**=p<0.0001; *p<0.001; two way ANOVA). Retinas were dissected 14 days after transection. TrkB mAb1 is H4H9816P2.
FIG. 13B shows retinal ganglion cell density in non-injured eyes dissected from homozygous, heterozygous, or wild-type TrkB rats.
Figures 13C, 14:
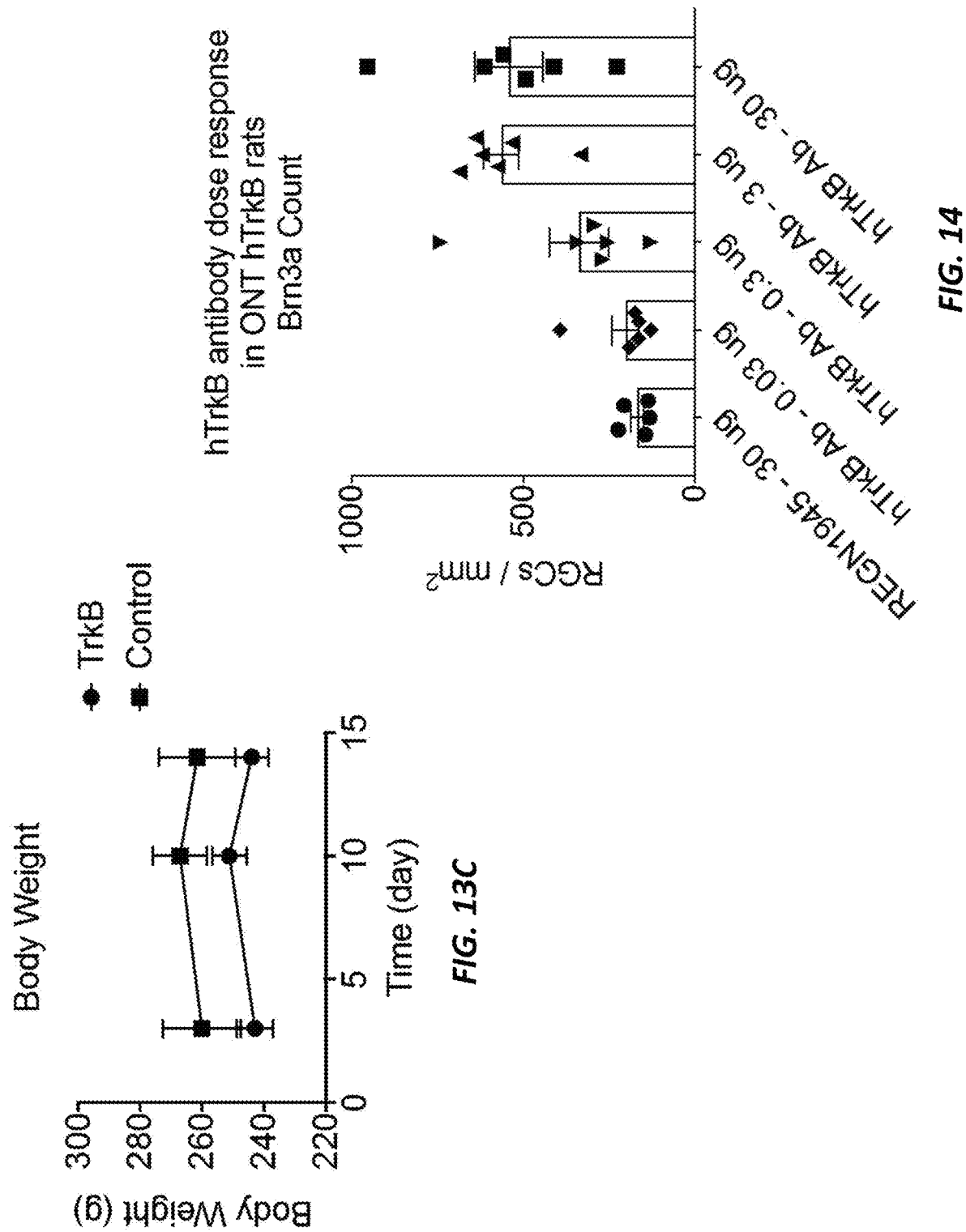
FIG. 13C shows the body weight of the human TRKB homozygous mice given TrkB agonist antibody (H4H9816P2; TrkB) or isotype control antibody (REGN1945; Control).
FIG. 14 shows retinal ganglion cell density in retinas dissected and stained for retinal ganglion cells in human TRKB homozygous rats given either TrkB agonist antibody (hTrkB; H4H9816P2) or isotype control antibody (REGN1945) intravitreally at 3 and 10 days after optic nerve transection. Retinas were dissected 14 days after transection.

Neuroprotective effect of TRKB Abs was next tested in humanized TrkB rats. The results in FIGS. 13A and 13B show that intravitreal injection of TRKB mAb in optic-nerve-transected humanized TrkB rats show significant neuroprotection of retinal ganglion cells. Human TRKB homozygous, human TRKB heterozygous, or wild-type TrkB rats were given either TrkB mAb1 or isotype control antibody intravitreally (3 μL) at 3 and 10 days after optic nerve transection. Fourteen days after transection, retinas were dissected and stained for RGCs. The rats were females that were 17-19 weeks old. As shown in FIG. 13A, rats treated with TrkB mAb1 (H4H9816P2) showed neuroprotection in all three genotypes compared to corresponding rats treated with isotype control antibody. Isotype-control-treated homozygous and heterozygous rats for human TRKB have higher RGC density than isotype-control-treated wild-type rats. FIG. 13B shows no RGC number difference in the naïve eyes between genotypes. FIG. 13C shows body weight of human TRKB homozygous mice given either TrkB agonist antibody (H4H9816P2) or isotype control antibody (REGN1945) at 14 days after transection.

Rat retinal whole-mount RGC isodensity maps were then created showing Brn3a labeled cells of non-injured and treated injured eyes in the three genotypes (data not shown). Whole mount reconstruction was prepared with the aid of motorized stage on fluorescence microscope (Nikon Eclipse Ti). RGCs were counted using an image analysis software (HALO®; Indica Labs, Corrales, NM, USA). Isodensity maps were generated through Matlab. Higher RGC density was observed with the humanized TrkB rats treated with TrkB mAb1 (H4H9816P2) compared to the isotype-control-treated rats (data not shown).

Taken together, the data shown in FIGS. 11A, 11B, 12A, 12B, and 13A-13C demonstrate that intravitreal administration of TRKB agonist mAb has a significant neuroprotective effect after optic nerve injury in humanized TrkB rats, in contrast to the small or no significant neuroprotective effect observed after optic nerve injury in humanized TrkB mice.

To further evaluate the effect of TRKB agonist antibodies on RGC survival in rats in the optic-nerve transection (ONT) model, a dose-response study was undertaken. Human TRKB homozygous rats (MAID100010; 75% SD, 25% DA) that were 1-9 months old were used. Six rats were used in each group. Human TRKB homozygous rats were given different doses of either TrkB mAb1 or isotype control antibody (REGN1945) intravitreally (3 μL) at 3 and 10 days after optic nerve transection. Fourteen days after transection, retinas were dissected and stained for RGCs. As shown in FIG. 14, TrkB mAb1 dose-dependently increased RGC survival in the TrkB humanized rats.

Figure 15B:
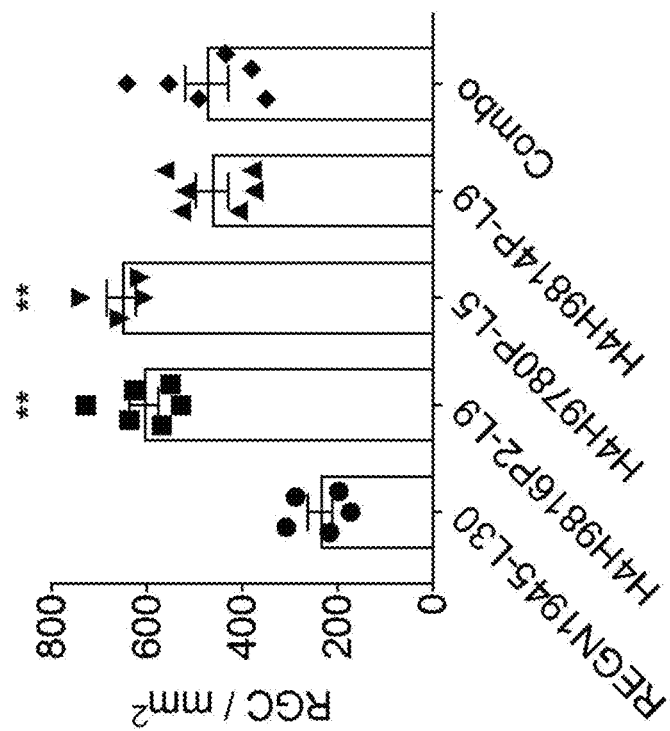
FIGS. 15A and 15B show retinal ganglion cell density in retinas dissected and stained for retinal ganglion cells in human TRKB homozygous rats given different TrkB agonist antibodies (H4H9816P2-L9, H4H9814P-L9, H4H9780P-L5, or a combination of all three) or isotype control antibody (REGN1945) intravitreally at 3 and 10 days after optic nerve transection (** p<0.01; Kruskal-Wallis test compared to isotype control antibody). Retinas were dissected 14 days after transection.
Figure 15A:
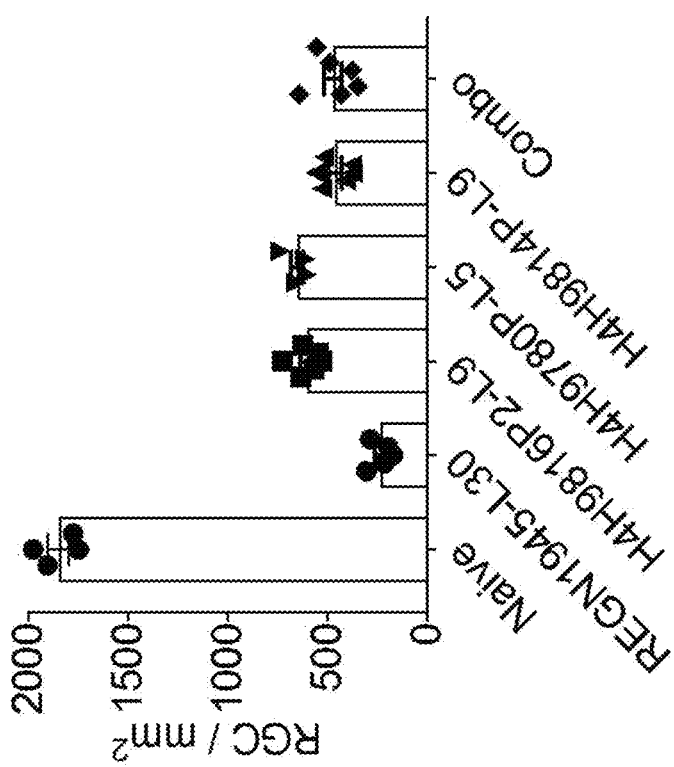

Next, the neuroprotective effect of different TrkB agonist antibodies was compared in human TRKB homozygous rats in the optic-nerve transection (ONT) model. Humanized TrkB rats (MAID100010; 75% SD, 25% DA) that were 8-10 weeks old were used. Five to six rats were used in each group. Human TRKB homozygous rats were given either H4H9816P2-L9 (10 μg), H4H9814P-L9 (10 μg), H4H9780P-L5 (10 μg), a combination of all three (3.3 μg each), or isotype control antibody (REGN1945; 10 μg) intravitreally (3 μL) at 3 and 10 days after optic nerve transection. Fourteen days after transection, retinas were dissected and stained for RGCs. The results are shown in FIGS. 15A and 15B. Each TrkB agonist antibody had a neuroprotective effect compared to the isotype control antibody. Body weight in each group was similar (data not shown).

Figure 16:
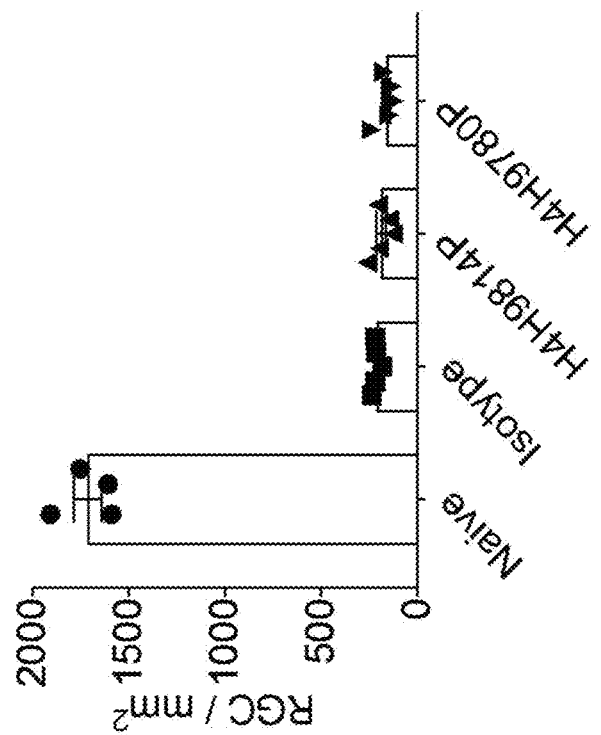
FIG. 16 shows retinal ganglion cell density in retinas dissected and stained for retinal ganglion cells in wild type rats given different TrkB agonist antibodies (H4H9780P and H4H9814P) or isotype control antibody (REGN1945) intravitreally at 3 and 10 days after optic nerve transection. Retinas were dissected 14 days after transection.

In contrast, the TrkB agonist antibodies H4H9780P and H4H9814P did not have any neuroprotective effect in wild type rats. Neuroprotective effect was assessed in wild type rats using the optic-nerve transection (ONT) model. Female wild type rats that were 8-10 weeks old were used. Five to six rats were used in each group. Wild type rats were given either H4H9780P (120 μg), H4H9814P (120 μg), or isotype control antibody (REGN1945; 120 μg) intravitreally (3 μL) at 3 and 10 days after optic nerve transection. Fourteen days after transection, retinas were dissected and stained for RGCs. As shown in FIG. 16, neither TrkB agonist antibody had a significant neuroprotective effect in wild type rats.

In addition, TrkB agonist antibody (H4H9780P) did not have a neuroprotective effect in human TRKB homozygous mice. Male human TRKB homozygous mice (MAID7139; 75% C57BL/6, 25% 129) that were 5 months old were used. Five to six mice were used in each group. Human TRKB homozygous mice were given either H4H9780P (40 μg per eye) or isotype control antibody (REGN1945; 40 μg per eye) intravitreally (1 μL) at 3 and 10 days after optic nerve transection. Fourteen days after transection, retinas were dissected and stained for RGCs. As shown in FIGS. 17A and 17B, the TrkB agonist antibody did not have a neuroprotective effect in human TRKB homozygous mice in contrast to the neuroprotective effect seen in human TRKB homozygous rats. FIG. 17C shows body weight of human TRKB homozygous mice given either H4H9780P or isotype control antibody at 14 days after transection.

We claim:

1. A genetically modified mouse whose genome comprises a genetically modified endogenous mouse TrkB locus comprising a humanized TrkB gene encoding a humanized tropomyosin receptor kinase B (TRKB) protein comprising:
   an endogenous mouse TRKB protein signal peptide;
   a human TRKB protein extracellular domain;
   an endogenous mouse TRKB protein transmembrane domain; and
   an endogenous mouse TRKB protein cytoplasmic domain,
   wherein the humanized TrkB gene is under the control of an endogenous mouse TrkB promoter, wherein the humanized TRKB protein comprises the amino acid sequence as set forth in SEQ ID NO: 4,
   wherein the humanized TrkB gene comprises a replacement of an endogenous mouse TrkB genomic sequence comprising a region starting from the codon in exon 2 encoding amino acid 32 through exon 10, including all introns between exons 2 and 10, with a corresponding human TrkB genomic sequence comprising a region starting from the codon in exon 2 encoding amino acid 32 through exon 10, including all introns between exons 2 and 10,
   wherein the genetically modified mouse expresses the humanized TRKB protein,
   wherein the genetically modified mouse is homozygous for the genetically modified endogenous mouse TrkB locus, and
   wherein the genetically modified mouse exhibits reduced (a) body weight and (b) total body fat mass upon treatment with a human TRKB agonist antibody relative to a control genetically modified mouse not treated with the antibody.

2. The genetically modified mouse of claim 1, wherein the human TRKB protein extracellular domain comprises the sequence set forth in SEQ ID NO: 60.

3. The genetically modified mouse of claim 1, wherein the human TRKB protein extracellular domain is encoded by the nucleotide sequence set forth in SEQ ID NO: 72.

4. The genetically modified mouse of claim 1, wherein the endogenous mouse TRKB protein signal peptide comprises the sequence set forth in SEQ ID NO: 51.

5. The genetically modified mouse of claim 1, wherein the endogenous mouse TRKB protein signal peptide is encoded by the nucleotide sequence set forth in SEQ ID NO: 63.

6. The genetically modified mouse of claim 1, wherein the endogenous mouse TRKB protein transmembrane domain comprises the sequence set forth in SEQ ID NO: 53.

7. The genetically modified mouse of claim 1, wherein the endogenous mouse TRKB protein transmembrane domain is encoded by the nucleotide sequence set forth in SEQ ID NO: 65.

8. The genetically modified mouse of claim 1, wherein the endogenous mouse TRKB protein cytoplasmic domain comprises the sequence set forth in SEQ ID NO: 54.

9. The genetically modified mouse of claim 1, wherein the endogenous mouse TRKB protein cytoplasmic domain is encoded by the nucleotide sequence set forth in SEQ ID NO: 66.

10. The genetically modified mouse of claim 1, wherein the endogenous mouse TRKB protein signal peptide comprises the sequence set forth in SEQ ID NO: 51, the endogenous mouse TRKB protein transmembrane domain comprises the sequence set forth in SEQ ID NO: 53, and the endogenous mouse TRKB protein cytoplasmic domain comprises the sequence set forth in SEQ ID NO: 54.

11. The genetically modified mouse of claim 1,
   wherein the endogenous mouse TRKB protein signal peptide is encoded by the nucleotide sequence set forth in SEQ ID NO: 63, the endogenous mouse TRKB protein transmembrane domain is encoded by the nucleotide sequence set forth in SEQ ID NO: 65, and the endogenous mouse TRKB protein cytoplasmic domain is encoded by the nucleotide sequence set forth in SEQ ID NO: 66.

12. The genetically modified mouse of claim 1, wherein the humanized TRKB protein is encoded by the nucleotide sequence set forth in SEQ ID NO: 12.

13. A method of assessing activity of a human-TRKB-targeting reagent in vivo, comprising:
   (a) administering the human-TRKB-targeting reagent to the genetically modified mouse of claim 1; and
   (b) assessing the activity of the human-TRKB-targeting reagent in the genetically modified mouse of step (a) as compared to an untreated control mouse.

14. A mouse cell isolated from the genetically modified mouse of claim 1, wherein the mouse cell's genome comprises the genetically modified endogenous mouse TrkB locus comprising the humanized TrkB gene encoding the humanized TRKB protein comprising the amino acid sequence as set forth in SEQ ID NO: 4, wherein the mouse cell expresses the humanized protein.

* * * * *

SEQUENCE LISTING

```
<160> NUMBER OF SEQ ID NOS: 125

<210> SEQ ID NO 1
<211> LENGTH: 821
<212> TYPE: PRT
<213> ORGANISM: Mus musculus
<220> FEATURE:
<221> NAME/KEY: MISC_FEATURE
<222> LOCATION: (1)..(31)
<223> OTHER INFORMATION: Signal Peptide
<220> FEATURE:
<221> NAME/KEY: MISC_FEATURE
<222> LOCATION: (32)..(429)
<223> OTHER INFORMATION: Extracellular Domain
<220> FEATURE:
<221> NAME/KEY: MISC_FEATURE
<222> LOCATION: (430)..(453)
<223> OTHER INFORMATION: Transmembrane Domain
```

```
<220> FEATURE:
<221> NAME/KEY: MISC_FEATURE
<222> LOCATION: (454)..(821)
<223> OTHER INFORMATION: Cytoplasmic Domain

<400> SEQUENCE: 1

Met Ser Pro Trp Leu Lys Trp His Gly Pro Ala Met Ala Arg Leu Trp
1               5                   10                  15

Gly Leu Cys Leu Leu Val Leu Gly Phe Trp Arg Ala Ser Leu Ala Cys
                20                  25                  30

Pro Thr Ser Cys Lys Cys Ser Ser Ala Arg Ile Trp Cys Thr Glu Pro
            35                  40                  45

Ser Pro Gly Ile Val Ala Phe Pro Arg Leu Glu Pro Asn Ser Val Asp
        50                  55                  60

Pro Glu Asn Ile Thr Glu Ile Leu Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala Tyr Lys Ala Phe Leu
                100                 105                 110

Lys Asn Ser Asn Leu Arg His Ile Asn Phe Thr Arg Asn Lys Leu Thr
                115                 120                 125

Ser Leu Ser Arg Arg His Phe Arg His Leu Asp Leu Ser Asp Leu Ile
            130                 135                 140

Leu Thr Gly Asn Pro Phe Thr Cys Ser Cys Asp Ile Met Trp Leu Lys
145                 150                 155                 160

Thr Leu Gln Glu Thr Lys Ser Ser Pro Asp Thr Gln Asp Leu Tyr Cys
                165                 170                 175

Leu Asn Glu Ser Ser Lys Asn Met Pro Leu Ala Asn Leu Gln Ile Pro
                180                 185                 190

Asn Cys Gly Leu Pro Ser Ala Arg Leu Ala Ala Pro Asn Leu Thr Val
            195                 200                 205

Glu Glu Gly Lys Ser Val Thr Leu Ser Cys Ser Val Gly Gly Asp Pro
210                 215                 220

Leu Pro Thr Leu Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
        275                 280                 285

Ile Thr Phe Leu Glu Ser Pro Thr Ser Asp His His Trp Cys Ile Pro
290                 295                 300

Phe Thr Val Arg Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
                340                 345                 350

His Met Asn Asn Gly Asp Tyr Thr Leu Met Ala Lys Asn Glu Tyr Gly
            355                 360                 365

Lys Asp Glu Arg Gln Ile Ser Ala His Phe Met Gly Arg Pro Gly Val
        370                 375                 380
```

-continued

```
Asp Tyr Glu Thr Asn Pro Asn Tyr Pro Glu Val Leu Tyr Glu Asp Trp
385                 390                 395                 400

Thr Thr Pro Thr Asp Ile Gly Asp Thr Thr Asn Lys Ser Asn Glu Ile
            405                 410                 415

Pro Ser Thr Asp Val Ala Asp Gln Ser Asn Arg Glu His Leu Ser Val
        420                 425                 430

Tyr Ala Val Val Ile Ala Ser Val Gly Phe Cys Leu Leu Val
    435                 440                 445

Met Leu Leu Leu Lys Leu Ala Arg His Ser Lys Phe Gly Met Lys
450                 455                 460

Gly Pro Ala Ser Val Ile Ser Asn Asp Asp Ser Ala Ser Pro Leu
465                 470                 475                 480

His His Ile Ser Asn Gly Ser Asn Thr Pro Ser Ser Glu Gly Gly
                485                 490                 495

Pro Asp Ala Val Ile Ile Gly Met Thr Lys Ile Pro Val Ile Glu Asn
            500                 505                 510

Pro Gln Tyr Phe Gly Ile Thr Asn Ser Gln Leu Lys Pro Asp Thr Phe
        515                 520                 525

Val Gln His Ile Lys Arg His Asn Ile Val Leu Lys Arg Glu Leu Gly
    530                 535                 540

Glu Gly Ala Phe Gly Lys Val Phe Leu Ala Glu Cys Tyr Asn Leu Cys
545                 550                 555                 560

Pro Glu Gln Asp Lys Ile Leu Val Ala Val Lys Thr Leu Lys Asp Ala
                565                 570                 575

Ser Asp Asn Ala Arg Lys Asp Phe His Arg Glu Ala Glu Leu Leu Thr
            580                 585                 590

Asn Leu Gln His Glu His Ile Val Lys Phe Tyr Gly Val Cys Val Glu
        595                 600                 605

Gly Asp Pro Leu Ile Met Val Phe Glu Tyr Met Lys His Gly Asp Leu
    610                 615                 620

Asn Lys Phe Leu Arg Ala His Gly Pro Asp Ala Val Leu Met Ala Glu
625                 630                 635                 640

Gly Asn Pro Pro Thr Glu Leu Thr Gln Ser Gln Met Leu His Ile Ala
                645                 650                 655

Gln Gln Ile Ala Ala Gly Met Val Tyr Leu Ala Ser Gln His Phe Val
            660                 665                 670

His Arg Asp Leu Ala Thr Arg Asn Cys Leu Val Gly Glu Asn Leu Leu
        675                 680                 685

Val Lys Ile Gly Asp Phe Gly Met Ser Arg Asp Val Tyr Ser Thr Asp
    690                 695                 700

Tyr Tyr Arg Val Gly Gly His Thr Met Leu Pro Ile Arg Trp Met Pro
705                 710                 715                 720

Pro Glu Ser Ile Met Tyr Arg Lys Phe Thr Thr Glu Ser Asp Val Trp
                725                 730                 735

Ser Leu Gly Val Val Leu Trp Glu Ile Phe Thr Tyr Gly Lys Gln Pro
            740                 745                 750

Trp Tyr Gln Leu Ser Asn Asn Glu Val Ile Glu Cys Ile Thr Gln Gly
        755                 760                 765

Arg Val Leu Gln Arg Pro Arg Thr Cys Pro Gln Glu Val Tyr Glu Leu
    770                 775                 780

Met Leu Gly Cys Trp Gln Arg Glu Pro His Thr Arg Lys Asn Ile Lys
785                 790                 795                 800

Ser Ile His Thr Leu Leu Gln Asn Leu Ala Lys Ala Ser Pro Val Tyr
```

805                 810                 815

Leu Asp Ile Leu Gly
            820

<210> SEQ ID NO 2
<211> LENGTH: 821
<212> TYPE: PRT
<213> ORGANISM: Rattus norvegicus
<220> FEATURE:
<221> NAME/KEY: MISC_FEATURE
<222> LOCATION: (1)..(31)
<223> OTHER INFORMATION: Signal Peptide
<220> FEATURE:
<221> NAME/KEY: MISC_FEATURE
<222> LOCATION: (32)..(429)
<223> OTHER INFORMATION: Extracellular Domain
<220> FEATURE:
<221> NAME/KEY: MISC_FEATURE
<222> LOCATION: (430)..(453)
<223> OTHER INFORMATION: Transmembrane Domain
<220> FEATURE:
<221> NAME/KEY: MISC_FEATURE
<222> LOCATION: (454)..(821)
<223> OTHER INFORMATION: Cytoplasmic Domain

<400> SEQUENCE: 2

Met Ser Pro Trp Pro Arg Trp His Gly Pro Ala Met Ala Arg Leu Trp
1               5                   10                  15

Gly Leu Cys Leu Leu Val Leu Gly Phe Trp Arg Ala Ser Leu Ala Cys
            20                  25                  30

Pro Met Ser Cys Lys Cys Ser Thr Thr Arg Ile Trp Cys Thr Glu Pro
        35                  40                  45

Ser Pro Gly Ile Val Ala Phe Pro Arg Leu Glu Pro Asn Ser Ile Asp
    50                  55                  60

Pro Glu Asn Ile Thr Glu Ile Leu Ile Ala Asn Gln Lys Arg Leu Glu
65                  70                  75                  80

Ile Ile Asn Glu Asp Asp Val Glu Ala Tyr Val Gly Leu Lys Asn Leu
                85                  90                  95

Thr Ile Val Asp Ser Gly Leu Lys Phe Val Ala Tyr Lys Ala Phe Leu
            100                 105                 110

Lys Asn Gly Asn Leu Arg His Ile Asn Phe Thr Arg Asn Lys Leu Thr
        115                 120                 125

Ser Leu Ser Arg Arg His Phe Arg His Leu Asp Leu Ser Asp Leu Ile
    130                 135                 140

Leu Thr Gly Asn Pro Phe Thr Cys Ser Cys Asp Ile Met Trp Leu Lys
145                 150                 155                 160

Thr Leu Gln Glu Thr Lys Ser Ser Pro Asp Thr Gln Asp Leu Tyr Cys
                165                 170                 175

Leu Asn Glu Ser Ser Lys Asn Thr Pro Leu Ala Asn Leu Gln Ile Pro
            180                 185                 190

Asn Cys Gly Leu Pro Ser Ala Arg Leu Ala Ala Pro Asn Leu Thr Val
        195                 200                 205

Glu Glu Gly Lys Ser Val Thr Ile Ser Cys Ser Val Gly Gly Asp Pro
    210                 215                 220

Leu Pro Thr Leu Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

```
Gly Glu Asp Gln Asp Ser Val Asn Leu Thr Val His Phe Ala Pro Thr
            275                 280                 285

Ile Thr Phe Leu Glu Ser Pro Thr Ser Asp His His Trp Cys Ile Pro
290                 295                 300

Phe Thr Val Arg Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
            325                 330                 335

Thr Asn His Thr Glu Tyr His Gly Cys Leu Gln Leu Asp Asn Pro Thr
            340                 345                 350

His Met Asn Asn Gly Asp Tyr Thr Leu Met Ala Lys Asn Glu Tyr Gly
            355                 360                 365

Lys Asp Glu Arg Gln Ile Ser Ala His Phe Met Gly Arg Pro Gly Val
370                 375                 380

Asp Tyr Glu Thr Asn Pro Asn Tyr Pro Glu Val Leu Tyr Glu Asp Trp
385                 390                 395                 400

Thr Thr Pro Thr Asp Ile Gly Asp Thr Thr Asn Lys Ser Asn Glu Ile
                405                 410                 415

Pro Ser Thr Asp Val Ala Asp Gln Thr Asn Arg Glu His Leu Ser Val
            420                 425                 430

Tyr Ala Val Val Ile Ala Ser Val Gly Phe Cys Leu Leu Val
            435                 440                 445

Met Leu Leu Leu Lys Leu Ala Arg His Ser Lys Phe Gly Met Lys
450                 455                 460

Gly Pro Ala Ser Val Ile Ser Asn Asp Asp Ser Ala Ser Pro Leu
465                 470                 475                 480

His His Ile Ser Asn Gly Ser Asn Thr Pro Ser Ser Glu Gly Gly
            485                 490                 495

Pro Asp Ala Val Ile Ile Gly Met Thr Lys Ile Pro Val Ile Glu Asn
            500                 505                 510

Pro Gln Tyr Phe Gly Ile Thr Asn Ser Gln Leu Lys Pro Asp Thr Phe
    515                 520                 525

Val Gln His Ile Lys Arg His Asn Ile Val Leu Lys Arg Glu Leu Gly
    530                 535                 540

Glu Gly Ala Phe Gly Lys Val Phe Leu Ala Glu Cys Tyr Asn Leu Cys
545                 550                 555                 560

Pro Glu Gln Asp Lys Ile Leu Val Ala Val Lys Thr Leu Lys Asp Ala
            565                 570                 575

Ser Asp Asn Ala Arg Lys Asp Phe His Arg Glu Ala Glu Leu Leu Thr
            580                 585                 590

Asn Leu Gln His Glu His Ile Val Lys Phe Tyr Gly Val Cys Val Glu
    595                 600                 605

Gly Asp Pro Leu Ile Met Val Phe Glu Tyr Met Lys His Gly Asp Leu
610                 615                 620

Asn Lys Phe Leu Arg Ala His Gly Pro Asp Ala Val Leu Met Ala Glu
625                 630                 635                 640

Gly Asn Pro Pro Thr Glu Leu Thr Gln Ser Gln Met Leu His Ile Ala
                645                 650                 655

Gln Gln Ile Ala Ala Gly Met Val Tyr Leu Ala Ser Gln His Phe Val
            660                 665                 670

His Arg Asp Leu Ala Thr Arg Asn Cys Leu Val Gly Glu Asn Leu Leu
            675                 680                 685
```

```
Val Lys Ile Gly Asp Phe Gly Met Ser Arg Asp Val Tyr Ser Thr Asp
        690             695                 700

Tyr Tyr Arg Val Gly Gly His Thr Met Leu Pro Ile Arg Trp Met Pro
705             710                 715                 720

Pro Glu Ser Ile Met Tyr Arg Lys Phe Thr Thr Glu Ser Asp Val Trp
                725                 730                 735

Ser Leu Gly Val Val Leu Trp Glu Ile Phe Thr Tyr Gly Lys Gln Pro
        740                 745                 750

Trp Tyr Gln Leu Ser Asn Asn Glu Val Ile Glu Cys Ile Thr Gln Gly
            755                 760                 765

Arg Val Leu Gln Arg Pro Arg Thr Cys Pro Gln Glu Val Tyr Glu Leu
770                 775                 780

Met Leu Gly Cys Trp Gln Arg Glu Pro His Thr Arg Lys Asn Ile Lys
785                 790                 795                 800

Asn Ile His Thr Leu Leu Gln Asn Leu Ala Lys Ala Ser Pro Val Tyr
                805                 810                 815

Leu Asp Ile Leu Gly
            820

<210> SEQ ID NO 3
<211> LENGTH: 838
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Signal Peptide
<220> FEATURE:
<221> NAME/KEY: MISC_FEATURE
<222> LOCATION: (32)..(430)
<223> OTHER INFORMATION: Extracellular Domain
<220> FEATURE:
<221> NAME/KEY: MISC_FEATURE
<222> LOCATION: (431)..(454)
<223> OTHER INFORMATION: Transmembrane Domain
<220> FEATURE:
<221> NAME/KEY: MISC_FEATURE
<222> LOCATION: (455)..(838)
<223> OTHER INFORMATION: Cytoplasmic Domain

<400> SEQUENCE: 3

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
                20                  25                  30

Pro Thr Ser Cys Lys Cys Ser Ala Ser Arg Ile Trp Cys Ser Asp Pro
                35                  40                  45

Ser Pro Gly Ile Val Ala Phe Pro Arg Leu Glu Pro Asn Ser Val Asp
        50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
```

```
            145                 150                 155                 160
Thr Leu Gln Glu Ala Lys Ser Ser Pro Asp Thr Gln Asp Leu Tyr Cys
                165                 170                 175
Leu Asn Glu Ser Ser Lys Asn Ile Pro Leu Ala Asn Leu Gln Ile Pro
                180                 185                 190
Asn Cys Gly Leu Pro Ser Ala Asn Leu Ala Ala Pro Asn Leu Thr Val
                195                 200                 205
Glu Glu Gly Lys Ser Ile Thr Leu Ser Cys Ser Val Ala Gly Asp Pro
            210                 215                 220
Val Pro Asn Met Tyr Trp Asp Val Gly Asn Leu Val Ser Lys His Met
225                 230                 235                 240
Asn Glu Thr Ser His Thr Gln Gly Ser Leu Arg Ile Thr Asn Ile Ser
                245                 250                 255
Ser Asp Asp Ser Gly Lys Gln Ile Ser Cys Val Ala Glu Asn Leu Val
                260                 265                 270
Gly Glu Asp Gln Asp Ser Val Asn Leu Thr Val His Phe Ala Pro Thr
            275                 280                 285
Ile Thr Phe Leu Glu Ser Pro Thr Ser Asp His His Trp Cys Ile Pro
            290                 295                 300
Phe Thr Val Lys Gly Asn Pro Lys Pro Ala Leu Gln Trp Phe Tyr Asn
305                 310                 315                 320
Gly Ala Ile Leu Asn Glu Ser Lys Tyr Ile Cys Thr Lys Ile His Val
                325                 330                 335
Thr Asn His Thr Glu Tyr His Gly Cys Leu Gln Leu Asp Asn Pro Thr
            340                 345                 350
His Met Asn Asn Gly Asp Tyr Thr Leu Ile Ala Lys Asn Glu Tyr Gly
            355                 360                 365
Lys Asp Glu Lys Gln Ile Ser Ala His Phe Met Gly Trp Pro Gly Ile
            370                 375                 380
Asp Asp Gly Ala Asn Pro Asn Tyr Pro Asp Val Ile Tyr Glu Asp Tyr
385                 390                 395                 400
Gly Thr Ala Ala Asn Asp Ile Gly Asp Thr Thr Asn Arg Ser Asn Glu
                405                 410                 415
Ile Pro Ser Thr Asp Val Thr Asp Lys Thr Gly Arg Glu His Leu Ser
                420                 425                 430
Val Tyr Ala Val Val Ile Ala Ser Val Val Gly Phe Cys Leu Leu
                435                 440                 445
Val Met Leu Phe Leu Leu Lys Leu Ala Arg His Ser Lys Phe Gly Met
450                 455                 460
Lys Asp Phe Ser Trp Phe Gly Phe Gly Lys Val Lys Ser Arg Gln Gly
465                 470                 475                 480
Val Gly Pro Ala Ser Val Ile Ser Asn Asp Asp Ser Ala Ser Pro
                485                 490                 495
Leu His His Ile Ser Asn Gly Ser Asn Thr Pro Ser Ser Ser Glu Gly
                500                 505                 510
Gly Pro Asp Ala Val Ile Ile Gly Met Thr Lys Ile Pro Val Ile Glu
            515                 520                 525
Asn Pro Gln Tyr Phe Gly Ile Thr Asn Ser Gln Leu Lys Pro Asp Thr
            530                 535                 540
Phe Val Gln His Ile Lys Arg His Asn Ile Val Leu Lys Arg Glu Leu
545                 550                 555                 560
Gly Glu Gly Ala Phe Gly Lys Val Phe Leu Ala Glu Cys Tyr Asn Leu
                565                 570                 575
```

-continued

```
Cys Pro Glu Gln Asp Lys Ile Leu Val Ala Val Lys Thr Leu Lys Asp
                580                 585                 590

Ala Ser Asp Asn Ala Arg Lys Asp Phe His Arg Glu Ala Glu Leu Leu
        595                 600                 605

Thr Asn Leu Gln His Glu His Ile Val Lys Phe Tyr Gly Val Cys Val
    610                 615                 620

Glu Gly Asp Pro Leu Ile Met Val Phe Glu Tyr Met Lys His Gly Asp
625                 630                 635                 640

Leu Asn Lys Phe Leu Arg Ala His Gly Pro Asp Ala Val Leu Met Ala
                645                 650                 655

Glu Gly Asn Pro Pro Thr Glu Leu Thr Gln Ser Gln Met Leu His Ile
            660                 665                 670

Ala Gln Gln Ile Ala Ala Gly Met Val Tyr Leu Ala Ser Gln His Phe
        675                 680                 685

Val His Arg Asp Leu Ala Thr Arg Asn Cys Leu Val Gly Glu Asn Leu
    690                 695                 700

Leu Val Lys Ile Gly Asp Phe Gly Met Ser Arg Asp Val Tyr Ser Thr
705                 710                 715                 720

Asp Tyr Tyr Arg Val Gly Gly His Thr Met Leu Pro Ile Arg Trp Met
                725                 730                 735

Pro Pro Glu Ser Ile Met Tyr Arg Lys Phe Thr Thr Glu Ser Asp Val
            740                 745                 750

Trp Ser Leu Gly Val Val Leu Trp Glu Ile Phe Thr Tyr Gly Lys Gln
        755                 760                 765

Pro Trp Tyr Gln Leu Ser Asn Asn Glu Val Ile Glu Cys Ile Thr Gln
    770                 775                 780

Gly Arg Val Leu Gln Arg Pro Arg Thr Cys Pro Gln Glu Val Tyr Glu
785                 790                 795                 800

Leu Met Leu Gly Cys Trp Gln Arg Glu Pro His Met Arg Lys Asn Ile
                805                 810                 815

Lys Gly Ile His Thr Leu Leu Gln Asn Leu Ala Lys Ala Ser Pro Val
            820                 825                 830

Tyr Leu Asp Ile Leu Gly
        835

<210> SEQ ID NO 4
<211> LENGTH: 822
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(31)
<223> OTHER INFORMATION: Signal Peptide
<220> FEATURE:
<221> NAME/KEY: MISC_FEATURE
<222> LOCATION: (1)..(31)
<223> OTHER INFORMATION: Mouse Sequence
<220> FEATURE:
<221> NAME/KEY: MISC_FEATURE
<222> LOCATION: (32)..(430)
<223> OTHER INFORMATION: Extracellular Domain
<220> FEATURE:
<221> NAME/KEY: MISC_FEATURE
<222> LOCATION: (32)..(432)
<223> OTHER INFORMATION: Human Sequence
<220> FEATURE:
<221> NAME/KEY: MISC_FEATURE
<222> LOCATION: (431)..(454)
<223> OTHER INFORMATION: Transmembrane Domain
```

```
<220> FEATURE:
<221> NAME/KEY: MISC_FEATURE
<222> LOCATION: (433)..(822)
<223> OTHER INFORMATION: Mouse Sequence
<220> FEATURE:
<221> NAME/KEY: MISC_FEATURE
<222> LOCATION: (455)..(822)
<223> OTHER INFORMATION: Cytoplasmic Domain

<400> SEQUENCE: 4
```

| | | | | | | | | | | | | | | |
|---|---|---|---|---|---|---|---|---|---|---|---|---|---|---|
| Met | Ser | Pro | Trp | Leu | Lys | Trp | His | Gly | Pro | Ala | Met | Ala | Arg | Leu | Trp |
| 1 | | | | 5 | | | | | 10 | | | | | 15 | |
| Gly | Leu | Cys | Leu | Leu | Val | Leu | Gly | Phe | Trp | Arg | Ala | Ser | Leu | Ala | Cys |
| | | | 20 | | | | | 25 | | | | | 30 | | |
| Pro | Thr | Ser | Cys | Lys | Cys | Ser | Ala | Ser | Arg | Ile | Trp | Cys | Ser | Asp | Pro |
| | | 35 | | | | | 40 | | | | | 45 | | | |
| Ser | Pro | Gly | Ile | Val | Ala | Phe | Pro | Arg | Leu | Glu | Pro | Asn | Ser | Val | Asp |
| 50 | | | | | 55 | | | | | 60 | | | | | |
| Pro | Glu | Asn | Ile | Thr | Glu | Ile | Phe | Ile | Ala | Asn | Gln | Lys | Arg | Leu | Glu |
| 65 | | | | | 70 | | | | | 75 | | | | | 80 |
| Ile | Ile | Asn | Glu | Asp | Asp | Val | Glu | Ala | Tyr | Val | Gly | Leu | Arg | Asn | Leu |
| | | | | 85 | | | | | 90 | | | | | 95 | |
| Thr | Ile | Val | Asp | Ser | Gly | Leu | Lys | Phe | Val | Ala | His | Lys | Ala | Phe | Leu |
| | | | 100 | | | | | 105 | | | | | 110 | | |
| Lys | Asn | Ser | Asn | Leu | Gln | His | Ile | Asn | Phe | Thr | Arg | Asn | Lys | Leu | Thr |
| | | 115 | | | | | 120 | | | | | 125 | | | |
| Ser | Leu | Ser | Arg | Lys | His | Phe | Arg | His | Leu | Asp | Leu | Ser | Glu | Leu | Ile |
| | 130 | | | | | 135 | | | | | 140 | | | | |
| Leu | Val | Gly | Asn | Pro | Phe | Thr | Cys | Ser | Cys | Asp | Ile | Met | Trp | Ile | Lys |
| 145 | | | | | 150 | | | | | 155 | | | | | 160 |
| Thr | Leu | Gln | Glu | Ala | Lys | Ser | Ser | Pro | Asp | Thr | Gln | Asp | Leu | Tyr | Cys |
| | | | | 165 | | | | | 170 | | | | | 175 | |
| Leu | Asn | Glu | Ser | Ser | Lys | Asn | Ile | Pro | Leu | Ala | Asn | Leu | Gln | Ile | Pro |
| | | | 180 | | | | | 185 | | | | | 190 | | |
| Asn | Cys | Gly | Leu | Pro | Ser | Ala | Asn | Leu | Ala | Ala | Pro | Asn | Leu | Thr | Val |
| | | 195 | | | | | 200 | | | | | 205 | | | |
| Glu | Glu | Gly | Lys | Ser | Ile | Thr | Leu | Ser | Cys | Ser | Val | Ala | Gly | Asp | Pro |
| | 210 | | | | | 215 | | | | | 220 | | | | |
| Val | Pro | Asn | Met | Tyr | Trp | Asp | Val | Gly | Asn | Leu | Val | Ser | Lys | His | Met |
| 225 | | | | | 230 | | | | | 235 | | | | | 240 |
| Asn | Glu | Thr | Ser | His | Thr | Gln | Gly | Ser | Leu | Arg | Ile | Thr | Asn | Ile | Ser |
| | | | | 245 | | | | | 250 | | | | | 255 | |
| Ser | Asp | Asp | Ser | Gly | Lys | Gln | Ile | Ser | Cys | Val | Ala | Glu | Asn | Leu | Val |
| | | | 260 | | | | | 265 | | | | | 270 | | |
| Gly | Glu | Asp | Gln | Asp | Ser | Val | Asn | Leu | Thr | Val | His | Phe | Ala | Pro | Thr |
| | | 275 | | | | | 280 | | | | | 285 | | | |
| Ile | Thr | Phe | Leu | Glu | Ser | Pro | Thr | Ser | Asp | His | His | Trp | Cys | Ile | Pro |
| | 290 | | | | | 295 | | | | | 300 | | | | |
| Phe | Thr | Val | Lys | Gly | Asn | Pro | Lys | Pro | Ala | Leu | Gln | Trp | Phe | Tyr | Asn |
| 305 | | | | | 310 | | | | | 315 | | | | | 320 |
| Gly | Ala | Ile | Leu | Asn | Glu | Ser | Lys | Tyr | Ile | Cys | Thr | Lys | Ile | His | Val |
| | | | | 325 | | | | | 330 | | | | | 335 | |
| Thr | Asn | His | Thr | Glu | Tyr | His | Gly | Cys | Leu | Gln | Leu | Asp | Asn | Pro | Thr |
| | | | 340 | | | | | 345 | | | | | 350 | | |
| His | Met | Asn | Asn | Gly | Asp | Tyr | Thr | Leu | Ile | Ala | Lys | Asn | Glu | Tyr | Gly |
| | | 355 | | | | | 360 | | | | | 365 | | | |

```
Lys Asp Glu Lys Gln Ile Ser Ala His Phe Met Gly Trp Pro Gly Ile
    370                 375                 380
Asp Asp Gly Ala Asn Pro Asn Tyr Pro Asp Val Ile Tyr Glu Asp Tyr
385                 390                 395                 400
Gly Thr Ala Ala Asn Asp Ile Gly Asp Thr Thr Asn Arg Ser Asn Glu
            405                 410                 415
Ile Pro Ser Thr Asp Val Thr Asp Lys Thr Gly Arg Glu His Leu Ser
                420                 425                 430
Val Tyr Ala Val Val Val Ile Ala Ser Val Val Gly Phe Cys Leu Leu
            435                 440                 445
Val Met Leu Leu Leu Leu Lys Leu Ala Arg His Ser Lys Phe Gly Met
450                 455                 460
Lys Gly Pro Ala Ser Val Ile Ser Asn Asp Asp Ser Ala Ser Pro
465                 470                 475                 480
Leu His His Ile Ser Asn Gly Ser Asn Thr Pro Ser Ser Ser Glu Gly
                485                 490                 495
Gly Pro Asp Ala Val Ile Ile Gly Met Thr Lys Ile Pro Val Ile Glu
            500                 505                 510
Asn Pro Gln Tyr Phe Gly Ile Thr Asn Ser Gln Leu Lys Pro Asp Thr
                515                 520                 525
Phe Val Gln His Ile Lys Arg His Asn Ile Val Leu Lys Arg Glu Leu
530                 535                 540
Gly Glu Gly Ala Phe Gly Lys Val Phe Leu Ala Glu Cys Tyr Asn Leu
545                 550                 555                 560
Cys Pro Glu Gln Asp Lys Ile Leu Val Ala Val Lys Thr Leu Lys Asp
                565                 570                 575
Ala Ser Asp Asn Ala Arg Lys Asp Phe His Arg Glu Ala Glu Leu Leu
            580                 585                 590
Thr Asn Leu Gln His Glu His Ile Val Lys Phe Tyr Gly Val Cys Val
                595                 600                 605
Glu Gly Asp Pro Leu Ile Met Val Phe Glu Tyr Met Lys His Gly Asp
            610                 615                 620
Leu Asn Lys Phe Leu Arg Ala His Gly Pro Asp Ala Val Leu Met Ala
625                 630                 635                 640
Glu Gly Asn Pro Pro Thr Glu Leu Thr Gln Ser Gln Met Leu His Ile
                645                 650                 655
Ala Gln Gln Ile Ala Ala Gly Met Val Tyr Leu Ala Ser Gln His Phe
            660                 665                 670
Val His Arg Asp Leu Ala Thr Arg Asn Cys Leu Val Gly Glu Asn Leu
        675                 680                 685
Leu Val Lys Ile Gly Asp Phe Gly Met Ser Arg Asp Val Tyr Ser Thr
        690                 695                 700
Asp Tyr Tyr Arg Val Gly Gly His Thr Met Leu Pro Ile Arg Trp Met
705                 710                 715                 720
Pro Pro Glu Ser Ile Met Tyr Arg Lys Phe Thr Thr Glu Ser Asp Val
                725                 730                 735
Trp Ser Leu Gly Val Val Leu Trp Glu Ile Phe Thr Tyr Gly Lys Gln
            740                 745                 750
Pro Trp Tyr Gln Leu Ser Asn Asn Glu Val Ile Glu Cys Ile Thr Gln
                755                 760                 765
Gly Arg Val Leu Gln Arg Pro Arg Thr Cys Pro Gln Glu Val Tyr Glu
        770                 775                 780
```

-continued

```
Leu Met Leu Gly Cys Trp Gln Arg Glu Pro His Thr Arg Lys Asn Ile
785                 790                 795                 800

Lys Ser Ile His Thr Leu Leu Gln Asn Leu Ala Lys Ala Ser Pro Val
            805                 810                 815

Tyr Leu Asp Ile Leu Gly
            820

<210> SEQ ID NO 5
<211> LENGTH: 822
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(31)
<223> OTHER INFORMATION: Signal Peptide
<220> FEATURE:
<221> NAME/KEY: MISC_FEATURE
<222> LOCATION: (1)..(31)
<223> OTHER INFORMATION: Rat Sequence
<220> FEATURE:
<221> NAME/KEY: MISC_FEATURE
<222> LOCATION: (32)..(430)
<223> OTHER INFORMATION: Extracellular Domain
<220> FEATURE:
<221> NAME/KEY: MISC_FEATURE
<222> LOCATION: (32)..(432)
<223> OTHER INFORMATION: Human Sequence
<220> FEATURE:
<221> NAME/KEY: MISC_FEATURE
<222> LOCATION: (431)..(454)
<223> OTHER INFORMATION: Transmembrane Domain
<220> FEATURE:
<221> NAME/KEY: MISC_FEATURE
<222> LOCATION: (433)..(822)
<223> OTHER INFORMATION: Rat Sequence
<220> FEATURE:
<221> NAME/KEY: MISC_FEATURE
<222> LOCATION: (455)..(822)
<223> OTHER INFORMATION: Cytoplasmic Domain

<400> SEQUENCE: 5

Met Ser Pro Trp Pro Arg Trp His Gly Pro Ala Met Ala Arg Leu Trp
1               5                   10                  15

Gly Leu Cys Leu Leu Val Leu Gly Phe Trp Arg Ala Ser Leu Ala Cys
                20                  25                  30

Pro Thr Ser Cys Lys Cys Ser Ala Ser Arg Ile Trp Cys Ser Asp Pro
            35                  40                  45

Ser Pro Gly Ile Val Ala Phe Pro Arg Leu Glu Pro Asn Ser Val Asp
    50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175
```

```
Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
            195                 200                 205

Glu Glu Gly Lys Ser Ile Thr Leu Ser Cys Ser Val Ala Gly Asp Pro
            210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
            275                 280                 285

Ile Thr Phe Leu Glu Ser Pro Thr Ser Asp His His Trp Cys Ile Pro
            290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Ile Ala Lys Asn Glu Tyr Gly
                355                 360                 365

Lys Asp Glu Lys Gln Ile Ser Ala His Phe Met Gly Trp Pro Gly Ile
            370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415

Ile Pro Ser Thr Asp Val Thr Asp Lys Thr Gly Arg Glu His Leu Ser
            420                 425                 430

Val Tyr Ala Val Val Val Ile Ala Ser Val Val Gly Phe Cys Leu Leu
            435                 440                 445

Val Met Leu Leu Leu Leu Lys Leu Ala Arg His Ser Lys Phe Gly Met
450                 455                 460

Lys Gly Pro Ala Ser Val Ile Ser Asn Asp Asp Ser Ala Ser Pro
465                 470                 475                 480

Leu His His Ile Ser Asn Gly Ser Asn Thr Pro Ser Ser Ser Glu Gly
                485                 490                 495

Gly Pro Asp Ala Val Ile Ile Gly Met Thr Lys Ile Pro Val Ile Glu
            500                 505                 510

Asn Pro Gln Tyr Phe Gly Ile Thr Asn Ser Gln Leu Lys Pro Asp Thr
            515                 520                 525

Phe Val Gln His Ile Lys Arg His Asn Ile Val Leu Lys Arg Glu Leu
530                 535                 540

Gly Glu Gly Ala Phe Gly Lys Val Phe Leu Ala Glu Cys Tyr Asn Leu
545                 550                 555                 560

Cys Pro Glu Gln Asp Lys Ile Leu Val Ala Val Lys Thr Leu Lys Asp
                565                 570                 575

Ala Ser Asp Asn Ala Arg Lys Asp Phe His Arg Glu Ala Glu Leu Leu
            580                 585                 590
```

```
Thr Asn Leu Gln His Glu His Ile Val Lys Phe Tyr Gly Val Cys Val
            595                 600                 605

Glu Gly Asp Pro Leu Ile Met Val Phe Glu Tyr Met Lys His Gly Asp
610                 615                 620

Leu Asn Lys Phe Leu Arg Ala His Gly Pro Asp Ala Val Leu Met Ala
625                 630                 635                 640

Glu Gly Asn Pro Pro Thr Glu Leu Thr Gln Ser Gln Met Leu His Ile
                645                 650                 655

Ala Gln Gln Ile Ala Ala Gly Met Val Tyr Leu Ala Ser Gln His Phe
            660                 665                 670

Val His Arg Asp Leu Ala Thr Arg Asn Cys Leu Val Gly Glu Asn Leu
        675                 680                 685

Leu Val Lys Ile Gly Asp Phe Gly Met Ser Arg Asp Val Tyr Ser Thr
    690                 695                 700

Asp Tyr Tyr Arg Val Gly Gly His Thr Met Leu Pro Ile Arg Trp Met
705                 710                 715                 720

Pro Pro Glu Ser Ile Met Tyr Arg Lys Phe Thr Thr Glu Ser Asp Val
                725                 730                 735

Trp Ser Leu Gly Val Val Leu Trp Glu Ile Phe Thr Tyr Gly Lys Gln
            740                 745                 750

Pro Trp Tyr Gln Leu Ser Asn Asn Glu Val Ile Glu Cys Ile Thr Gln
        755                 760                 765

Gly Arg Val Leu Gln Arg Pro Arg Thr Cys Pro Gln Glu Val Tyr Glu
    770                 775                 780

Leu Met Leu Gly Cys Trp Gln Arg Glu Pro His Thr Arg Lys Asn Ile
785                 790                 795                 800

Lys Asn Ile His Thr Leu Leu Gln Asn Leu Ala Lys Ala Ser Pro Val
                805                 810                 815

Tyr Leu Asp Ile Leu Gly
            820

<210> SEQ ID NO 6
<211> LENGTH: 8744
<212> TYPE: DNA
<213> ORGANISM: Mus musculus

<400> SEQUENCE: 6
gtctggaggg tgctatgcta tgcgtgtgtg cgtgtgtgtg cgcgcgcgcg tgtgtgagcg      60
tgtgtgtttt tggatttcat actaattttc tggagtttct gccctgctc tgcgtcagcc     120 ctcacgtcac ttcgccagca gtagcagagg cggcggcggc ggcggccgcc ggttagagcc     180
cagtcgctgc ttcagctgct gttgctgctt ctgcagcgct ctgctccctg cgcttgctac     240
gggaggccgg ggaagccgcg cggacagtcc tcggtggcct gggccggcac tgtcctgcta     300
ccgcagttgc tccccagccc tgaggtgcgc accgatatcg atattcgtgc cggtttagcg     360
gttctgcgac ccaaagagtc cagggagatc caccgagtgg tgcctggcgt ataggactat     420
gcagccgcct tgtggctcgg agcagcggcc cgcgatgtcc cagccactgt gaaccatttg     480
gtcagcgcca acctgctcag ccccagcacc gacaggctca gcctctggta cgctccactc     540
cgcgggaggc caccagcacc aagcagcaag agggcgcagg gaaggcctcc ccctccggc     600 ggggacgcc tggctcagcg tagggacacg cactccgact gactggcact ggcagctcgg     660
gatgtcgccc tggctgaagt ggcatggacc cgccatggcg cggctctggg gcttatgcct     720
gctggtcttg ggcttctgga gggcctctct cgcctgcccg acgtcctgca aatgcagttc     780
```

```
cgctaggatt tggtgtactg agccttctcc aggcatcgtg gcattcccga ggttggaacc      840
taacagcgtt gacccggaga acatcacgga aattctcatt gcaaaccaga aaaggctaga      900
aatcatcaat gaagatgacg ttgaagctta cgtggggctg agaaacctta caattgtgga      960
ttccggctta agtttgtgg cttacaaagc gtttctgaaa acagcaacc tgcggcacat       1020
aaatttcaca cgaaacaagc tgacgagttt gtccaggaga catttccgcc accttgactt     1080
gtctgacctg atcctgacgg gtaatccgtt cacgtgctcc tgcgacatca tgtggctcaa     1140
gactctccag gagactaaat ccagccccga cactcaggat ttgtactgcc tcaatgagag     1200
cagcaagaac atgcccctgg cgaacctgca gatacccaat tgtggtctgc catctgcacg     1260
tctggctgct cctaacctca ccgtggagga aggaaagtct gtgaccctt cctgcagtgt      1320
gggggtgac ccactcccca ccttgtactg ggacgttggg aatttggttt ccaagcacat      1380
gaatgaaaca agccacacac agggctcctt aaggataacg aacatttcat ctgatgacag     1440
tggaaagcaa atctcttgtg tggcagaaaa ccttgtagga gaagatcaag attctgtgaa     1500
cctcactgtg cattttgcgc caactatcac gtttctcgag tctccaacct cagatcacca     1560
ctggtgcatt ccattcactg tgagaggcaa ccccaagcct gcgcttcagt ggttctacaa     1620
tggggccata ctgaatgagt ccaagtacat ctgtactaag atcccacgtca ccaatcacac    1680
ggagtaccat ggctgcctcc agctggataa ccccactcat atgaataacg gagactacac     1740
cctgatggcc aagaacagt atgggaagga tgagagacag atctccgctc acttcatggg     1800
ccggcctgga gtcgactacg agacaaaccc aaattaccct gaagtcctct atgaagactg     1860
gaccacgcca actgacattg gggatactac gaacaaaagt aatgaaatcc cctccacgga    1920
tgttgctgac caaagcaatc gggagcatct ctcggtctat gccgtggtgg tgattgcatc    1980
tgtggtggga ttctgcctgc tggtgatgtt gctcctgctc aagttggcga gcattccaa     2040
gtttggcatg aaaggcccag cttcggtcat cagcaacgac gatgactctg ccagccccct    2100
ccaccacatc tccaatggga gtaacactcc atcttcttcg gagggcggtc ccgacgctgt    2160
cattattgga atgaccaaga ttcctgttat tgaaaacccc cagtactttg gcatcaccaa    2220
cagtcagctc aagccagaca catttgttca gcatatcaag agacacaaca tcgttctgaa    2280
gagggaactt gggggaaggag ccttcgggaa agttttcctt gccgagtgct acaacctctg    2340
cccagagcag gataagatcc tggtggctgt gaagacgctg aaggacgcca gcgacaatgc    2400
acgcaaggac tttcatcggg aagctgagct gctgaccaac ctccagcacg agcacattgt    2460
caagttctac ggtgtctgtg tggagggcga cccactcatc atggtctttg agtacatgaa    2520
gcacggggac ctcaacaagt tccttagggc acacgggccc gacgcagtgc tgatggcaga    2580
gggtaacccg cccacagagc tgacgcagtc gcagatgctg cacatcgctc agcaaatcgc    2640
agcaggtatg gtctacctgg cgtcccaaca ctttgtgcac cgtgacctgg ccacccggaa    2700
ctgcctggtg ggagagaacc tgctggtgaa aattggggac tttgggatgt cccgagatgt    2760
gtacagcacc gactactatc gggtcggtgg ccacacaatg ttgcccatcc gatggatgcc    2820
tccagagagc atcatgtaca ggaaattcac caccgagagc gacgtctgga gcctgggcgt    2880
tgtgttgtgg gagatcttca cctacggcaa gcagccctgg tatcagctat cgaacaatga    2940
ggtgatagag tgcatcaccc agggaagagt ccttcagcgg cctcgaacgt gtccccagga    3000
ggtgtatgag ctcatgcttg gatgctggca gcgggaacca cacacccgga gaacatcaa     3060
gagcatccac acccctcctc agaacttggc caaggcatct cccgtctacc tggatatcct    3120
aggctagggt cctccttctg cccagaccgt ccttcccaag gccctcctca gactggccta    3180
```

```
cacgacgaac ctcttgactg ccgctgacgt catgaccttg ctgtccttcg ctctgacagt      3240
gttgacagga ccaggagcgg ctctttgggg gaggcagtgt gtgcttctcc atccacagac      3300
agtattaact cgcttctggc attgtctctt tctctccctt gggtttgttt ctttcttttg      3360
ccccttcccc ttttatcatt atttattcat ttatttattt tctggtcttc accgcttcac      3420
ggccctcagt ctctccttga ccaatctggc ttctgcattc ctattaactg tacatagaca      3480
aaggccttaa caaacctaat ttgttatatc agcagacact ccagtttgcc caccacaact      3540
aacaatgcct tgttgtattc ctgcctttga cgtggatgaa aaaagggaa aaaaaaatca       3600 aacatctgac ttaagctgtc acttccgatg tacagacgtg gggcgtttct atggattcac      3660
ttctatttat tatttattaa tttatttatt tatcactctt cttattgttt tctggtggtt      3720
ttaacctatg tgtgagaagg aaaagttgtg tacaatctgg gaaaacttta tcagtgggaa      3780
atgaaaacga gagcgagcaa gcgagcaaga gagggagaga gagagagaag cgttaccata      3840
aaccacggca tgagcgagac agagacaagc catgggatca gtcgggagtc cgttgtgctt      3900
aggaaaaccc agcagccatt agctggggga gcatgttcgg ctctgtcccc caagcacctt      3960
tctgaggagg acacaggatg ttgaactctg cttcacgggc agagcttcta atgacagata      4020
ctggcttgca ctggaaagac agttcccacg ggacctggac ggacaacaca tcctacattc      4080
agacattgtg gtcgggcacg gtgacagagt tgatccgttt ctcaagtgtt atctaccaag      4140
cttttgtgaa gttccatcga aggaggtaga ttcttgctca gatataattt caggaaaacc      4200
cgagtccttg acaaagacag gagacgctct caatttggag gcaagtttct cttaccttga      4260 acttttttcag acagcaactc cgcccagccc ccatcttcca ctctcacctg tcttgtaact      4320
gtgcaaacaa aagtgtgcat ggtctttgtc aattgatacc tatgtgcacg tgtgcagaaa      4380
ctgttgttcc agctggggtg tctgattagg agggcagatc cataaaaggt ctaacctagg      4440
caacttcggg aaaggagacc agatcagtag ctggaggcac tctccagtag gcggtgaggg      4500
gtttactgag taggcatgct gaagcccgga tattcaccca tctcaaaccc cccgggctgc      4560
aggacaggca caggccatcc ctgaggagaa ggggagccct tttgggatac cacctgaggt      4620
tatgttcagt gtgctctggt caagtccctt gctcggggct ctgtttgggg agagtggttt      4680
cattccaagg tactcattat tagtatgctg ttttgttaac tatactccat taaaaagtta      4740
aaaaaaaaaa gaattaagcc ttgacactgt atggctgaca ggaggctgtg cccagactga      4800
gcctggagat ttgcgcccgc acatggtcat tggttttccg aaaagagagg gtaaatttat      4860
atagaaattt acaggtattt gggtagtcat ttagaccgag ggagaccagt gtttccattt      4920
ctctgcgccc cctctgtgag gggaagttcg atacacttga cacctttata aacggagcca      4980
gataggaagg gagtgactta attcaccta gaacatttca tttggtgttt atttctgaag       5040
gtgcaagagc tctgtgtagg tttcatttgt gcccgagcat ttctggagca ctgtgttttc      5100
tagcagaaac tccgagagcc agttctcaca atgaaacttt aaaacctgtg taaattgaca      5160
gagagcagaa ggcgatccaa gaggcccact caagtgagtg gtggcacgag gcacatgcgg      5220
tggccctttc tgttgtgctg gcccatgaga gatgggagct attttgtcct cttcgtccat      5280
taaaacaaac ccctccagaa tacctatagt aatataatga aagccatatc tctgtgatct      5340
ataccgtcag gtatagatca ttaaaggacc catggtactg tcaggcactg tggaaccgtg      5400
aggcagcgga aaggcaaggg cacatttgta catgttcctc tagcttccgc cagccgtgac      5460
ctatgaactc acataggccg gttgctccta gtctgacggg ctgccctggg aggaaaagct      5520
```

```
gcaagatgct cagcagagag caaaggagag gatagtcttg gaaaaggcca aggttgggga    5580
tgccatacag gattacacca aagggctgta ctgagaatgt gggagcattc cattccagt     5640 ttgtattttc ctcagcaaga aaaagagca gatagaaggg cagaggagga tagagaggaa    5700
gagaaaggag agggagaaga gagcagagaa gagagagaga gagagagaga gagagaatct    5760 ttatacttt tggcaagtcc tcgaaggtct caaaatgaaa gtgtctatgc aagtgcaaat    5820
ttttacagtt atttatacta attattatta ttgttattaa ttattattat tactagtctg    5880
ttgtctcaag aatatgtgca gatttcagag cattaaagag tatttggttt cttttaaagt    5940
agttgggtga gccaaggaca ccttaaaata attgtcactg ttcatctgct atcgcctttc    6000
tcatggtatt ttaagtttta gaaagaaac attcttgttc taaaacatat ccctctccat    6060
agatgacaaa aaaaaatggt gttagcaaac cgaaacctcc cccgattcct gtctgacatc    6120
cgatccattt ctcaactgct tgatgatttc cgagcgcttt ttgcatatgt tgtcaaaata    6180
ttcatattat tttggtgagg gaatggagac tcagaaactc agaggacaaa cataagcttc    6240
accgaagtct gtctgccaga tacaaactaa catacaaaca agacagccgg gaaggaaatg    6300
tgctggtagc gtgtctgtgg agcagggtgg gggttagaac agaaggagac ctgggcagtg    6360
cacgcagaag agatgttaca tcatgtgctt ctgctcctgg cttctgctga ctcccaactt    6420
tgcgctcagc ctcatttaga aaacgcttca aacactgctc ttcagggttc tgtcagaact    6480
cacacacacg tgctcacacc agcccgctt gtgacgtttt tatgtacttc tatataaata    6540
tatacataat atatgttata aacacttgat ttatacatat acaaatgcac acatgtagtg    6600
tgtttgtgtg tttatgtata aacatatagg ctcatggtaa tagaataatt ataagtaggg    6660
tgcaatatga ataatttgct taatatttgc taagtaacca aaactttcca acgtcatgtg    6720
gcagttcata tttccactct cagtgtgggt aaggatgggc tacaccacac tttcagctct    6780
gtgcagccct tggatggaag atgtgttgaa aaaaaaatca catcttccct gaaacaactg    6840
actgaaagcc atcctctaca ttgaatctgt tctctggctc tttgcaaagg agaaatgcag    6900
acaaatggtc tccttgtgtc ccagtcctgg gaaggagaag tgggttttct cttcttgcac    6960
atttgggccg tgctcacctt tcctggctct atgcccttta cactgggctc agagatgaag    7020
cagtctagac ccaagctgca gggctgtagg gaggcaaatg tcttcgaggc tgatagcaaa    7080
gcatccaaaa atctatagca agatgcgcag cttgaagtca ctcctcatcc acacggcaag    7140
caagagccag ggcatgcagt gctgtccatc tctaggactg ggcagtgggg tccccggtca    7200
agggcagtct ttccctaagc ctctcctttt gcaaatggca ctgccagcag tacctggcat    7260
taagtcacga aaaatttcta aaatggcagc acagaccegt gtgccctcat tgctctgccc    7320
ccacatgcct catcattaga gggctccagt ttttcaaactt gactttccat ttggccctgt    7380
atcgtggtta aaggaaatct caacagaggg atggccaatt gacctaaatc cccagatgtc    7440
caagtttgca gtgaaagcca gttcttccca aatgtataac tggaatgtag ggactcaggt    7500
tgtgatactt catacaggaa tctcagatgt tattgtaaag aactgggttg ggagggattc    7560
atcactaagc caacaataat gcaggagggc gtggctgatc gttaagccaa tagtagtgca    7620
ggagggcgtg gctgctgtga gggctggaat ccatctctgc tgctaaagtt cagggttctc    7680
aactcttttc agctgttgca gcccttcact tctttccctt cggcgttatt tatttgtgta    7740
tttatttatt tatttatta tttatctatc tatctatcaa cttttggtcc attcatcacc    7800
aacataaagc aaaaacaatt ttttacatat atgtaaatgt gttgcaagtg aaacactgtg    7860
aatctcacaa ccacctccta gcaactatgc tgccatcttg acgtgcgtct caggagtcga    7920
```

```
gacgggaaaa gacgaggacg tcattttgca gcctacgcat tctgggccag gtccgtgttc    7980
gttttatttc tttagtctgt gagttaagaa aacaatccga gtggagggtg acggatgttc    8040
ggcaagttcg gtgaagcagc acgagctctt tgcagctata ggttcgagca agaagaaaaa    8100
ccatgggaga tggagaaggg aaatttgatg gaggggtggg gtggggtggg ggctctgtct    8160
tacagctcgt gtagcttact gttgcttaaa aatgtataca acagctggaa atgttttcaa    8220
cacaaggtat ttgaaataaa tgtgaatctt aaatatgtac tcccttaagg aatgaacata    8280
ttatggtgaa atattgctcc cccgcgtccc ctacaaatct gcctagagat gtggatacct    8340
acatttgctt aagcatcaga ccagtgtttg tatatacccg ggccatacac actcatctcg    8400
acgtctctct gcggatgtat ttccccttca ctggtgacct ggtatttaga actccgtctt    8460
ttcagttggt ttatttccct ttaatgtgat gtctctgtgc cgattattac cggttcttac    8520 ttgttttttgc aatccgtttt gaggtccagt gttttactga gactcattgc atcttggctg    8580
atttcaaagt gacacccgaa tacagtgttt aaaaaaaaag tttgtttgta aatcatgtga    8640
ccagcttctc tcaccctgac atggaatgtc tcttgtacta cagtgtattt aataataaaa    8700
gaaaaaaatg atgtcttaca ataaataaca tcttccacaa gagg                     8744

<210> SEQ ID NO 7
<211> LENGTH: 4750
<212> TYPE: DNA
<213> ORGANISM: Rattus norvegicus

<400> SEQUENCE: 7
tgtgcgtgcg tgcgtgtgtg tgtgtgtgtg tgtgtgtgtg tgtgtgtgtg tgtgtgtgtg      60
tgagcgtgtg tgttttttgga tttcatacta atttttctgga gtttctgccc ctgctctgcg    120
tcagccctca cgtcacttcg ccagcagtag cagaggcggc ggcggccgcc ggttagagcc     180
cagtcgctgc ttcagctgct gttgctgctt ctgcggcgct ctgctccctg cgctggctac     240
gggaggccgg gggagccgcg ccgacagtcc tctgtggcca gggccggcac tgtcctgcta     300
ccgcagttgc tccccagccc tgaggtgcgc accgatatcg atatccgtgc cggtttagcg     360
gttctgcgac ccaaagagtc cagggagagc caccgagtgg cgcctggcgt ataggaccat     420
gcagccgcct tgtggcttgg agcagcggcc cgtgatgttc cagccactgt gaaccatttg     480
gtcagcgcca acctgctcag ccccagcacc gacaggctca gcctctggta cgctcctctc     540
ggcgggaggc catcagcacc aagcagcaag agggctcagg gaaggcctcc cccctccggc     600
gggggacgcc tggctcagcg tagggacacg cactctgact gactggcact ggcagctcgg     660
gatgtcgccc tggccgaggt ggcatggacc cgccatggcg cggctctggg gcttatgctt     720
gctggtcttg ggcttctgga gggcttctct tgcctgcccc atgtcctgca aatgcagcac     780
cactaggatt tggtgtaccg agccttctcc tggcatcgtg gcatttccga ggttggaacc    840
taacagcatt gacccagaga acatcaccga aattctcatt gcaaaccaga aaaggttaga    900
aatcatcaat gaagatgatg tcgaagctta cgtggggctg aaaaacctta caattgtgga    960
ttccggctta aagtttgtgg cttacaaggc gtttctgaag aacggcaacc tgcggcacat   1020
caatttcact cgaaacaagc tgacgagttt gtccaggaga catttccgcc accttgactt   1080
gtctgacctg atcctgacgg gtaatccgtt cacgtgttcc tgtgacatca tgtggctcaa   1140
gactctccag gagacgaaat ccagcccga cactcaggat ttgtattgcc tcaatgagag    1200
cagcaagaat acccctctgg cgaacctgca gattcccaat tgtggtctgc cgtctgcacg   1260
```

-continued

```
tctggccgct cctaacctca cggtggagga agggaagtct gtgaccattt cctgcagcgt      1320
cgggggtgac ccgctcccca ccttgtactg ggacgttggg aatttggttt ccaaacacat      1380
gaatgaaaca agccacacac agggctcctt aaggataaca acatttcat cggatgacag       1440
tgggaaacaa atctcttgtg tggcagaaaa cctcgttgga gaagatcaag actctgtgaa      1500
cctcactgtg cattttgcac caaccatcac atttctcgaa tctccaacct cagaccacca      1560
ctggtgcatc ccattcactg tgagaggcaa ccccaagcca gcacttcagt ggttctacaa      1620
cggagccata ctgaatgaat ccaagtacat ctgtaccaaa atacacgtca ccaatcacac      1680
ggagtaccac ggctgcctcc agctggataa ccccactcat atgaataatg agactacac      1740
cctaatggcc aagaatgaat atgggaagga cgagagacag atttctgctc acttcatggg     1800
ccggcctgga gttgactatg agacaaaccc aaattaccct gaagtcctct atgaagactg     1860
gaccacgcca actgacatcg gggatactac aaacaaaagt aatgagatcc cctccacgga     1920
tgttgctgac caaaccaatc gggagcatct ctcggtctat gccgtggtgg tgattgcctc    1980
tgtggtagga ttctgcctgc tggtgatgct gcttctgctc aagttggcga gacattccaa    2040
gtttggcatg aaaggcccag cttccgtcat cagcaacgac gatgactctg ccagccctct    2100
ccaccacatc tccaacggga gcaacactcc gtcttcttcg gagggcgggc ccgatgctgt    2160
catcattggg atgaccaaga tccctgtcat tgaaaacccc cagtacttcg gtatcaccaa    2220
cagccagctc aagccggaca catttgttca gcacatcaag agacacaaca tcgttctgaa    2280
gagggagctt ggagaaggag cctttgggaa agttttccta gcggagtgct ataacctctg    2340
ccccgagcag gataagatcc tggtggccgt gaagacgctg aaggacgcca gcgacaatgc    2400
tcgcaaggac tttcatcgcg aagccgagct gctgaccaac ctccagcacg agcacattgt    2460
caagttctac ggtgtctgtg tggagggcga cccactcatc atggtctttg agtacatgaa    2520
gcacggggac ctcaacaagt tccttagggc acacgggcca gatgcagtgc tgatggcaga    2580
gggtaacccg cccaccgagc tgacgcagtc gcagatgctg cacatcgctc agcaaatcgc    2640
agcaggcatg gtctacctgg catcccaaca cttcgtgcac cgagacctgg ccaccggaa     2700
ctgcttggta ggagagaacc tgctggtgaa aattgggga ttcgggatgt cccgggatgt     2760
atacagcacc gactactacc gggttggtgg ccacacaatg ttgcccatcc gatggatgcc    2820
tccagagagc atcatgtaca ggaaattcac caccgagagt gacgtctgga gcctgggagt    2880
tgtgttgtgg gagatcttca cctacggcaa gcagccctgg tatcagctat caaacaacga    2940
ggtgatagaa tgcatcaccc agggcagagt ccttcagcgg cctcgcacgt gtccccagga    3000
ggtgtacgag ctgatgctgg gatgctggca gcgggaacca cacacaagga agaacatcaa    3060
gaacatccac acactccttc agaacttggc gaaggcgtcg cccgtctacc tggacatcct    3120
aggctagact ccctcttctc ccagacggcc cttcccaagg caccctcag acctcttaac     3180
tgccgctgat gtcaccacct tgctgtcctt cgctctgaca gtgttaacaa gacaaggagc    3240
ggctctccgg ggtgaggcag tgcgcacttc cccatccaca gacagtatcg actcgcttct    3300
ggctttgtcg ctttctctcc ctttggtttg tttctttctt ttgcccattc tccatttatt    3360
tatttattta tttatttatt tatttattta tttatctatc tatctatcta tctatctatc    3420
tatttattta tttattggtc ttcactgctt catggtcctc ggcctctctc cttgaccgat    3480
ctggcttctg tactcctatt cactgtacat agacaaaggc cttaacaaac ctgatttgtt    3540
atatcagcag acactccagt ttgcccacca caactaacaa tgccttgttg tattcctgcc    3600
tttgatgtgg atgaaaaaaa gggaaaaaaa aataatcaaa catctgactt aaaccgtcac    3660
```

-continued

```
ttccgatgta cagacacggg gcgtttctat ggattcactt ctatctatct atttatttat    3720
ttatctattt atttatttct cttctttgtt gttttccggt ggttttagcc tgtgtatgag    3780
aagggaaagt catgtacagt ctgggaaaac tttatctgtg ggaaatggaa accagaaagg    3840
gaaagaagct ttaccataaa gcacagcagg agtgagacac agaaaagcca ttggatcagc    3900
cagagtccgt cctgcatagg aaaacccagc agccatcagg ctggaggatc atgttcggca    3960
ctgaccccg aggacctttc tgaggaggac acagaatgtt aaactctgca tcatggacac     4020
agtttccgat cacagatact ggccttcaat ggaaaaaaaa aaaacccag atagttcttg     4080
tgagacctgg acagcacgtc caacatccag acattgtggt cgggcacagt gacagagttg    4140
atgcatttct cacgggttat tctacagagc ttttgtcaag tccaatggaa ggaggtagat    4200
tcttgttcag atatgattc gggaaaaaacc gagtccttga caaagacagg agacaccctc    4260
agttgggagg caagtttctc ttaccttgga ctttctcaca cagcaattct caccccacc    4320
ccctccactc tcacctgtct tgtaactgtg caaacaaaag tgtgcatggt ctttgtcagt    4380
tgatacctt gtgcacctct gtgcagaaac tgctgtctgt cccggctgtg gtacccgatc     4440
agtggggtag atccacgaaa ggtctcattt taggccgctt tgggaaggta accagatcgg    4500
tagctggaag cactctccag taggtggcga agggtgagtg ggtctgctga agcctgcata    4560
tcttcaccca cctcaaaccc accgggctgc acagggaca ggcacaggcc acccctgagg     4620
gacagggaag ctctcttggg ataccacctg agtttacatt cagtgtgctc aggtcaagtc    4680
tctcgctcgg ggctctgttt cggggagaat ggtttcattc caacgcactc attatcagga    4740
ttctgttttc                                                          4750
```

<210> SEQ ID NO 8
<211> LENGTH: 4057
<212> TYPE: DNA
<213> ORGANISM: Homo sapiens

<400> SEQUENCE: 8

```
gggagcagga gcctcgctgg ctgcttcgct cgcgctctac gcgctcagtc cccggcggta      60
gcaggagcct ggacccaggc gccggcggcg ggcgtgaggc gccggagccc ggcctcgagg     120
tgcataccgg accccattc gcatctaaca aggaatctgc gccccagaga gtcccggacg     180
ccgccggtcg gtgcccggcg cgccgggcca tgcagcgacg gccgccgcgg agctccgagc    240
agcggtagcg ccccctgta aagcggttcg ctatgccggg accactgtga accctgccgc     300
ctgccggaac actcttcgct ccggaccagc tcagcctctg ataagctgga ctcggcacgc    360
ccgcaacaag caccgaggag ttaagagagc cgcaagcgca gggaaggcct ccccgcacgg    420
gtggggaaa gcgccggtg cagcgcgggg acaggcactc gggctggcac tggctgctag     480
ggatgtcgtc ctggataagg tggcatggac ccgccatggc gcggctctgg ggcttctgct    540
ggctggttgt gggcttctgg agggccgctt tcgcctgtcc cacgtcctgc aaatgcagtg    600
cctctcggat ctggtgcagc gaccttctc ctggcatcgt ggcatttccg agattggagc     660
ctaacagtgt agatcctgag aacatcaccg aaattttcat cgcaaaccag aaaaggttag    720
aaatcatcaa cgaagatgat gttgaagctt atgtgggact gagaaatctg acaattgtgg    780
attctggatt aaaatttgtg gctcataaag catttctgaa aacagcaac ctgcagcaca     840
tcaatttac ccgaaacaaa ctgacgagtt tgtctaggaa acatttccgt caccttgact    900
tgtctgaact gatcctggtg ggcaatccat ttacatgctc ctgtgacatt atgtggatca    960
```

```
agactctcca agaggctaaa tccagtccag acactcagga tttgtactgc ctgaatgaaa    1020
gcagcaagaa tattcccctg gcaaacctgc agatacccaa ttgtggtttg ccatctgcaa    1080
atctggccgc acctaacctc actgtggagg aaggaaagtc tatcacatta tcctgtagtg    1140
tggcaggtga tccggttcct aatatgtatt gggatgttgg taacctggtt tccaaacata    1200
tgaatgaaac aagccacaca cagggctcct taaggataac taacatttca tccgatgaca    1260
gtgggaagca gatctcttgt gtggcggaaa atcttgtagg agaagatcaa gattctgtca    1320
acctcactgt gcattttgca ccaactatca catttctcga atctccaacc tcagaccacc    1380
actggtgcat tccattcact gtgaaaggca accccaaacc agcgcttcag tggttctata    1440
acggggcaat attgaatgag tccaaataca tctgtactaa aatacatgtt accaatcaca    1500
cggagtacca cggctgcctc cagctggata atcccactca catgaacaat ggggactaca    1560
ctctaatagc caagaatgag tatgggaagg atgagaaaca gatttctgct cacttcatgg    1620
gctggcctgg aattgacgat ggtgcaaacc caaattatcc tgatgtaatt tatgaagatt    1680
atggaactgc agcgaatgac atcggggaca ccacgaacag aagtaatgaa atcccttcca    1740
cagacgtcac tgataaaacc ggtcgggaac atctctcggt ctatgctgtg gtggtgattg    1800
cgtctgtggt gggattttgc cttttggtaa tgctgtttct gcttaagttg gcaagacact    1860
ccaagtttgg catgaaagat ttctcatggt ttggatttgg gaaagtaaaa tcaagacaag    1920
gtgttggccc agcctccgtt atcagcaatg atgatgactc tgccagccca ctccatcaca    1980
tctccaatgg gagtaacact ccatcttctt cggaaggtgg cccagatgct gtcattattg    2040
gaatgaccaa gatccctgtc attgaaaatc cccagtactt tggcatcacc aacagtcagc    2100
tcaagccaga cacatttgtt cagcacatca gcgacataa cattgttctg aaaagggagc    2160
taggcgaagg agccttttgga aaagtgttcc tagctgaatg ctataacctc tgtcctgagc    2220
aggacaagat cttggtggca gtgaagaccc tgaaggatgc cagtgacaat gcacgcaagg    2280
acttccaccg tgaggccgag ctcctgacca acctccagca tgagcacatc gtcaagttct    2340
atggcgtctg cgtggagggc acccccctca tcatggtctt tgagtacatg aagcatgggg    2400
acctcaacaa gttcctcagg gcacacggcc ctgatgccgt gctgatggct gagggcaacc    2460
cgcccacgga actgacgcag tcgcagatgc tgcatatagc ccagcagatc gccgcgggca    2520
tggtctacct ggcgtcccag cacttcgtgc accgcgattt ggccaccagg aactgcctgg    2580
tcggggagaa cttgctggtg aaaatcgggg actttgggat gtcccgggac gtgtacagca    2640
ctgactacta cagggtcggt ggccacacaa tgctgcccat tcgctggatg cctccagaga    2700
gcatcatgta caggaaattc acgacggaaa gcgacgtctg gagcctgggg gtcgtgttgt    2760
gggagatttt cacctatggc aaacagccct ggtaccagct gtcaaacaat gaggtgatag    2820
agtgtatcac tcagggccga gtcctgcagc gaccccgcac gtgcccccag gaggtgtatg    2880
agctgatgct ggggtgctgg cagcgagagc cccacgagg gaagaacatc aagggcatcc    2940
ataccctcct tcagaacttg gccaaggcat ctccggtcta cctggacatt ctaggctagg    3000
gcccttttcc ccagaccgat ccttcccaac gtactcctca gacgggctga gaggatgaac    3060
atcttttaac tgccgctgga ggccaccaag ctgctctcct tcactctgac agtattaaca    3120
tcaaagactc cgagaagctc tcgagggaag cagtgtgtac ttcttcatcc atagacacag    3180
tattgacttc ttttttggcat tatctctttc tctcttccca tctcccttgg ttgttccttt    3240
ttcttttttt aaattttctt tttcttcttt ttttcgtct tccctgcttc acgattctta    3300
ccctttcttt tgaatcaatc tggcttctgc attactatta actctgcata gacaaaggcc    3360
```

```
ttaacaaacg taatttgtta tatcagcaga cactccagtt tgcccaccac aactaacaat    3420
gccttgttgt attcctgcct ttgatgtgga tgaaaaaaag ggaaaacaaa tatttcactt    3480
aaactttgtc acttctgctg tacagatatc gagagtttct atggattcac ttctatttat    3540
ttattattat tactgttctt attgttttttg gatggcttaa gcctgtgtat aaaaaagaaa    3600
acttgtgttc aatctgtgaa gcctttatct atgggagatt aaaaccagag agaaagaaga    3660
tttattatga accgcaatat gggaggaaca aagacaacca ctgggatcag ctggtgtcag    3720
tccctactta ggaaatactc agcaactgtt agctgggaag aatgtattcg gccacttccc    3780
ctgaggacct ttctgaggag taaaaagact actggcctct gtgccatgga tgattcttttt    3840 cccatcacca gaaatgatag cgtgcagtag agagcaaaga tggcttccgt gagacacaag    3900
atggcgcata gtgtgctcgg acacagttttt gtcttcgtag gttgtgatga tagcactggt    3960
ttgtttctca agcgctatcc acagaacctt tgtcaacttc agttgaaaag aggtggattc    4020
atgtccagag ctcatttcgg ggtcaggtgg gaaagcc                             4057
```

<210> SEQ ID NO 9
<211> LENGTH: 2466
<212> TYPE: DNA
<213> ORGANISM: Mus musculus
<220> FEATURE:
<221> NAME/KEY: misc_feature
<222> LOCATION: (1)..(93)
<223> OTHER INFORMATION: Signal Peptide
<220> FEATURE:
<221> NAME/KEY: misc_feature
<222> LOCATION: (94)..(1287)
<223> OTHER INFORMATION: Extracellular Domain
<220> FEATURE:
<221> NAME/KEY: misc_feature
<222> LOCATION: (1288)..(1359)
<223> OTHER INFORMATION: Transmembrane Domain
<220> FEATURE:
<221> NAME/KEY: misc_feature
<222> LOCATION: (1360)..(2463)
<223> OTHER INFORMATION: Cytoplasmic Domain

<400> SEQUENCE: 9

```
atgtcgccct ggctgaagtg gcatggaccc gccatggcgc ggctctgggg cttatgcctg     60
ctggtcttgg gcttctggag ggcctctctc gcctgcccga cgtcctgcaa atgcagttcc    120
gctaggattt ggtgtactga gccttctcca ggcatcgtgg cattcccgag gttggaacct    180
aacagcgttg acccggagaa catcacggaa attctcattg caaaccagaa aaggctagaa    240
atcatcaatg aagatgacgt tgaagcttac gtggggctga gaaaccttac aattgtggat    300
tccggcttaa agtttgtggc ttacaaagcg tttctgaaaa acagcaacct gcggcacata    360
aatttcacac gaaacaagct gacgagtttg tccaggagac atttccgcca ccttgacttg    420
tctgacctga tcctgacggg taatccgttc acgtgctcct gcgacatcat gtggctcaag    480
actctccagg agactaaatc cagccccgac actcaggatt tgtactgcct caatgagagc    540
agcaagaaca tgcccctggc gaacctgcag ataccccaatt gtggtctgcc atctgcacgt    600
ctggctgctc ctaacctcac cgtggaggaa ggaaagtctg tgacccttttc ctgcagtgtg    660 gggggtgacc cactccccac cttgtactgg gacgttggga atttggtttc caagcacatg    720
aatgaaacaa gccacacaca gggctcctta aggataacga acatttcatc tgatgacagt    780
ggaaagcaaa tctcttgtgt ggcagaaaac cttgtaggag aagatcaaga ttctgtgaac    840
ctcactgtgc attttgcgcc aactatcacg tttctcgagt ctccaacctc agatcaccac    900
```

```
tggtgcattc cattcactgt gagaggcaac cccaagcctg cgcttcagtg gttctacaat    960
ggggccatac tgaatgagtc caagtacatc tgtactaaga tccacgtcac caatcacacg   1020
gagtaccatg gctgcctcca gctggataac cccactcata tgaataacgg agactacacc   1080
ctgatggcca agaacgagta tgggaaggat gagagacaga tctccgctca cttcatgggc   1140
cggcctggag tcgactacga gacaaaccca aattaccctg aagtcctcta tgaagactgg   1200
accacgccaa ctgacattgg ggatactacg aacaaaagta atgaaatccc ctccacggat   1260
gttgctgacc aaagcaatcg ggagcatctc tcggtctatg ccgtggtggt gattgcatct   1320
gtggtgggat tctgcctgct ggtgatgttg ctcctgctca agttggcgag acattccaag   1380
tttggcatga aaggcccagc ttcggtcatc agcaacgacg atgactctgc cagcccctc    1440
caccacatct ccaatgggag taacactcca tcttcttcgg agggcggtcc cgacgctgtc   1500
attattggaa tgaccaagat tcctgttatt gaaaaccccc agtactttgg catcaccaac   1560
agtcagctca agccagacac atttgttcag catatcaaga dacacaacat cgttctgaag   1620
agggaacttg gggaaggagc cttcgggaaa gttttccttg ccgagtgcta caacctctgc   1680
ccagagcagg ataagatcct ggtggctgtg aagacgctga aggacgccag cgacaatgca   1740
cgcaaggact ttcatcggga agctgagctg ctgaccaacc tccagcacga gcacattgtc   1800
aagttctacg gtgtctgtgt ggagggcgac ccactcatca tggtctttga gtacatgaag   1860
cacggggacc tcaacaagtt ccttagggca cacgggcccg acgcagtgct gatggcagag   1920
ggtaacccgc ccacagagct gacgcagtcg cagatgctgc acatcgctca gcaaatcgca   1980
gcaggtatgg tctacctggc gtcccaacac tttgtgcacc gtgacctggc cacccggaac   2040
tgcctggtgg gagagaacct gctggtgaaa attgggggact ttgggatgtc ccgagatgtg   2100
tacagcaccg actactatcg ggtcggtggc cacacaatgt tgcccatccg atggatgcct   2160
ccagagagca tcatgtacag gaaattcacc accgagagcg acgtctggag cctgggcgtt   2220
gtgttgtggg agatcttcac ctacggcaag cagcccctgg tatcagctatc gaacaatgag   2280
gtgatagagt gcatcaccca gggaagagtc cttcagcggc ctcgaacgtg tccccaggag   2340
gtgtatgagc tcatgcttgg atgctggcag cgggaaccac acacccggaa gaacatcaag   2400
agcatccaca ccctccttca gaacttggcc aaggcatctc ccgtctacct ggatatccta   2460
ggctag                                                              2466
```

<210> SEQ ID NO 10
<211> LENGTH: 2466
<212> TYPE: DNA
<213> ORGANISM: Rattus norvegicus
<220> FEATURE:
<221> NAME/KEY: misc_feature
<222> LOCATION: (1)..(93)
<223> OTHER INFORMATION: Signal Peptide
<220> FEATURE:
<221> NAME/KEY: misc_feature
<222> LOCATION: (94)..(1287)
<223> OTHER INFORMATION: Extracellular Domain
<220> FEATURE:
<221> NAME/KEY: misc_feature
<222> LOCATION: (1288)..(1359)
<223> OTHER INFORMATION: Transmembrane Domain
<220> FEATURE:
<221> NAME/KEY: misc_feature
<222> LOCATION: (1360)..(2463)
<223> OTHER INFORMATION: Cytoplasmic Domain

<400> SEQUENCE: 10

```
atgtcgccct ggccgaggtg gcatggaccc gccatggcgc ggctctgggg cttatgcttg    60
```

```
ctggtcttgg gcttctggag ggcttctctt gcctgcccca tgtcctgcaa atgcagcacc      120
actaggattt ggtgtaccga gccttctcct ggcatcgtgg catttccgag gttggaacct      180
aacagcattg acccagagaa catcaccgaa attctcattg caaaccagaa aaggttagaa      240
atcatcaatg aagatgatgt cgaagcttac gtggggctga aaaaccttac aattgtggat      300
tccggcttaa agtttgtggc ttacaaggcg tttctgaaga acggcaacct gcggcacatc      360
aatttcactc gaaacaagct gacgagtttg tccaggagac atttccgcca ccttgacttg      420
tctgacctga tcctgacggg taatccgttc acgtgttcct gtgacatcat gtggctcaag      480
actctccagg agacgaaatc cagccccgac actcaggatt tgtattgcct caatgagagc      540
agcaagaata cccctctggc gaacctgcag attcccaatt gtggtctgcc gtctgcacgt      600
ctggccgctc ctaacctcac ggtggaggaa gggaagtctg tgaccatttc ctgcagcgtc      660
gggggtgacc cgctccccac cttgtactgg gacgttggga atttggtttc caaacacatg      720
aatgaaacaa gccacacaca gggctcctta aggataacaa acatttcatc ggatgacagt      780
gggaaacaaa tctcttgtgt ggcagaaaac ctcgttggag aagatcaaga ctctgtgaac      840
ctcactgtgc attttgcacc aaccatcaca tttctcgaat ctccaacctc agaccaccac      900
tggtgcatcc cattcactgt gagaggcaac cccaagccag cacttcagtg gttctacaac      960
ggagccatac tgaatgaatc caagtacatc tgtaccaaaa tacacgtcac caatcacacg     1020
gagtaccacg gctgcctcca gctggataac cccactcata tgaataatgg agactacacc     1080
ctaatggcca agaatgaata tgggaaggac gagagacaga tttctgctca cttcatgggc     1140
cggcctggag ttgactatga gacaaaccca aattaccctg aagtcctcta tgaagactgg     1200
accacgccaa ctgacatcgg ggatactaca acaaaagta atgagatccc ctccacggat     1260
gttgctgacc aaaccaatcg ggagcatctc tcggtctatg ccgtggtggt gattgcctct     1320
gtggtaggat tctgcctgct ggtgatgctg cttctgctca gttggcgag acattccaag     1380 tttggcatga aaggcccagc ttccgtcatc agcaacgacg atgactctgc cagccctctc     1440
caccacatct ccaacgggag caacactccg tcttcttcgg agggcgggcc cgatgctgtc     1500
atcattggga tgaccaagat ccctgtcatt gaaaaccccc agtacttcgg tatcaccaac     1560
agccagctca gccggacac atttgttcag cacatcaaga gacacaacat cgttctgaag     1620
agggagcttg gagaaggagc ctttgggaaa gttttcctag cggagtgcta taacctctgc     1680
cccgagcagg ataagatcct ggtggccgtg aagacgctga aggacgccag cgacaatgct     1740
cgcaaggact tcatcgcga agccgagctg ctgaccaacc tccagcacga gcacattgtc     1800
aagttctacg gtgtctgtgt ggagggcgac ccactcatca tggtctttga gtacatgaag     1860 cacgggacc tcaacaagtt ccttagggca cacgggccag atgcagtgct gatgcagag     1920 ggtaacccgc ccaccgagct gacgcagtcg cagatgctgc acatcgctca gcaaatcgca     1980
gcaggcatgt tctacctggc atcccaacac ttcgtgcacc gagacctggc cacccggaac     2040
tgcttggtag agagaacct gctggtgaaa attggggact tcgggatgtc ccgggatgta     2100
tacagcaccg actactaccg ggttggtggc cacacaatgt tgcccatccg atggatgcct     2160
ccagagagca tcatgtacag gaaattcacc accgagagtg acgtctggag cctgggagtt     2220
gtgttgtggg agatcttcac ctacggcaag cagccctggt atcagctatc aaacaacgag     2280
gtgatagaat gcatcaccca gggcagagtc cttcagcggc ctcgcacgtg tccccaggag     2340
gtgtacgagc tgatgctggg atgctggcag cgggaaccac acacaaggaa gaacatcaag     2400
```

| | |
|---|---|
| aacatccaca cactccttca gaacttggcg aaggcgtcgc ccgtctacct ggacatccta | 2460 |
| ggctag | 2466 |

```
<210> SEQ ID NO 11
<211> LENGTH: 2517
<212> TYPE: DNA
<213> ORGANISM: Homo sapiens
<220> FEATURE:
<221> NAME/KEY: misc_feature
<222> LOCATION: (1)..(93)
<223> OTHER INFORMATION: Signal Peptide
<220> FEATURE:
<221> NAME/KEY: misc_feature
<222> LOCATION: (94)..(1290)
<223> OTHER INFORMATION: Extracellular Domain
<220> FEATURE:
<221> NAME/KEY: misc_feature
<222> LOCATION: (1291)..(1362)
<223> OTHER INFORMATION: Transmembrane Domain
<220> FEATURE:
<221> NAME/KEY: misc_feature
<222> LOCATION: (1363)..(2514)
<223> OTHER INFORMATION: Cytoplasmic Domain
```

<400> SEQUENCE: 11

| | |
|---|---|
| atgtcgtcct ggataaggtg gcatggaccc gccatggcgc ggctctgggg cttctgctgg | 60 |
| ctggttgtgg gcttctggag ggccgctttc gcctgtccca cgtcctgcaa atgcagtgcc | 120 |
| tctcggatct ggtgcagcga cccttctcct ggcatcgtgg catttccgag attggagcct | 180 |
| aacagtgtag atcctgagaa catcaccgaa attttcatcg caaaccagaa aaggttagaa | 240 |
| atcatcaacg aagatgatgt tgaagcttat gtgggactga aaatctgac aattgtggat | 300 |
| tctggattaa aatttgtggc tcataaagca tttctgaaaa acagcaacct gcagcacatc | 360 |
| aatttttaccc gaaacaaact gacgagtttg tctaggaaac atttccgtca ccttgacttg | 420 |
| tctgaactga tcctggtggg caatccattt acatgctcct gtgacattat gtggatcaag | 480 |
| actctccaag aggctaaatc cagtccagac actcaggatt tgtactgcct gaatgaaagc | 540 |
| agcaagaata ttcccctggc aaacctgcag atacccaatt gtggtttgcc atctgcaaat | 600 |
| ctggccgcac ctaacctcac tgtggaggaa ggaaagtcta tcacattatc ctgtagtgtg | 660 |
| gcaggtgatc cggttcctaa tatgtattgg gatgttggta acctggtttc caaacatatg | 720 |
| aatgaaacaa gccacacaca gggctcctta aggataacta acatttcatc cgatgacagt | 780 |
| gggaagcaga tctcttgtgt ggcggaaaat cttgtaggag aagatcaaga ttctgtcaac | 840 |
| ctcactgtgc attttgcacc aactatcaca tttctcgaat ctccaacctc agaccaccac | 900 |
| tggtgcattc cattcactgt gaaaggcaac cccaaaccag cgcttcagtg gttctataac | 960 |
| ggggcaatat tgaatgagtc caaatacatc tgtactaaaa tacatgttac caatcacacg | 1020 |
| gagtaccacg gctgcctcca gctggataat cccactcaca tgaacaatgg ggactacact | 1080 |
| ctaatagcca agaatgagta tgggaaggat gagaaacaga tttctgctca cttcatgggc | 1140 |
| tggcctggaa ttgacgatgg tgcaaaccca aattatcctg atgtaattta tgaagattat | 1200 |
| ggaactgcag cgaatgacat cggggacacc acgaacagaa gtaatgaaat cccttccaca | 1260 |
| gacgtcactg ataaaaccgg tcgggaacat ctctcggtct atgctgtggt ggtgattgcg | 1320 |
| tctgtggtgg gattttgcct tttggtaatg ctgtttctgc ttaagttggc aagacactcc | 1380 |
| aagtttggca tgaaagattt ctcatggttt ggatttggga agtaaaaatc aagacaaggt | 1440 |
| gttggcccag cctccgttat cagcaatgat gatgactctg ccagcccact ccatcacatc | 1500 |
| tccaatggga gtaacactcc atcttcttcg gaaggtggcc cagatgctgt cattattgga | 1560 |

-continued

```
atgaccaaga tccctgtcat tgaaaatccc cagtactttg gcatcaccaa cagtcagctc    1620
aagccagaca catttgttca gcacatcaag cgacataaca ttgttctgaa aagggagcta    1680
ggcgaaggag cctttggaaa agtgttccta gctgaatgct ataacctctg tcctgagcag    1740
gacaagatct tggtggcagt gaagaccctg aaggatgcca gtgacaatgc acgcaaggac    1800
ttccaccgtg aggccgagct cctgaccaac ctccagcatg agcacatcgt caagttctat    1860
ggcgtctgcg tggagggcga ccccctcatc atggtctttg agtacatgaa gcatgggac    1920 ctcaacaagt tcctcagggc acacggccct gatgccgtgc tgatggctga gggcaacccg    1980
cccacggaac tgacgcagtc gcagatgctg catatagccc agcagatcgc cgcgggcatg    2040
gtctacctgg cgtcccagca cttcgtgcac cgcgatttgg ccaccaggaa ctgcctggtc    2100
ggggagaact tgctggtgaa aatcggggac tttgggatgt cccgggacgt gtacagcact    2160
gactactaca gggtcggtgg ccacacaatg ctgcccattc gctggatgcc tccagagagc    2220
atcatgtaca ggaaattcac gacggaaagc gacgtctgga gcctgggggt cgtgttgtgg    2280
gagattttca cctatggcaa acagccctgg taccagctgt caaacaatga ggtgatagag    2340
tgtatcactc agggccgagt cctgcagcga ccccgcacgt gccccagga ggtgtatgag    2400 ctgatgctgg ggtgctggca gcgagagccc cacatgagga agaacatcaa gggcatccat    2460
accctccttc agaacttggc caaggcatct ccggtctacc tggacattct aggctag    2517
```

<210> SEQ ID NO 12
<211> LENGTH: 2469
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(93)
<223> OTHER INFORMATION: Signal Peptide
<220> FEATURE:
<221> NAME/KEY: misc_feature
<222> LOCATION: (1)..(93)
<223> OTHER INFORMATION: Mouse Sequence
<220> FEATURE:
<221> NAME/KEY: misc_feature
<222> LOCATION: (94)..(1290)
<223> OTHER INFORMATION: Extracellular Domain
<220> FEATURE:
<221> NAME/KEY: misc_feature
<222> LOCATION: (94)..(1296)
<223> OTHER INFORMATION: Human Sequence
<220> FEATURE:
<221> NAME/KEY: misc_feature
<222> LOCATION: (1291)..(1362)
<223> OTHER INFORMATION: Transmembrane Domain
<220> FEATURE:
<221> NAME/KEY: misc_feature
<222> LOCATION: (1297)..(2466)
<223> OTHER INFORMATION: Mouse Sequence
<220> FEATURE:
<221> NAME/KEY: misc_feature
<222> LOCATION: (1363)..(2466)
<223> OTHER INFORMATION: Cytoplasmic Domain

<400> SEQUENCE: 12

```
atgtcgccct ggctgaagtg gcatggaccc gccatggcgc ggctctgggg cttatgcctg      60
ctggtcttgg gcttctggag ggcctctctc gcctgtccca cgtcctgcaa atgcagtgcc     120
tctcggatct ggtgcagcga cccttctcct ggcatcgtgg catttccgag attggagcct     180
aacagtgtag atcctgagaa catcaccgaa attttcatcg caaaccagaa aaggttagaa     240
```

```
atcatcaacg aagatgatgt tgaagcttat gtgggactga gaaatctgac aattgtggat      300
tctggattaa aatttgtggc tcataaagca tttctgaaaa acagcaacct gcagcacatc      360
aattttaccc gaaacaaact gacgagtttg tctaggaaac atttccgtca ccttgacttg      420
tctgaactga tcctggtggg caatccattt acatgctcct gtgacattat gtggatcaag      480
actctccaag aggctaaatc cagtccagac actcaggatt tgtactgcct gaatgaaagc      540
agcaagaata ttcccctggc aaacctgcag atacccaatt gtggtttgcc atctgcaaat      600
ctggccgcac ctaacctcac tgtggaggaa ggaaagtcta tcacattatc ctgtagtgtg      660
gcaggtgatc cggttcctaa tatgtattgg gatgttggta acctggtttc caaacatatg      720
aatgaaacaa gccacacaca gggctcctta aggataacta acatttcatc cgatgacagt      780
gggaagcaga tctcttgtgt ggcggaaaat cttgtaggag aagatcaaga ttctgtcaac      840
ctcactgtgc attttgcacc aactatcaca tttctcgaat ctccaacctc agaccaccac      900
tggtgcattc cattcactgt gaaaggcaac cccaaaccag cgcttcagtg gttctataac      960
ggggcaatat tgaatgagtc aaatacatc tgtactaaaa tacatgttac caatcacacg      1020
gagtaccacg gctgcctcca gctggataat cccactcaca tgaacaatgg ggactacact      1080
ctaatagcca agaatgagta tgggaaggat gagaaacaga tttctgctca cttcatgggc      1140
tggcctggaa ttgacgatgg tgcaaaccca aattatcctg atgtaattta tgaagattat      1200
ggaactgcag cgaatgacat cggggacacc acgaacagaa gtaatgaaat cccttccaca      1260
gacgtcactg ataaaaccgg tcgggaacat ctctcggtct atgccgtggt ggtgattgca      1320
tctgtggtgg gattctgcct gctggtgatg ttgctcctgc tcaagttggc gagacattcc      1380
aagtttggca tgaaaggccc agcttcggtc atcagcaacg acgatgactc tgccagcccc      1440
ctccaccaca tctccaatgg gagtaacact ccatcttctt cggagggcgg tcccgacgct      1500
gtcattattg gaatgaccaa gattcctgtt attgaaaacc cccagtactt tggcatcacc      1560
aacagtcagc tcaagccaga cacatttgtt cagcatatca agagacacaa catcgttctg      1620
aagagggaac ttgggaagg agccttcggg aaagttttcc ttgccgagtg ctacaacctc      1680
tgcccagagc aggataagat cctggtggct gtgaagacgc tgaaggacgc cagcgacaat      1740
gcacgcaagg acttcatcg ggaagctgag ctgctgacca cctccagca cgagcacatt      1800 gtcaagttct acggtgtctg tgtggagggc gacccactca tcatggtctt tgagtacatg      1860
aagcacgggg acctcaacaa gttccttagg gcacacgggc ccgacgcagt gctgatggca      1920
gagggtaacc cgcccacaga gctgacgcag tcgcagatgc tgcacatcgc tcagcaaatc      1980
gcagcaggta tggtctacct ggcgtcccaa cactttgtgc accgtgacct ggccacccgg      2040
aactgcctgg tgggagagaa cctgctggtg aaaattgggg actttgggat gtcccgagat      2100
gtgtacagca ccgactacta tcgggtcggt ggccacacaa tgttgcccat ccgatggatg      2160
cctccagaga gcatcatgta caggaaattc accaccgaga gcgacgtctg gagcctgggc      2220
gttgtgttgt gggagatctt cacctacggc aagcagccct ggtatcagct atcgaacaat      2280
gaggtgatag agtgcatcac ccagggaaga gtccttcagc ggcctcgaac gtgtccccag      2340
gaggtgtatg agctcatgct tggatgctgg cagcgggaac cacacacccg gaagaacatc      2400
aagagcatcc acacctcct tcagaacttg gccaaggcat ctccgtcta cctggatatc      2460 ctaggctag                                                              2469
```

<210> SEQ ID NO 13
<211> LENGTH: 2469

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(93)
<223> OTHER INFORMATION: Signal Peptide
<220> FEATURE:
<221> NAME/KEY: misc_feature
<222> LOCATION: (1)..(93)
<223> OTHER INFORMATION: Rat Sequence
<220> FEATURE:
<221> NAME/KEY: misc_feature
<222> LOCATION: (94)..(1290)
<223> OTHER INFORMATION: Extracellular Domain
<220> FEATURE:
<221> NAME/KEY: misc_feature
<222> LOCATION: (94)..(1296)
<223> OTHER INFORMATION: Human Sequence
<220> FEATURE:
<221> NAME/KEY: misc_feature
<222> LOCATION: (1291)..(1362)
<223> OTHER INFORMATION: Transmembrane Domain
<220> FEATURE:
<221> NAME/KEY: misc_feature
<222> LOCATION: (1297)..(2466)
<223> OTHER INFORMATION: Rat Sequence
<220> FEATURE:
<221> NAME/KEY: misc_feature
<222> LOCATION: (1363)..(2466)
<223> OTHER INFORMATION: Cytoplasmic Domain

<400> SEQUENCE: 13
atgtcgccct ggccgaggtg gcatggaccc gccatggcgc ggctctgggg cttatgcttg      60
ctggtcttgg gcttctggag gcttctctt gcctgtccca cgtcctgcaa atgcagtgcc     120
tctcggatct ggtgcagcga cccttctcct ggcatcgtgg catttccgag attggagcct     180
aacagtgtag atcctgagaa catcaccgaa atttcatcg caaaccagaa aaggttagaa     240
atcatcaacg aagatgatgt tgaagcttat gtgggactga aaatctgac aattgtggat     300 tctggattaa aatttgtggc tcataaagca tttctgaaaa acagcaacct gcagcacatc     360
aattttaccc gaaacaaact gacgagtttg tctaggaaac attccgtca ccttgacttg     420 tctgaactga tcctggtggg caatccattt acatgctcct gtgacattat gtggatcaag     480
actctccaag aggctaaatc cagtccagac actcaggatt tgtactgcct gaatgaaagc     540
agcaagaata ttcccctggc aaacctgcag atacccaatt gtggtttgcc atctgcaaat     600
ctggccgcac ctaacctcac tgtggaggaa ggaaagtcta tcacattatc ctgtagtgtg     660
gcaggtgatc cggttcctaa tatgtattgg gatgttgta acctggtttc caaacatatg     720
aatgaaacaa gccacacaca gggctcctta aggataacta acatttcatc cgatgacagt     780
gggaagcaga tctcttgtgt ggcggaaaat cttgtaggag aagatcaaga ttctgtcaac     840
ctcactgtgc attttgcacc aactatcaca tttctcgaat ctccaacctc agaccaccac     900
tggtgcattc cattcactgt gaaaggcaac cccaaaccag cgcttcagtg gttctataac     960
ggggcaatat tgaatgagtc caaatacatc tgtactaaaa tacatgttac caatcacacg    1020
gagtaccacg gctgcctcca gctggataat cccactcaca tgaacaatgg ggactacact    1080
ctaatagcca agaatgagta tgggaaggat gagaaacaga tttctgctca cttcatgggc    1140
tggcctggaa ttgacgatgg tgcaaaccca aattatcctg atgtaattta tgaagattat    1200
ggaactgcag cgaatgacat cggggacacc acgaacagaa gtaatgaaat cccttccaca    1260
gacgtcactg ataaaaccgg tcgggaacat ctctcggtct atgccgtggt ggtgattgcc    1320
```

-continued

```
tctgtggtag gattctgcct gctggtgatg ctgcttctgc tcaagttggc gagacattcc    1380
aagtttggca tgaaaggccc agcttccgtc atcagcaacg acgatgactc tgccagccct    1440
ctccaccaca tctccaacgg gagcaacact ccgtcttctt cggagggcgg gcccgatgct    1500
gtcatcattg ggatgaccaa gatccctgtc attgaaaacc cccagtactt cggtatcacc    1560
aacagccagc tcaagccgga cacatttgtt cagcacatca agagacacaa catcgttctg    1620
aagagggagc ttggagaagg agcctttggg aaagttttcc tagcggagtg ctataacctc    1680
tgccccgagc aggataagat cctggtggcc gtgaagacgc tgaaggacgc cagcgacaat    1740
gctcgcaagg actttcatcg cgaagccgag ctgctgacca acctccagca cgagcacatt    1800
gtcaagttct acggtgtctg tgtggagggc gacccactca tcatggtctt tgagtacatg    1860
aagcacgggg acctcaacaa gttccttagg gcacacgggc cagatgcagt gctgatggca    1920
gagggtaacc cgcccaccga gctgacgcag tcgcagatgc tgcacatcgc tcagcaaatc    1980
gcagcaggca tggtctacct ggcatcccaa cacttcgtgc accgagacct ggccacccgg    2040
aactgcttgg taggagagaa cctgctggtg aaaattgggg acttcgggat gtcccgggat    2100
gtatacagca ccgactacta ccgggttggt ggccacacaa tgttgcccat ccgatggatg    2160
cctccagaga gcatcatgta caggaaattc accaccgaga gtgacgtctg gagcctggga    2220
gttgtgttgt gggagatctt cacctacggc aagcagccct ggtatcagct atcaaacaac    2280
gaggtgatag aatgcatcac ccagggcaga gtccttcagc ggcctcgcac gtgtccccag    2340
gaggtgtacg agctgatgct gggatgctgg cagcgggaac cacacacaag gaagaacatc    2400
aagaacatcc acacactcct tcagaacttg gcgaaggcgt cgcccgtcta cctggacatc    2460
ctaggctag                                                            2469
```

```
<210> SEQ ID NO 14
<211> LENGTH: 22
<212> TYPE: DNA
<213> ORGANISM: Artificial Sequence
<220> FEATURE:
<223> OTHER INFORMATION: Synthetic

<400> SEQUENCE: 14
aggtgggtag gtcctggaag tg                                                22

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
aatgctgtcc caagagtggg                                                   20

<210> SEQ ID NO 16
<211> LENGTH: 21
<212> TYPE: DNA
<213> ORGANISM: Artificial Sequence
<220> FEATURE:
<223> OTHER INFORMATION: Synthetic

<400> SEQUENCE: 16
gtcctgcatc ccttgtcttt g                                                 21

<210> SEQ ID NO 17
<211> LENGTH: 21
```

```
<212> TYPE: DNA
<213> ORGANISM: Artificial Sequence
<220> FEATURE:
<223> OTHER INFORMATION: Synthetic

<400> SEQUENCE: 17
atgtgggcgt tgtgcagtct c                                           21

<210> SEQ ID NO 18
<211> LENGTH: 24
<212> TYPE: DNA
<213> ORGANISM: Artificial Sequence
<220> FEATURE:
<223> OTHER INFORMATION: Synthetic

<400> SEQUENCE: 18
cgctgcagtg cattgaactc agca                                        24

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
ctgtggaggg acgtgaccag                                             20

<210> SEQ ID NO 20
<211> LENGTH: 22
<212> TYPE: DNA
<213> ORGANISM: Artificial Sequence
<220> FEATURE:
<223> OTHER INFORMATION: Synthetic

<400> SEQUENCE: 20
tccgctagga tttggtgtac tg                                          22

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
agccttctcc aggcatcgtg gcat                                        24

<210> SEQ ID NO 22
<211> LENGTH: 19
<212> TYPE: DNA
<213> ORGANISM: Artificial Sequence
<220> FEATURE:
<223> OTHER INFORMATION: Synthetic

<400> SEQUENCE: 22
tccgggtcaa cgctgttag                                              19

<210> SEQ ID NO 23
<211> LENGTH: 18
<212> TYPE: DNA
<213> ORGANISM: Artificial Sequence
<220> FEATURE:
<223> OTHER INFORMATION: Synthetic

<400> SEQUENCE: 23
```
tcctgcgagg gttctgac                                                    18

<210> SEQ ID NO 24
<211> LENGTH: 29
<212> TYPE: DNA
<213> ORGANISM: Artificial Sequence
<220> FEATURE:
<223> OTHER INFORMATION: Synthetic

<400> SEQUENCE: 24
tgggtgctca tatgccagag aaattgtca                                        29

<210> SEQ ID NO 25
<211> LENGTH: 22
<212> TYPE: DNA
<213> ORGANISM: Artificial Sequence
<220> FEATURE:
<223> OTHER INFORMATION: Synthetic

<400> SEQUENCE: 25
cgatctgtga tggcctgctt ac                                               22

<210> SEQ ID NO 26
<211> LENGTH: 22
<212> TYPE: DNA
<213> ORGANISM: Artificial Sequence
<220> FEATURE:
<223> OTHER INFORMATION: Synthetic

<400> SEQUENCE: 26
gggctcaggc aggtatatgt tg                                               22

<210> SEQ ID NO 27
<211> LENGTH: 27
<212> TYPE: DNA
<213> ORGANISM: Artificial Sequence
<220> FEATURE:
<223> OTHER INFORMATION: Synthetic

<400> SEQUENCE: 27
acagatgctg tcccaaacat agcaaga                                          27

<210> SEQ ID NO 28
<211> LENGTH: 23
<212> TYPE: DNA
<213> ORGANISM: Artificial Sequence
<220> FEATURE:
<223> OTHER INFORMATION: Synthetic

<400> SEQUENCE: 28
ccaaccctaa gccagtgaaa cag                                              23

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
gtgctggaga ccaggagact                                                  20

<210> SEQ ID NO 30
<211> LENGTH: 28
<212> TYPE: DNA
<213> ORGANISM: Artificial Sequence

```
<220> FEATURE:
<223> OTHER INFORMATION: Synthetic

<400> SEQUENCE: 30
tgccatactc agtttatacg gtgctgac                                           28

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
gcctggtggc tcagtcaatg                                                    20

<210> SEQ ID NO 32
<211> LENGTH: 19
<212> TYPE: DNA
<213> ORGANISM: Artificial Sequence
<220> FEATURE:
<223> OTHER INFORMATION: Synthetic

<400> SEQUENCE: 32
gcagacactg gatgggtca                                                     19

<210> SEQ ID NO 33
<211> LENGTH: 26
<212> TYPE: DNA
<213> ORGANISM: Artificial Sequence
<220> FEATURE:
<223> OTHER INFORMATION: Synthetic

<400> SEQUENCE: 33
ccattcgcga gttatgagaa gctgca                                             26

<210> SEQ ID NO 34
<211> LENGTH: 22
<212> TYPE: DNA
<213> ORGANISM: Artificial Sequence
<220> FEATURE:
<223> OTHER INFORMATION: Synthetic

<400> SEQUENCE: 34
acagggttag ctggtgaatg ga                                                 22

<210> SEQ ID NO 35
<211> LENGTH: 19
<212> TYPE: DNA
<213> ORGANISM: Artificial Sequence
<220> FEATURE:
<223> OTHER INFORMATION: Synthetic

<400> SEQUENCE: 35
tcggagcaca ggactacag                                                     19

<210> SEQ ID NO 36
<211> LENGTH: 25
<212> TYPE: DNA
<213> ORGANISM: Artificial Sequence
<220> FEATURE:
<223> OTHER INFORMATION: Synthetic

<400> SEQUENCE: 36
caagaggaac tgtgtccagg aaagc                                              25
```

```
<210> SEQ ID NO 37
<211> LENGTH: 22
<212> TYPE: DNA
<213> ORGANISM: Artificial Sequence
<220> FEATURE:
<223> OTHER INFORMATION: Synthetic

<400> SEQUENCE: 37
agcgtgcctc acctaacctc ta                                              22

<210> SEQ ID NO 38
<211> LENGTH: 19
<212> TYPE: DNA
<213> ORGANISM: Artificial Sequence
<220> FEATURE:
<223> OTHER INFORMATION: Synthetic

<400> SEQUENCE: 38
gcacagcact gtaaaggca                                                  19

<210> SEQ ID NO 39
<211> LENGTH: 29
<212> TYPE: DNA
<213> ORGANISM: Artificial Sequence
<220> FEATURE:
<223> OTHER INFORMATION: Synthetic

<400> SEQUENCE: 39
acggaactcg aaggaattgg tattgttgt                                       29

<210> SEQ ID NO 40
<211> LENGTH: 23
<212> TYPE: DNA
<213> ORGANISM: Artificial Sequence
<220> FEATURE:
<223> OTHER INFORMATION: Synthetic

<400> SEQUENCE: 40
acacagctat gggagaaaga ctg                                             23

<210> SEQ ID NO 41
<211> LENGTH: 23
<212> TYPE: DNA
<213> ORGANISM: Artificial Sequence
<220> FEATURE:
<223> OTHER INFORMATION: Synthetic

<400> SEQUENCE: 41
ccggttggcg agtgcgcatg cac                                             23

<210> SEQ ID NO 42
<211> LENGTH: 23
<212> TYPE: DNA
<213> ORGANISM: Artificial Sequence
<220> FEATURE:
<223> OTHER INFORMATION: Synthetic

<400> SEQUENCE: 42
ccttccggtt ggcgagtgcg cat                                             23

<210> SEQ ID NO 43
<211> LENGTH: 23
<212> TYPE: DNA
<213> ORGANISM: Artificial Sequence
<220> FEATURE:
<223> OTHER INFORMATION: Synthetic
```

```
<400> SEQUENCE: 43
ccaagggtgc gttgatggat cta                                              23

<210> SEQ ID NO 44
<211> LENGTH: 23
<212> TYPE: DNA
<213> ORGANISM: Artificial Sequence
<220> FEATURE:
<223> OTHER INFORMATION: Synthetic

<400> SEQUENCE: 44
gaatgccaag ggtgcgttga tgg                                              23

<210> SEQ ID NO 45
<211> LENGTH: 23
<212> TYPE: DNA
<213> ORGANISM: Artificial Sequence
<220> FEATURE:
<223> OTHER INFORMATION: Synthetic

<400> SEQUENCE: 45
ctgggtgatt gggactgaga aag                                              23

<210> SEQ ID NO 46
<211> LENGTH: 24
<212> TYPE: DNA
<213> ORGANISM: Artificial Sequence
<220> FEATURE:
<223> OTHER INFORMATION: Synthetic

<400> SEQUENCE: 46
cagccttgaa agtatggctt gggc                                             24

<210> SEQ ID NO 47
<211> LENGTH: 18
<212> TYPE: DNA
<213> ORGANISM: Artificial Sequence
<220> FEATURE:
<223> OTHER INFORMATION: Synthetic

<400> SEQUENCE: 47
gcactcgcca accggaag                                                    18

<210> SEQ ID NO 48
<211> LENGTH: 23
<212> TYPE: DNA
<213> ORGANISM: Artificial Sequence
<220> FEATURE:
<223> OTHER INFORMATION: Synthetic

<400> SEQUENCE: 48
gaccagctca cccttactta tgg                                              23

<210> SEQ ID NO 49
<211> LENGTH: 23
<212> TYPE: DNA
<213> ORGANISM: Artificial Sequence
<220> FEATURE:
<223> OTHER INFORMATION: Synthetic

<400> SEQUENCE: 49
actgaatgcc aagggtgcgt tga                                              23

<210> SEQ ID NO 50
```

```
<211> LENGTH: 23
<212> TYPE: DNA
<213> ORGANISM: Artificial Sequence
<220> FEATURE:
<223> OTHER INFORMATION: Synthetic

<400> SEQUENCE: 50
tcttggaaat ccgctgaaga gtt                                        23

<210> SEQ ID NO 51
<211> LENGTH: 31
<212> TYPE: PRT
<213> ORGANISM: Mus musculus

<400> SEQUENCE: 51

Met Ser Pro Trp Leu Lys Trp His Gly Pro Ala Met Ala Arg Leu Trp
1               5                   10                  15

Gly Leu Cys Leu Leu Val Leu Gly Phe Trp Arg Ala Ser Leu Ala
            20                  25                  30

<210> SEQ ID NO 52
<211> LENGTH: 398
<212> TYPE: PRT
<213> ORGANISM: Mus musculus

<400> SEQUENCE: 52

Cys Pro Thr Ser Cys Lys Cys Ser Ser Ala Arg Ile Trp Cys Thr Glu
1               5                   10                  15

Pro Ser Pro Gly Ile Val Ala Phe Pro Arg Leu Glu Pro Asn Ser Val
            20                  25                  30

Asp Pro Glu Asn Ile Thr Glu Ile Leu Ile Ala Asn Gln Lys Arg Leu
        35                  40                  45

Glu Ile Ile Asn Glu Asp Asp Val Glu Ala Tyr Val Gly Leu Arg Asn
    50                  55                  60

Leu Thr Ile Val Asp Ser Gly Leu Lys Phe Val Ala Tyr Lys Ala Phe
65                  70                  75                  80

Leu Lys Asn Ser Asn Leu Arg His Ile Asn Phe Thr Arg Asn Lys Leu
                85                  90                  95

Thr Ser Leu Ser Arg Arg His Phe Arg His Leu Asp Leu Ser Asp Leu
            100                 105                 110

Ile Leu Thr Gly Asn Pro Phe Thr Cys Ser Cys Asp Ile Met Trp Leu
        115                 120                 125

Lys Thr Leu Gln Glu Thr Lys Ser Ser Pro Asp Thr Gln Asp Leu Tyr
    130                 135                 140

Cys Leu Asn Glu Ser Ser Lys Asn Met Pro Leu Ala Asn Leu Gln Ile
145                 150                 155                 160

Pro Asn Cys Gly Leu Pro Ser Ala Arg Leu Ala Ala Pro Asn Leu Thr
                165                 170                 175

Val Glu Glu Gly Lys Ser Val Thr Leu Ser Cys Ser Val Gly Gly Asp
            180                 185                 190

Pro Leu Pro Thr Leu Tyr Trp Asp Val Gly Asn Leu Val Ser Lys His
        195                 200                 205

Met Asn Glu Thr Ser His Thr Gln Gly Ser Leu Arg Ile Thr Asn Ile
    210                 215                 220

Ser Ser Asp Asp Ser Gly Lys Gln Ile Ser Cys Val Ala Glu Asn Leu
225                 230                 235                 240

Val Gly Glu Asp Gln Asp Ser Val Asn Leu Thr Val His Phe Ala Pro
                245                 250                 255
```

```
Thr Ile Thr Phe Leu Glu Ser Pro Thr Ser Asp His His Trp Cys Ile
            260                 265                 270
Pro Phe Thr Val Arg Gly Asn Pro Lys Pro Ala Leu Gln Trp Phe Tyr
            275                 280                 285
Asn Gly Ala Ile Leu Asn Glu Ser Lys Tyr Ile Cys Thr Lys Ile His
            290                 295                 300
Val Thr Asn His Thr Glu Tyr His Gly Cys Leu Gln Leu Asp Asn Pro
305                 310                 315                 320
Thr His Met Asn Asn Gly Asp Tyr Thr Leu Met Ala Lys Asn Glu Tyr
            325                 330                 335
Gly Lys Asp Glu Arg Gln Ile Ser Ala His Phe Met Gly Arg Pro Gly
            340                 345                 350
Val Asp Tyr Glu Thr Asn Pro Asn Tyr Pro Glu Val Leu Tyr Glu Asp
            355                 360                 365
Trp Thr Thr Pro Thr Asp Ile Gly Asp Thr Thr Asn Lys Ser Asn Glu
            370                 375                 380
Ile Pro Ser Thr Asp Val Ala Asp Gln Ser Asn Arg Glu His
385                 390                 395

<210> SEQ ID NO 53
<211> LENGTH: 24
<212> TYPE: PRT
<213> ORGANISM: Mus musculus

<400> SEQUENCE: 53

Leu Ser Val Tyr Ala Val Val Ile Ala Ser Val Val Gly Phe Cys
1               5                   10                  15
Leu Leu Val Met Leu Leu Leu Leu
                20

<210> SEQ ID NO 54
<211> LENGTH: 368
<212> TYPE: PRT
<213> ORGANISM: Mus musculus

<400> SEQUENCE: 54

Lys Leu Ala Arg His Ser Lys Phe Gly Met Lys Gly Pro Ala Ser Val
1               5                   10                  15
Ile Ser Asn Asp Asp Ser Ala Ser Pro Leu His His Ile Ser Asn
            20                  25                  30
Gly Ser Asn Thr Pro Ser Ser Glu Gly Gly Pro Asp Ala Val Ile
            35                  40                  45
Ile Gly Met Thr Lys Ile Pro Val Ile Glu Asn Pro Gln Tyr Phe Gly
            50                  55                  60
Ile Thr Asn Ser Gln Leu Lys Pro Asp Thr Phe Val Gln His Ile Lys
65                  70                  75                  80
Arg His Asn Ile Val Leu Lys Arg Glu Leu Gly Glu Gly Ala Phe Gly
                85                  90                  95
Lys Val Phe Leu Ala Glu Cys Tyr Asn Leu Cys Pro Glu Gln Asp Lys
            100                 105                 110
Ile Leu Val Ala Val Lys Thr Leu Lys Asp Ala Ser Asp Asn Ala Arg
            115                 120                 125
Lys Asp Phe His Arg Glu Ala Glu Leu Leu Thr Asn Leu Gln His Glu
            130                 135                 140
His Ile Val Lys Phe Tyr Gly Val Cys Val Glu Gly Asp Pro Leu Ile
145                 150                 155                 160
```

Met Val Phe Glu Tyr Met Lys His Gly Asp Leu Asn Lys Phe Leu Arg
                165                 170                 175

Ala His Gly Pro Asp Ala Val Leu Met Ala Glu Gly Asn Pro Pro Thr
            180                 185                 190

Glu Leu Thr Gln Ser Gln Met Leu His Ile Ala Gln Gln Ile Ala Ala
        195                 200                 205

Gly Met Val Tyr Leu Ala Ser Gln His Phe Val His Arg Asp Leu Ala
    210                 215                 220

Thr Arg Asn Cys Leu Val Gly Glu Asn Leu Leu Val Lys Ile Gly Asp
225                 230                 235                 240

Phe Gly Met Ser Arg Asp Val Tyr Ser Thr Asp Tyr Tyr Arg Val Gly
                245                 250                 255

Gly His Thr Met Leu Pro Ile Arg Trp Met Pro Pro Glu Ser Ile Met
            260                 265                 270

Tyr Arg Lys Phe Thr Thr Glu Ser Asp Val Trp Ser Leu Gly Val Val
        275                 280                 285

Leu Trp Glu Ile Phe Thr Tyr Gly Lys Gln Pro Trp Tyr Gln Leu Ser
    290                 295                 300

Asn Asn Glu Val Ile Glu Cys Ile Thr Gln Gly Arg Val Leu Gln Arg
305                 310                 315                 320

Pro Arg Thr Cys Pro Gln Glu Val Tyr Glu Leu Met Leu Gly Cys Trp
                325                 330                 335

Gln Arg Glu Pro His Thr Arg Lys Asn Ile Lys Ser Ile His Thr Leu
            340                 345                 350

Leu Gln Asn Leu Ala Lys Ala Ser Pro Val Tyr Leu Asp Ile Leu Gly
        355                 360                 365

<210> SEQ ID NO 55
<211> LENGTH: 31
<212> TYPE: PRT
<213> ORGANISM: Rattus norvegicus

<400> SEQUENCE: 55

Met Ser Pro Trp Pro Arg Trp His Gly Pro Ala Met Ala Arg Leu Trp
1               5                   10                  15

Gly Leu Cys Leu Leu Val Leu Gly Phe Trp Arg Ala Ser Leu Ala
            20                  25                  30

<210> SEQ ID NO 56
<211> LENGTH: 398
<212> TYPE: PRT
<213> ORGANISM: Rattus norvegicus

<400> SEQUENCE: 56

Cys Pro Met Ser Cys Lys Cys Ser Thr Thr Arg Ile Trp Cys Thr Glu
1               5                   10                  15

Pro Ser Pro Gly Ile Val Ala Phe Pro Arg Leu Glu Pro Asn Ser Ile
            20                  25                  30

Asp Pro Glu Asn Ile Thr Glu Ile Leu Ile Ala Asn Gln Lys Arg Leu
        35                  40                  45

Glu Ile Ile Asn Glu Asp Asp Val Glu Ala Tyr Val Gly Leu Lys Asn
    50                  55                  60

Leu Thr Ile Val Asp Ser Gly Leu Lys Phe Val Ala Tyr Lys Ala Phe
65                  70                  75                  80

Leu Lys Asn Gly Asn Leu Arg His Ile Asn Phe Thr Arg Asn Lys Leu
                85                  90                  95

```
Thr Ser Leu Ser Arg Arg His Phe Arg His Leu Asp Leu Ser Asp Leu
            100                 105                 110

Ile Leu Thr Gly Asn Pro Phe Thr Cys Ser Cys Asp Ile Met Trp Leu
            115                 120                 125

Lys Thr Leu Gln Glu Thr Lys Ser Ser Pro Asp Thr Gln Asp Leu Tyr
130                 135                 140

Cys Leu Asn Glu Ser Ser Lys Asn Thr Pro Leu Ala Asn Leu Gln Ile
145                 150                 155                 160

Pro Asn Cys Gly Leu Pro Ser Ala Arg Leu Ala Ala Pro Asn Leu Thr
                165                 170                 175

Val Glu Glu Gly Lys Ser Val Thr Ile Ser Cys Ser Val Gly Gly Asp
            180                 185                 190

Pro Leu Pro Thr Leu Tyr Trp Asp Val Gly Asn Leu Val Ser Lys His
            195                 200                 205

Met Asn Glu Thr Ser His Thr Gln Gly Ser Leu Arg Ile Thr Asn Ile
            210                 215                 220

Ser Ser Asp Asp Ser Gly Lys Gln Ile Ser Cys Val Ala Glu Asn Leu
225                 230                 235                 240

Val Gly Glu Asp Gln Asp Ser Val Asn Leu Thr Val His Phe Ala Pro
                245                 250                 255

Thr Ile Thr Phe Leu Glu Ser Pro Thr Ser Asp His His Trp Cys Ile
            260                 265                 270

Pro Phe Thr Val Arg Gly Asn Pro Lys Pro Ala Leu Gln Trp Phe Tyr
            275                 280                 285

Asn Gly Ala Ile Leu Asn Glu Ser Lys Tyr Ile Cys Thr Lys Ile His
            290                 295                 300

Val Thr Asn His Thr Glu Tyr His Gly Cys Leu Gln Leu Asp Asn Pro
305                 310                 315                 320

Thr His Met Asn Asn Gly Asp Tyr Thr Leu Met Ala Lys Asn Glu Tyr
                325                 330                 335

Gly Lys Asp Glu Arg Gln Ile Ser Ala His Phe Met Gly Arg Pro Gly
            340                 345                 350

Val Asp Tyr Glu Thr Asn Pro Asn Tyr Pro Glu Val Leu Tyr Glu Asp
            355                 360                 365

Trp Thr Thr Pro Thr Asp Ile Gly Asp Thr Thr Asn Lys Ser Asn Glu
370                 375                 380

Ile Pro Ser Thr Asp Val Ala Asp Gln Thr Asn Arg Glu His
385                 390                 395

<210> SEQ ID NO 57
<211> LENGTH: 24
<212> TYPE: PRT
<213> ORGANISM: Rattus norvegicus

<400> SEQUENCE: 57

Leu Ser Val Tyr Ala Val Val Val Ile Ala Ser Val Val Gly Phe Cys
1               5                   10                  15

Leu Leu Val Met Leu Leu Leu Leu
            20

<210> SEQ ID NO 58
<211> LENGTH: 368
<212> TYPE: PRT
<213> ORGANISM: Rattus norvegicus

<400> SEQUENCE: 58
```

Lys Leu Ala Arg His Ser Lys Phe Gly Met Lys Gly Pro Ala Ser Val
1               5                   10                  15

Ile Ser Asn Asp Asp Ser Ala Ser Pro Leu His His Ile Ser Asn
            20                  25                  30

Gly Ser Asn Thr Pro Ser Ser Glu Gly Gly Pro Asp Ala Val Ile
            35                  40                  45

Ile Gly Met Thr Lys Ile Pro Val Ile Glu Asn Pro Gln Tyr Phe Gly
50                  55                  60

Ile Thr Asn Ser Gln Leu Lys Pro Asp Thr Phe Val Gln His Ile Lys
65                  70                  75                  80

Arg His Asn Ile Val Leu Lys Arg Glu Leu Gly Glu Gly Ala Phe Gly
                85                  90                  95

Lys Val Phe Leu Ala Glu Cys Tyr Asn Leu Cys Pro Glu Gln Asp Lys
            100                 105                 110

Ile Leu Val Ala Val Lys Thr Leu Lys Asp Ala Ser Asp Asn Ala Arg
            115                 120                 125

Lys Asp Phe His Arg Glu Ala Glu Leu Leu Thr Asn Leu Gln His Glu
            130                 135                 140

His Ile Val Lys Phe Tyr Gly Val Cys Val Glu Gly Asp Pro Leu Ile
145                 150                 155                 160

Met Val Phe Glu Tyr Met Lys His Gly Asp Leu Asn Lys Phe Leu Arg
                165                 170                 175

Ala His Gly Pro Asp Ala Val Leu Met Ala Glu Gly Asn Pro Pro Thr
            180                 185                 190

Glu Leu Thr Gln Ser Gln Met Leu His Ile Ala Gln Gln Ile Ala Ala
            195                 200                 205

Gly Met Val Tyr Leu Ala Ser Gln His Phe Val His Arg Asp Leu Ala
210                 215                 220

Thr Arg Asn Cys Leu Val Gly Glu Asn Leu Leu Val Lys Ile Gly Asp
225                 230                 235                 240

Phe Gly Met Ser Arg Asp Val Tyr Ser Thr Asp Tyr Tyr Arg Val Gly
                245                 250                 255

Gly His Thr Met Leu Pro Ile Arg Trp Met Pro Pro Glu Ser Ile Met
            260                 265                 270

Tyr Arg Lys Phe Thr Thr Glu Ser Asp Val Trp Ser Leu Gly Val Val
            275                 280                 285

Leu Trp Glu Ile Phe Thr Tyr Gly Lys Gln Pro Trp Tyr Gln Leu Ser
            290                 295                 300

Asn Asn Glu Val Ile Glu Cys Ile Thr Gln Gly Arg Val Leu Gln Arg
305                 310                 315                 320

Pro Arg Thr Cys Pro Gln Glu Val Tyr Glu Leu Met Leu Gly Cys Trp
                325                 330                 335

Gln Arg Glu Pro His Thr Arg Lys Asn Ile Lys Asn Ile His Thr Leu
            340                 345                 350

Leu Gln Asn Leu Ala Lys Ala Ser Pro Val Tyr Leu Asp Ile Leu Gly
            355                 360                 365

<210> SEQ ID NO 59
<211> LENGTH: 31
<212> TYPE: PRT
<213> ORGANISM: Homo sapiens

<400> SEQUENCE: 59

Met Ser Ser Trp Ile Arg Trp His Gly Pro Ala Met Ala Arg Leu Trp

```
                1               5                    10                   15
            Gly Phe Cys Trp Leu Val Val Gly Phe Trp Arg Ala Ala Phe Ala
                         20                   25                   30

<210> SEQ ID NO 60
<211> LENGTH: 399
<212> TYPE: PRT
<213> ORGANISM: Homo sapiens

<400> SEQUENCE: 60

Cys Pro Thr Ser Cys Lys Cys Ser Ala Ser Arg Ile Trp Cys Ser Asp
1               5                   10                  15

Pro Ser Pro Gly Ile Val Ala Phe Pro Arg Leu Glu Pro Asn Ser Val
            20                  25                  30

Asp Pro Glu Asn Ile Thr Glu Ile Phe Ile Ala Asn Gln Lys Arg Leu
        35                  40                  45

Glu Ile Ile Asn Glu Asp Asp Val Glu Ala Tyr Val Gly Leu Arg Asn
    50                  55                  60

Leu Thr Ile Val Asp Ser Gly Leu Lys Phe Val Ala His Lys Ala Phe
65                  70                  75                  80

Leu Lys Asn Ser Asn Leu Gln His Ile Asn Phe Thr Arg Asn Lys Leu
                85                  90                  95

Thr Ser Leu Ser Arg Lys His Phe Arg His Leu Asp Leu Ser Glu Leu
            100                 105                 110

Ile Leu Val Gly Asn Pro Phe Thr Cys Ser Cys Asp Ile Met Trp Ile
        115                 120                 125

Lys Thr Leu Gln Glu Ala Lys Ser Ser Pro Asp Thr Gln Asp Leu Tyr
    130                 135                 140

Cys Leu Asn Glu Ser Ser Lys Asn Ile Pro Leu Ala Asn Leu Gln Ile
145                 150                 155                 160

Pro Asn Cys Gly Leu Pro Ser Ala Asn Leu Ala Ala Pro Asn Leu Thr
                165                 170                 175

Val Glu Glu Gly Lys Ser Ile Thr Leu Ser Cys Ser Val Ala Gly Asp
            180                 185                 190

Pro Val Pro Asn Met Tyr Trp Asp Val Gly Asn Leu Val Ser Lys His
        195                 200                 205

Met Asn Glu Thr Ser His Thr Gln Gly Ser Leu Arg Ile Thr Asn Ile
    210                 215                 220

Ser Ser Asp Asp Ser Gly Lys Gln Ile Ser Cys Val Ala Glu Asn Leu
225                 230                 235                 240

Val Gly Glu Asp Gln Asp Ser Val Asn Leu Thr Val His Phe Ala Pro
                245                 250                 255

Thr Ile Thr Phe Leu Glu Ser Pro Thr Ser Asp His His Trp Cys Ile
            260                 265                 270

Pro Phe Thr Val Lys Gly Asn Pro Lys Pro Ala Leu Gln Trp Phe Tyr
        275                 280                 285

Asn Gly Ala Ile Leu Asn Glu Ser Lys Tyr Ile Cys Thr Lys Ile His
    290                 295                 300

Val Thr Asn His Thr Glu Tyr His Gly Cys Leu Gln Leu Asp Asn Pro
305                 310                 315                 320

Thr His Met Asn Asn Gly Asp Tyr Thr Leu Ile Ala Lys Asn Glu Tyr
                325                 330                 335

Gly Lys Asp Glu Lys Gln Ile Ser Ala His Phe Met Gly Trp Pro Gly
            340                 345                 350
```

```
Ile Asp Asp Gly Ala Asn Pro Asn Tyr Pro Asp Val Ile Tyr Glu Asp
            355                 360                 365

Tyr Gly Thr Ala Ala Asn Asp Ile Gly Asp Thr Thr Asn Arg Ser Asn
            370                 375                 380

Glu Ile Pro Ser Thr Asp Val Thr Asp Lys Thr Gly Arg Glu His
385                 390                 395

<210> SEQ ID NO 61
<211> LENGTH: 24
<212> TYPE: PRT
<213> ORGANISM: Homo sapiens

<400> SEQUENCE: 61

Leu Ser Val Tyr Ala Val Val Ile Ala Ser Val Val Gly Phe Cys
1               5                   10                  15

Leu Leu Val Met Leu Phe Leu Leu
            20

<210> SEQ ID NO 62
<211> LENGTH: 384
<212> TYPE: PRT
<213> ORGANISM: Homo sapiens

<400> SEQUENCE: 62

Lys Leu Ala Arg His Ser Lys Phe Gly Met Lys Asp Phe Ser Trp Phe
1               5                   10                  15

Gly Phe Gly Lys Val Lys Ser Arg Gln Gly Val Gly Pro Ala Ser Val
            20                  25                  30

Ile Ser Asn Asp Asp Ser Ala Ser Pro Leu His His Ile Ser Asn
            35                  40                  45

Gly Ser Asn Thr Pro Ser Ser Ser Glu Gly Gly Pro Asp Ala Val Ile
50                  55                  60

Ile Gly Met Thr Lys Ile Pro Val Ile Glu Asn Pro Gln Tyr Phe Gly
65                  70                  75                  80

Ile Thr Asn Ser Gln Leu Lys Pro Asp Thr Phe Val Gln His Ile Lys
                85                  90                  95

Arg His Asn Ile Val Leu Lys Arg Glu Leu Gly Glu Gly Ala Phe Gly
            100                 105                 110

Lys Val Phe Leu Ala Glu Cys Tyr Asn Leu Cys Pro Glu Gln Asp Lys
        115                 120                 125

Ile Leu Val Ala Val Lys Thr Leu Lys Asp Ala Ser Asp Asn Ala Arg
    130                 135                 140

Lys Asp Phe His Arg Glu Ala Glu Leu Leu Thr Asn Leu Gln His Glu
145                 150                 155                 160

His Ile Val Lys Phe Tyr Gly Val Cys Val Glu Gly Asp Pro Leu Ile
                165                 170                 175

Met Val Phe Glu Tyr Met Lys His Gly Asp Leu Asn Lys Phe Leu Arg
            180                 185                 190

Ala His Gly Pro Asp Ala Val Leu Met Ala Glu Gly Asn Pro Pro Thr
        195                 200                 205

Glu Leu Thr Gln Ser Gln Met Leu His Ile Ala Gln Gln Ile Ala Ala
    210                 215                 220

Gly Met Val Tyr Leu Ala Ser Gln His Phe Val His Arg Asp Leu Ala
225                 230                 235                 240

Thr Arg Asn Cys Leu Val Gly Glu Asn Leu Leu Val Lys Ile Gly Asp
                245                 250                 255
```

```
Phe Gly Met Ser Arg Asp Val Tyr Ser Thr Asp Tyr Tyr Arg Val Gly
            260                 265                 270

Gly His Thr Met Leu Pro Ile Arg Trp Met Pro Pro Glu Ser Ile Met
        275                 280                 285

Tyr Arg Lys Phe Thr Thr Glu Ser Asp Val Trp Ser Leu Gly Val Val
        290                 295                 300

Leu Trp Glu Ile Phe Thr Tyr Gly Lys Gln Pro Trp Tyr Gln Leu Ser
305                 310                 315                 320

Asn Asn Glu Val Ile Glu Cys Ile Thr Gln Gly Arg Val Leu Gln Arg
                325                 330                 335

Pro Arg Thr Cys Pro Gln Glu Val Tyr Glu Leu Met Leu Gly Cys Trp
            340                 345                 350

Gln Arg Glu Pro His Met Arg Lys Asn Ile Lys Gly Ile His Thr Leu
        355                 360                 365

Leu Gln Asn Leu Ala Lys Ala Ser Pro Val Tyr Leu Asp Ile Leu Gly
        370                 375                 380

<210> SEQ ID NO 63
<211> LENGTH: 93
<212> TYPE: DNA
<213> ORGANISM: Mus musculus

<400> SEQUENCE: 63
atgtcgccct ggctgaagtg gcatggaccc gccatggcgc ggctctgggg cttatgcctg      60
ctggtcttgg gcttctggag ggcctctctc gcc                                  93

<210> SEQ ID NO 64
<211> LENGTH: 1194
<212> TYPE: DNA
<213> ORGANISM: Mus musculus

<400> SEQUENCE: 64
tgcccgacgt cctgcaaatg cagttccgct aggatttggt gtactgagcc ttctccaggc      60
atcgtggcat tcccgaggtt ggaacctaac agcgttgacc cggagaacat cacggaaatt     120
ctcattgcaa accagaaaag gctagaaatc atcaatgaag atgacgttga agcttacgtg     180
gggctgagaa accttacaat tgtggattcc ggcttaaagt ttgtggctta caaagcgttt     240
ctgaaaaaca gcaacctgcg gcacataaat ttcacacgaa acaagctgac gagtttgtcc     300
aggagacatt tccgccacct tgacttgtct gacctgatcc tgacgggtaa tccgttcacg     360
tgctcctgcg acatcatgtg gctcaagact ctccaggaga ctaaatccag ccccgacact     420
caggatttgt actgcctcaa tgagagcagc aagaacatgc ccctggcgaa cctgcagata     480
cccaattgtg gtctgccatc tgcacgtctg gctgctccta acctcaccgt ggaggaagga     540
aagtctgtga ccctttcctg cagtgtgggg ggtgacccac tccccacctt gtactgggac     600
gttgggaatt tggtttccaa gcacatgaat gaaacaagcc acacacaggg ctccttaagg     660
ataacgaaca tttcatctga tgacagtgga aagcaaatct cttgtgtggc agaaaacctt     720
gtaggagaag atcaagattc tgtgaacctc actgtgcatt ttgcgccaac tatcacgttt     780
ctcgagtctc caacctcaga tcaccactgg tgcattccat tcactgtgag aggcaacccc     840
aagcctgcgc ttcagtggtt ctacaatggg gccatactga atgagtccaa gtacatctgt     900
actaagatcc acgtcaccaa tcacacggag taccatggct gcctccagct ggataaccc      960 actcatatga ataacggaga ctacaccctg atggccaaga cgagtatgg gaaggatgag    1020 agacagatct ccgctcactt catgggccgg cctggagtcg actacgagac aaacccaaat    1080
```

| taccctgaag tcctctatga agactggacc acgccaactg acattgggga tactacgaac | 1140 |
| aaaagtaatg aaatcccctc cacggatgtt gctgaccaaa gcaatcggga gcat | 1194 |

<210> SEQ ID NO 65
<211> LENGTH: 72
<212> TYPE: DNA
<213> ORGANISM: Mus musculus

<400> SEQUENCE: 65

| ctctcggtct atgccgtggt ggtgattgca tctgtggtgg gattctgcct gctggtgatg | 60 |
| ttgctcctgc tc | 72 |

<210> SEQ ID NO 66
<211> LENGTH: 1104
<212> TYPE: DNA
<213> ORGANISM: Mus musculus

<400> SEQUENCE: 66

| aagttggcga gacattccaa gtttggcatg aaaggcccag cttcggtcat cagcaacgac | 60 |
| gatgactctg ccagccccct ccaccacatc tccaatggga gtaacactcc atcttcttcg | 120 |
| gagggcggtc ccgacgctgt cattattgga atgaccaaga ttcctgttat tgaaaacccc | 180 |
| cagtactttg gcatcaccaa cagtcagctc aagccagaca catttgttca gcatatcaag | 240 |
| agacacaaca tcgttctgaa gagggaactt ggggaaggag ccttcgggaa agttttcctt | 300 |
| gccgagtgct acaacctctg cccagagcag gataagatcc tggtggctgt gaagacgctg | 360 |
| aaggacgcca gcgacaatgc acgcaaggac tttcatcggg aagctgagct gctgaccaac | 420 |
| ctccagcacg agcacattgt caagttctac ggtgtctgtg tggagggcga cccactcatc | 480 |
| atggtctttg agtacatgaa gcacgggggac ctcaacaagt tccttagggc acacgggccc | 540 |
| gacgcagtgc tgatggcaga gggtaacccg cccacagagc tgacgcagtc gcagatgctg | 600 |
| cacatcgctc agcaaatcgc agcaggtatg gtctacctgg cgtcccaaca ctttgtgcac | 660 |
| cgtgacctgg ccacccggaa ctgcctggtg ggagagaacc tgctggtgaa aattggggac | 720 |
| tttgggatgt cccgagatgt gtacagcacc gactactatc gggtcggtgg ccacacaatg | 780 |
| ttgcccatcc gatggatgcc tccagagagc atcatgtaca ggaaattcac caccgagagc | 840 |
| gacgtctgga gcctgggcgt tgtgttgtgg gagatcttca cctacggcaa gcagccctgg | 900 |
| tatcagctat cgaacaatga ggtgatagag tgcatcaccc agggaagagt ccttcagcgg | 960 |
| cctcgaacgt gtccccagga ggtgtatgag ctcatgcttg gatgctggca gcgggaacca | 1020 |
| cacacccgga gaacatcaa gagcatccac accctccttc agaacttggc caaggcatct | 1080 |
| cccgtctacc tggatatcct aggc | 1104 |

<210> SEQ ID NO 67
<211> LENGTH: 93
<212> TYPE: DNA
<213> ORGANISM: Rattus norvegicus

<400> SEQUENCE: 67

| atgtcgccct ggccgaggtg gcatggaccc gccatggcgc ggctctgggg cttatgcttg | 60 |
| ctggtcttgg gcttctggag ggcttctctt gcc | 93 |

<210> SEQ ID NO 68
<211> LENGTH: 1194
<212> TYPE: DNA

<213> ORGANISM: Rattus norvegicus

<400> SEQUENCE: 68

```
tgccccatgt cctgcaaatg cagcaccact aggatttggt gtaccgagcc ttctcctggc    60
atcgtggcat ttccgaggtt ggaacctaac agcattgacc cagagaacat caccgaaatt   120
ctcattgcaa accagaaaag gttagaaatc atcaatgaag atgatgtcga agcttacgtg   180
gggctgaaaa accttacaat tgtggattcc ggcttaaagt ttgtggctta caaggcgttt   240
ctgaagaacg gcaacctgcg gcacatcaat ttcactcgaa acaagctgac gagtttgtcc   300
aggagacatt tccgccacct tgacttgtct gacctgatcc tgacgggtaa tccgttcacg   360
tgttcctgtg acatcatgtg gctcaagact ctccaggaga cgaaatccag ccccgacact   420
caggatttgt attgcctcaa tgagagcagc aagaataccc ctctggcgaa cctgcagatt   480
cccaattgtg gtctgccgtc tgcacgtctg gccgctccta acctcacggt ggaggaaggg   540
aagtctgtga ccatttcctg cagcgtcggg ggtgacccgc tccccacctt gtactgggac   600
gttgggaatt tggtttccaa acacatgaat gaaacaagcc acacacaggg ctccttaagg   660
ataacaaaca tttcatcgga tgacagtggg aaacaaatct cttgtgtggc agaaaacctc   720
gttggagaag atcaagactc tgtgaacctc actgtgcatt ttgcaccaac catcacattt   780
ctcgaatctc caacctcaga ccaccactgg tgcatcccat tcactgtgag aggcaacccc   840
aagccagcac ttcagtggtt ctacaacgga gccatactga tgaatccaa gtacatctgt   900
accaaaatac acgtcaccaa tcacacggag taccacggct gcctccagct ggataacccc   960
actcatatga ataatggaga ctacacccta atggccaaga tgaatatgg gaaggacgag  1020
agacagattt ctgctcactt catgggccgg cctggagttg actatgagac aaacccaaat  1080
tacccctgaag tcctctatga agactggacc acgccaactg catcggggga tactacaaac  1140
aaaagtaatg agatcccctc cacggatgtt gctgaccaaa ccaatcggga gcat         1194
```

<210> SEQ ID NO 69
<211> LENGTH: 72
<212> TYPE: DNA
<213> ORGANISM: Rattus norvegicus

<400> SEQUENCE: 69

```
ctctcggtct atgccgtggt ggtgattgcc tctgtggtag gattctgcct gctggtgatg    60
ctgcttctgc tc                                                       72
```

<210> SEQ ID NO 70
<211> LENGTH: 1104
<212> TYPE: DNA
<213> ORGANISM: Rattus norvegicus

<400> SEQUENCE: 70

```
aagttggcga gacattccaa gtttggcatg aaaggcccag cttccgtcat cagcaacgac    60
gatgactctg ccagccctct ccaccacatc tccaacggga gcaacactcc gtcttcttcg   120
gagggcgggc ccgatgctgt catcattggg atgaccaaga tccctgtcat tgaaaacccc   180
cagtacttcg gtatcaccaa cagccagctc aagccggaca catttgttca gcacatcaag   240
agacacaaca tcgttctgaa gagggagctt ggagaaggag cctttgggaa agttttccta   300
gcggagtgct ataacctctg ccccgagcag gataagatcc tggtggccgt gaagacgctg   360
aaggacgcca gcgacaatgc tcgcaaggac tttcatcgcg aagccgagct gctgaccaac   420
ctccagcacg agcacattgt caagttctac ggtgtctgtg tggagggcga cccactcatc   480
```

```
atggtctttg agtacatgaa gcacggggac ctcaacaagt tccttagggc acacgggcca      540
gatgcagtgc tgatggcaga gggtaacccg cccaccgagc tgacgcagtc gcagatgctg      600
cacatcgctc agcaaatcgc agcaggcatg gtctacctgg catcccaaca cttcgtgcac      660
cgagacctgg ccaccggaa ctgcttggta ggagagaacc tgctggtgaa aattggggac       720
ttcgggatgt cccgggatgt atacagcacc gactactacc gggttggtgg ccacacaatg      780
ttgcccatcc gatggatgcc tccagagagc atcatgtaca ggaaattcac caccgagagt      840
gacgtctgga gcctgggagt tgtgttgtgg gagatcttca cctacggcaa gcagccctgg      900
tatcagctat caaacaacga ggtgatagaa tgcatcaccc agggcagagt ccttcagcgg      960
cctcgcacgt gtccccagga ggtgtacgag ctgatgctgg gatgctggca gcgggaacca     1020
cacacaagga agaacatcaa gaacatccac acactccttc agaacttggc gaaggcgtcg     1080
cccgtctacc tggacatcct aggc                                            1104

<210> SEQ ID NO 71
<211> LENGTH: 93
<212> TYPE: DNA
<213> ORGANISM: Homo sapiens

<400> SEQUENCE: 71
atgtcgtcct ggataaggtg gcatggaccc gccatggcgc ggctctgggg cttctgctgg       60
ctggttgtgg gcttctggag ggccgctttc gcc                                   93

<210> SEQ ID NO 72
<211> LENGTH: 1197
<212> TYPE: DNA
<213> ORGANISM: Homo sapiens

<400> SEQUENCE: 72
tgtcccacgt cctgcaaatg cagtgcctct cggatctggt gcagcgaccc ttctcctggc       60
atcgtggcat ttccgagatt ggagcctaac agtgtagatc ctgagaacat caccgaaatt      120
ttcatcgcaa accagaaaag gttagaaatc atcaacgaag atgatgttga agcttatgtg      180
ggactgagaa atctgacaat tgtggattct ggattaaaat ttgtggctca taaagcattt      240
ctgaaaaaca gcaacctgca gcacatcaat tttacccgaa acaaactgac gagtttgtct      300
aggaaacatt tccgtcacct tgacttgtct gaactgatcc tggtgggcaa tccatttaca      360
tgctcctgtg acattatgtg gatcaagact ctccaagagg ctaaatccag tccagacact      420
caggatttgt actgcctgaa tgaaagcagc aagaatattc ccctggcaaa cctgcagata      480
cccaattgtg gtttgccatc tgcaaatctg gccgcaccta acctcactgt ggaggaagga      540
aagtctatca cattatcctg tagtgtggca ggtgatccgg ttcctaatat gtattgggat      600
gttggtaacc tggtttccaa acatatgaat gaaacaagcc acacacaggg ctccttaagg      660
ataactaaca tttcatccga tgacagtggg aagcagatct cttgtgtggc ggaaaatctt      720
gtaggagaag atcaagattc tgtcaacctc actgtgcatt ttgcaccaac tatcacattt      780
ctcgaatctc caacctcaga ccaccactgg tgcattccat tcactgtgaa aggcaacccc      840
aaaccagcgc ttcagtggtt ctataacgg gcaattga tgagtccaa atacatctgt        900 actaaaatac atgttaccaa tcacacggag taccacggct gcctccagct ggataatccc      960
actcacatga acaatgggga ctacactcta atagccaaga atgagtatgg gaaggatgag     1020
aaacagattt ctgctcactt catgggctgg cctggaattg acgatggtgc aaacccaaat     1080
```

```
tatcctgatg taatttatga agattatgga actgcagcga atgacatcgg ggacaccacg    1140
aacagaagta atgaaatccc ttccacagac gtcactgata aaaccggtcg ggaacat      1197
```

<210> SEQ ID NO 73
<211> LENGTH: 72
<212> TYPE: DNA
<213> ORGANISM: Homo sapiens

<400> SEQUENCE: 73

```
ctctcggtct atgctgtggt ggtgattgcg tctgtggtgg gattttgcct tttggtaatg    60
ctgtttctgc tt                                                        72
```

<210> SEQ ID NO 74
<211> LENGTH: 1152
<212> TYPE: DNA
<213> ORGANISM: Homo sapiens

<400> SEQUENCE: 74

```
aagttggcaa gacactccaa gtttggcatg aaagatttct catggtttgg atttgggaaa    60
gtaaaatcaa gacaaggtgt tggcccagcc tccgttatca gcaatgatga tgactctgcc   120
agcccactcc atcacatctc caatgggagt aacactccat cttcttcgga aggtggccca   180
gatgctgtca ttattggaat gaccaagatc cctgtcattg aaaatcccca gtactttggc   240
atcaccaaca gtcagctcaa gccagacaca tttgttcagc acatcaagcg acataacatt   300
gttctgaaaa gggagctagg cgaaggagcc tttggaaaag tgttcctagc tgaatgctat   360
aacctctgtc ctgagcagga caagatcttg gtggcagtga gaccctgaa ggatgccagt   420 gacaatgcac gcaaggactt ccaccgtgag gccgagctcc tgaccaacct ccagcatgag   480
cacatcgtca agttctatgg cgtctgcgtg gagggcgacc ccctcatcat ggtctttgag   540
tacatgaagc atgggacct caacaagttc ctcagggcac acggccctga tgccgtgctg   600
atggctgagg gcaacccgcc cacggaactg acgcagtcgc agatgctgca tatagcccag   660
cagatcgccg cgggcatggt ctacctggcg tcccagcact tcgtgcaccg cgatttggcc   720
accaggaact gcctggtcgg ggagaacttg ctggtgaaaa tcggggactt tgggatgtcc   780
cgggacgtgt acagcactga ctactacagg gtcggtggcc acacaatgct gcccattcgc   840
tggatgcctc cagagagcat catgtacagg aaattcacga cggaaagcga cgtctggagc   900 ctggggtcg tgttgtggga gattttcacc tatggcaaac agccctggta ccagctgtca   960
aacaatgagg tgatagagtg tatcactcag ggccgagtcc tgcagcgacc ccgcacgtgc  1020
ccccaggagg tgtatgagct gatgctgggg tgctggcagc gagagcccca catgaggaag  1080
aacatcaagg gcatccatac cctccttcag aacttggcca aggcatctcc ggtctacctg  1140
gacattctag gc                                                      1152
```

<210> SEQ ID NO 75
<211> LENGTH: 822
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Signal Peptide
<220> FEATURE:
<221> NAME/KEY: MISC_FEATURE
<222> LOCATION: (32)..(430)
<223> OTHER INFORMATION: Extracellular Domain
<220> FEATURE:
<221> NAME/KEY: MISC_FEATURE

```
<222> LOCATION: (431)..(454)
<223> OTHER INFORMATION: Transmembrane Domain
<220> FEATURE:
<221> NAME/KEY: MISC_FEATURE
<222> LOCATION: (455)..(822)
<223> OTHER INFORMATION: Cytoplasmic Domain

<400> SEQUENCE: 75
```

Met Ser Ser Trp Ile Arg Trp His Gly Pro Ala Met Ala Arg Leu Trp
1               5                  10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Val Asp
    50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
    210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
        275                 280                 285

Ile Thr Phe Leu Glu Ser Pro Thr Ser Asp His His Trp Cys Ile Pro
    290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Ile Ala Lys Asn Glu Tyr Gly
        355                 360                 365

Lys Asp Glu Lys Gln Ile Ser Ala His Phe Met Gly Trp Pro Gly Ile

```
           370                 375                 380
Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415

Ile Pro Ser Thr Asp Val Thr Asp Lys Thr Gly Arg Glu His Leu Ser
                420                 425                 430

Val Tyr Ala Val Val Ile Ala Ser Val Val Gly Phe Cys Leu Leu
                435                 440                 445

Val Met Leu Phe Leu Leu Lys Leu Ala Arg His Ser Lys Phe Gly Met
                450                 455                 460

Lys Gly Pro Ala Ser Val Ile Ser Asn Asp Asp Ser Ala Ser Pro
465                 470                 475                 480

Leu His His Ile Ser Asn Gly Ser Asn Thr Pro Ser Ser Glu Gly
                485                 490                 495

Gly Pro Asp Ala Val Ile Ile Gly Met Thr Lys Ile Pro Val Ile Glu
                500                 505                 510

Asn Pro Gln Tyr Phe Gly Ile Thr Asn Ser Gln Leu Lys Pro Asp Thr
                515                 520                 525

Phe Val Gln His Ile Lys Arg His Asn Ile Val Leu Lys Arg Glu Leu
                530                 535                 540

Gly Glu Gly Ala Phe Gly Lys Val Phe Leu Ala Glu Cys Tyr Asn Leu
545                 550                 555                 560

Cys Pro Glu Gln Asp Lys Ile Leu Val Ala Val Lys Thr Leu Lys Asp
                565                 570                 575

Ala Ser Asp Asn Ala Arg Lys Asp Phe His Arg Glu Ala Glu Leu Leu
                580                 585                 590

Thr Asn Leu Gln His Glu His Ile Val Lys Phe Tyr Gly Val Cys Val
                595                 600                 605

Glu Gly Asp Pro Leu Ile Met Val Phe Glu Tyr Met Lys His Gly Asp
                610                 615                 620

Leu Asn Lys Phe Leu Arg Ala His Gly Pro Asp Ala Val Leu Met Ala
625                 630                 635                 640

Glu Gly Asn Pro Pro Thr Glu Leu Thr Gln Ser Gln Met Leu His Ile
                645                 650                 655

Ala Gln Gln Ile Ala Ala Gly Met Val Tyr Leu Ala Ser Gln His Phe
                660                 665                 670

Val His Arg Asp Leu Ala Thr Arg Asn Cys Leu Val Gly Glu Asn Leu
                675                 680                 685

Leu Val Lys Ile Gly Asp Phe Gly Met Ser Arg Asp Val Tyr Ser Thr
                690                 695                 700

Asp Tyr Tyr Arg Val Gly Gly His Thr Met Leu Pro Ile Arg Trp Met
705                 710                 715                 720

Pro Pro Glu Ser Ile Met Tyr Arg Lys Phe Thr Thr Glu Ser Asp Val
                725                 730                 735

Trp Ser Leu Gly Val Val Leu Trp Glu Ile Phe Thr Tyr Gly Lys Gln
                740                 745                 750

Pro Trp Tyr Gln Leu Ser Asn Asn Glu Val Ile Glu Cys Ile Thr Gln
                755                 760                 765

Gly Arg Val Leu Gln Arg Pro Arg Thr Cys Pro Gln Glu Val Tyr Glu
                770                 775                 780

Leu Met Leu Gly Cys Trp Gln Arg Glu Pro His Met Arg Lys Asn Ile
785                 790                 795                 800
```

Lys Gly Ile His Thr Leu Leu Gln Asn Leu Ala Lys Ala Ser Pro Val
            805                 810                 815

Tyr Leu Asp Ile Leu Gly
            820

<210> SEQ ID NO 76
<211> LENGTH: 8498
<212> TYPE: DNA
<213> ORGANISM: Homo sapiens

<400> SEQUENCE: 76

| | | | | | |
|---|---|---|---|---|---|
| cctcgaggtg | cataccggac | ccccattcgc | atctaacaag | gaatctgcgc | cccagagagt | 60 |
| cccgggagcg | ccgccggtcg | gtgcccggcg | cgccgggcca | tgcagcgacg | gccgccgcgg | 120 |
| agctccgagc | agcggtagcg | ccccccctgta | aagcggttcg | ctatgccggg | gccactgtga | 180 |
| accctgccgc | ctgccggaac | actcttcgct | ccggaccagc | tcagcctctg | ataagctgga | 240 |
| ctcggcacgc | ccgcaacaag | caccgaggag | ttaagagagc | cgcaagcgca | gggaaggcct | 300 |
| ccccgcacgg | gtgggggaaa | gcggccggtg | cagcgcgggg | acaggcactc | gggctggcac | 360 |
| tggctgctag | ggatgtcgtc | ctggataagg | tggcatggac | ccgccatggc | gcggctctgg | 420 |
| ggcttctgct | ggctggttgt | gggcttctgg | agggccgctt | tcgcctgtcc | cacgtcctgc | 480 |
| aaatgcagtg | cctctcggat | ctggtgcagc | gaccccttctc | ctggcatcgt | ggcatttccg | 540 |
| agattggagc | ctaacagtgt | agatcctgag | aacatcaccg | aaattttcat | cgcaaaccag | 600 |
| aaaaggttag | aaatcatcaa | cgaagatgat | gttgaagctt | atgtgggact | gagaaatctg | 660 |
| acaattgtgg | attctggatt | aaaatttgtg | gctcataaag | catttctgaa | aacagcaac | 720 |
| ctgcagcaca | tcaattttac | ccgaaacaaa | ctgacgagtt | tgtctaggaa | acatttccgt | 780 |
| caccttgact | tgtctgaact | gatcctggtg | ggcaatccat | ttacatgctc | ctgtgacatt | 840 |
| atgtggatca | agactctcca | agaggctaaa | tccagtccag | acactcagga | tttgtactgc | 900 |
| ctgaatgaaa | gcagcaagaa | tattcccctg | gcaaacctgc | agataccccaa | ttgtggtttg | 960 |
| ccatctgcaa | atctggccgc | acctaacctc | actgtggagg | aaggaaagtc | tatcacatta | 1020 |
| tcctgtagtg | tggcaggtga | tccggttcct | aatatgtatt | gggatgttgg | taacctggtt | 1080 |
| tccaaacata | tgaatgaaac | aagccacaca | cagggctcct | taaggataac | taacatttca | 1140 |
| tccgatgaca | gtgggaagca | gatctcttgt | gtggcgaaa | atcttgtagg | agaagatcaa | 1200 |
| gattctgtca | acctcactgt | gcattttgca | ccaactatca | catttctcga | atctccaacc | 1260 |
| tcagaccacc | actggtgcat | tccattcact | gtgaaaggca | accccaaacc | agcgcttcag | 1320 |
| tggttctata | cgggggcaat | attgaatgag | tccaaataca | tctgtactaa | aatacatgtt | 1380 |
| accaatcaca | cggagtacca | cggctgcctc | cagctggata | tcccactcca | catgaacaat | 1440 |
| ggggactaca | ctctaatagc | caagaatgag | tatgggaagg | atgagaaaca | gatttctgct | 1500 |
| cacttcatgg | gctggcctgg | aattgacgat | ggtgcaaacc | caattatcc | tgatgtaatt | 1560 |
| tatgaagatt | atggaactgc | agcgaatgac | atcggggaca | ccacgaacag | aagtaatgaa | 1620 |
| atcccttcca | cagacgtcac | tgataaaacc | ggtcgggaac | atctctcggt | ctatgctgtg | 1680 |
| gtggtgattg | cgtctgtggt | gggattttgc | cttttggtaa | tgctgtttct | gcttaagttg | 1740 |
| gcaagacact | ccaagtttgg | catgaaaggc | ccagcctccg | ttatcagcaa | tgatgatgac | 1800 |
| tctgccagcc | cactccatca | catctccaat | gggagtaaca | ctccatcttc | ttcggaaggt | 1860 |
| ggcccagatg | ctgtcattat | tggaatgacc | aagatccctg | tcattgaaaa | tccccagtac | 1920 |

```
tttggcatca ccaacagtca gctcaagcca gacacatttg ttcagcacat caagcgacat    1980
aacattgttc tgaaaaggga gctaggcgaa ggagcctttg aaaagtgtt  cctagctgaa    2040 tgctataacc tctgtcctga gcaggacaag atcttggtgg cagtgaagac cctgaaggat    2100
gccagtgaca atgcacgcaa ggacttccac cgtgaggccg agctcctgac caacctccag    2160
catgagcaca tcgtcaagtt ctatggcgtc tgcgtggagg gcgaccccct catcatggtc    2220
tttgagtaca tgaagcatgg ggacctcaac aagttcctca gggcacacgg ccctgatgcc    2280
gtgctgatgg ctgagggcaa cccgcccacg gaactgacgc agtcgcagat gctgcatata    2340
gcccagcaga tcgccgcggg catggtctac ctggcgtccc agcacttcgt gcaccgcgat    2400
ttggccacca ggaactgcct ggtcggggag aacttgctgg tgaaaatcgg ggactttggg    2460
atgtcccggg acgtgtacag cactgactac tacagggtcg gtggccacac aatgctgccc    2520
attcgctgga tgcctccaga gagcatcatg tacaggaaat tcacgacgga aagcgacgtc    2580
tggagcctgg gggtcgtgtt gtgggagatt ttcaccbatg gcaaacagcc ctggtaccag    2640
ctgtcaaaca atgaggtgat agagtgtatc actcagggcc gagtcctgca gcgacccgc     2700 acgtgccccc aggaggtgta tgagctgatg ctggggtgct ggcagcgaga gccccacatg    2760
aggaagaaca tcaagggcat ccataccctc cttcagaact tggccaaggc atctccggtc    2820
tacctggaca ttctaggcta gggccctttt ccccagaccg atccttccca acgtactcct    2880
cagacgggct gagaggatga acatcttta  actgccgctg gaggccacca agctgctctc    2940
cttcactctg acagtattaa catcaaagac tccgagaagc tctcgaggga agcagtgtgt    3000
acttcttcat ccatagacac agtattgact tcttttggc  attatctctt tctctctttc    3060
catctccctt ggttgttcct ttttcttttt ttaaatttc  tttttcttt  tttttcgtc     3120 ttccctgctt cacgattctt acccttctt  ttgaatcaat ctggcttctg cattactatt    3180
aactctgcat agacaaaggc cttaacaaac gtaatttgtt atatcagcag acactccagt    3240
ttgcccacca caactaacaa tgccttgttg tattcctgcc tttgatgtgg atgaaaaaaa    3300
gggaaaacaa atatttcact taaactttgt cacttctgct gtacagatat cgagagtttc    3360
tatggattca cttctatta  tttattatta ttactgttct tattgttttt ggatggctta    3420
agcctgtgta taaaaagaa  aacttgtgtt caatctgtga agcctttatc tatgggagat    3480
taaaaccaga gagaaagaag atttattatg aaccgcaata tgggaggaac aaagacaacc    3540
actgggatca gctggtgtca gtccctactt aggaaatact cagcaactgt agctgggaa     3600 gaatgtattc ggcaccttcc cctgaggacc tttctgagga gtaaaaagac tactggcctc    3660
tgtgccatgg atgattcttt tcccatcacc agaaatgata gcgtgcagta gagagcaaag    3720
atggcttccg tgagacacaa gatggcgcat agtgtgctcg gacacagttt tgtcttcgta    3780
ggttgtgatg atagcactgg tttgtttctc aagcgctatc cacagaacct tgtcaacttc    3840
cagttgaaaa gaggtggatt catgtccaga gctcatttcg gggtcaggtg gaaagccaa     3900 gaacttggaa aagataagac aagctataaa ttcggaggca gtttctttt  acaatgaact    3960 tttcagatct cacttccctc cgaccctaa  cttccatgcc cacccgtcct tttaactgtg    4020
caagcaaaat tgtgcatggt cttcgtcgat taataccttg tgtgcagaca ctactgctcc    4080
agacgtcgtt tccctgatag gtagagcaga tccataaaaa ggtatgactt atacaattag    4140
gggaagctaa tggagtttat tagctgagta tcaatgtctc tgcgttgtac ggtggtgatg    4200
ggttttaatg aatatggacc ctgaagcctg gaaatcctca tccacgtcga acccacagga    4260
ctgtgggaag ggcagaatca atccctaagg gaaaggaaac ctcaccctga gggcatcaca    4320
```

```
tgcactcatg ttcagtgtac acaggtcaag tcccttgctc tgggctctag ttgggagagt    4380
ggtttcattc caagtgtact ccattgtcag tatgctgttt ttgtttcctt cactccattc    4440
aaaaagtcaa atacaaaat ttggcacagc atgccaacgg gaggctgtgc ccagaccaag     4500
cactggaagt gtgcttctag gcatagtcat tggttttgca aaaagagggc tcaaatttaa    4560
atagaaattt acagctattt gaatggtcag ataccaag aaagaaaaat atttctgttc      4620
ctcaagaaaa cttgctaccc tctgtgaggg gaattttgct aaacttgaca tctttataac    4680
atgagccaga ttgaaaggga gtgattttca ttcatcttag gtcatgttat ttcatatttg    4740
tttctgaagg tgcgatagct ctgttttagg ttttgcttgc gcctgttaat tactggaaca    4800 ccttatttt cattaaaggc tttgaaagcc aattctcaaa aattcaaaag tgcaaattaa     4860
cagaacaaaa ggaaatccag tagcaactgc agtcaagcga gggagttgac aagataaacc    4920
ttacgtccat tcaagttata tgctggccta tgagagatga gagttgggtc gtttgttctc    4980
tttgttgatg attttaaaaa aaccctctag aatacacata ataacataat gaaagccata    5040
tctccatgat atatatgtgc acatatatat acatacatgt gcatgtatgt atcatattaa    5100
ggacccatgg tactcttaaa acactgtaga actctgtgac gcagtaagga aggggcagat    5160
ttgtacaaaa acttttctag attccatcag caaaaaccaa cacaggtttg tcacgctgca    5220
tgtctggcca gctaatctcg ggggaaaagc tacaagttat ttattttatt ttaagagaat    5280
aaagtaggta ataatttaag ggatcaaatt caaggaggaa tgtgcaattt tagagcaaag    5340
atttgtttaa ggcaaatgag actttgggag catcccattc cagttttgtc ttttttttct    5400
ctgaaagaaa aaagcaaaaa ataaaataaa attccactta taccttctga caagtcccta    5460
aaggtcttga aataaaaggt tctatgcaag tgcaaagttt tatagttatt tttattgctg    5520
attattacta ttactatctc tgttgtctta agagtatgtg ctgatttcag agacatctca    5580
aattgaaaga atatcagatt gcttttaaag tagctgaacg agccacagaa tatctgaaat    5640
tattcattgt tgttcctcca ccacccctt tctcatggtc tgattttag aagagtggca     5700 tcctcgttct aaaatgtaat gatcaccaaa tacggcctttc catcaaattt gtgaaaacta   5760
caacagtata acagtgacaa acctaattct ctagcccaaa cctggtctga caatcatttc    5820
catttagaag tcattgaata gttttccaaa cactttccat gtgtgttagc aaattattcc    5880
tattttgtgt agatgaggac gttgagactc agagacattc agaggcacgc tagaggtctc    5940
cagcctagct tccagcacca ttgggactga atccaagtac tctcactctg aacttcgtgg    6000
ttctgtccac tagagactct aatatgcaaa caagcagttc aggaaagaaa gcatgctaac    6060
acattcatga agcagtatat gaagttagaa gaacaaaagg aaatacagga gatgacaagc    6120
aactgagata ttgtgatata taatcatgct cttagcttca gctaaattca gctaaattct    6180
tgtacactga accaatgtca taatcaggct tatttagaaa acactttgaa ctatgctata    6240
aaagattata tcagaattca tattatacat gtgttcacat cagcgctacc tgtgatgttt    6300 tcatgtatt atgtatgtgt tataaatact tgatttatac atatacaaat gcacatacgt     6360
agtgtgtttg tgtgtttatg tataaattta taggcacaca ataatagagg taattataag    6420
taggatgcgg tatgaataat ttgcttaaaa tatgctaaat aaccaaaact gtttaacgtc    6480
atgttgctgt tagtgcttcc atactccacg tgggtaggac tacatcacac ttttcaactc    6540
tgtgcagtac tgcatgggtg gaagacatat ttaagataat gtgcttccca aaacaactga    6600
ataaaagcca tcccactaca ttgagtgctt tctctggctc cttgcaaaga aagatacttt    6660
```

| | |
|---|---|
| ttgtaatggt ccaggaaagg aacattgctt tcttttgtc tttcagcaca tttgtattat | 6720 |
| gctcaccttg tctctgtctc actgtgaccc ctttacactt gagttcagag ttcaagcatt | 6780 |
| ccaaatataa attggaatgt tggcagccca gtggcttgaa ggccaatgat gagcagtcca | 6840 |
| agacccaca gcgagatgag caactcttag gaattcccac atcctagagt gaatgcacca | 6900 |
| actaacagta tagaatgctg tccttttcaa agcgtcctaa cagcaggatt acctggtcaa | 6960 |
| gtatggactt tctttgaatc tttcttttca caaattggac tgcctgtaat accaataaca | 7020 |
| ttgttgtatc taactaaata aatgactgca tatacacaca taccctcaat tctcttgctt | 7080 |
| ccccatttc ttttcatcc cctgtctcag gactttatt ttcaatgttg accttggtt | 7140 |
| tggccatata tcactgttat aggaaatctc atgagaggaa tggctagtga cccaactctc | 7200 |
| caaatgtcta agttagtagt tacagctgat ttttatgat gcataattgg aatgtggagc | 7260 |
| ctctgaggtt gtgatagctt gtacatgaat ttcaaatgtc attctaaaga atgaggggtg | 7320 |
| ggagggattt atagttagaa acgacagtgc aggaagggt attttcttgt tgtcagggct | 7380 |
| ggaatgaatc actgctgctc aagtcaaagg ttcttgaata tccttagttt ttgcatttcc | 7440 |
| cctccttttc ctttgacctt tattatttta attatgtatt tatttattta tttatatact | 7500 |
| tttgctccat tcagcacaaa cacaaagcaa agcaaaaaaa aaaatatata tatatatatc | 7560 |
| tgtatatgtg ttgtaggcaa aacactgtga atttcacaac aaccaccacc aagcaactat | 7620 |
| tttgccatct taacatacat ctcaggagac gaaatgagaa aagatgggga tgtcattttt | 7680 |
| tagtctatgc gtttgaggcc aggtccatgt ttatttattt ctttagtcta tgcattaatg | 7740 |
| aaaatgatcc tgagtggagg ttagctgaac gttcaatgta ctggagcaag catcataaaa | 7800 |
| gctgctagta gccatgtgtt tgaacaggaa aaatattaca gaaaatgaaa tgtaaaggcc | 7860 |
| tatatcttgc agcttgtata tcttactatt gcttaaaaaa tgtataaagc agctggaaat | 7920 |
| gtttaaaata caaggtcttt gaattaaatg tggattttaa atatgtaatc ccttgacaaa | 7980 |
| tgaccaaatt atggtgaact attgctccct gcgttctttg atcattacct atgacttaca | 8040 |
| aatctgcctg gagatgtgga cattctgcat ttgcttctgt atctggagag atgtttgtat | 8100 |
| atatccaggc cgtatacaca cacatttcca tatctctcta cagatatatt tcccttcaa | 8160 |
| tcgtgacctg gtatttggaa ctctcctttt catttggctt atcttccttt taatgtgatg | 8220 |
| tctctgtgct aatacttacc agttcttgtt ttgcaatctg ttttgaggtc cattgcttta | 8280 |
| ctaagaccca ctgcatcttg gctgatttca aagtgacacc tgaatacagt gtttaaaaaa | 8340 |
| aaaaagttt tgtttgtaaa tcatgtgacc agcttctctc aacctgacat ggaaagtctc | 8400 |
| ttgtactaca gtgtatttaa taaaaatgat gtcttacaat aaataacata ctccaaaaga | 8460 |
| gagactaaaa atgaaaaaaa aaaaaaaaaa aaaaaaaa | 8498 |

```
<210> SEQ ID NO 77
<211> LENGTH: 2469
<212> TYPE: DNA
<213> ORGANISM: Homo sapiens
<220> FEATURE:
<221> NAME/KEY: misc_feature
<222> LOCATION: (1)..(93)
<223> OTHER INFORMATION: Signal Peptide
<220> FEATURE:
<221> NAME/KEY: misc_feature
<222> LOCATION: (94)..(1290)
<223> OTHER INFORMATION: Extracellular Domain
<220> FEATURE:
<221> NAME/KEY: misc_feature
<222> LOCATION: (1291)..(1362)
<223> OTHER INFORMATION: Transmembrane Domain
```

<220> FEATURE:
<221> NAME/KEY: misc_feature
<222> LOCATION: (1363)..(2466)
<223> OTHER INFORMATION: Cytoplasmic Domain

<400> SEQUENCE: 77

```
atgtcgtcct ggataaggtg gcatggaccc gccatggcgc ggctctgggg cttctgctgg      60
ctggttgtgg gcttctggag ggccgctttc gcctgtccca cgtcctgcaa atgcagtgcc     120
tctcggatct ggtgcagcga cccttctcct ggcatcgtgg catttccgag attggagcct     180
aacagtgtag atcctgagaa catcaccgaa attttcatcg caaaccagaa aaggttagaa     240
atcatcaacg aagatgatgt tgaagcttat gtgggactga aaatctgac aattgtggat      300
tctggattaa aatttgtggc tcataaagca tttctgaaaa cagcaacct gcagcacatc      360
aatttttaccc gaaacaaact gacgagtttg tctaggaaac atttccgtca ccttgacttg    420
tctgaactga tcctggtggg caatccattt acatgctcct gtgacattat gtggatcaag    480
actctccaag aggctaaatc cagtccgac actcaggatt gtactgcct gaatgaaagc      540
agcaagaata ttccctggc aaacctgcag atacccaatt gtggtttgcc atctgcaaat    600
ctggccgcac ctaacctcac tgtggaggaa ggaaagtcta tcacattatc ctgtagtgtg    660
gcaggtgatc cggttcctaa tatgtattgg gatgttggta acctggtttc caaacatatg    720
aatgaaacaa gccacacaca gggctcctta aggataacta acatttcatc cgatgacagt    780
gggaagcaga tctcttgtgt ggcggaaaat cttgtaggag aagatcaaga ttctgtcaac    840
ctcactgtgc attttgcacc aactatcaca tttctcgaat ctccaacctc agaccaccac    900
tggtgcattc cattcactgt gaaaggcaac cccaaaccag cgcttcagtg gttctataac    960
ggggcaatat tgaatgagtc caaatacatc tgtactaaaa tacatgttac caatcacacg   1020
gagtaccacg gctgcctcca gctggataat cccactcaca tgaacaatgg ggactacact   1080
ctaatagcca agaatgagta tgggaaggat gagaaacaga tttctgctca cttcatgggc   1140
tggcctggaa ttgacgatgg tgcaaaccca aattatcctg atgtaattta tgaagattat   1200
ggaactgcag cgaatgacat cggggacacc acgaacagaa gtaatgaaat ccttccaca   1260
gacgtcactg ataaaaccgg tcgggaacat ctctcggtct atgctgtggt ggtgattgcg    1320
tctgtggtgg gattttgcct tttggtaatg ctgtttctgc ttaagttggc aagacactcc    1380
aagtttggca tgaaaggccc agcctccgtt atcagcaatg atgatgactc tgccagccca    1440
ctccatcaca tctccaatgg gagtaacact ccatcttctt cggaaggtgg cccagatgct    1500
gtcattattg gaatgaccaa gatccctgtc attgaaaatc cccagtactt tggcatcacc    1560
aacagtcagc tcaagccaga cacatttgtt cagcacatca gcgacataa cattgttctg    1620
aaaagggagc taggcgaagg agcctttgga aaagtgttcc tagctgaatg ctataacctc    1680
tgtcctgagc aggacaagat cttggtggca gtgaagaccc tgaaggatgc cagtgacaat    1740
gcacgcaagg acttccaccg tgaggccgag ctcctgacca acctccagca tgagcacatc    1800
gtcaagttct atggcgtctg cgtggagggc gacccctca tcatggtctt tgagtacatg    1860
aagcatgggg acctcaacaa gttcctcagg gcacacggcc ctgatgccgt gctgatggct    1920
gagggcaacc cgcccacgga actgacgcag tcgcagatgc tgcatatagc ccagcagatc    1980
gccgcgggca tggtctacct ggcgtcccag cacttcgtgc accgcgattt ggccaccagg    2040
aactgcctgg tcggggagaa cttgctgtg aaaatcgggg actttgggat gtcccgggac    2100
gtgtacagca ctgactacta cagggtcggt ggccacacaa tgctgcccat tcgctggatg    2160
```

```
cctccagaga gcatcatgta caggaaattc acgacggaaa gcgacgtctg gagcctgggg    2220
gtcgtgttgt gggagatttt cacctatggc aaacagccct ggtaccagct gtcaaacaat    2280
gaggtgatag agtgtatcac tcagggccga gtcctgcagc gaccccgcac gtgccccag     2340 gaggtgtatg agctgatgct ggggtgctgg cagcgagagc cccacatgag gaagaacatc    2400
aagggcatcc ataccctcct tcagaacttg gccaaggcat ctccggtcta cctggacatt    2460
ctaggctag                                                             2469
```

<210> SEQ ID NO 78
<211> LENGTH: 354
<212> TYPE: DNA
<213> ORGANISM: Artificial Sequence
<220> FEATURE:
<223> OTHER INFORMATION: Synthetic

<400> SEQUENCE: 78

```
caggtgcagc tggtggagtc tgggggaggc gtggtccagc ctgggaggtc cctgagactc      60
tcctgtgcag cctctggatt cagcttcagt agctttggca tgcactgggt ccgccaggct     120
ccaggcaagg gactggagtg ggtgtcagtt atatcatatg atggaattaa tacatactat     180
acagactccg tgaagggccg attcaccatc tccagagaca attccaagaa cacgctgtat     240
ctgcaaatga acggcctgag agctgaggac acggctcttt attactgtgt gcaagggtca     300
attggaaccg ttttttgaata ctggggccag ggaaccctgg tcaccgtctc ctca          354
```

<210> SEQ ID NO 79
<211> LENGTH: 118
<212> TYPE: PRT
<213> ORGANISM: Artificial Sequence
<220> FEATURE:
<223> OTHER INFORMATION: Synthetic

<400> SEQUENCE: 79

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Phe
            20                  25                  30

Gly Met His Trp Val Arg Gln Ala Pro Gly Lys Gly Leu Glu Trp Val
        35                  40                  45

Ser Val Ile Ser Tyr Asp Gly Ile Asn Thr Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Gly Leu Arg Ala Glu Asp Thr Ala Leu Tyr Tyr Cys
                85                  90                  95

Val Gln Gly Ser Ile Gly Thr Val Phe Glu Tyr Trp Gly Gln Gly Thr
            100                 105                 110

Leu Val Thr Val Ser Ser
        115

<210> SEQ ID NO 80
<211> LENGTH: 24
<212> TYPE: DNA
<213> ORGANISM: Artificial Sequence
<220> FEATURE:
<223> OTHER INFORMATION: Synthetic

<400> SEQUENCE: 80

```
ggattcagct tcagtagctt tggc                                             24
```

<210> SEQ ID NO 81
<211> LENGTH: 8
<212> TYPE: PRT
<213> ORGANISM: Artificial Sequence
<220> FEATURE:
<223> OTHER INFORMATION: Synthetic

<400> SEQUENCE: 81

Gly Phe Ser Phe Ser Ser Phe Gly
1               5

<210> SEQ ID NO 82
<211> LENGTH: 24
<212> TYPE: DNA
<213> ORGANISM: Artificial Sequence
<220> FEATURE:
<223> OTHER INFORMATION: Synthetic

<400> SEQUENCE: 82
atatcatatg atggaattaa taca                                          24

<210> SEQ ID NO 83
<211> LENGTH: 8
<212> TYPE: PRT
<213> ORGANISM: Artificial Sequence
<220> FEATURE:
<223> OTHER INFORMATION: Synthetic

<400> SEQUENCE: 83

Ile Ser Tyr Asp Gly Ile Asn Thr
1               5

<210> SEQ ID NO 84
<211> LENGTH: 33
<212> TYPE: DNA
<213> ORGANISM: Artificial Sequence
<220> FEATURE:
<223> OTHER INFORMATION: Synthetic

<400> SEQUENCE: 84
gtgcaagggt caattggaac cgttttttgaa tac                               33

<210> SEQ ID NO 85
<211> LENGTH: 11
<212> TYPE: PRT
<213> ORGANISM: Artificial Sequence
<220> FEATURE:
<223> OTHER INFORMATION: Synthetic

<400> SEQUENCE: 85

Val Gln Gly Ser Ile Gly Thr Val Phe Glu Tyr
1               5                   10

<210> SEQ ID NO 86
<211> LENGTH: 321
<212> TYPE: DNA
<213> ORGANISM: Artificial Sequence
<220> FEATURE:
<223> OTHER INFORMATION: Synthetic

<400> SEQUENCE: 86
gacatccaga tgacccagtc tccatcctcc ctgtctgcat ctgtaggaga cagagtcacc   60
atcacttgcc gggcgagtca gggcattagc aattatttag cctggtatca gcagaaacca  120
gggaaagttc ctaaactcct gatctatgct gcatccactt tacaatcagg ggtcccatct  180

```
cggttcggtg gcagtggatc tgggacagat ttcactctca ccatcagcag cctgcagcct    240
gaagatgttg caacttatta ctgtcaaaag tataccagtg ccccattcac tttcggccct    300
gggaccaaag tggatatcaa a                                              321
```

```
<210> SEQ ID NO 87
<211> LENGTH: 107
<212> TYPE: PRT
<213> ORGANISM: Artificial Sequence
<220> FEATURE:
<223> OTHER INFORMATION: Synthetic

<400> SEQUENCE: 87
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Gly Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Thr Ser Ala Pro Phe
                85                  90                  95

Thr Phe Gly Pro Gly Thr Lys Val Asp Ile Lys
            100                 105

```
<210> SEQ ID NO 88
<211> LENGTH: 18
<212> TYPE: DNA
<213> ORGANISM: Artificial Sequence
<220> FEATURE:
<223> OTHER INFORMATION: Synthetic

<400> SEQUENCE: 88
cagggcatta gcaattat                                                   18

<210> SEQ ID NO 89
<211> LENGTH: 6
<212> TYPE: PRT
<213> ORGANISM: Artificial Sequence
<220> FEATURE:
<223> OTHER INFORMATION: Synthetic

<400> SEQUENCE: 89
```

Gln Gly Ile Ser Asn Tyr
1               5

```
<210> SEQ ID NO 90
<211> LENGTH: 9
<212> TYPE: DNA
<213> ORGANISM: Artificial Sequence
<220> FEATURE:
<223> OTHER INFORMATION: Synthetic

<400> SEQUENCE: 90 gctgcatcc                                                              9

<210> SEQ ID NO 91
<211> LENGTH: 3
<212> TYPE: PRT
```

```
<213> ORGANISM: Artificial Sequence
<220> FEATURE:
<223> OTHER INFORMATION: Synthetic

<400> SEQUENCE: 91

Ala Ala Ser
1

<210> SEQ ID NO 92
<211> LENGTH: 27
<212> TYPE: DNA
<213> ORGANISM: Artificial Sequence
<220> FEATURE:
<223> OTHER INFORMATION: Synthetic

<400> SEQUENCE: 92
caaaagtata ccagtgcccc attcact                                          27

<210> SEQ ID NO 93
<211> LENGTH: 9
<212> TYPE: PRT
<213> ORGANISM: Artificial Sequence
<220> FEATURE:
<223> OTHER INFORMATION: Synthetic

<400> SEQUENCE: 93

Gln Lys Tyr Thr Ser Ala Pro Phe Thr
1               5

<210> SEQ ID NO 94
<211> LENGTH: 366
<212> TYPE: DNA
<213> ORGANISM: Artificial Sequence
<220> FEATURE:
<223> OTHER INFORMATION: Synthetic

<400> SEQUENCE: 94
gaggtgcagc tggtggagtc tgggggaggc ttggtccagc ctggggggtc cctaaaactc       60
tcctgtacag cctctgggtt caccttcagt ggctctgtta ttcactgggt ccgccaggct      120
tccgggaaag gctggagtg gattggccgt attagaaaca aggctaacag ttacgcgaca       180
gcatatggtg cgtcggtgac aggcaggttc accatctcca gagatgattc aaagaacacg      240
gcgtatctgc aaatgaacag cctgaaaacc gaggacacgg ccgttttatta ctgtactttc     300 ccgggtgtag tgggacgagg aggttttgac tactggggcc agggcaccct ggtcaccgtc      360
tcctca                                                                366

<210> SEQ ID NO 95
<211> LENGTH: 122
<212> TYPE: PRT
<213> ORGANISM: Artificial Sequence
<220> FEATURE:
<223> OTHER INFORMATION: Synthetic

<400> SEQUENCE: 95

Glu Val Gln Leu Val Glu Ser Gly Gly Gly Leu Val Gln Pro Gly Gly
1               5                   10                  15

Ser Leu Lys Leu Ser Cys Thr Ala Ser Gly Phe Thr Phe Ser Gly Ser
            20                  25                  30

Val Ile His Trp Val Arg Gln Ala Ser Gly Lys Gly Leu Glu Trp Ile
        35                  40                  45

Gly Arg Ile Arg Asn Lys Ala Asn Ser Tyr Ala Thr Ala Tyr Gly Ala
    50                  55                  60
```

Ser Val Thr Gly Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Val Tyr
                 85                  90                  95

Tyr Cys Thr Phe Pro Gly Val Val Gly Arg Gly Gly Phe Asp Tyr Trp
            100                 105                 110

Gly Gln Gly Thr Leu Val Thr Val Ser Ser
        115                 120

<210> SEQ ID NO 96
<211> LENGTH: 24
<212> TYPE: DNA
<213> ORGANISM: Artificial Sequence
<220> FEATURE:
<223> OTHER INFORMATION: Synthetic

<400> SEQUENCE: 96
gggttcacct tcagtggctc tgtt                                          24

<210> SEQ ID NO 97
<211> LENGTH: 8
<212> TYPE: PRT
<213> ORGANISM: Artificial Sequence
<220> FEATURE:
<223> OTHER INFORMATION: Synthetic

<400> SEQUENCE: 97

Gly Phe Thr Phe Ser Gly Ser Val
1               5

<210> SEQ ID NO 98
<211> LENGTH: 30
<212> TYPE: DNA
<213> ORGANISM: Artificial Sequence
<220> FEATURE:
<223> OTHER INFORMATION: Synthetic

<400> SEQUENCE: 98
attagaaaca aggctaacag ttacgcgaca                                    30

<210> SEQ ID NO 99
<211> LENGTH: 10
<212> TYPE: PRT
<213> ORGANISM: Artificial Sequence
<220> FEATURE:
<223> OTHER INFORMATION: Synthetic

<400> SEQUENCE: 99

Ile Arg Asn Lys Ala Asn Ser Tyr Ala Thr
1               5                   10

<210> SEQ ID NO 100
<211> LENGTH: 39
<212> TYPE: DNA
<213> ORGANISM: Artificial Sequence
<220> FEATURE:
<223> OTHER INFORMATION: Synthetic

<400> SEQUENCE: 100
actttcccgg gtgtagtggg acgaggaggt tttgactac                          39

<210> SEQ ID NO 101
<211> LENGTH: 13
<212> TYPE: PRT

<213> ORGANISM: Artificial Sequence
<220> FEATURE:
<223> OTHER INFORMATION: Synthetic

<400> SEQUENCE: 101

Thr Phe Pro Gly Val Gly Arg Gly Gly Phe Asp Tyr
1               5                   10

<210> SEQ ID NO 102
<211> LENGTH: 339
<212> TYPE: DNA
<213> ORGANISM: Artificial Sequence
<220> FEATURE:
<223> OTHER INFORMATION: Synthetic

<400> SEQUENCE: 102

```
gacatcgtga tgacccagtc tccagactcc ctggctgtgt ctctgggcga gggggccacc      60
atcaactgca tgtccagcca gagtgtttta ttcagctcca acaataagaa ctacttagct     120
tggtaccaac agaaaccagg acagcctcct aagttgctct tttactgggc atctacccgg     180
gaatccgggg tccctgaccg attcggtggc agcgggtctg ggacagattt ctctctcacc     240
atcaacagcc tgcagactga agatgtggca gtttattact gtctccaata ttatagtatt     300
ccgtggacgt tcggccaagg gaccaaggtg gaaatcaaa                            339
```

<210> SEQ ID NO 103
<211> LENGTH: 113
<212> TYPE: PRT
<213> ORGANISM: Artificial Sequence
<220> FEATURE:
<223> OTHER INFORMATION: Synthetic

<400> SEQUENCE: 103

Asp Ile Val Met Thr Gln Ser Pro Asp Ser Leu Ala Val Ser Leu Gly
1               5                   10                  15

Glu Gly Ala Thr Ile Asn Cys Met Ser Ser Gln Ser Val Leu Phe Ser
                20                  25                  30

Ser Asn Asn Lys Asn Tyr Leu Ala Trp Tyr Gln Gln Lys Pro Gly Gln
            35                  40                  45

Pro Pro Lys Leu Leu Phe Tyr Trp Ala Ser Thr Arg Glu Ser Gly Val
    50                  55                  60

Pro Asp Arg Phe Gly Gly Ser Gly Ser Gly Thr Asp Phe Ser Leu Thr
65                  70                  75                  80

Ile Asn Ser Leu Gln Thr Glu Asp Val Ala Val Tyr Tyr Cys Leu Gln
                85                  90                  95

Tyr Tyr Ser Ile Pro Trp Thr Phe Gly Gln Gly Thr Lys Val Glu Ile
            100                 105                 110

Lys

<210> SEQ ID NO 104
<211> LENGTH: 36
<212> TYPE: DNA
<213> ORGANISM: Artificial Sequence
<220> FEATURE:
<223> OTHER INFORMATION: Synthetic

<400> SEQUENCE: 104

```
cagagtgttt tattcagctc caacaataag aactac                               36
```

<210> SEQ ID NO 105
<211> LENGTH: 12

```
<212> TYPE: PRT
<213> ORGANISM: Artificial Sequence
<220> FEATURE:
<223> OTHER INFORMATION: Synthetic

<400> SEQUENCE: 105

Gln Ser Val Leu Phe Ser Ser Asn Asn Lys Asn Tyr
1               5                   10

<210> SEQ ID NO 106
<211> LENGTH: 9
<212> TYPE: DNA
<213> ORGANISM: Artificial Sequence
<220> FEATURE:
<223> OTHER INFORMATION: Synthetic

<400> SEQUENCE: 106 tgggcatct                                                                     9

<210> SEQ ID NO 107
<211> LENGTH: 3
<212> TYPE: PRT
<213> ORGANISM: Artificial Sequence
<220> FEATURE:
<223> OTHER INFORMATION: Synthetic

<400> SEQUENCE: 107

Trp Ala Ser
1

<210> SEQ ID NO 108
<211> LENGTH: 27
<212> TYPE: DNA
<213> ORGANISM: Artificial Sequence
<220> FEATURE:
<223> OTHER INFORMATION: Synthetic

<400> SEQUENCE: 108
ctccaatatt atagtattcc gtggacg                                                27

<210> SEQ ID NO 109
<211> LENGTH: 9
<212> TYPE: PRT
<213> ORGANISM: Artificial Sequence
<220> FEATURE:
<223> OTHER INFORMATION: Synthetic

<400> SEQUENCE: 109

Leu Gln Tyr Tyr Ser Ile Pro Trp Thr
1               5

<210> SEQ ID NO 110
<211> LENGTH: 381
<212> TYPE: DNA
<213> ORGANISM: Artificial Sequence
<220> FEATURE:
<223> OTHER INFORMATION: Synthetic

<400> SEQUENCE: 110
gaggtgcagc tggtggagtc tgggggaggc ttggtacagc ctggagggtc cctgacactc            60
tcctgtgcag cctctggatt caatttccgt gattatgaaa tgatctgggt ccgccagact           120
ccagggaagg ggctggagtg gatttcatac attagtaata gtggttatac catatactac           180
gcagactctg tgaagggccg attcaccatc tccagagaca cgccaggaa ctcaatatat           240 ctgcaagtga acagcctgag agccgaggac acggctgttt attactgttc gagacgtact           300
```

```
actatgattc ggggcattag ggcgtactac tattacggtc tggacgtctg gggccaaggg    360
accacggtca ccgtctcctc a                                              381
```

<210> SEQ ID NO 111
<211> LENGTH: 127
<212> TYPE: PRT
<213> ORGANISM: Artificial Sequence
<220> FEATURE:
<223> OTHER INFORMATION: Synthetic

<400> SEQUENCE: 111

```
Glu Val Gln Leu Val Glu Ser Gly Gly Gly Leu Val Gln Pro Gly Gly
1               5                   10                  15

Ser Leu Thr Leu Ser Cys Ala Ala Ser Gly Phe Asn Phe Arg Asp Tyr
            20                  25                  30

Glu Met Ile Trp Val Arg Gln Thr Pro Gly Lys Gly Leu Glu Trp Ile
        35                  40                  45

Ser Tyr Ile Ser Asn Ser Gly Tyr Thr Ile Tyr Tyr Ala Asp Ser Val
    50                  55                  60

Lys Gly Arg Phe Thr Ile Ser Arg Asp Asn Ala Arg Asn Ser Ile Tyr
65                  70                  75                  80

Leu Gln Val Asn Ser Leu Arg Ala Glu Asp Thr Ala Val Tyr Tyr Cys
                85                  90                  95

Ser Arg Arg Thr Thr Met Ile Arg Gly Ile Arg Ala Tyr Tyr Tyr Tyr
            100                 105                 110

Gly Leu Asp Val Trp Gly Gln Gly Thr Thr Val Thr Val Ser Ser
        115                 120                 125
```

<210> SEQ ID NO 112
<211> LENGTH: 24
<212> TYPE: DNA
<213> ORGANISM: Artificial Sequence
<220> FEATURE:
<223> OTHER INFORMATION: Synthetic

<400> SEQUENCE: 112

```
ggattcaatt tccgtgatta tgaa                                           24
```

<210> SEQ ID NO 113
<211> LENGTH: 8
<212> TYPE: PRT
<213> ORGANISM: Artificial Sequence
<220> FEATURE:
<223> OTHER INFORMATION: Synthetic

<400> SEQUENCE: 113

```
Gly Phe Asn Phe Arg Asp Tyr Glu
1               5
```

<210> SEQ ID NO 114
<211> LENGTH: 24
<212> TYPE: DNA
<213> ORGANISM: Artificial Sequence
<220> FEATURE:
<223> OTHER INFORMATION: Synthetic

<400> SEQUENCE: 114

```
attagtaata gtggttatac cata                                           24
```

<210> SEQ ID NO 115
<211> LENGTH: 8

```
<212> TYPE: PRT
<213> ORGANISM: Artificial Sequence
<220> FEATURE:
<223> OTHER INFORMATION: Synthetic

<400> SEQUENCE: 115

Ile Ser Asn Ser Gly Tyr Thr Ile
1               5

<210> SEQ ID NO 116
<211> LENGTH: 60
<212> TYPE: DNA
<213> ORGANISM: Artificial Sequence
<220> FEATURE:
<223> OTHER INFORMATION: Synthetic

<400> SEQUENCE: 116
tcgagacgta ctactatgat cggggcatt agggcgtact actattacgg tctggacgtc     60

<210> SEQ ID NO 117
<211> LENGTH: 20
<212> TYPE: PRT
<213> ORGANISM: Artificial Sequence
<220> FEATURE:
<223> OTHER INFORMATION: Synthetic

<400> SEQUENCE: 117

Ser Arg Arg Thr Thr Met Ile Arg Gly Ile Arg Ala Tyr Tyr Tyr Tyr
1               5                   10                  15

Gly Leu Asp Val
            20

<210> SEQ ID NO 118
<211> LENGTH: 324
<212> TYPE: DNA
<213> ORGANISM: Artificial Sequence
<220> FEATURE:
<223> OTHER INFORMATION: Synthetic

<400> SEQUENCE: 118
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccgtca    180
aggttcagtg gcagtggatc tgggacagat ttcactctca ccatcagcag tctgcaacct    240
gaagattttg caacttacta ctgtcaacag agttacagta cccctccgat caccttcggc    300
caagggacac gactggagat taaa                                          324

<210> SEQ ID NO 119
<211> LENGTH: 108
<212> TYPE: PRT
<213> ORGANISM: Artificial Sequence
<220> FEATURE:
<223> OTHER INFORMATION: Synthetic

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

Ile Thr Phe Gly Gln Gly Thr Arg Leu Glu Ile Lys
            100                 105

<210> SEQ ID NO 120
<211> LENGTH: 18
<212> TYPE: DNA
<213> ORGANISM: Artificial Sequence
<220> FEATURE:
<223> OTHER INFORMATION: Synthetic

<400> SEQUENCE: 120
cagagcatta gcagctat                                                 18

<210> SEQ ID NO 121
<211> LENGTH: 6
<212> TYPE: PRT
<213> ORGANISM: Artificial Sequence
<220> FEATURE:
<223> OTHER INFORMATION: Synthetic

<400> SEQUENCE: 121

Gln Ser Ile Ser Ser Tyr
1               5

<210> SEQ ID NO 122
<211> LENGTH: 9
<212> TYPE: DNA
<213> ORGANISM: Artificial Sequence
<220> FEATURE:
<223> OTHER INFORMATION: Synthetic

<400> SEQUENCE: 122 gctgcatcc                                                            9

<210> SEQ ID NO 123
<211> LENGTH: 3
<212> TYPE: PRT
<213> ORGANISM: Artificial Sequence
<220> FEATURE:
<223> OTHER INFORMATION: Synthetic

<400> SEQUENCE: 123

Ala Ala Ser
1

<210> SEQ ID NO 124
<211> LENGTH: 30
<212> TYPE: DNA
<213> ORGANISM: Artificial Sequence
<220> FEATURE:
<223> OTHER INFORMATION: Synthetic

<400> SEQUENCE: 124
caacagagtt acagtacccc tccgatcacc                                    30

<210> SEQ ID NO 125
<211> LENGTH: 10
<212> TYPE: PRT
<213> ORGANISM: Artificial Sequence
```

```
<220> FEATURE:
<223> OTHER INFORMATION: Synthetic

<400> SEQUENCE: 125

Gln Gln Ser Tyr Ser Thr Pro Pro Ile Thr
1               5                   10
```